US007521541B2

(12) United States Patent
Eigenbrot et al.

(10) Patent No.: US 7,521,541 B2
(45) Date of Patent: Apr. 21, 2009

(54) CYSTEINE ENGINEERED ANTIBODIES AND CONJUGATES

(75) Inventors: Charles W. Eigenbrot, Burlingame, CA (US); Jagath Reddy Junutula, Fremont, CA (US); Henry Lowman, El Granada, CA (US); Helga E. Raab, San Francisco, CA (US); Richard Vandlen, Hillsborough, CA (US)

(73) Assignee: Genetech Inc., South San Francisco, CA (US)

( * ) Notice: Subject to any disclaimer, the term of this patent is extended or adjusted under 35 U.S.C. 154(b) by 0 days.

(21) Appl. No.: 11/233,258

(22) Filed: Sep. 22, 2005

(65) Prior Publication Data

US 2007/0092940 A1 Apr. 26, 2007

Related U.S. Application Data

(60) Provisional application No. 60/696,353, filed on Jun. 30, 2005, provisional application No. 60/612,468, filed on Sep. 23, 2004.

(51) Int. Cl.
*C07K 16/00* (2006.01)

(52) U.S. Cl. .................. 530/387.1; 424/133.1

(58) Field of Classification Search ........................ None
See application file for complete search history.

(56) References Cited

U.S. PATENT DOCUMENTS

| 5,219,996 A | * | 6/1993 | Bodmer et al. | ............ 530/387.3 |
| 6,248,564 B1 | | 6/2001 | Walter et al. | |
| 6,753,165 B1 | | 6/2004 | Cox et al. | |
| 7,097,840 B2 | * | 8/2006 | Erickson et al. | ............ 424/178.1 |
| 2004/0005324 A1 | * | 1/2004 | Pilkington et al. | ....... 424/159.1 |
| 2004/0229310 A1 | | 11/2004 | Simmons | |
| 2004/0235068 A1 | * | 11/2004 | Levinson | .................... 435/7.23 |
| 2005/0048572 A1 | | 3/2005 | Reilly et al. | |

FOREIGN PATENT DOCUMENTS

| WO | WO/89/01974 | * | 3/1989 |
| WO | 94/06474 | | 3/1994 |
| WO | 03/049704 A2 | | 6/2003 |
| WO | 03/060080 A2 | | 7/2003 |
| WO | 2004/050849 A2 | | 6/2004 |

OTHER PUBLICATIONS

Carter, P., Presta, L., Gorman, C.M., Ridgway, J.B.B., Henner, D., Wong, W.L., Rowland, A.M., Kotts, C., Carver, M.E., and Shepard, H.M. Humanization of an anti-p185 her2 antibody for human cancer therapy. Proceedings of the National Academy of Sciences, 1992. vol. 89, pp. 4285-4289.*
Rudikoff, S., Giusti, A.M., Cook, W.D., and Scharff, M.D. Single amino acid substitution altering antigen-binding specificity. Proceedings of the National Academy of Sciences, 1982. vol. 79, pp. 1979-1983.*
MacCallum, R.M., Martin, A.C.R., and Thornton, J.M. Antibody-antigen independent interactions: contact analysis and binding site topography. Journal of Molecular Biology, 1996. vol. 262, pp. 732-745.*
Wu, H., Nie, Y., Huse, W.D., and Watkins, J.D. Humanization of a murine monoclonal antibody by simultaneous optimization of framework and CDR residues. Journal of Molecular Biology, 1999. vol. 294, pp. 151-162.*
Kabat, E.A., Wu, T.T., Reid-Miller, M., Perry, H.M., and Gottesman, K.S., eds. Sequences of Proteins of Immunological Interest, 1987. 4th ed. US Department of Health and Human Services, Public Health Service, National Institutes of Health, pp. 160 and 294.*
All drugs online. Retrieved from the Internet <URL:http://www.all-drugs-online.com/Drugs/Oncology/1377.aspx> Retrieved on Jan. 5, 2009.*
Biopharma. Retrieved from the Interent <URL: http://www.biopharma.com/Samples/184.html> Retrieved on Jan. 5, 2009.*
Baca et al., "Antibody Humanization Using Monovalent Phage Display" *Journal of Biological Chemistry* 272(16):10678-10684 (1997).
Bernhard et al., "Cysteine analogs of recombinant barley ribosome inactivating protein form antibody conjugates with enhanced stability and potency in vitro" *Bioconjug Chem.* (5) 2:126-132 (Mar. 1994).
Better et al., "Gelonin analogs with engineered cysteine residues form antibody immunoconjugates with unique properties" *J Biol Chem.* 269(13):9644-9650 (Apr. 1, 1994).
*CellTiter-Glo Luminescent Cell Viability Assay* (Technical Bulletin No. 288). Madison, WI:Promega Corp., pp. 1-11 (Feb. 2004).
Chang et al., "High-Level Secretion of Human Growth Hormone by *Escherichia coli*" *Gene* 55:189-196 (1987).
Chmura et al., "Antibodies with infinite affinity" *Proc Natl Acad Sci U S A.* 98(15):8480-8484. (Jul. 17, 2001).
Collaborative Computational Project, No. 4, "The CCP4 Suite: Programs for Protein Crystallography" *Acta. Cryst.* D50-760-763 (1994).
Dennis et al., "Albumin binding as a general strategy for improving the pharmacokinetics of proteins" *Journal of Biological Chemistry* 277(38):35035-35043 (Sep. 20, 2002).
Doronina et al., "Development of potent monoclonal antibody auristatin conjugates for cancer therapy" *Nature Biotechnology* 21:778-784 (2003).

(Continued)

*Primary Examiner*—Larry R. Helms
*Assistant Examiner*—Meera Natarajan
(74) *Attorney, Agent, or Firm*—Alex Andrus

(57) ABSTRACT

Antibodies are engineered by replacing one or more amino acids of a parent antibody with non cross-linked, highly reactive cysteine amino acids. Antibody fragments may also be engineered with one or more cysteine amino acids to form cysteine engineered antibody fragments (ThioFab). Methods of design, preparation, screening, and selection of the cysteine engineered antibodies are provided. Cysteine engineered antibodies (Ab), optionally with an albumin-binding peptide (ABP) sequence, are conjugated with one or more drug moieties (D) through a linker (L) to form cysteine engineered antibody-drug conjugates having Formula I:

$$Ab-(L-D)_p \qquad I$$

where p is 1 to 4. Diagnostic and therapeutic uses for cysteine engineered antibody drug compounds and compositions are disclosed.

68 Claims, 26 Drawing Sheets

OTHER PUBLICATIONS

Eigenbrot et al., "X-Ray Structures of the Antigen-Binding Domains From Three Variants of Humanized Anti-p185$^{HER2}$ Antibody 4D5 and Comparison With Molecular Modeling" *J. Mol. Biol.* 229:969-995 (1993).

Gerstner et al., "Sequence Plasticity in the Antigen-binding Site of a Therapeutic Anti-HER2 Antibody" *J. Mol. Biol.* 321:851-862 (2002).

Greenwood et al., "Engineering multiple-domain forms of the therapeutic antibody CAMPATH-1H: effects on complement lysis" *Therapeutic Immunology* 1(5):247-255 (Oct. 1994).

Ho et al., "Site-Directed Mutagenesis by Overlap Extension Using the Polymerase Chain Reaction" *Gene* 77(1):51-59 (1989).

Ito et al., "A general method for introducing a series of mutations into cloned DNA using the polymerase chain reaction" *Gene* 102(1):67-70 (Jun. 15, 1991).

Kanno et al., "Assembling of engineered IgG-binding protein on gold surface for highly oriented antibody immobilization" *J Biotechnol.* 76(2-3):207-214 (Jan. 21, 2000).

King et al., "Facile synthesis of maleimide bifunctional linkers" *Tetrahedron Letters* 43:1987-1990 (2002).

Lambert, J. "Drug-conjugated monoclonal antibodies for the treatment of cancer" *Curr Opin Pharmacol.* 5(5):543-549 (Oct. 2005).

Lewis et al., "Maleimidocysteineamido-DOTA derivatives: new reagents for radiometal chelate conjugation to antibody sulfhydryl groups undergo pH-dependent cleavage reactions" *Bioconjug Chem.* 9(1):72-86 (Jan. 1998).

Lowman, H., "Phage display of peptide libraries on protein scaffolds" *Methods in Molecular Biology*, Chapter 24, 87:249-264 (1998).

Lund et al., "Expression and characterization of truncated forms of humanized L243 IgG1. Architectural features can influence synthesis of its oligosaccharide chains and affect superoxide production triggered through human Fcgamma receptor I" *Eur J Biochem.* 267(24):7246-7257 (Dec. 2000).

Olafsen et al., "Characterization of engineered anti-p185HER-2 (scFv-CH3) 2 antibody fragments (minibodies) for tumor targeting" *Protein Eng Des Sel.* 17(4):315-323 (Apr. 2004).

Payne, Gillian, "Progress in Immunoconjugate Cancer Therapeutics" *Cancer Cell* 3:207-212 (2003).

Roux et al., "Comparisons of the ability of human IgG3 hinge mutants, IgM, IgE, and IgA2, to form small immune complexes: a role for flexibility and geometry" *J Immunol.* 161(8):4083-4090 (Oct. 15, 1998).

Senter, P. et al., "Immunoconjugates comprised of drugs with impaired cellular permeability: a new approach to targeted therapy, Abstract No. 623, presented on Mar. 28, 2004, Proceedings of the American Association for Cancer Research" 45:36 (2004).

Singh et al., "Labeling of antibodies by in situ modification of thiol groups generated from selenol-catalyzed reduction of native disulfide bonds" *Analytical Biochemistry* 304(2):147-156 (May 15, 2002).

Sun et al., "Enabling ScFvs as multi-drug carriers: a dendritic approach" *Biorg Med Chem.* 11(8):1761-1768 (Apr. 17, 2003).

Sun et al., "Syntheses of dendritic linkers containing chlorambucil residues for the preparation of antibody-multidrug immunconjugates" *Bioorg Med Chem Lett.* 12(16):2213-2215 (Aug. 19, 2002).

Tu et al., "Protein footprinting at cysteines: probing ATP-modulated contacts in cysteine-substitution mutants of yeast DNA topoisomerase II" *Proc Natl Acad Sci U S A.* 96(9):4862-4867 (Apr. 27, 1999).

Wu et al., "Arming antibodies: prospects and challenges for immunoconjugates" *Nat Biotechnol.* 23(9):1137-1146 (Sep. 23, 2005).

Zhang et al., "Complete disulfide bond assignment of recombinant immunoglobulin G4 monoclonal antibody" *Analytical Biochemistry* 311(1):1-9 (Dec. 1, 2002).

Corneillie et al, "Converting Weak Binders into Infinite Binders" *Bioconjugate Chem* 15:1389-1390 (2004).

Hafner et al., "Noncompetitive Immunoassay of Small Analytes at the Femtomolar Level by Affinity Probe Capillary Electrophoresis: Direct Analysis of Digoxin Using a Uniform-Labeled scFv Immunoreagent" *Anal. Chem* 72:5779-5786 (2000).

Renard et al., "Deriving Topological Constraints from Functional Data for the Design of Reagentless Fluorescent Immunosensors" *J. Mol. Biol.* 326:167-175 (2003).

Schelte et al., "Differential Reactivity of Maleimide and Bromoacetyl Functions with Thiols: Application to the Preparation of Liposomal Diepitope Constructs" *Bioconjugate Chem* 11:118-123 (2000).

Shopes, Bob, "A Genetically Engineered Human IgG With Limited Flexibility Fully Initiates Cytolysis Via Complement" *Molecular Immunology* 30:603-609 (1993).

Trail et al., "Monoclonal Antibody Drug Immunoconjugates for Targeted Treatment of Cancer" *Cancer Immunol. Immunother* 52:328-337 (2003).

Stimmel et al., "Site-specific Conjugation on Serine—Cysteine Variant Monoclonal Antibodies" *Journal of Biological Chemistry* 275(39) (2000).

* cited by examiner

Sequential Numbering

```
                10        20        30
4d5v7fabH   EVQLVESGGGLVQPGGSLRLSCAASGFNIKDTYIHW
            ***********************************
4d5v7fabH   EVQLVESGGGLVQPGGSLRLSCAASGFNIKDTYIHW
                10        20        30
```

Kabat Numbering

```
                40        50        60        70        80
4d5v7fabH   VRQAPGKGLEWVARIYPTNGYTRYADSVKGRFTISADTSKNTAYLQMNSL
            *************************************************
4d5v7fabH   VRQAPGKGLEWVARIYPTNGYTRYADSVKGRFTISADTSKNTAYLQMNSL
                40        50    a   60        70        80  abc 90       100       110       120       130
4d5v7fabH   RAEDTAVYYCSRWGGDGFYAMDYWGQGTLVTVSSASTKGPSVFPLAPSSK
            *************************************************
4d5v7fabH   RAEDTAVYYCSRWGGDGFYAMDYWGQGTLVTVSSASTKGPSVFPLAPSSK
                    90       100abc    110       120

140       150       160       170       180
4d5v7fabH   STSGGTAALGCLVKDYFPEPVTVSWNSGALTSGVHTFPAVLQSSGLYSLS
            *************************************************
4d5v7fabH   STSGGTAALGCLVKDYFPEPVTVSWNSGALTSGVHTFPAVLQSSGLYSLS
                130       140       150       160       170

190       200       210       220
4d5v7fabH   SVVTVPSSSLGTQTYICNVNHKPSNTKVDKKVEPKSC
            ************************************
4d5v7fabH   SVVTVPSSSLGTQTYICNVNHKPSNTKVDKKVEPKSC
                180       190       200       210
```

Figure 1B

CYSTEINE ENGINEERED ANTIBODIES AND CONJUGATES

This non-provisional application filed under 37 CFR §1.53 (b), claims the benefit under 35 USC §119(e) of U.S. Provisional Application Ser. No. 60/612,468 filed on Sep. 23, 2004 and U.S. Provisional Application Ser. No. 60/696,353 filed on Jun. 30, 2005, each of which are incorporated by reference in their entirety.

FIELD OF THE INVENTION

The invention relates generally to antibodies engineered with reactive cysteine residues and more specifically to antibodies with therapeutic or diagnostic applications. The cysteine engineered antibodies may be conjugated with chemotherapeutic drugs, toxins, affinity ligands such as biotin, and detection labels such as fluorophores. The invention also relates to methods of using antibodies and antibody-drug conjugate compounds for in vitro, in situ, and in vivo diagnosis or treatment of mammalian cells, or associated pathological conditions.

BACKGROUND OF THE INVENTION

Antibody therapy has been established for the targeted treatment of patients with cancer, immunological and angiogenic disorders. In attempts to discover effective cellular targets for cancer diagnosis and therapy with antibodies, researchers have sought to identify transmembrane or otherwise tumor-associated polypeptides that are specifically expressed on the surface of cancer cells as compared to normal, non-cancerous cell(s). The identification of such tumor-associated cell surface antigen polypeptides, i.e. tumor associated antigens (TAA), has given rise to the ability to specifically target cancer cells for destruction via antibody-based therapies.

The use of antibody-drug conjugates (ADC), i.e. immunoconjugates, for the local delivery of cytotoxic or cytostatic agents, i.e. drugs to kill or inhibit tumor cells in the treatment of cancer (Lambert, J. (2005) Curr. Opinion in Pharmacology 5:543-549; Wu et al (2005) Nature Biotechnology 23(9): 1137-1146; Payne, G. (2003) Cancer Cell 3:207-212; Syrigos and Epenetos (1999) Anticancer Research 19:605-614; Niculescu-Duvaz and Springer (1997) Adv. Drug Del. Rev. 26:151-172; U.S. Pat. No. 4,975,278) theoretically allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al (1986) Lancet pp. (Mar. 15, 1986):603-05; Thorpe, (1985) "Antibody Carriers Of Cytotoxic Agents In Cancer Therapy: A Review," in Monoclonal Antibodies '84: Biological And Clinical Applications, A. Pinchera et al (ed.s), pp. 475-506). Maximal efficacy with minimal toxicity is sought thereby. Efforts to design and refine ADC have focused on the selectivity of monoclonal antibodies (mAbs) as well as drug-linking and drug-releasing properties (Lambert, J. (2005) Curr. Opinion in Pharmacology 5:543-549;. Both polyclonal antibodies and monoclonal antibodies have been reported as useful in these strategies (Rowland et al (1986) Cancer Immunol. Immunother., 21:183-87). Drugs used in these methods include daunomycin, doxorubicin, methotrexate, and vindesine (Rowland et al (1986) supra). Toxins used in antibody-toxin conjugates include bacterial toxins such as diphtheria toxin, plant toxins such as ricin, small molecule toxins such as geldanamycin (Mandler et al (2000) J. of the Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al (1996) Proc. Natl. Acad. Sci. USA 93:8618-8623), and calicheamicin (Lode et al (1998) Cancer Res. 58:2928; Hinman et al (1993) Cancer Res. 53:3336-3342). The toxins may effect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

An antibody-radioisotope conjugate has been approved. ZEVALIN® (ibritumomab tiuxetan, Biogen/Idec) is composed of a murine IgG1 kappa monoclonal antibody directed against the CD20 antigen found on the surface of normal and malignant B lymphocytes and $^{111}$In or $^{90}$Y radioisotope bound by a thiourea linker-chelator (Wiseman et al (2000) Eur. J. Nucl. Med. 27(7):766-77; Wiseman et al (2002) Blood 99(12):4336-42; Witzig et al (2002) J. Clin. Oncol. 20(10): 2453-63; Witzig et al (2002) J. Clin. Oncol. 20(15):3262-69). Although ZEVALIN® has activity against B-cell non-Hodgkin's Lymphoma (NHL), administration results in severe and prolonged cytopenias in most patients. MYLOTARG™ (gemtuzumab ozogamicin, Wyeth Pharmaceuticals), an antibody-drug conjugate composed of a hu CD33 antibody linked to calicheamicin, was approved in 2000 for the treatment of acute myeloid leukemia by injection (Drugs of the Future (2000) 25(7):686; U.S. Pat. Nos. 4,970,198; 5,079,233; 5,585,089; 5,606,040; 5,693,762; 5,739,116; 5,767,285; 5,773,001). Cantuzumab mertansine (Immunogen, Inc.), an antibody-drug conjugate composed of the huC242 antibody linked via the disulfide linker SPP to the maytansinoid drug moiety, DM1 (Xie et al (2004) J. of Pharm. and Exp. Ther. 308(3):1073-1082), is advancing into Phase II trials for the treatment of cancers that express CanAg, such as colon, pancreatic, gastric, and others. MLN-2704 (Millennium Pharm., BZL Biologics, Immunogen Inc.), an antibody-drug conjugate composed of the anti-prostate specific membrane antigen (PSMA) monoclonal antibody linked to the maytansinoid drug moiety, DM1, is under development for the potential treatment of prostate tumors. The auristatin peptides, auristatin E (AE) and monomethyl-lauristatin (MMAE), synthetic analogs of dolastatin (WO 02/088172), have been conjugated to: (i) chimeric monoclonal antibodies cBR96 (specific to Lewis Y on carcinomas); (ii) cAC10 which is specific to CD30 on hematological malignancies (Klussman, et al (2004), Bioconjugate Chemistry 15(4):765-773; Doronina et al (2003) Nature Biotechnology 21(7):778-784; Francisco et al (2003) Blood 102(4):1458-1465; US 2004/0018194; (iii) anti-CD20 antibodies such as rituxan (WO 04/032828) for the treatment of CD20-expressing cancers and immune disorders; (iv) anti-EphB2R antibodies 2H9 and anti-IL-8 for treatment of colorectal cancer (Mao et al (2004) Cancer Research 64(3):781-788); (v) E-selectin antibody (Bhaskar et al (2003) Cancer Res. 63:6387-6394); and (vi) other anti-CD30 antibodies (WO 03/043583). Variants of auristatin E are disclosed in U.S. Pat. Nos. 5,767, 237 and 6,124,431. Monomethyl auristatin E conjugated to monoclonal antibodies are disclosed in Senter et al, Proceedings of the American Association for Cancer Research, Volume 45, Abstract Number 623, presented Mar. 28, 2004. Auristatin analogs MMAE and MMAF have been conjugated to various antibodies (WO 2005/081711).

Conventional means of attaching, i.e. linking through covalent bonds, a drug moiety to an antibody generally leads to a heterogeneous mixture of molecules where the drug moieties are attached at a number of sites on the antibody. For example, cytotoxic drugs have typically been conjugated to antibodies through the often-numerous lysine residues of an antibody, generating a heterogeneous antibody-drug conjugate mixture. Depending on reaction conditions, the heterogeneous mixture typically contains a distribution of antibodies with from 0 to about 8, or more, attached drug moieties. In addition, within each subgroup of conjugates with a particular integer ratio of drug moieties to antibody, is a potentially heterogeneous mixture where the drug moiety is attached at various sites on the antibody. Analytical and preparative methods are inadequate to separate and characterize the antibody-drug conjugate species molecules within the heterogeneous mixture resulting from a conjugation reaction. Antibodies are large, complex and structurally diverse biomolecules, often with many reactive functional groups. Their reactivities with linker reagents and drug-linker intermediates are dependent on factors such as pH, concentration, salt concentration, and co-solvents. Furthermore, the multi-step conjugation process may be nonreproducible due to difficulties in controlling the reaction conditions and characterizing reactants and intermediates.

Cysteine thiols are reactive at neutral pH, unlike most amines which are protonated and less nucleophilic near pH 7. Since free thiol (RSH, sulfhydryl) groups are relatively reactive, proteins with cysteine residues often exist in their oxidized form as disulfide-linked oligomers or have internally bridged disulfide groups. Extracellular proteins generally do not have free thiols (Garman, 1997, Non-Radioactive Labelling: A Practical Approach, Academic Press, London, at page 55). The amount of free thiol in a protein may be estimated by the standard Ellman's assay. Immunoglobulin M is an example of a disulfide-linked pentamer, while immunoglobulin G is an example of a protein with internal disulfide bridges bonding the subunits together. In proteins such as this, reduction of the disulfide bonds with a reagent such as dithiothreitol (DTT) or selenol (Singh et al (2002) Anal. Biochem. 304:147-156) is required to generate the reactive free thiol. This approach may result in loss of antibody tertiary structure and antigen binding specificity.

Antibody cysteine thiol groups are generally more reactive, i.e. more nucleophilic, towards electrophilic conjugation reagents than antibody amine or hydroxyl groups. Cysteine residues have been introduced into proteins by genetic engineering techniques to form covalent attachments to ligands or to form new intramolecular disulfide bonds (Better et al (1994) J. Biol. Chem. 13:9644-9650; Bernhard et al (1994) Bioconjugate Chem. 5:126-132; Greenwood et al (1994) Therapeutic Immunology 1:247-255; Tu et al (1999) Proc. Natl. Acad. Sci USA 96:4862-4867; Kanno et al (2000) J. of Biotechnology, 76:207-214; Chmura et al (2001) Proc. Nat. Acad. Sci. USA 98(15):8480-8484; U.S. Pat. No. 6,248,564). However, designing in cysteine thiol groups by the mutation of various amino acid residues of a protein to cysteine amino acids is potentially problematic, particularly in the case of unpaired (free Cys) residues or those which are relatively accessible for reaction or oxidation. In concentrated solutions of the protein, whether in the periplasm of E. coli, culture supernatants, or partially or completely purified protein, unpaired Cys residues on the surface of the protein can pair and oxidize to form intermolecular disulfides, and hence protein dimers or multimers. Disulfide dimer formation renders the new Cys unreactive for conjugation to a drug, ligand, or other label. Furthermore, if the protein oxidatively forms an intramolecular disulfide bond between the newly engineered Cys and an existing Cys residue, both Cys groups are unavailable for active site participation and interactions. Furthermore, the protein may be rendered inactive or non-specific, by misfolding or loss of tertiary structure (Zhang et al (2002) Anal. Biochem. 311:1-9).

SUMMARY

The compounds of the invention include cysteine engineered antibodies where one or more amino acids of a parent antibody are replaced with a free cysteine amino acid. A cysteine engineered antibody comprises one or more free cysteine amino acids having a thiol reactivity value in the range of 0.6 to 1.0. A free cysteine amino acid is a cysteine residue which has been engineered into the parent antibody and is not part of a disulfide bridge.

In one aspect, the cysteine engineered antibody is prepared by a process comprising:
 (a) replacing one or more amino acid residues of a parent antibody by cysteine; and
 (b) determining the thiol reactivity of the cysteine engineered antibody by reacting the cysteine engineered antibody with a thiol-reactive reagent.

The cysteine engineered antibody may be more reactive than the parent antibody with the thiol-reactive reagent.

The free cysteine amino acid residues may be located in the heavy or light chains, or in the constant or variable domains. Antibody fragments, e.g. Fab, may also be engineered with one or more cysteine amino acids replacing amino acids of the antibody fragment, to form cysteine engineered antibody fragments.

Another aspect of the invention provides a method of preparing (making) a cysteine engineered antibody, comprising:
 (a) introducing one or more cysteine amino acids into a parent antibody in order to generate the cysteine engineered antibody; and
 (b) determining the thiol reactivity of the cysteine engineered antibody with a thiol-reactive reagent;
wherein the cysteine engineered antibody is more reactive than the parent antibody with the thiol-reactive reagent.

Step (a) of the method of preparing a cysteine engineered antibody may comprise:
 (i) mutagenizing a nucleic acid sequence encoding the cysteine engineered antibody;
 (ii) expressing the cysteine engineered antibody; and
 (iii) isolating and purifying the cysteine engineered antibody.

Step (b) of the method of preparing a cysteine engineered antibody may comprise expressing the cysteine engineered antibody on a viral particle selected from a phage or a phagemid particle.

Step (b) of the method of preparing a cysteine engineered antibody may also comprise:
 (i) reacting the cysteine engineered antibody with a thiol-reactive affinity reagent to generate an affinity labelled, cysteine engineered antibody; and
 (ii) measuring the binding of the affinity labelled, cysteine engineered antibody to a capture media.

Another aspect of the invention is a method of screening cysteine engineered antibodies with highly reactive, unpaired cysteine amino acids for thiol reactivity comprising:
 (a) introducing one or more cysteine amino acids into a parent antibody in order to generate a cysteine engineered antibody;
 (b) reacting the cysteine engineered antibody with a thiol-reactive affinity reagent to generate an affinity labelled, cysteine engineered antibody; and
 (c) measuring the binding of the affinity labelled, cysteine engineered antibody to a capture media; and (d) determining the thiol reactivity of the cysteine engineered antibody with the thiol-reactive reagent.

Step (a) of the method of screening cysteine engineered antibodies may comprise:

(i) mutagenizing a nucleic acid sequence encoding the cysteine engineered antibody;

(ii) expressing the cysteine engineered antibody; and (iii) isolating and purifying the cysteine engineered antibody.

Step (b) of the method of screening cysteine engineered antibodies may comprise expressing the cysteine engineered antibody on a viral particle selected from a phage or a phagemid particle.

Step (b) of the method of screening cysteine engineered antibodies may also comprise:

(i) reacting the cysteine engineered antibody with a thiol-reactive affinity reagent to generate an affinity labelled, cysteine engineered antibody; and (ii) measuring the binding of the affinity labelled, cysteine engineered antibody to a capture media.

Cysteine engineered antibodies may be useful in the treatment of cancer and include antibodies specific for cell surface and transmembrane receptors, and tumor-associated antigens (TAA). Such antibodies may be used as naked antibodies (unconjugated to a drug or label moiety) or as Formula I antibody-drug conjugates (ADC).

Embodiments of the methods for preparing and screening a cysteine engineered antibody include where the parent antibody is an antibody fragment, such as hu4D5Fabv8. The parent antibody may also be a fusion protein comprising an albumin-binding peptide sequence (ABP). The parent antibody may also be a humanized antibody selected from huMAb4D5-1, huMAb4D5-2, huMAb4D5-3, huMAb4D5-4, huMAb4D5-5, huMAb4D5-6, huMAb4D5-7 and huMAb4D5-8 (trastuzumab).

Cysteine engineered antibodies of the invention may be site-specifically and efficiently coupled with a thiol-reactive reagent. The thiol-reactive reagent may be a multifunctional linker reagent, a capture label reagent, a fluorophore reagent, or a drug-linker intermediate.

The cysteine engineered antibody may be labeled with a detectable label, immobilized on a solid phase support and/or conjugated with a drug moiety.

Another aspect of the invention is an antibody-drug conjugate compound comprising a cysteine engineered antibody (Ab), and a drug moiety (D) wherein the cysteine engineered antibody is attached through one or more free cysteine amino acids by a linker moiety (L) to D; the compound having Formula I:

where p is 1, 2, 3, or 4; and wherein the cysteine engineered antibody is prepared by a process comprising replacing one or more amino acid residues of a parent antibody by one or more free cysteine amino acids. Drug moieties include, but are not limited to a maytansinoid, an auristatin, a dolastatin, a trichothecene, CC1065, a calicheamicin and other enediyne antibiotics, a taxane, an anthracycline, and stereoisomers, isosteres, analogs or derivatives thereof. Exemplary drug moieties include DM1, MMAE, and MMAF.

The antibody-drug conjugate of Formula I may further comprise an albumin-binding peptide (ABP) sequence; the composition having Formula Ia:

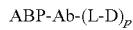

Another aspect of the invention is a composition comprising a cysteine engineered antibody or a cysteine engineered antibody-drug conjugate and a physiologically or pharmaceutically acceptable carrier or diluent. This composition for therapeutic use is sterile and may be lyophilized.

Another aspect of the invention includes diagnostic and therapeutic uses for the compounds and compositions disclosed herein. Pharmaceutical compositions include combinations of Formula I compounds and one or more chemotherapeutic agents.

Another aspect of the invention is a method for killing or inhibiting the proliferation of tumor cells or cancer cells comprising treating the cells with an amount of an antibody-drug conjugate of the invention, or a pharmaceutically acceptable salt or solvate thereof, being effective to kill or inhibit the proliferation of the tumor cells or cancer cells.

Other aspects of the invention include methods for treating: cancer; an autoimmune disease; or an infectious disease comprising administering to a patient in need thereof an effective amount of the antibody-drug conjugate compound of the invention, or a pharmaceutically acceptable salt or solvate thereof.

Another aspect of the invention is a method for the treatment of cancer in a mammal, wherein the cancer is characterized by the overexpression of an ErbB receptor. The mammal optionally does not respond, or responds poorly, to treatment with an unconjugated anti-ErbB antibody. The method comprises administering to the mammal a therapeutically effective amount of an antibody-drug conjugate compound of the invention.

Another aspect of the invention is a method of inhibiting the growth of tumor cells that overexpress a growth factor receptor selected from the group consisting of HER2 receptor and EGF receptor comprising administering to a patient an antibody-drug conjugate compound which binds specifically to said growth factor receptor and a chemotherapeutic agent wherein said antibody-drug conjugate and said chemotherapeutic agent are each administered in amounts effective to inhibit growth of tumor cells in the patient.

Another aspect of the invention is a method for the treatment of a human patient susceptible to or diagnosed with a disorder characterized by overexpression of ErbB2 receptor, comprising administering an effective amount of a combination of an antibody-drug conjugate compound and a chemotherapeutic agent.

Another aspect of the invention is an assay method for detecting cancer cells comprising: exposing cells to an antibody-drug conjugate compound, and determining the extent of binding of the antibody-drug conjugate compound to the cells.

Another aspect of the invention is an article of manufacture comprising an antibody-drug conjugate compound; a container; and a package insert or label indicating that the compound can be used to treat cancer.

BRIEF DESCRIPTION OF THE DRAWINGS

FIG. 1B shows a sequential numbering scheme (top row), starting at the N-terminus in comparison with the Kabat numbering scheme (bottom row) for 4D5v7fabH. Kabat numbering insertions are noted by a, b, c.

DETAILED DESCRIPTION OF EXEMPLARY EMBODIMENTS

Figure 1A:
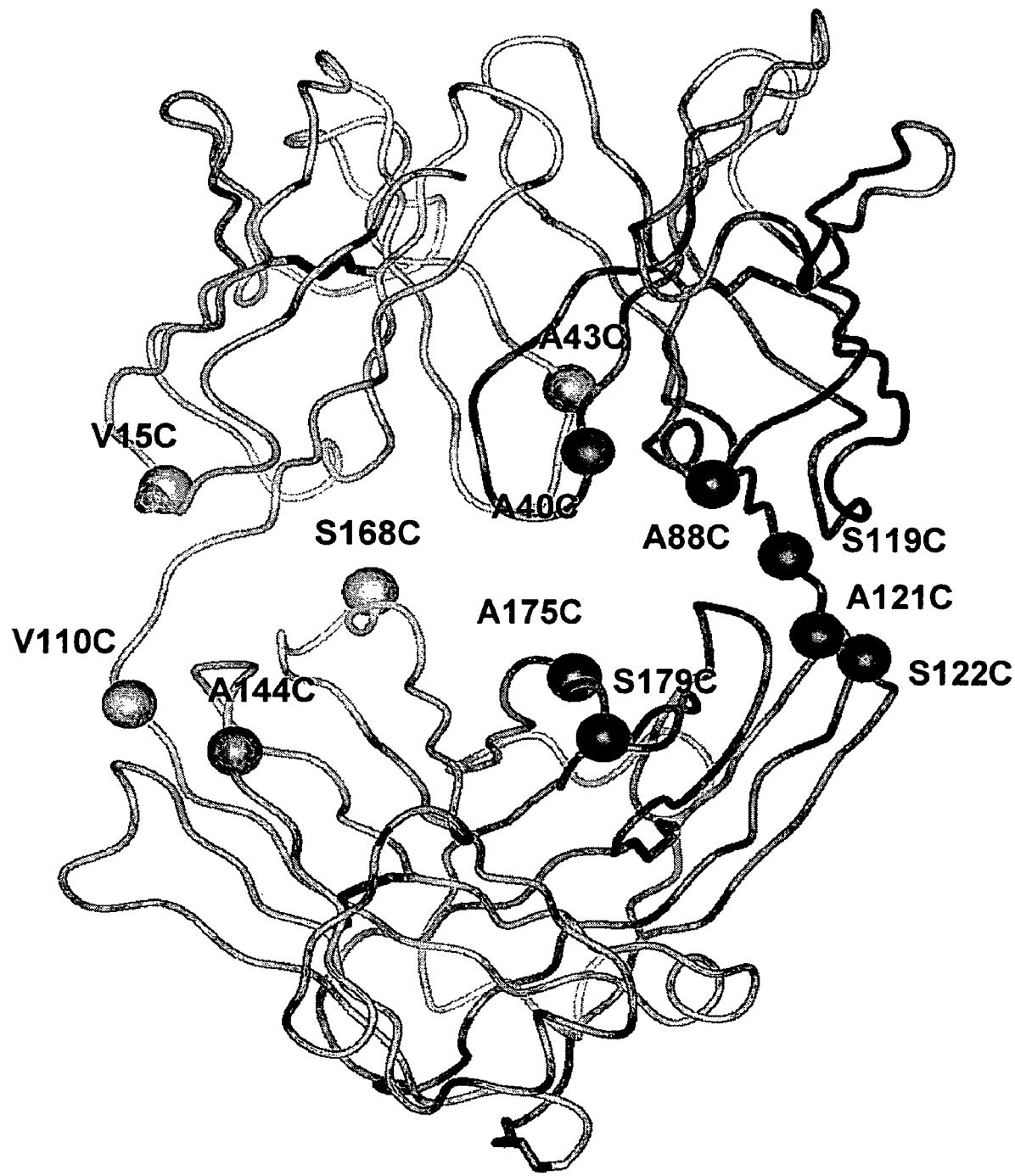
FIG. 1A shows a three-dimensional representation of the hu4D5Fabv7 antibody fragment derived by X-ray crystal coordinates. The structure positions of the exemplary engineered Cys residues of the heavy and light chains are numbered (according to a sequential numbering system).

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

Unless defined otherwise, technical and scientific terms used herein have the same meaning as commonly understood by one of ordinary skill in the art to which this invention belongs, and are consistent with: Singleton et al (1994) Dictionary of Microbiology and Molecular Biology, 2nd Ed., J. Wiley & Sons, New York, N.Y.; and Janeway, C., Travers, P., Walport, M., Shlomchik (2001) Immunobiology, 5th Ed., Garland Publishing, New York.

Definitions

Unless stated otherwise, the following terms and phrases as used herein are intended to have the following meanings:

When trade names are used herein, applicants intend to independently include the trade name product formulation, the generic drug, and the active pharmaceutical ingredient(s) of the trade name product.

The term "antibody" herein is used in the broadest sense and specifically covers monoclonal antibodies, polyclonal antibodies, dimers, multimers, multispecific antibodies (e.g., bispecific antibodies), and antibody fragments, so long as they exhibit the desired biological activity (Miller et al (2003) Jour. of Immunology 170:4854-4861). Antibodies may be murine, human, humanized, chimeric, or derived from other species. An antibody is a protein generated by the immune system that is capable of recognizing and binding to a specific antigen. (Janeway, C., Travers, P., Walport, M., Shlomchik (2001) Immuno Biology, 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In one aspect, however, the immunoglobulin is of human, murine, or rabbit origin.

"Antibody fragments" comprise a portion of a full length antibody, generally the antigen binding or variable region thereof. Examples of antibody fragments include Fab, Fab', F(ab')$_2$, and Fv fragments; diabodies; linear antibodies; minibodies (Olafsen et al (2004) Protein Eng. Design & Sel. 17(4):315-323), fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al (1975) *Nature* 256:495, or may be made by recombinant DNA methods (see for example: U.S. Pat. Nos. 4,816,567; 5,807,715). The monoclonal antibodies may also be isolated from phage antibody libraries using the techniques described in Clackson et al (1991) Nature, 352:624-628; Marks et al (1991) J. Mol. Biol., 222:581-597; for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) Proc. Natl. Acad. Sci. USA, 81:6851-6855). Chimeric antibodies of interest herein include "primatized" antibodies comprising variable domain antigen-binding sequences derived from a non-human primate (e.g., Old World Monkey, Ape etc) and human constant region sequences.

An "intact antibody" herein is one comprising a VL and VH domains, as well as a light chain constant domain (CL)

and heavy chain constant domains, CH1, CH2 and CH3. The constant domains may be native sequence constant domains (e.g., human native sequence constant domains) or amino acid sequence variant thereof. The intact antibody may have one or more "effector functions" which refer to those biological activities attributable to the Fc constant region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors such as B cell receptor and BCR.

Depending on the amino acid sequence of the constant domain of their heavy chains, intact antibodies can be assigned to different "classes." There are five major classes of intact immunoglobulin antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called $\alpha$, $\delta$, $\epsilon$, $\gamma$, and $\mu$, respectively. The subunit structures and three-dimensional configurations of different classes of immunoglobulins are well known. Ig forms include hinge-modifications or hingeless forms (Roux et al (1998) J. Immunol. 161:4083-4090; Lund et al (2000) Eur. J. Biochem. 267:7246-7256; US 2005/0048572; US 2004/0229310).

An "ErbB receptor" is a receptor protein tyrosine kinase which belongs to the ErbB receptor family whose members are important mediators of cell growth, differentiation and survival. The ErbB receptor family includes four distinct members including epidermal growth factor receptor (EGFR, ErbB1, HER1), HER2 (ErbB2 or p185neu), HER3 (ErbB3) and HER4 (ErbB4 or tyro2). A panel of anti-ErbB2 antibodies has been characterized using the human breast tumor cell line SKBR3 (Hudziak et al (1989) Mol. Cell. Biol. 9(3): 1165-1172. Maximum inhibition was obtained with the antibody called 4D5 which inhibited cellular proliferation by 56%. Other antibodies in the panel reduced cellular proliferation to a lesser extent in this assay. The antibody 4D5 was further found to sensitize ErbB2-overexpressing breast tumor cell lines to the cytotoxic effects of TNF-$\alpha$ (U.S. Pat. No. 5,677,171). The anti-ErbB2 antibodies discussed in Hudziak et al. are further characterized in Fendly et al (1990) Cancer Research 50:1550-1558; Kotts et al. (1990) In Vitro 26(3):59A; Sarup et al. (1991) Growth Regulation 1:72-82; Shepard et al. J. (1991) Clin. Immunol. 11(3):117-127; Kumar et al. (1991) Mol. Cell. Biol. 11(2):979-986; Lewis et al. (1993) Cancer Immunol. Immunother. 37:255-263; Pietras et al. (1994) Oncogene 9:1829-1838; Vitetta et al. (1994) Cancer Research 54:5301-5309; Sliwkowski et al. (1994) J. Biol. Chem. 269(20):14661-14665; Scott et al. (1991) J. Biol. Chem. 266:14300-5; D'souza et al. Proc. Natl. Acad. Sci. (1994) 91:7202-7206; Lewis et al. (1996) Cancer Research 56:1457-1465; and Schaefer et al. (1997) Oncogene 15:1385-1394.

The ErbB receptor will generally comprise an extracellular domain, which may bind an ErbB ligand; a lipophilic transmembrane domain; a conserved intracellular tyrosine kinase domain; and a carboxyl-terminal signaling domain harboring several tyrosine residues which can be phosphorylated. The ErbB receptor may be a "native sequence" ErbB receptor or an "amino acid sequence variant" thereof. Preferably, the ErbB receptor is native sequence human ErbB receptor. Accordingly, a "member of the ErbB receptor family" is EGFR (ErbB1), ErbB2, ErbB3, ErbB4 or any other ErbB receptor currently known or to be identified in the future.

The terms "ErbB1", "epidermal growth factor receptor", "EGFR" and "HER1" are used interchangeably herein and refer to EGFR as disclosed, for example, in Carpenter et al (1987) Ann. Rev. Biochem., 56:881-914, including naturally occurring mutant forms thereof (e.g., a deletion mutant EGFR as in Humphrey et al (1990) Proc. Nat. Acad. Sci. (USA) 87:4207-4211). The term erbB1 refers to the gene encoding the EGFR protein product. Antibodies against HER1 are described, for example, in Murthy et al (1987) Arch. Biochem. Biophys., 252:549-560 and in WO 95/25167.

The term "ERRP", "EGF-Receptor Related Protein", "EGFR Related Protein" and "epidermal growth factor receptor related protein" are used interchangeably herein and refer to ERRP as disclosed, for example in U.S. Pat. No. 6,399,743 and US Publication No. 2003/0096373.

The expressions "ErbB2" and "HER2" are used interchangeably herein and refer to human HER2 protein described, for example, in Semba et al (1985) Proc. Nat. Acad. Sci. (USA) 82:6497-6501 and Yamamoto et al (1986) Nature, 319:230-234 (Genebank accession number X03363). The term "erbB2" refers to the gene encoding human ErbB2 and "neu" refers to the gene encoding rat p185neu. Preferred ErbB2 is native sequence human ErbB2.

"ErbB3" and "HER3" refer to the receptor polypeptide as disclosed, for example, in U.S. Pat. Nos. 5,183,884 and 5,480,968 as well as Kraus et al (1989) Proc. Nat. Acad. Sci. (USA) 86:9193-9197. Antibodies against ErbB3 are known in the art and are described, for example, in U.S. Pat. Nos. 5,183,884, 5,480,968 and in WO 97/35885.

The terms "ErbB4" and "HER4" herein refer to the receptor polypeptide as disclosed, for example, in EP Pat Application No 599,274; Plowman et al (1993) Proc. Natl. Acad. Sci. USA 90:1746-1750; and Plowman et al (1993) Nature 366: 473-475, including isoforms thereof, e.g., as disclosed in WO 99/19488. Antibodies against HER4 are described, for example, in WO 02/18444.

Antibodies to ErbB receptors are available commercially from a number of sources, including, for example, Santa Cruz Biotechnology, Inc., California, USA.

The term "amino acid sequence variant" refers to polypeptides having amino acid sequences that differ to some extent from a native sequence polypeptide. Ordinarily, amino acid sequence variants will possess at least about 70% sequence identity with at least one receptor binding domain of a native ErbB ligand or with at least one ligand binding domain of a native ErbB receptor, and preferably, they will be at least about 80%, more preferably, at least about 90% homologous by sequence with such receptor or ligand binding domains. The amino acid sequence variants possess substitutions, deletions, and/or insertions at certain positions within the amino acid sequence of the native amino acid sequence. Amino acids are designated by the conventional names, one-letter and three-letter codes.

"Sequence identity" is defined as the percentage of residues in the amino acid sequence variant that are identical after aligning the sequences and introducing gaps, if necessary, to achieve the maximum percent sequence identity. Methods and computer programs for the alignment are well known in the art. One such computer program is "Align 2," authored by Genentech, Inc., which was filed with user documentation in the United States Copyright Office, Washington, D.C. 20559, on Dec. 10, 1991.

"Antibody-dependent cell-mediated cytotoxicity" and "ADCC" refer to a cell-mediated reaction in which nonspecific cytotoxic cells that express Fc receptors (FcRs) (e.g., Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells in summarized is Table 3 on page 464 of Ravetch and Kinet, (1991) "Annu. Rev. Immunol." 9:457-92. To assess ADCC activity of a molecule of interest, an in vitro ADCC assay, such as that described in U.S. Pat. Nos. 5,500,362 and 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al (1998) PROC. NAT. ACAD. SCI. (USA) (USA) 95:652-656.

"Human effector cells" are leukocytes which express one or more constant region receptors (FcRs) and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g., from blood or PBMCs as described herein.

The terms "Fc receptor" or "FcR" are used to describe a receptor that binds to the Fc constant region of an antibody. The preferred FcR is a native sequence human FcR. Moreover, a preferred FcR is one which binds an IgG antibody (a gamma receptor) and includes receptors of the FcγRI, FcγRII, and Fcγ RIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (See review M. in *Daëron*, "Annu. Rev. Immunol." 15:203-234 (1997)). FcRs are reviewed in Ravetch and Kinet, "Annu. Rev. Immunol"., 9:457-92 (1991); Capel et al (1994) Immunomethods 4:25-34; and de Haas et al (1995) J. Lab. Clin. Med. 126:330-41. Other FcRs, including those to be identified in the future, are encompassed by the term "FcR" herein. The term also includes the neonatal receptor, FcRn, which is responsible for the transfer of maternal IgGs to the fetus (Guyer et al (1976) J. Immunol., 117:587 and Kim et al (1994) J. Immunol. 24:249).

"Complement dependent cytotoxicity" or "CDC" refers to the ability of a molecule to lyse a target in the presence of complement. The complement activation pathway is initiated by the binding of the first component of the complement system (C1q) to a molecule (e.g., an antibody) complexed with a cognate antigen. To assess complement activation, a CDC assay, e.g., as described in Gazzano-Santoro et al *J. Immunol. Methods,* 202:163 (1996), may be performed.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end. The constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al (1991) Sequences of Proteins of Immunological Interest, 5th Ed. Public Health Service, National Institutes of Health, Bethesda, Md.). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g., residues 24-34 (L1), 50-56 (L2) and 89-97 (L3) in the light chain variable domain and 31-35 (H1), 50-65 (H2) and 95-102 (H3) in the heavy chain variable domain; Kabat et al supra) and/or those residues from a "hypervariable loop" (e.g., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk (1987) J. Mol. Biol., 196:901-917). "Framework Region" or "FR" residues are those variable domain residues other than the hypervariable region residues as herein defined.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-binding sites and is still capable of cross-linking antigen.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')2 antibody fragments originally were produced as pairs of Fab' fragments which have hinge cysteines between them. Other chemical couplings of antibody fragments are also known.

The "light chains" of antibodies from any vertebrate species can be assigned to one of two clearly distinct types, called kappa (κ) and lambda (λ), based on the amino acid sequences of their constant domains.

"Single-chain Fv" or "scFv" antibody fragments comprise the $V_H$ and $V_L$ domains of antibody, wherein these domains are present in a single polypeptide chain. Preferably, the Fv polypeptide further comprises a polypeptide linker between the VH and VL domains which enables the scFv to form the desired structure for antigen binding. For a review of scFv, see Plückthun in The Pharmacology of Monoclonal Antibodies, vol. 113, Rosenburg and Moore eds., Springer-Verlag, New York, pp. 269-315 (1994). Anti-ErbB2 antibody scFv fragments are described in WO 93/16185; U.S. Pat. Nos. 5,571,894; and 5,587,458.

The term "diabodies" refers to small antibody fragments with two antigen-binding sites, which fragments comprise a variable heavy domain (VH) connected to a variable light domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al (1993) Proc. Natl. Acad. Sci. USA 90:6444-6448.

"Humanized" forms of non-human (e.g., rodent) antibodies are chimeric antibodies that contain minimal sequence derived from non-human immunoglobulin. Humanization is a method to transfer the murine antigen binding information to a non-immunogenic human antibody acceptor, and has resulted in many therapeutically useful drugs. The method of humanization generally begins by transferring all six murine complementarity determining regions (CDRs) onto a human antibody framework (Jones et al, (1986) Nature 321:522-525). These CDR-grafted antibodies generally do not retain their original affinity for antigen binding, and in fact, affinity is often severely impaired. Besides the CDRs, select non-human antibody framework residues must also be incorporated to maintain proper CDR conformation (Chothia et al (1989) Nature 342:877). The transfer of key mouse framework residues to the human acceptor in order to support the structural conformation of the grafted CDRs has been shown to restore antigen binding and affinity (Riechmann et al (1992) J. Mol. Biol. 224, 487-499; Foote and Winter, (1992) J. Mol. Biol. 224:487-499; Presta et al (1993) J. Immunol. 151, 2623-2632; Werther et al (1996) J. Immunol. Methods 157:4986-4995; and Presta et al (2001) Thromb. Haemost. 85:379-389). For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see U.S. Pat. No. 6,407,213; Jones et al (1986) Nature, 321:522-525; Riechmann et al (1988) Nature 332:323-329; and Presta, (1992) Curr. Op. Struct. Biol., 2:593-596.

A "free cysteine amino acid" refers to a cysteine amino acid residue which has been engineered into a parent antibody, has a thiol functional group (—SH), and is not paired as an intramolecular or intermolecular disulfide bridge.

The term "thiol reactivity value" is a quantitative characterization of the reactivity of free cysteine amino acids. The thiol reactivity value is the percentage of a free cysteine amino acid in a cysteine engineered antibody which reacts with a thiol-reactive reagent, and converted to a maximum value of 1. For example, a free cysteine amino acid on a cysteine engineered antibody which reacts in 100% yield with a thiol-reactive reagent, such as a biotin-maleimide reagent, to form a biotin-labelled antibody has a thiol reactivity value of 1.0. Another cysteine amino acid engineered into the same or different parent antibody which reacts in 80% yield with a thiol-reactive reagent has a thiol reactivity value of 0.8. Another cysteine amino acid engineered into the same or different parent antibody which fails totally to react with a thiol-reactive reagent has a thiol reactivity value of 0. Determination of the thiol reactivity value of a particular cysteine may be conducted by ELISA assay, mass spectroscopy, liquid chromatography, autoradiography, or other quantitative analytical tests.

A "parent antibody" is an antibody comprising an amino acid sequence from which one or more amino acid residues are replaced by one or more cysteine residues. The parent antibody may comprise a native or wild type sequence. The parent antibody may have pre-existing amino acid sequence modifications (such as additions, deletions and/or substitutions) relative to other native, wild type, or modified forms of an antibody. A parent antibody may be directed against a target antigen of interest, e.g. a biologically important polypeptide. Antibodies directed against nonpolypeptide antigens (such as tumor-associated glycolipid antigens; see U.S. Pat. No. 5,091,178) are also contemplated.

Exemplary parent antibodies include antibodies having affinity and selectivity for cell surface and transmembrane receptors and tumor-associated antigens (TAA).

Other exemplary parent antibodies include those selected from, and without limitation, anti-estrogen receptor antibody, anti-progesterone receptor antibody, anti-p53 antibody, anti-HER-2/neu antibody, anti-EGFR antibody, anti-cathepsin D antibody, anti-Bcl-2 antibody, anti-E-cadherin antibody, anti-CA125 antibody, anti-CA15-3 antibody, anti-CA19-9 antibody, anti-c-erbB-2 antibody, anti-P-glycoprotein antibody, anti-CEA antibody, anti-retinoblastoma protein antibody, anti-ras oncoprotein antibody, anti-Lewis X antibody, anti-Ki-67 antibody, anti-PCNA antibody, anti-CD3 antibody, anti-CD4 antibody, anti-CD5 antibody, anti-CD7 antibody, anti-CD8 antibody, anti-CD9/p24 antibody, anti-CD10 antibody, anti-CD11c antibody, anti-CD13 antibody, anti-CD14 antibody, anti-CD15 antibody, anti-CD19 antibody, anti-CD20 antibody, anti-CD22 antibody, anti-CD23 antibody, anti-CD30 antibody, anti-CD31 antibody, anti-CD33 antibody, anti-CD34 antibody, anti-CD35 antibody, anti-CD38 antibody, anti-CD41 antibody, anti-LCA/CD45 antibody, anti-CD45RO antibody, anti-CD45RA antibody, anti-CD39 antibody, anti-CD100 antibody, anti-CD95/Fas antibody, anti-CD99 antibody, anti-CD106 antibody, anti-ubiquitin antibody, anti-CD71 antibody, anti-c-myc antibody, anti-cytokeratins antibody, anti-vimentins antibody, anti-HPV proteins antibody, anti-kappa light chains antibody, anti-lambda light chains antibody, anti-melanosomes antibody, anti-prostate specific antigen antibody, anti-S-100 antibody, anti-tau antigen antibody, anti-fibrin antibody, anti-keratins antibody and anti-Tn-antigen antibody.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An antibody "which binds" a molecular target or an antigen of interest, e.g., ErbB2 antigen, is one capable of binding that antigen with sufficient affinity such that the antibody is useful in targeting a cell expressing the antigen. Where the antibody is one which binds ErbB2, it will usually preferentially bind ErbB2 as opposed to other ErbB receptors, and may be one which does not significantly cross-react with other proteins such as EGFR, ErbB3 or ErbB4. In such embodiments, the extent of binding of the antibody to these non-ErbB2 proteins (e.g., cell surface binding to endogenous receptor) will be less than 10% as determined by fluorescence activated cell sorting (FACS) analysis or radioimmunoprecipitation (RIA). Sometimes, the anti-ErbB2 antibody will not significantly cross-react with the rat neu protein, e.g., as described in Schecter et al. (1984) Nature 312:513 and Drebin et al (1984) Nature 312:545-548.

Molecular targets for antibodies encompassed by the present invention include CD proteins and their ligands, such as, but not limited to: (i) CD3, CD4, CD8, CD19, CD20, CD22, CD34, CD40, CD79α (CD79a), and CD79β (CD79b); (ii) members of the ErbB receptor family such as the EGF receptor, HER2, HER3 or HER4 receptor; (iii) cell adhesion molecules such as LFA-1, Mac 1, p150,95, VLA-4, ICAM-1, VCAM and αv/β3 integrin, including either alpha or beta subunits thereof (e.g. anti-CD11a, anti-CD18 or anti-CD11b antibodies); (iv) growth factors such as VEGF; IgE; blood group antigens; flk2/flt3 receptor; obesity (OB) receptor; mpl receptor; CTLA-4; protein C, BR3, c-met, tissue factor, β7 etc; and (v) cell surface and transmembrane tumor-associated antigens (TAA).

Unless indicated otherwise, the term "monoclonal antibody 4D5" refers to an antibody that has antigen binding residues of, or derived from, the murine 4D5 antibody (ATCC CRL 10463). For example, the monoclonal antibody 4D5 may be murine monoclonal antibody 4D5 or a variant thereof, such as a humanized 4D5. Exemplary humanized 4D5 antibodies include huMAb4D5-1, huMAb4D5-2, huMAb4D5-3, huMAb4D5-4, huMAb4D5-5, huMAb4D5-6, huMAb4D5-7 and huMAb4D5-8 (trastuzumab, HERCEPTIN®) as in U.S. Pat. No. 5,821,337.

The terms "treat" or "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can, for example, be measured by assessing the time to disease progression (TTP) and/or determining the response rate (RR).

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

An "ErbB-expressing cancer" is one comprising cells which have ErbB protein present at their cell surface. An "ErbB2-expressing cancer" is one which produces sufficient levels of ErbB2 at the surface of cells thereof, such that an anti-ErbB2 antibody can bind thereto and have a therapeutic effect with respect to the cancer.

A cancer which "overexpresses" an antigenic receptor is one which has significantly higher levels of the receptor, such as ErbB2, at the cell surface thereof, compared to a noncancerous cell of the same tissue type. Such overexpression may be caused by gene amplification or by increased transcription or translation. Receptor overexpression may be determined in a diagnostic or prognostic assay by evaluating increased levels of the receptor protein present on the surface of a cell (e.g., via an immunohistochemistry assay; IHC). Alternatively, or additionally, one may measure levels of receptor-encoding nucleic acid in the cell, e.g., via fluorescent in situ hybridization (FISH; see WO 98/45479), southern blotting, or polymerase chain reaction (PCR) techniques, such as real time quantitative PCR (RT-PCR).

The tumors overexpressing ErbB2 (HER2) are rated by immunohistochemical scores corresponding to the number of copies of HER2 molecules expressed per cell, and can been determined biochemically: 0=0-10,000 copies/cell, 1+=at least about 200,000 copies/cell, 2+=at least about 500,000 copies/cell, 3+=about $1-2 \times 10^6$ copies/cell. Overexpression of HER2 at the 3+ level, which leads to ligand-independent activation of the tyrosine kinase (Hudziak et al (1987) *Proc. Natl. Acad. Sci. USA,* 84:7159-7163), occurs in approximately 30% of breast cancers, and in these patients, relapse-free survival and overall survival are diminished (Slamon et al (1989) *Science,* 244:707-712; Slamon et al (1987) *Science,* 235:177-182).

The term "cytotoxic agent" as used herein refers to a substance that inhibits or prevents the function of cells and/or causes destruction of cells. The term is intended to include radioactive isotopes (e.g., $^{211}$At, $^{131}$I, $^{125}$I, $^{90}$Y, $^{186}$Re, $^{188}$Re, $^{153}$Sm, $^{212}$Bi, $^{32}$P, $^{60}$C, and radioactive isotopes of Lu), chemotherapeutic agents, and toxins such as small molecule toxins or enzymatically active toxins of bacterial, fungal, plant or animal origin, including synthetic analogs and derivatives thereof.

An "autoimmune disease" herein is a disease or disorder arising from and directed against an individual's own tissues or organs or a co-segregate or manifestation thereof or resulting condition therefrom. In many of these autoimmune and inflammatory disorders, a number of clinical and laboratory markers may exist, including, but not limited to, hypergammaglobulinemia, high levels of autoantibodies, antigen-antibody complex deposits in tissues, benefit from corticosteroid or immunosuppressive treatments, and lymphoid cell aggregates in affected tissues. Without being limited to any one theory regarding B-cell mediated autoimmune disease, it is believed that B cells demonstrate a pathogenic effect in human autoimmune diseases through a multitude of mechanistic pathways, including autoantibody production, immune complex formation, dendritic and T-cell activation, cytokine synthesis, direct chemokine release, and providing a nidus for ectopic neo-lymphogenesis. Each of these pathways may participate to different degrees in the pathology of autoimmune diseases. An autoimmune disease can be an organ-specific disease (i.e., the immune response is specifically directed against an organ system such as the endocrine system, the hematopoietic system, the skin, the cardiopulmonary system, the gastrointestinal and liver systems, the renal system, the thyroid, the ears, the neuromuscular system, the central nervous system, etc.) or a systemic disease which can affect multiple organ systems (for example, systemic lupus erythematosus (SLE), rheumatoid arthritis, polymyositis, etc.).

The term "cytostatic" refers to the effect of limiting the function of cells, such as limiting cellular growth or proliferation of cells.

A "chemotherapeutic agent" is a chemical compound useful in the treatment of cancer. Examples of chemotherapeutic agents include Erlotinib (TARCEVA®, Genentech/OSI Pharm.), Bortezomib (VELCADE®, Millenium Pharm.), Fulvestrant (FASLODEX®, Astrazeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (GSK572016, GlaxoSmithKline), Lonafarnib (SCH 66336), Sorafenib (BAY43-9006, Bayer Labs.), and Gefitinib (IRESSA®, Astrazeneca), AG1478, AG1571 (SU 5271; Sugen), alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1 (Angew Chem Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, anthramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above.

Also included in this definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON toremifene; (ii) aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; (iii) anti-androgens such as flutamide, nilutamide, bicalutamide, leuprolide, and goserelin; as well as troxacitabine (a 1,3-dioxolane nucleoside cytosine analog); (iv) aromatase inhibitors; (v) protein kinase inhibitors; (vi) lipid kinase inhibitors; (vii) antisense oligonucleotides, particularly those which inhibit expression of genes in signaling pathways implicated in abherant cell proliferation, such as, for example, PKC-alpha, Ralf and H-Ras; (viii) ribozymes such as a VEGF expression inhibitor (e.g., ANGIOZYME® ribozyme) and a HER2 expression inhibitor; (ix) vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; (x) anti-angiogenic agents such as bevacizumab (AVASTIN®, Genentech); and (xi) pharmaceutically acceptable salts, acids or derivatives of any of the above.

As used herein, the term "EGFR-targeted drug" refers to a therapeutic agent that binds to EGFR and, optionally, inhibits EGFR activation. Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBITUX®) and reshaped human 225 (H225) (see, WO 96/40210, Imclone Systems Inc.); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF (see WO 98/50433, Abgenix). The anti-EGFR antibody may be conjugated with a cytotoxic agent, thus generating an immunoconjugate (see, e.g., EP 659,439A2, Merck Patent GmbH). Examples of small molecules that bind to EGFR include ZD1839 or Gefitinib (IRESSA™; Astra Zeneca), Erlotinib HCl (CP-358774, TARCEVA™; Genentech/OSI) and AG1478, AG1571 (SU 5271; Sugen).

Protein kinase inhibitors include tyrosine kinase inhibitors which inhibits to some extent tyrosine kinase activity of a tyrosine kinase such as an ErbB receptor. Examples of such inhibitors include the EGFR-targeted drugs noted in the preceding paragraph as well as quinazolines such as PD 153035, 4-(3-chloroanilino) quinazoline, pyridopyrimidines, pyrimidopyrimidines, pyrrolopyrimidines, such as CGP 59326, CGP 60261 and CGP 62706, and pyrazolopyrimidines, 4-(phenylamino)-7H-pyrrolo[2,3-d]pyrimidines, curcumin (diferuloyl methane, 4,5-bis (4-fluoroanilino)phthalimide), tyrphostines containing nitrothiophene moieties; PD-0183805 (Warner-Lambert); antisense molecules (e.g., those that bind to ErbB-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-ErbB inhibitors such as CI-1033 (Pfizer); Affinitac (ISIS 3521; Isis/Lilly); Imatinib mesylate (Gleevec; Novartis); PKI 166 (Novartis); GW2016 (Glaxo SmithKline); CI-1033 (Pfizer); EKB-569 (Wyeth); Semaxanib (Sugen); ZD6474 (AstraZeneca); PTK-787 (Novartis/Schering AG); INC-1C11 (Imclone); or as described in any of the following patent publications: WO 99/09016 (American Cyanamid); WO 98/43960 (American Cyanamid); WO 97/38983 (Warner Lambert); WO 99/06378 (Warner Lambert); WO 99/06396 (Warner Lambert); WO 96/30347 (Pfizer, Inc); WO 96/33978 (Zeneca); WO 96/3397 (Zeneca); and WO 96/33980 (Zeneca).

An "anti-angiogenic agent" refers to a compound which blocks, or interferes with to some degree, the development of blood vessels. The anti-angiogenic factor may, for instance, be a small molecule or antibody that binds to a growth factor or growth factor receptor involved in promoting angiogenesis. The preferred anti-angiogenic factor herein is an antibody that binds to Vascular Endothelial Growth Factor (VEGF).

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-$\alpha$ and -$\beta$; mullerian-inhibiting substance; mouse gonadotropin-associated peptide; inhibin; activin; vascular endothelial growth factor; integrin; thrombopoietin (TPO); nerve growth factors such as NGF-$\beta$; platelet-growth factor; transforming growth factors (TGFs) such as TGF-$\alpha$ and TGF-$\beta$; insulin-like growth factor-I and -II; erythropoietin (EPO); osteoinductive factors; interferons such as interferon-$\alpha$, -$\beta$, and -$\gamma$; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1$\alpha$, IL-2, IL-3, IL-4, IL-5, IL-6, IL-7, IL-8, IL-9, IL-10, IL-11, IL-12; a tumor necrosis factor such as TNF-$\alpha$ or TNF-$\beta$; and other polypeptide factors including LIF and kit ligand (KL). As used herein, the term cytokine includes proteins from natural sources or from recombinant cell culture and biologically active equivalents of the native sequence cytokines.

The term "prodrug" as used in this application refers to a precursor or derivative form of a pharmaceutically active substance that is less cytotoxic to tumor cells compared to the parent drug and is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al "Prodrugs: A Chemical Approach to Targeted Drug Delivery," *Directed Drug Delivery*, Borchardt et al (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

A "liposome" is a small vesicle composed of various types of lipids, phospholipids and/or surfactant which is useful for delivery of a drug (such as the anti-ErbB2 antibodies disclosed herein and, optionally, a chemotherapeutic agent) to a mammal. The components of the liposome are commonly arranged in a bilayer formation, similar to the lipid arrangement of biological membranes.

The term "package insert" is used to refer to instructions customarily included in commercial packages of therapeutic products, that contain information about the indications, usage, dosage, administration, contraindications and/or warnings concerning the use of such therapeutic products.

"Phage display" is a technique by which variant polypeptides are displayed as fusion proteins to a coat protein on the surface of phage, e.g., filamentous phage, particles. One utility of phage display lies in the fact that large libraries of randomized protein variants can be rapidly and efficiently sorted for those sequences that bind to a target molecule with high affinity. Display of peptide and protein libraries on phage has been used for screening millions of polypeptides for ones with specific binding properties. Polyvalent phage display methods have been used for displaying small random peptides and small proteins, typically through fusions to either pIII or pVIII of filamentous phage (Wells and Lowman, (1992) Curr. Opin. Struct. Biol., 3:355-362, and references cited therein). In monovalent phage display, a protein or peptide library is fused to a phage coat protein or a portion thereof, and expressed at low levels in the presence of wild type protein. Avidity effects are reduced relative to polyvalent phage so that sorting is on the basis of intrinsic ligand affinity, and phagemid vectors are used, which simplify DNA manipulations. Lowman and Wells, *Methods: A companion to Methods in Enzymology*, 3:205-0216 (1991). Phage display includes techniques for producing antibody-like molecules (Janeway, C., Travers, P., Walport, M., Shlomchik (2001) *Immunobiology*, 5th Ed., Garland Publishing, New York, p627-628; Lee et al ).

A "phagemid" is a plasmid vector having a bacterial origin of replication, e.g., ColE1, and a copy of an intergenic region of a bacteriophage. The phagemid may be used on any known bacteriophage, including filamentous bacteriophage and lambdoid bacteriophage. The plasmid will also generally contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid may form infectious or non-infectious phage particles. This term includes phagemids which contain a phage coat protein gene or fragment thereof linked to a heterologous polypeptide gene as a gene fusion such that the heterologous polypeptide is displayed on the surface of the phage particle.

"Linker", "Linker Unit", or "link" means a chemical moiety comprising a covalent bond or a chain of atoms that covalently attaches an antibody to a drug moiety. In various embodiments, a linker is specified as L. Linkers include a divalent radical such as an alkyldiyl, an arylene, a heteroarylene, moieties such as: —$(CR_2)_nO(CR_2)_n$—, repeating units of alkyloxy (e.g. polyethylenoxy, PEG, polymethyleneoxy) and alkylamino (e.g. polyethyleneamino, Jeffamine™); and diacid ester and amides including succinate, succinamide, diglycolate, malonate, and caproamide.

The term "label" means any moiety which can be covalently attached to an antibody and that functions to: (i) provide a detectable signal; (ii) interact with a second label to modify the detectable signal provided by the first or second label, e.g. FRET (fluorescence resonance energy transfer); (iii) stabilize interactions or increase affinity of binding, with antigen or ligand; (iv) affect mobility, e.g. electrophoretic mobility, or cell-permeability, by charge, hydrophobicity, shape, or other physical parameters, or (v) provide a capture moiety, to modulate ligand affinity, antibody/antigen binding, or ionic complexation.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The phrase "pharmaceutically acceptable salt," as used herein, refers to pharmaceutically acceptable organic or inorganic salts of an ADC. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

"Pharmaceutically acceptable solvate" refers to an association of one or more solvent molecules and an ADC. Examples of solvents that form pharmaceutically acceptable solvates include, but are not limited to, water, isopropanol, ethanol, methanol, DMSO, ethyl acetate, acetic acid, and ethanolamine.

The following abbreviations are used herein and have the indicated definitions: BME is beta-mercaptoethanol, Boc is N-(t-butoxycarbonyl), cit is citrulline (2-amino-5-ureido pentanoic acid), dap is dolaproine, DCC is 1,3-dicyclohexylcarbodiimide, DCM is dichloromethane, DEA is diethylamine, DEAD is diethylazodicarboxylate, DEPC is diethylphosphorylcyanidate, DIAD is diisopropylazodicarboxylate, DIEA is N,N-diisopropylethylamine, dil is dolaisoleucine, DMA is dimethylacetamide, DMAP is 4-dimethylaminopyridine, DME is ethyleneglycol dimethyl ether (or 1,2-dimethoxyethane), DMF is N,N-dimethylformamide, DMSO is dimethylsulfoxide, doe is dolaphenine, dov is N,N-dimethylvaline, DTNB is 5,5'-dithiobis (2-nitrobenzoic acid), DTPA is diethylenetriaminepentaacetic acid, DTT is dithiothreitol, EDCI is 1-(3-dimethylaminopropyl)-3-ethylcarbodiimide hydrochloride, EEDQ is 2-ethoxy-1-ethoxycarbonyl-1,2-dihydroquinoline, ES-MS is electrospray mass spectrometry, EtOAc is ethyl acetate, Fmoc is N-(9-fluorenylmethoxycarbonyl), gly is glycine, HATU is O-(7-azabenzotriazol-1-yl)-N,N,N',N'-tetramethyluronium hexafluorophosphate, HOBt is 1-hydroxybenzotriazole, HPLC is high pressure liquid chromatography, ile is isoleucine, lys is lysine, MeCN ($CH_3CN$) is acetonitrile, MeOH is methanol, Mtr is 4-anisyldiphenylmethyl (or 4-methoxytrityl), nor is (1S, 2R)-(+)-norephedrine, PAB is p-aminobenzylcarbamoyl, PBS is phosphate-buffered saline (pH 7), PEG is polyethylene glycol, Ph is phenyl, Pnp is p-nitrophenyl, MC is 6-maleimidocaproyl, phe is L-phenylalanine, PyBrop is bromo tris-pyrrolidino phosphonium hexafluorophosphate, SEC is size-exclusion chromatography, Su is succinimide, TFA is trifluoroacetic acid, TLC is thin layer chromatography, UV is ultraviolet, and val is valine.

Cysteine Engineered Antibodies

The compounds of the invention include cysteine engineered antibodies where one or more amino acids of a wild-type or parent antibody are replaced with a cysteine amino acid. Any form of antibody may be so engineered, i.e. mutated. For example, a parent Fab antibody fragment may be engineered to form a cysteine engineered Fab, referred to herein as "ThioFab." Similarly, a parent monoclonal antibody may be engineered to form a "ThioMab." It should be noted that a single site mutation yields a single engineered cysteine residue in a ThioFab, while a single site mutation yields two engineered cysteine residues in a ThioMab, due to the dimeric nature of the IgG antibody. Mutants with replaced ("engineered") cysteine (Cys) residues are evaluated for the reactivity of the newly introduced, engineered cysteine thiol groups. The thiol reactivity value is a relative, numerical term in the range of 0 to 1.0 and can be measured for any cysteine engineered antibody. Thiol reactivity values of cysteine engineered antibodies of the invention are in the ranges of 0.6 to 1.0; 0.7 to 1.0; or 0.8 to 1.0.

The design, selection, and preparation methods of the invention enable cysteine engineered antibodies which are reactive with electrophilic functionality. These methods further enable antibody conjugate compounds such as antibody-drug conjugate (ADC) compounds with drug molecules at designated, designed, selective sites. Reactive cysteine residues on an antibody surface allow specifically conjugating a drug moiety through a thiol reactive group such as maleimide or haloacetyl. The nucleophilic reactivity of the thiol functionality of a Cys residue to a maleimide group is about 1000 times higher compared to any other amino acid functionality in a protein, such as amino group of lysine residues or the N-terminal amino group. Thiol specific functionality in iodoacetyl and maleimide reagents may react with amine groups, but higher pH (>9.0) and longer reaction times are required (Garman, 1997, Non-Radioactive Labelling: A Practical Approach, Academic Press, London).

Cysteine engineered antibodies of the invention preferably retain the antigen binding capability of their wild type, parent antibody counterparts. Thus, cysteine engineered antibodies are capable of binding, preferably specifically, to antigens. Such antigens include, for example, tumor-associated antigens (TAA), cell surface receptor proteins and other cell surface molecules, transmembrane proteins, signalling proteins, cell survival regulatory factors, cell proliferation regulatory factors, molecules associated with (for e.g., known or suspected to contribute functionally to) tissue development or differentiation, lymphokines, cytokines, molecules involved in cell cycle regulation, molecules involved in vasculogenesis and molecules associated with (for e.g., known or suspected to contribute functionally to) angiogenesis. The tumor-associated antigen may be a cluster differentiation factor (i.e., a CD protein). An antigen to which a cysteine engineered antibody is capable of binding may be a member of a subset of one of the above-mentioned categories, wherein the other subset(s) of said category comprise other molecules/antigens that have a distinct characteristic (with respect to the antigen of interest).

The parent antibody may also be a humanized antibody selected from huMAb4D5-1, huMAb4D5-2, huMAb4D5-3, huMAb4D5-4, huMAb4D5-5, huMAb4D5-6, huMAb4D5-7 and huMAb4D5-8 (Trastuzumab, HERCEPTIN®) as described in Table 3 of U.S. Pat. No. 5,821,337, expressly incorporated herein by reference; humanized 520C9 (WO 93/21319) and humanized 2C4 antibodies as described herein.

Cysteine engineered antibodies of the invention may be site-specifically and efficiently coupled with a thiol-reactive reagent. The thiol-reactive reagent may be a multifunctional linker reagent, a capture, i.e. affinity, label reagent (e.g. a biotin-linker reagent), a detection label (e.g. a fluorophore reagent), a solid phase immobilization reagent (e.g. SEPHAROSE™, polystyrene, or glass), or a drug-linker intermediate. One example of a thiol-reactive reagent is N-ethyl maleimide (NEM). In an exemplary embodiment, reaction of a ThioFab with a biotin-linker reagent provides a biotinylated ThioFab by which the presence and reactivity of the engineered cysteine residue may be detected and measured. Reaction of a ThioFab with a multifunctional linker reagent provides a ThioFab with a functionalized linker which may be further reacted with a drug moiety reagent or other label. Reaction of a ThioFab with a drug-linker intermediate provides a ThioFab drug conjugate.

The exemplary methods described here may be applied generally to the identification and production of antibodies, and more generally, to other proteins through application of the design and screening steps described herein.

Such an approach may be applied to the conjugation of other thiol-reactive agents in which the reactive group is, for example, a maleimide, an iodoacetamide, a pyridyl disulfide, or other thiol-reactive conjugation partner (Haugland, 2003, Molecular Probes Handbook of Fluorescent Probes and Research Chemicals, Molecular Probes, Inc.; Brinkley, 1992, Bioconjugate Chem. 3:2; Garman, 1997, Non-Radioactive Labelling: A Practical Approach, Academic Press, London; Means (1990) Bioconjugate Chem. 1:2; Hermanson, G. in Bioconjugate Techniques (1996) Academic Press, San Diego, pp. 40-55, 643-671). The partner may be a cytotoxic agent (e.g. a toxin such as doxorubicin or pertussis toxin), a fluorophore such as a fluorescent dye like fluorescein or rhodamine, a chelating agent for an imaging or radiotherapeutic metal, a peptidyl or non-peptidyl label or detection tag, or a clearance-modifying agent such as various isomers of polyethylene glycol, a peptide that binds to a third component, or another carbohydrate or lipophilic agent.

The sites identified on the exemplary antibody fragment, hu4D5Fabv8, herein are primarily in the constant domain of an antibody which is well conserved across all species of antibodies. These sites should be broadly applicable to other antibodies, without further need of structural design or knowledge of specific antibody structures, and without interference in the antigen binding properties inherent to the variable domains of the antibody.

Cysteine engineered antibodies which may be useful in the treatment of cancer include, but are not limited to, antibodies against cell surface receptors and tumor-associated antigens (TAA). Such antibodies may be used as naked antibodies (unconjugated to a drug or label moiety) or as Formula I antibody-drug conjugates (ADC). Tumor-associated antigens are known in the art, and can prepared for use in generating antibodies using methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

Examples of TAA include, but are not limited to, TAA (1)-(36) listed below. For convenience, information relating to these antigens, all of which are known in the art, is listed below and includes names, alternative names, Genbank accession numbers and primary reference(s), following nucleic acid and protein sequence identification conventions of the National Center for Biotechnology Information (NCBI). Nucleic acid and protein sequences corresponding to TAA (1)-(36) are available in public databases such as GenBank. Tumor-associated antigens targeted by antibodies include all amino acid sequence variants and isoforms possessing at least about 70%, 80%, 85%, 90%, or 95% sequence identity relative to the sequences identified in the cited references, or which exhibit substantially the same biological properties or characteristics as a TAA having a sequence found in the cited references. For example, a TAA having a variant sequence generally is able to bind specifically to an antibody that binds specifically to the TAA with the corresponding sequence listed. The sequences and disclosure in the reference specifically recited herein are expressly incorporated by reference.

Tumor-Associated Antigens (1)-(36):

(1) BMPR1B (bone morphogenetic protein receptor-type IB, Genbank accession no. NM_001203) ten Dijke, P., et al Science 264 (5155):101-104 (1994), Oncogene 14 (11): 1377-1382 (1997)); WO2004063362 (Claim 2); WO2003042661 (Claim 12); US 2003134790-A1 (Page 38-39); WO2002102235 (Claim 13; Page 296); WO2003055443 (Page 91-92); WO200299122 (Example 2; Page 528-530); WO2003029421 (Claim 6); WO2003024392 (Claim 2; FIG. 112); WO200298358 (Claim 1; Page 183); WO200254940 (Page 100-101); WO200259377 (Page 349-350); WO200230268 (Claim 27; Page 376); WO200148204 (Example; FIG. 4) NP_001194 bone morphogenetic protein receptor, type IB /pid=NP_001194.1—Cross-references: MIM:603248; NP_001194.1; AY065994

(2) E16 (LAT1, SLC7A5, Genbank accession no. NM_003486) Biochem. Biophys. Res. Commun. 255 (2), 283-288 (1999), Nature 395 (6699):288-291 (1998), Gaugitsch, H. W., et al (1992) J. Biol. Chem. 267 (16): 11267-11273); WO2004048938 (Example 2); WO2004032842 (Example IV); WO2003042661 (Claim 12); WO2003016475 (Claim 1); WO200278524 (Example 2); WO200299074 (Claim 19; Page 127-129); WO200286443 (Claim 27; Pages 222, 393); WO2003003906 (Claim 10; Page 293); WO200264798 (Claim 33; Page 93-95); WO200014228 (Claim 5; Page 133-136); US2003224454 (FIG. 3); WO2003025138 (Claim 12; Page 150); NP_003477 solute carrier family 7 (cationic amino acid transporter, y+system), member 5/pid=NP_003477.3-*Homo sapiens* Cross-references: *MIM:*600182; NP_003477.3; NM_015923; NM_003486_1

Figure 2A:
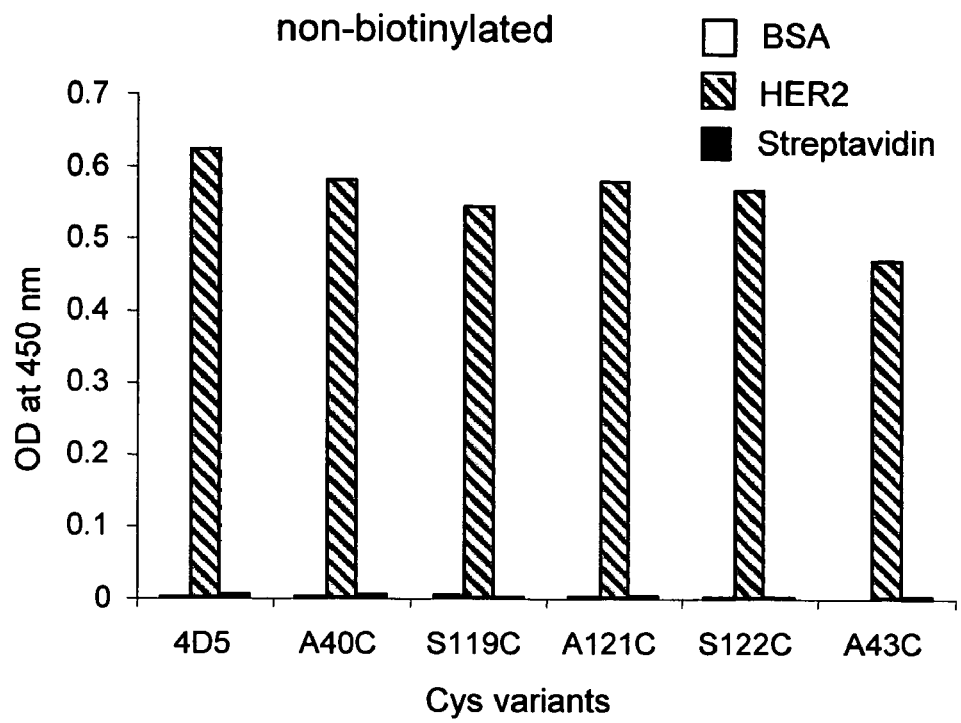
FIGS. 2A and 2B show binding measurements with detection of absorbance at 450 nm of hu4D5Fabv8 and hu4D5Fabv8 Cys mutant (ThioFab) phage variants: (A) non-biotinylated phage-hu4D5Fabv8 and (B) biotinylated phage-hu4D5Fabv8 (B) by the PHESELECTOR assay for interactions with BSA (open bar), HER2 (striped bar) or streptavidin (solid bar).
Figure 13A:
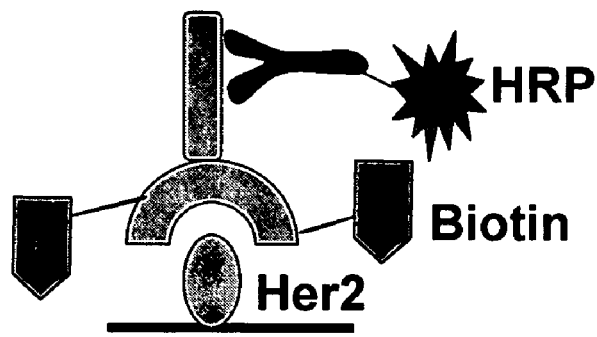
FIG. 13A shows a cartoon depiction of biotinylated antibody binding to immobilized HER2 with binding of HRP labeled secondary antibody for absorbance detection.

(3) STEAP1 (six transmembrane epithelial antigen of prostate, Genbank accession no. NM_012449) Cancer Res. 61 (15), 5857-5860 (2001), Hubert, R. S., et al (1999) Proc. Natl. Acad. Sci. U.S.A. 96 (25):14523-14528); WO2004065577 (Claim 6); WO2004027049 (FIG. 1L); EP1394274 (Example 11); WO2004016225 (Claim 2); WO2003042661 (Claim 12); US2003157089 (Example 5); US2003185830 (Example 5); US2003064397 (FIG. 2); WO200289747 (Example 5; Page 618-619); WO2003022995 (Example 9; FIG. 13A, Example 53; Page 173, Example 2; FIG. 2A); NP_036581 six transmembrane epithelial antigen of the prostate Cross-references: MIM:604415; NP_036581.1; NM_012449_1

Figure 12:
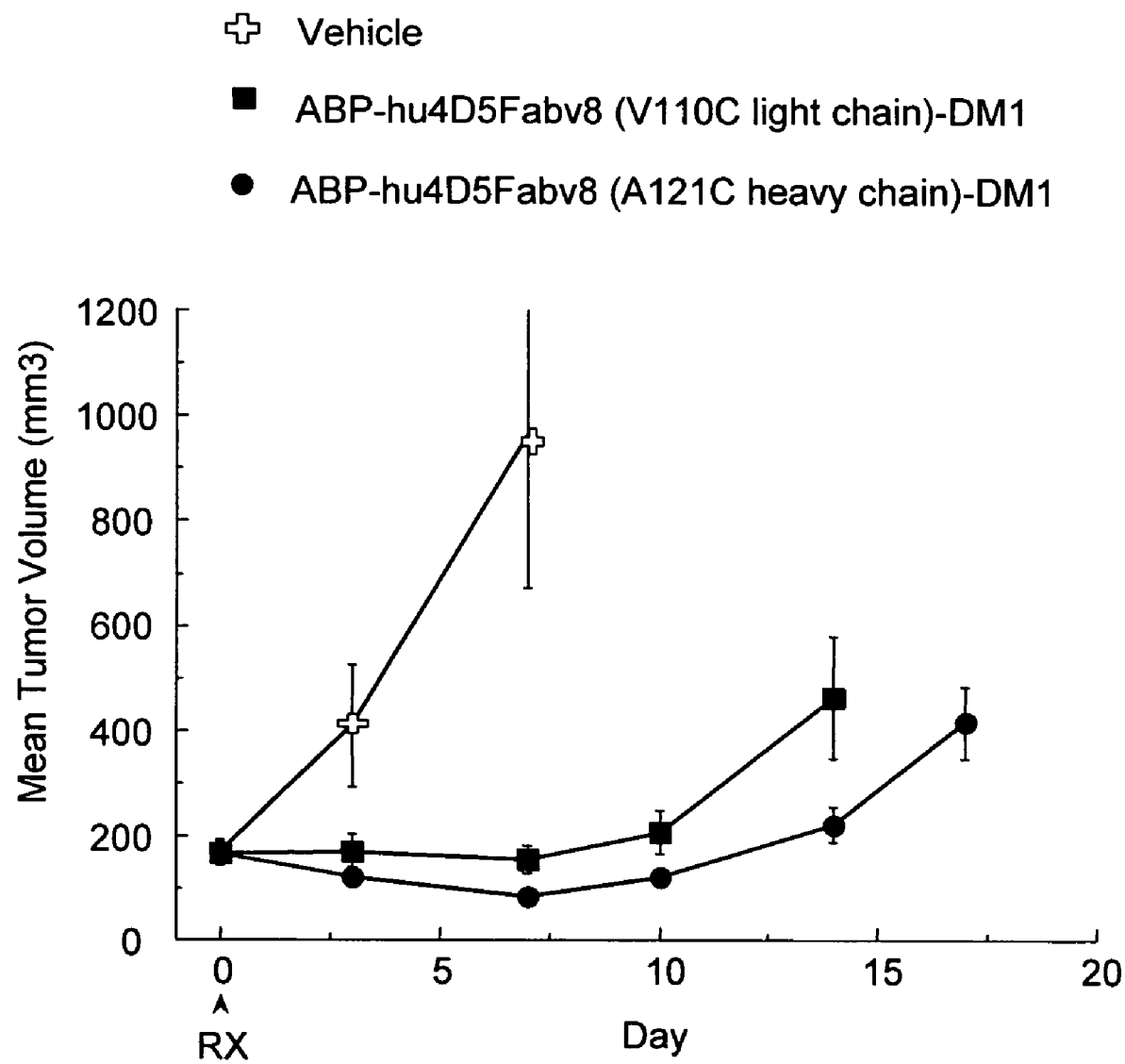
FIG. 12 shows the mean tumor volume change over time in athymic nude mice with MMTV-HER2 Fo5 mammary tumor allografts, dosed on Day 0 with: ✟Vehicle (Buffer); -■- ABP-hu4D5Fabv8 cysteine mutant (V110C light chain)-DM1; and -●- ABP-hu4D5Fabv8 cysteine mutant (A121C heavy chain)-DM1.

(4) 0772P (CA125, MUC16, Genbank accession no. AF361486) J. Biol. Chem. 276 (29):27371-27375 (2001)); WO2004045553 (Claim 14); WO200292836 (Claim 6; FIG. 12); WO200283866 (Claim 15; Page 116-121); US2003124140 (Example 16); Cross-references: GI:34501467; AAK74120.3; AF361486_1

(5) MPF (MPF, MSLN, SMR, megakaryocyte potentiating factor, mesothelin, Genbank accession no. NM_005823) Yamaguchi, N., et al Biol. Chem. 269 (2), 805-808 (1994), Proc. Natl. Acad. Sci. U.S.A. 96 (20):11531-11536 (1999), Proc. Natl. Acad. Sci. U.S.A. 93 (1):136-140(1996), J. Biol. Chem. 270 (37):21984-21990 (1995)); WO2003101283 (Claim 14); (WO2002102235 (Claim 13; Page 287-288); WO2002101075 (Claim 4; Page 308-309); WO200271928 (Page 320-321); WO9410312 (Page 52-57); Cross-references: MIM:601051; NP_005814.2; NM_005823_1

(6) Napi3b (NAPI-3B, NPIIb, SLC34A2, solute carrier family 34 (sodium phosphate), member 2, type II sodium-dependent phosphate transporter 3b, Genbank accession no. NM_006424) J. Biol. Chem. 277 (22):19665-19672

(2002), Genomics 62 (2):281-284 (1999), Feild, J. A., et al (1999) Biochem. Biophys. Res. Commun. 258 (3):578-582); WO2004022778 (Claim 2); EP1394274 (Example 11); WO2002102235 (Claim 13; Page 326); EP875569 (Claim 1; Page 17-19); WO200157188 (Claim 20; Page 329); WO2004032842 (Example IV); WO200175177 (Claim 24; Page 139-140); Cross-references: MIM: 604217; NP_006415.1; NM_006424_1

(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B, Genbank accession no. AB040878) Nagase T., et al (2000) DNA Res. 7 (2):143-150); WO2004000997 (Claim 1); WO2003003984 (Claim 1); WO200206339 (Claim 1; Page 50); WO200188133 (Claim 1; Page 41-43, 48-58); WO2003054152 (Claim 20); WO2003101400 (Claim 11); Accession: Q9P283; EMBL; AB040878; BAA95969.1. Genew; HGNC: 10737;

(8) PSCA hlg (2700050C12Rik, C530008O16Rik, RIKEN cDNA 2700050C12, RIKEN cDNA 2700050C12 gene, Genbank accession no. AY358628); Ross et al (2002) Cancer Res. 62:2546-2553; US2003129192 (Claim 2); US2004044180 (Claim 12); US2004044179 (Claim 11); US2003096961 (Claim 11); US2003232056 (Example 5); WO2003105758 (Claim 12); US2003206918 (Example 5); EP1347046 (Claim 1); WO2003025148 (Claim 20); Cross-references: GI:37182378; AAQ88991.1; AY358628_1

Figure 6:
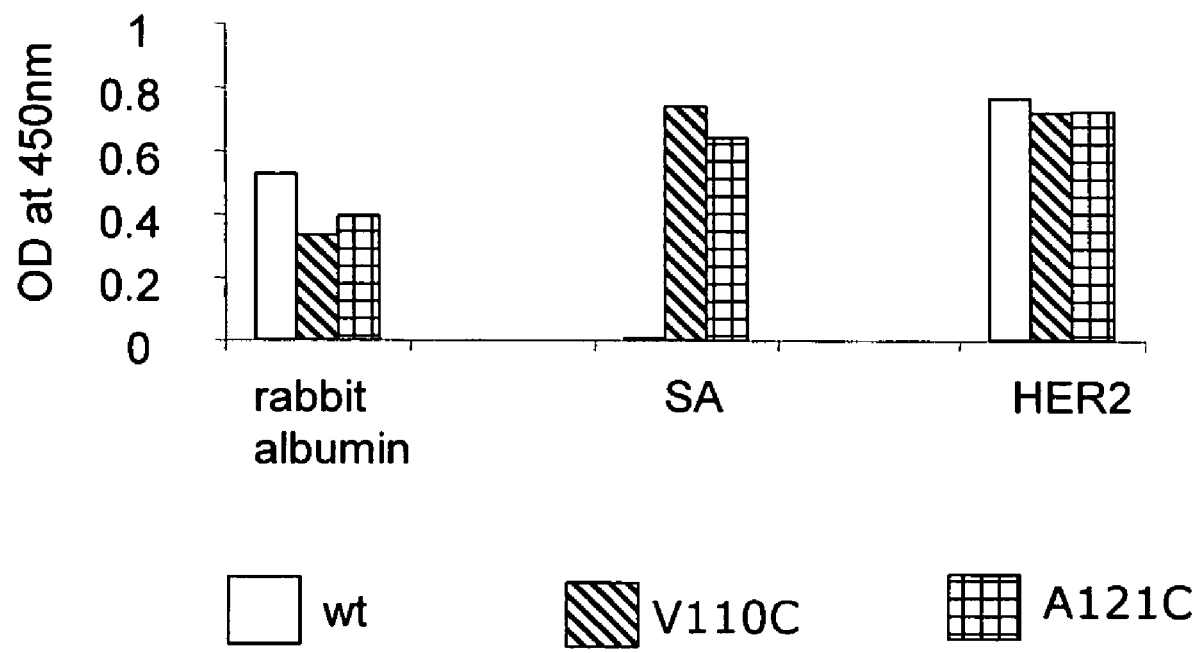
FIG. 6 shows ELISA analysis with detection of absorbance at 450 nm of biotinylated ABP-hu4D5Fabv8 wild type (wt), and ABP-hu4D5Fabv8 cysteine mutants V110C and A121C for binding with rabbit albumin, streptavidin (SA), and HER2.

(9) ETBR (Endothelin type B receptor, Genbank accession no. AY275463); Nakamuta M., et al Biochem. Biophys. Res. Commun. 177, 34-39, 1991; Ogawa Y., et al Biochem. Biophys. Res. Commun. 178, 248-255, 1991; Arai H., et al Jpn. Circ. J. 56, 1303-1307, 1992; Arai H., et al J. Biol. Chem. 268, 3463-3470, 1993; Sakamoto A., Yanagisawa M., et al Biochem. Biophys. Res. Commun. 178, 656-663, 1991; Elshourbagy N. A., et al J. Biol. Chem. 268, 3873-3879, 1993; Haendler B., et al J. Cardiovasc. Pharmacol. 20, s1-S4, 1992; Tsutsumi M., et al Gene 228, 43-49, 1999; Strausberg R. L., et al Proc. Natl. Acad. Sci. U.S.A. 99, 16899-16903, 2002; Bourgeois C., et al J. Clin. Endocrinol. Metab. 82, 3116-3123, 1997; Okamoto Y., et al Biol. Chem. 272, 21589-21596, 1997; Verheij J. B., et al Am. J. Med. Genet. 108, 223-225, 2002; Hofstra R. M. W., et al Eur. J. Hum. Genet. 5, 180-185, 1997; Puffenberger E. G., et al Cell 79, 1257-1266, 1994; Attie T., et al, Hum. Mol. Genet. 4, 2407-2409, 1995; Auricchio A., et al Hum. Mol. Genet. 5:351-354, 1996; Amiel J., et al Hum. Mol. Genet. 5, 355-357, 1996; Hofstra R. M. W., et al Nat. Genet. 12, 445-447, 1996; Svensson P. J., et al Hum. Genet. 103, 145-148, 1998; Fuchs S., et al Mol. Med. 7, 115-124, 2001; Pingault V., et al (2002) Hum. Genet. 111, 198-206; WO2004045516 (Claim 1); WO2004048938 (Example 2); WO2004040000 (Claim 151); WO2003087768 (Claim 1); WO2003016475 (Claim 1); WO2003016475 (Claim 1); WO200261087 (FIG. 1); WO2003016494 (FIG. 6); WO2003025138 (Claim 12; Page 144); WO200198351 (Claim 1; Page 124-125); EP522868 (Claim 8; FIG. 2); WO200177172 (Claim 1; Page 297-299); US2003109676; U.S. Pat. No. 6,518,404 (FIG. 3); U.S. Pat. No. 5,773,223 (Claim 1a; Col 31-34); WO2004001004;

(10) MSG783 (RNF124, hypothetical protein FLJ20315, Genbank accession no. NM_017763); WO2003104275 (Claim 1); WO2004046342 (Example 2); WO2003042661 (Claim 12); WO2003083074 (Claim 14; Page 61); WO2003018621 (Claim 1); WO2003024392 (Claim 2; FIG. 93); WO200166689 (Example 6); Cross-references: LocusID:54894; NP_060233.2; NM_017763_1

Figure 4A:
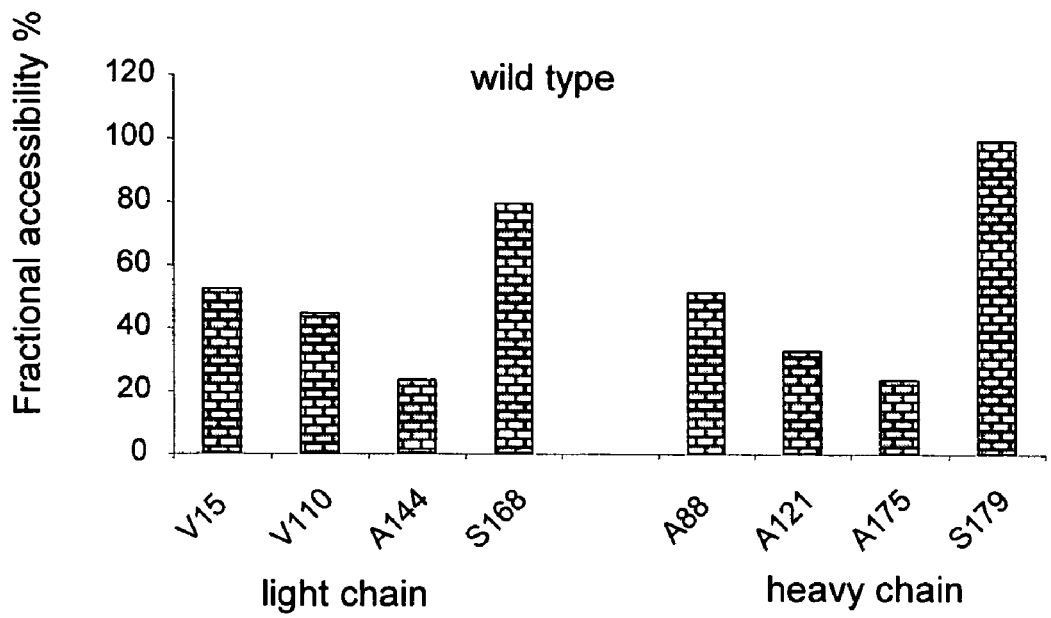
FIG. 4A shows Fractional Surface Accessibility values of residues on wild type hu4D5Fabv8. Light chain sites are on the left side and heavy chain sites are on the right side.
Figure 4B:
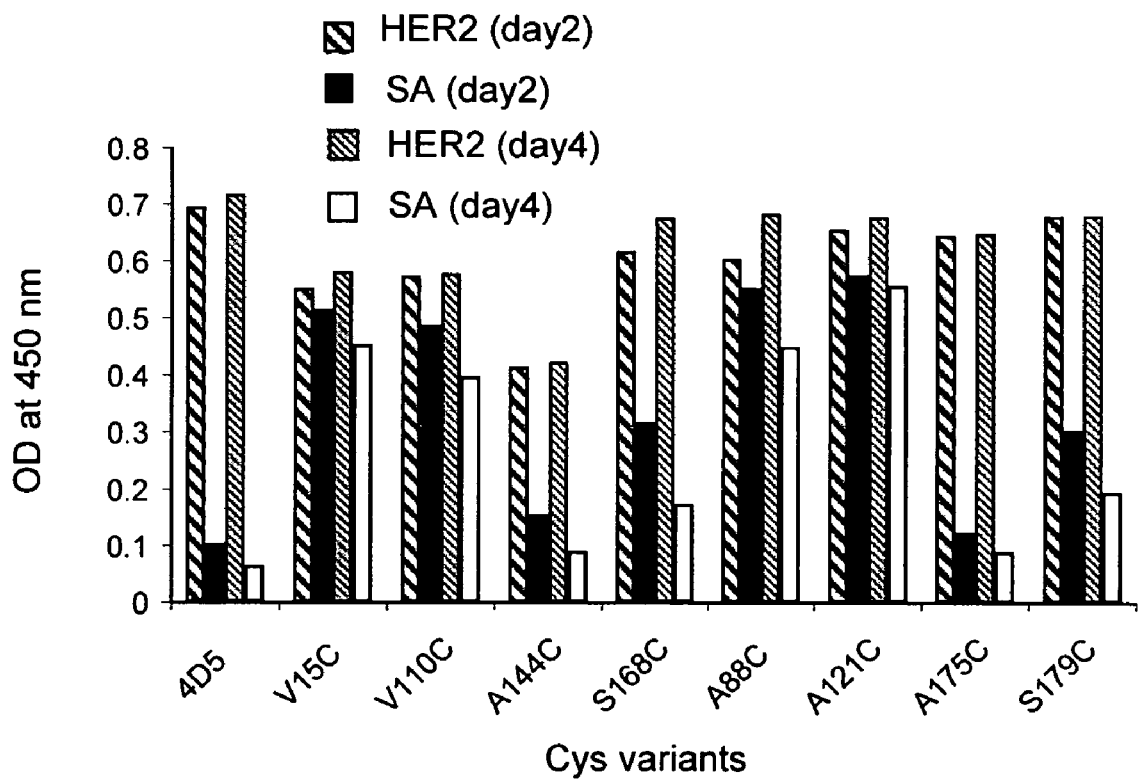
FIG. 4B shows binding measurements with detection of absorbance at 450 nm of biotinylated hu4D5Fabv8 (left) and hu4D5Fabv8 Cys mutant (ThioFab) variants for interactions with HER2 (day 2), streptavidin (SA) (day 2), HER2 (day 4), and SA (day 4). Phage-hu4D5Fabv8 Cys variants were isolated and stored at 4° C. Biotin conjugation was carried out either at day 2 or day 4 followed by PHESELECTOR analyses to monitor their interaction with Her2 and streptavidin as described in Example 2, and probe the stability of reactive thiol groups on engineered ThioFab variants.
Figure 10:
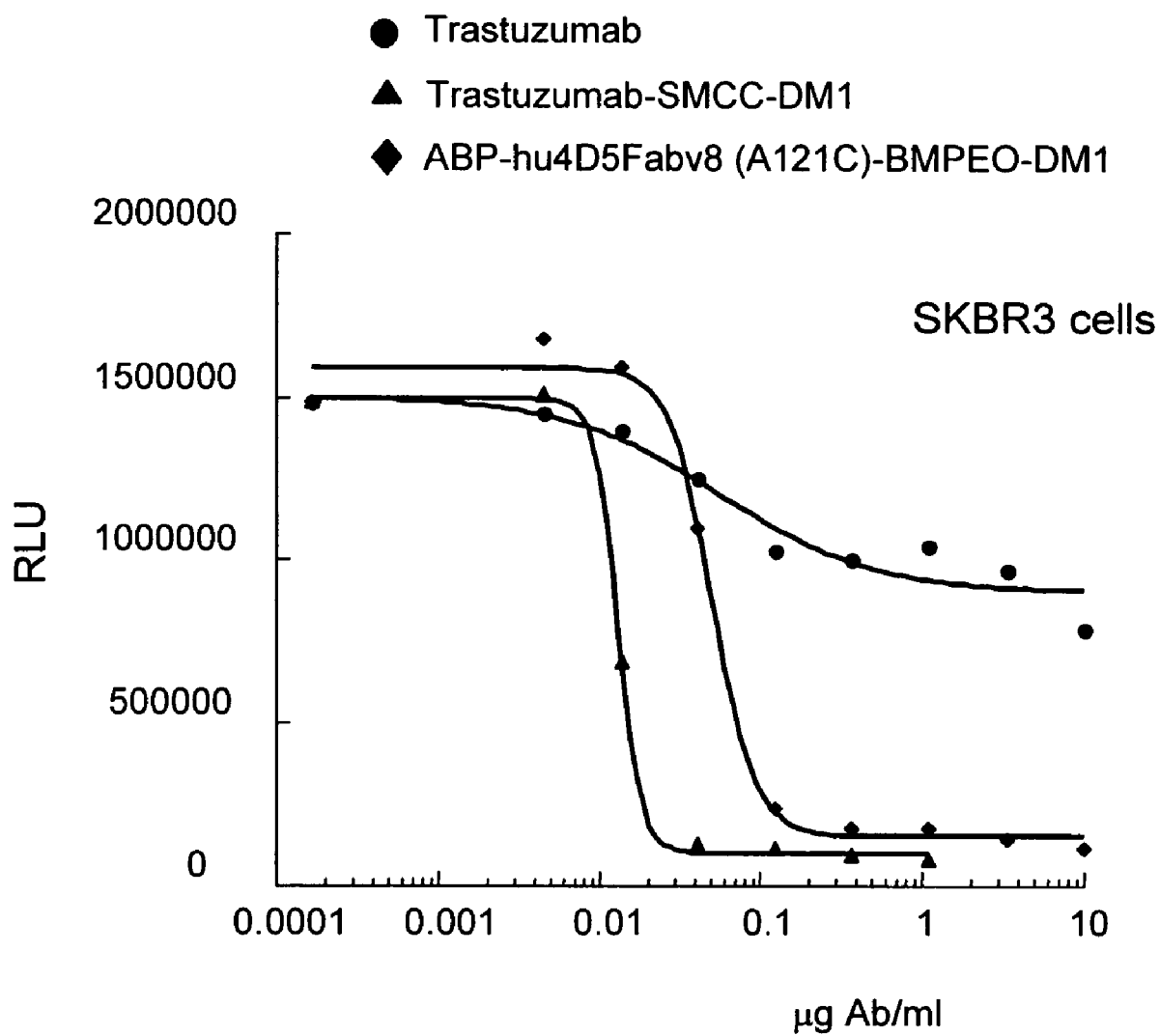
FIG. 10 shows an in vitro, cell proliferation assay of SK-BR-3 cells treated with -●- trastuzumab; -▲- trastuzumab-SMCC-DM1; and -♦- hu4D5Fabv8 cysteine mutant-(A121C)-BMPEO-DM1.

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138) Lab. Invest. 82 (11):1573-1582 (2002)); WO2003087306; US2003064397 (Claim 1; FIG. 1); WO200272596 (Claim 13; Page 54-55); WO200172962 (Claim 1; FIG. 4B); WO2003104270 (Claim 11); WO2003104270 (Claim 16); US2004005598 (Claim 22); WO2003042661 (Claim 12); US2003060612 (Claim 12; FIG. 10); WO200226822 (Claim 23; FIG. 2); WO200216429 (Claim 12; FIG. 10); Cross-references: GI:22655488; AAN04080.1; AF455138_1

(12) TrpM4 (BR22450, FLJ20041, TRPM4, TRPM4B, transient receptor potential cation channel, subfamily M, member 4, Genbank accession no. NM_017636) Xu, X. Z., et al Proc. Natl. Acad. Sci. U.S.A. 98 (19):10692-10697 (2001), Cell 109 (3):397-407 (2002), J. Biol. Chem. 278 (33): 30813-30820 (2003)); US2003143557 (Claim 4); WO200040614 (Claim 14; Page 100-103); WO200210382 (Claim 1; FIG. 9A); WO2003042661 (Claim 12); WO200230268 (Claim 27; Page 391); US2003219806 (Claim 4); WO200162794 (Claim 14; FIG. 1A-D); Cross-references: MIM:606936; NP_060106.2; NM_017636_1

(13) CRIPTO (CR, CR1, CRGF, CRIPTO, TDGF1, teratocarcinoma-derived growth factor, Genbank accession no. NP_003203 or NM_003212) Ciccodicola, A., et al EMBO J. 8 (7):1987-1991 (1989), Am. J. Hum. Genet. 49 (3):555-565 (1991)); US2003224411 (Claim 1); WO2003083041 (Example 1); WO2003034984 (Claim 12); WO200288170 (Claim 2; Page 52-53); WO2003024392 (Claim 2; FIG. 58); WO200216413 (Claim 1; Page 94-95, 105); WO200222808 (Claim 2; FIG. 1); U.S. 5,854,399 (Example 2; Col 17-18); U.S. Pat. No. 5,792,616 (FIG. 2); Cross-references: MIM:187395; NP_003203.1; NM_003212_1

Figure 9:
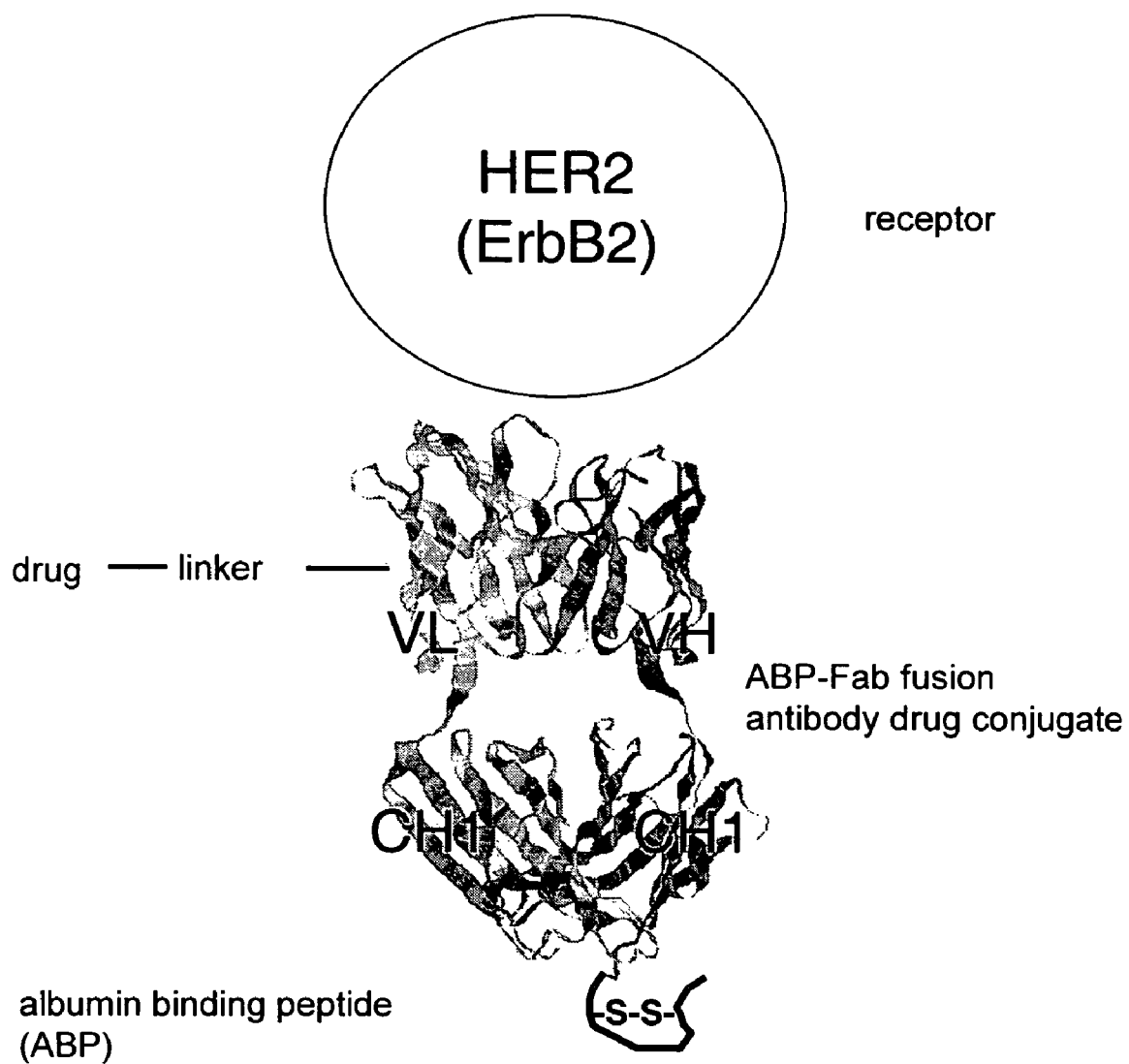
FIG. 9 shows an exemplary representation of an ABP-ThioFab fusion protein drug conjugate binding to a HER2 receptor antigen. ABP=albumin binding protein.

(14) CD21 (CR2 (Complement receptor 2) or C3DR (C3d/Epstein Barr virus receptor) or Hs.73792 Genbank accession no. M26004) Fujisaku et al (1989) J. Biol. Chem. 264 (4):2118-2125); Weis J. J., et al J. Exp. Med. 167, 1047-1066, 1988; Moore M., et al Proc. Natl. Acad. Sci. U.S.A. 84, 9194-9198, 1987; Barel M., et al Mol. Immunol. 35, 1025-1031, 1998; Weis J. J., et al Proc. Natl. Acad. Sci. U.S.A. 83, 5639-5643, 1986; Sinha S. K., et al (1993) J. Immunol. 150, 5311-5320; WO2004045520 (Example 4); US2004005538 (Example 1); WO2003062401 (Claim 9); WO2004045520 (Example 4); WO9102536 (FIG. 9.1-9.9); WO2004020595 (Claim 1); Accession: P20023; Q13866; Q14212; EMBL; M26004; AAA35786.1.

(15) CD79b (CD79B, CD79β, IGb (immunoglobulin-associated beta), B29, Genbank accession no. NM_000626 or 11038674) Proc. Natl. Acad. Sci. U.S.A. (2003) 100 (7): 4126-4131, Blood (2002) 100 (9):3068-3076, Muller et al (1992) Eur. J. Immunol. 22 (6):1621-1625); WO2004016225 (Claim 2, FIG. 140); WO2003087768, US2004101874 (Claim 1, page 102); WO2003062401 (Claim 9); WO200278524 (Example 2); US2002150573 (Claim 5, page 15); U.S. Pat. No. 5,644,033; WO2003048202 (Claim 1, pages 306 and 309); WO 99/558658, U.S. Pat. No. 6,534,482 (Claim 13, FIG. 17A/B); WO200055351 (Claim 11, pages 1145-1146); Cross-references: MIM:147245; NP_000617.1; NM_000626_1

(16) FcRH2 (IFGP4, IRTA4, SPAP1A (SH2 domain containing phosphatase anchor protein 1a), SPAP1B, SPAP1C, Genbank accession no. NM_030764, AY358130) Genome Res. 13 (10):2265-2270 (2003), Immunogenetics 54 (2):87-95 (2002), Blood 99 (8):2662-2669 (2002), Proc. Natl. Acad. Sci. U.S.A. 98 (17):9772-9777 (2001), Xu, M. J., et al (2001) Biochem. Biophys. Res. Commun. 280 (3):768-775; WO2004016225 (Claim 2); WO2003077836; WO200138490 (Claim 5; FIG. 18D-1-18D-2); WO2003097803 (Claim 12); WO2003089624 (Claim 25); Cross-references: MIM:606509; NP_110391.2; NM_030764_1

Figure 7:
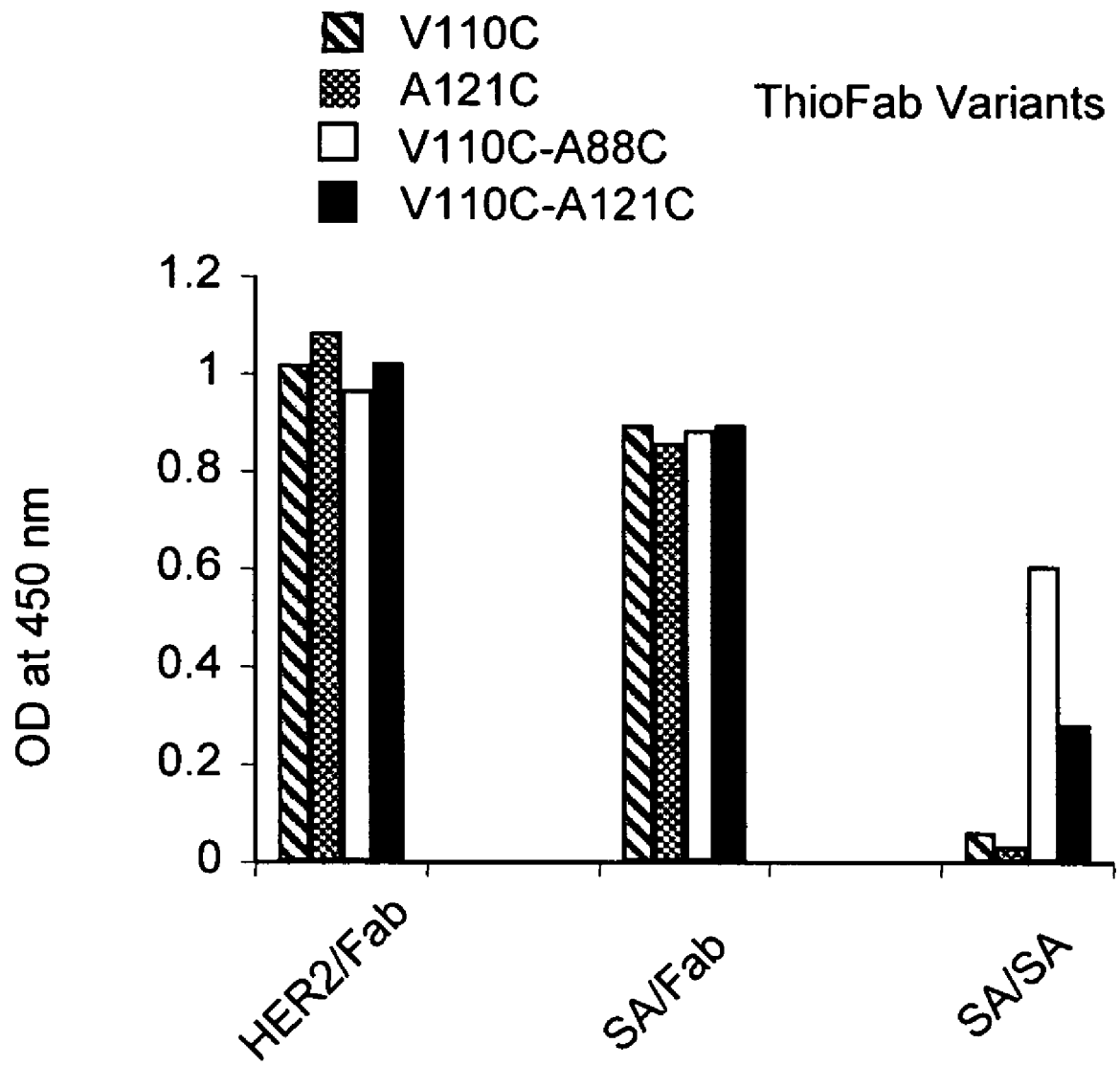
FIG. 7 shows ELISA analysis with detection of absorbance at 450 nm of biotinylated ABP-hu4D5Fabv8 cysteine mutants (ThioFab variants): (left to right) single Cys variants ABP-V110C, ABP-A121C, and double Cys variants ABP-V110C-A88C and ABP-V110C-A121C for binding with rabbit albumin, HER2 and streptavidin (SA), and probing with Fab-HRP or SA-HRP.

(17) HER2 (ErbB2, Genbank accession no. M11730) Coussens L., et al Science (1985) 230(4730):1132-1139); Yamamoto T., et al Nature 319, 230-234, 1986; Semba K., et al Proc. Natl. Acad. Sci. U.S.A. 82, 6497-6501, 1985; Swiercz J. M., et al J. Cell Biol. 165, 869-880, 2004; Kuhns J. J., et al J. Biol. Chem. 274, 36422-36427, 1999; Cho H.—S., et al Nature 421, 756-760, 2003; Ehsani A., et al (1993) Genomics 15, 426-429; WO2004048938 (Example 2); WO2004027049 (FIG. 1I); WO2004009622; WO2003081210; WO2003089904 (Claim 9); WO2003016475 (Claim 1); US2003118592; WO2003008537 (Claim 1); WO2003055439 (Claim 29; FIG. 1A-B); WO2003025228 (Claim 37; FIG. 5C); WO200222636 (Example 13; Page 95-107); WO200212341 (Claim 68; FIG. 7); WO200213847 (Page 71-74); WO200214503 (Page 114-117); WO200153463 (Claim 2; Page 41-46); WO200141787 (Page 15); WO200044899 (Claim 52; FIG. 7); WO200020579 (Claim 3; FIG. 2); U.S. Pat. No. 5,869,445 (Claim 3; Col 31-38); WO9630514 (Claim 2; Page 56-61); EP1439393 (Claim 7); WO2004043361 (Claim 7); WO2004022709; WO200100244 (Example 3; FIG. 4); Accession: P04626; EMBL; M11767; AAA35808.1. EMBL; M11761; AAA35808.1.

Figure 8:
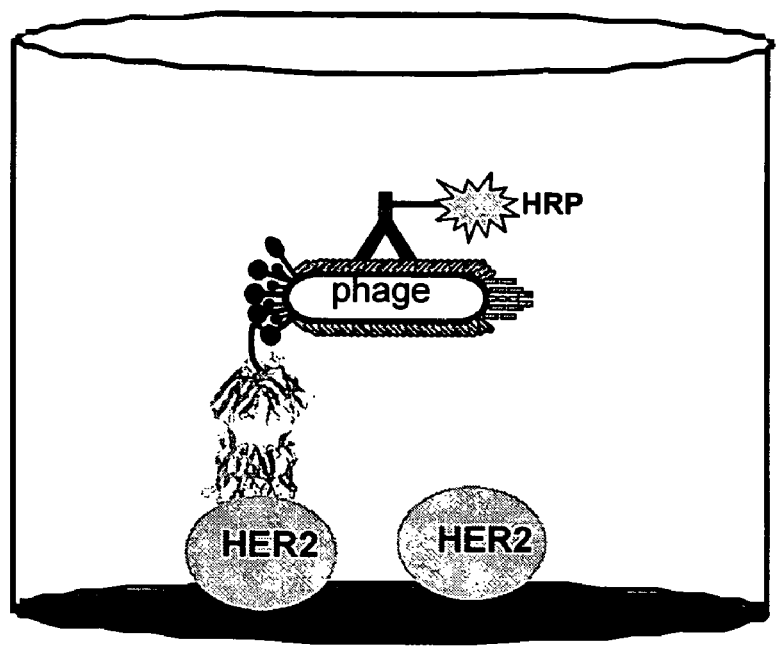
FIG. 8 shows binding of biotinylated ThioFab phage and an anti-phage HRP antibody to HER2 (top) and Streptavidin (bottom).
Figure 8:
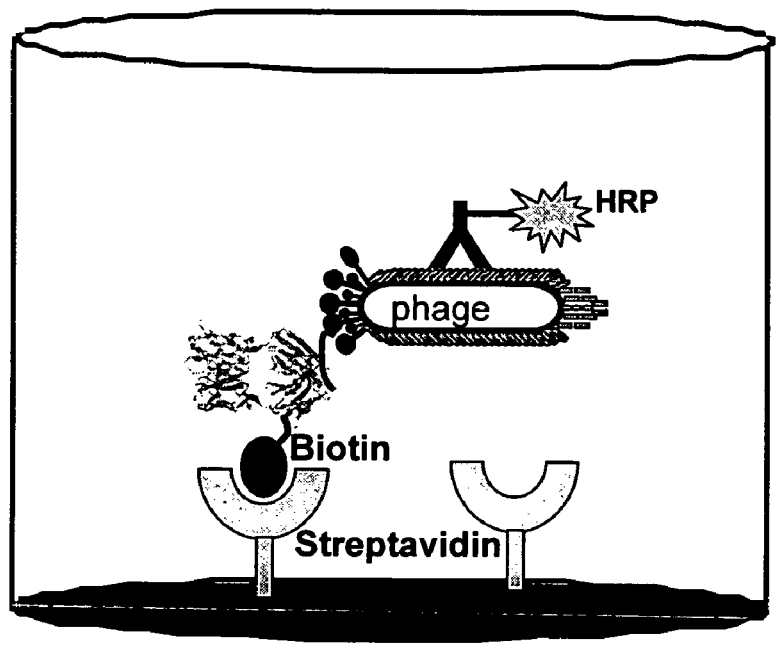

(18) NCA (CEACAM6, Genbank accession no. M18728); Barnett T., et al Genomics 3, 59-66, 1988; Tawaragi Y., et al Biochem. Biophys. Res. Commun. 150, 89-96, 1988; Strausberg R. L., et al Proc. Natl. Acad. Sci. U.S.A. 99:16899-16903, 2002; WO2004063709; EP1439393 (Claim 7); WO2004044178 (Example 4); WO2004031238; WO2003042661 (Claim 12); WO200278524 (Example 2); WO200286443 (Claim 27; Page 427); WO200260317 (Claim 2); Accession: P40199; Q14920; EMBL; M29541; AAA59915.1. EMBL; M18728;

(19) MDP (DPEP1, Genbank accession no. BC017023) Proc. Natl. Acad. Sci. U.S.A. 99 (26):16899-16903 (2002)); WO2003016475 (Claim 1); WO200264798 (Claim 33; Page 85-87); JP05003790 (FIG. 6-8); WO9946284 (FIG. 9); Cross-references: MIM:179780; AAH17023.1; BC017023_1

(20) IL20Rα (IL20Ra, ZCYTOR7, Genbank accession no. AF184971); Clark H. F., et al Genome Res. 13, 2265-2270, 2003; Mungall A. J., et al Nature 425, 805-811, 2003; Blumberg H., et al Cell 104, 9-19, 2001; Dumoutier L., et al J. Immunol. 167, 3545-3549, 2001; Parrish-Novak J., et al J. Biol. Chem. 277, 47517-47523, 2002; Pletnev S., et al (2003) Biochemistry 42:12617-12624; Sheikh F., et al (2004) J. Immunol. 172, 2006-2010; EP1394274 (Example 11); US2004005320 (Example 5); WO2003029262 (Page 74-75); WO2003002717 (Claim 2; Page 63); WO200222153 (Page 45-47); US2002042366 (Page 20-21); WO200146261 (Page 57-59); WO200146232 (Page 63-65); WO9837193 (Claim 1; Page 55-59); Accession: Q9UHF4; Q6UWA9; Q96SH8; EMBL; AF184971; AAF01320.1.

(21) Brevican (BCAN, BEHAB, Genbank accession no. AF229053) Gary S. C., et al Gene 256, 139-147, 2000; Clark H. F., et al Genome Res. 13, 2265-2270, 2003; Strausberg R. L., et al Proc. Natl. Acad. Sci. U.S.A. 99, 16899-16903, 2002; US2003186372 (Claim 11); US2003186373 (Claim 11); US2003119131 (Claim 1; FIG. 52); US2003119122 (Claim 1; FIG. 52); US2003119126 (Claim 1); US2003119121 (Claim 1; FIG. 52); US2003119129 (Claim 1); US2003119130 (Claim 1); US2003119128 (Claim 1; FIG. 52); US2003119125 (Claim 1); WO2003016475 (Claim 1); WO200202634 (Claim 1);

(22) EphB2R (DRT, ERK, Hek5, EPHT3, Tyro5, Genbank accession no. NM_004442) Chan, J. and Watt, V. M., Oncogene 6 (6), 1057-1061 (1991) Oncogene 10 (5):897-905 (1995), Annu. Rev. Neurosci. 21:309-345 (1998), Int. Rev. Cytol. 196:177-244 (2000)); WO2003042661 (Claim 12); WO200053216 (Claim 1; Page 41); WO2004065576 (Claim 1); WO2004020583 (Claim 9); WO2003004529 (Page 128-132); WO200053216 (Claim 1; Page 42); Cross-references: MIM:600997; NP_004433.2; NM_004442_1

(23) ASLG659 (B7h, Genbank accession no. AX092328) US20040101899 (Claim 2); WO2003104399 (Claim 11); WO2004000221 (FIG. 3); US2003165504 (Claim 1); US2003124140 (Example 2); US2003065143 (FIG. 60); WO2002102235 (Claim 13; Page 299); US2003091580 (Example 2); WO200210187 (Claim 6; FIG. 10); WO200194641 (Claim 12; FIG. 7b); WO200202624 (Claim 13; FIG. 1A-1B); US2002034749 (Claim 54; Page 45-46); WO200206317 (Example 2; Page 320-321, Claim 34; Page 321-322); WO200271928 (Page 468469); WO200202587 (Example 1; FIG. 1); WO200140269 (Example 3; Pages 190-192); WO200036107 (Example 2; Page 205-207); WO2004053079 (Claim 12); WO2003004989 (Claim 1); WO200271928 (Page 233-234, 452-453); WO 0116318;

(24) PSCA (Prostate stem cell antigen precursor, Genbank accession no. AJ297436) Reiter R. E., et al Proc. Natl. Acad. Sci. U.S.A. 95, 1735-1740, 1998; Gu Z., et al Oncogene 19, 1288-1296, 2000; Biochem. Biophys. Res. Commun. (2000) 275(3):783-788; WO2004022709; EP1394274 (Example 11); US2004018553 (Claim 17); WO2003008537 (Claim 1); WO200281646 (Claim 1; Page 164); WO2003003906 (Claim 10; Page 288); WO200140309 (Example 1; FIG. 17); US2001055751 (Example 1; FIG. 1b); WO200032752 (Claim 18; FIG. 1); WO9851805 (Claim 17; Page 97); WO9851824 (Claim 10; Page 94); WO9840403 (Claim 2; FIG. 1B); Accession: O43653; EMBL; AF043498; AAC39607.1.

(25) GEDA (Genbank accession No. AY260763); AAP14954 lipoma HMGIC fusion-partner-like protein/pid=AAP14954.1—*Homo sapiens* Species: *Homo sapiens* (human) WO2003054152 (Claim 20); WO2003000842 (Claim 1); WO2003023013 (Example 3, Claim 20); US2003194704 (Claim 45); Cross-references: GI:30102449; AAP14954.1; AY260763_1

(26) BAFF-R (B cell-activating factor receptor, BLyS receptor 3, BR3, Genbank accession No. AF116456); BAFF receptor/pid=NP-443177.1—Homo sapiens Thompson, J. S., et al Science 293 (5537), 2108-2111 (2001); WO2004058309; WO2004011611; WO2003045422 (Example; Page 32-33); WO2003014294 (Claim 35; FIG. 6B); WO2003035846 (Claim 70; Page 615-616);

WO200294852 (Col 136-137); WO200238766 (Claim 3; Page 133); WO200224909 (Example 3; FIG. 3); Cross-references: MIM:606269; NP_443177.1; NM_052945_1; AF132600

(27) CD22 (B-cell receptor CD22-β-form, BL-CAM, Lyb-8, Lyb8, SIGLEC-2, FLJ22814, Genbank accession No. AK026467); Wilson et al (1991) J. Exp. Med. 173:137-146; WO2003072036 (Claim 1; FIG. 1); Cross-references: MIM:107266; NP_001762.1; NM_001771_1

(28) CD79a (CD79A, CD79a, immunoglobulin-associated alpha, a B cell-specific protein that covalently interacts with Ig beta (CD79B) and forms a complex on the surface with Ig M molecules, transduces a signal involved in B-cell differentiation), pI: 4.84, MW: 25028 TM: 2 [P] Gene Chromosome: 19q13.2, Genbank accession No. NP_001774.10) WO2003088808, US20030228319; WO2003062401 (Claim 9); US2002150573 (Claim 4, pages 13-14); WO9958658 (Claim 13, FIG. 16); WO9207574 (FIG. 1); U.S. Pat. No. 5,644,033; Ha et al (1992) J. Immunol. 148(5):1526-1531; Mueller et al (1992) Eur. J. Biochem. 22:1621-1625; Hashimoto et al (1994) Immunogenetics 40(4):287-295; Preud'homme et al (1992) Clin. Exp. Immunol. 90(1):141-146; Yu et al (1992) J. Immunol. 148(2) 633-637; Sakaguchi et al (1988) EMBO J. 7(11):3457-3464;

(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia); 372 aa, pI: 8.54 MW: 41959 TM: 7 [P] Gene Chromosome: 11q23.3, Genbank accession No. NP_001707.1) WO2004040000; WO2004015426; US2003105292 (Example 2); U.S. Pat. No. 6,555,339 (Example 2); WO200261087 (FIG. 1); WO200157188 (Claim 20, page 269); WO200172830 (pages 12-13); WO200022129 (Example 1, pages 152-153, Example 2, pages 254-256); WO9928468 (Claim 1, page 38); U.S. Pat. No. 5,440,021 (Example 2, col 49-52); WO9428931 (pages 56-58); WO9217497 (Claim 7, FIG. 5); Dobner et al (1992) Eur. J. Immunol. 22:2795-2799; Barella et al (1995) Biochem. J. 309:773-779;

(30) HLA-DOB (Beta subunit of MHC class II molecule (Ia antigen) that binds peptides and presents them to CD4+ T lymphocytes); 273 aa, pI: 6.56 MW: 30820 TM: 1 [P] Gene Chromosome: 6p21.3, Genbank accession No. NP_002111.1) Tonnelle et al (1985) EMBO J. 4(11): 2839-2847; Jonsson et al (1989) Immunogenetics 29(6): 411-413; Beck et al (1992) J. Mol. Biol. 228:433-441; Strausberg et al (2002) Proc. Natl. Acad. Sci USA 99:16899-16903; Servenius et al (1987) J. Biol. Chem. 262:8759-8766; Beck et al (1996) J. Mol. Biol. 255:1-13; Naruse et al (2002) Tissue Antigens 59:512-519; WO9958658 (Claim 13, FIG. 15); U.S. Pat. No. 6,153,408 (Col 35-38); U.S. Pat. No. 5,976,551 (col 168-170); U.S. Pat. No. 6,011,146 (col 145-146); Kasahara et al (1989) Immunogenetics 30(1):66-68; Larhammar et al (1985) J. Biol. Chem. 260(26):14111-14119;

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability); 422 aa, pI: 7.63, MW: 47206 TM: 1 [P] Gene Chromosome: 17p13.3, Genbank accession No. NP_002552.2) Le et al (1997) FEBS Lett. 418(1-2):195-199; WO2004047749; WO2003072035 (Claim 10); Touchman et al (2000) Genome Res. 10:165-173; WO200222660 (Claim 20); WO2003093444 (Claim 1); WO2003087768 (Claim 1); WO2003029277 (page 82);

(32) CD72 (B-cell differentiation antigen CD72, Lyb-2) PROTEIN SEQUENCE Full maeaity... tafrfpd (1... 359; 359 aa), pI: 8.66, MW: 40225 TM: 1 [P] Gene Chromosome: 9 p13.3, Genbank accession No. NP_001773.1) WO2004042346 (Claim 65); WO2003026493 (pages 51-52, 57-58); WO200075655 (pages 105-106); Von Hoegen et al (1990) J. Immunol. 144(12):4870-4877; Strausberg et al (2002) Proc. Natl. Acad. Sci USA 99:16899-16903;

(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis); 661 aa, pI: 6.20, MW: 74147 TM: 1 [P] Gene Chromosome: 5q 12, Genbank accession No. NP_005573.1) US2002193567; WO9707198 (Claim 11, pages 39-42); Miura et al (1996) Genomics 38(3):299-304; Miura et al (1998) Blood 92:2815-2822; WO2003083047; WO9744452 (Claim 8, pages 57-61); WO200012130 (pages 24-26);

(34) FcRH1 (Fc receptor-like protein 1, a putative receptor for the immunoglobulin Fc domain that contains C2 type Ig-like and ITAM domains, may have a role in B-lymphocyte differentiation); 429 aa, pI: 5.28, MW: 46925 TM: 1 [P] Gene Chromosome: 1q21-1q22, Genbank accession No. NP_443170.1) WO2003077836; WO200138490 (Claim 6, FIG. 18E-1-18-E-2); Davis et al (2001) Proc. Natl. Acad. Sci USA 98(17):9772-9777; WO2003089624 (Claim 8); EP1347046 (Claim 1); WO2003089624 (Claim 7);

(35) IRTA2 (Immunoglobulin superfamily receptor translocation associated 2, a putative immunoreceptor with possible roles in B cell development and lymphomagenesis; deregulation of the gene by translocation occurs in some B cell malignancies); 977 aa, pI: 6.88 MW: 106468 TM: 1 [P] Gene Chromosome: 1q21, Genbank accession No. Human:AF343662, AF343663, AF343664, AF343665, AF369794, AF397453, AK090423, AK090475, AL834187, AY358085; Mouse:AK089756, AY158090, AY506558; NP_112571.1 WO2003024392 (Claim 2, FIG. 97); Nakayama et al (2000) Biochem. Biophys. Res. Commun. 277(1):124-127; WO2003077836; WO200138490 (Claim 3, FIG. 18B-1-18B-2);

(36) TENB2 (TMEFF2, tomoregulin, TPEF, HPP1, TR, putative transmembrane proteoglycan, related to the EGF/heregulin family of growth factors and follistatin); 374 aa, NCBI Accession: AAD55776, AAF91397, AAG49451, NCBI RefSeq: NP_057276; NCBI Gene: 23671; OMIM: 605734; SwissProt Q9UIK5; Genbank accession No. AF179274; AY358907, CAF85723, CQ782436 WO2004074320 (SEQ ID NO 810); JP2004113151 (SEQ ID NOS 2, 4, 8); WO2003042661 (SEQ ID NO 580); WO2003009814 (SEQ ID NO 411); EP1295944 (pages 69-70); WO200230268 (page 329); WO200190304 (SEQ ID NO 2706); US2004249130; US2004022727; WO2004063355; US2004197325; US2003232350; US2004005563; US2003124579; Horie et al (2000) Genomics 67:146-152; Uchida et al (1999) Biochem. Biophys. Res. Commun. 266:593-602; Liang et al (2000) Cancer Res. 60:4907-12; Glynne-Jones et al (2001) Int J Cancer. October 15; 94(2):178-84.

The parent antibody may also be a fusion protein comprising an albumin-binding peptide (ABP) sequence (Dennis et al. (2002) "Albumin Binding As A General Strategy For Improving The Pharmacokinetics Of Proteins" J Biol. Chem. 277:35035-35043; WO 01/45746). Antibodies of the invention include fusion proteins with ABP sequences taught by: (i) Dennis et al (2002) J Biol. Chem. 277:35035-35043 at Tables III and IV, page 35038; (ii) US 20040001827 at [0076] SEQ ID NOS: 9-22; and (iii) WO 01/45746 at pages 12-13, SEQ ID NOS: z1-z14, and all of which are incorporated herein by reference.

Mutagenesis

DNA encoding an amino acid sequence variant of the starting polypeptide is prepared by a variety of methods known in the art. These methods include, but are not limited to, preparation by site-directed (or oligonucleotide-mediated) mutagenesis, PCR mutagenesis, and cassette mutagenesis of an earlier prepared DNA encoding the polypeptide. Variants of recombinant antibodies may be constructed also by restriction fragment manipulation or by overlap extension PCR with synthetic oligonucleotides. Mutagenic primers encode the cysteine codon replacement(s). Standard mutagenesis techniques can be employed to generate DNA encoding such mutant cysteine engineered antibodies. General guidance can be found in Sambrook et al Molecular Cloning, A Laboratory Manual, Cold Spring Harbor Laboratory Press, Cold Spring Harbor, N.Y., 1989; and Ausubel et al Current Protocols in Molecular Biology, Greene Publishing and Wiley-Interscience, New York, N.Y., 1993.

Site-directed mutagenesis is one method for preparing substitution variants, i.e. mutant proteins. This technique is well known in the art (see for example, Carter (1985) et al Nucleic Acids Res. 13:4431-4443; Ho et al (1989) Gene (Amst.) 77:51-59; and Kunkel et al (1987) Proc. Natl. Acad. Sci. USA 82:488). Briefly, in carrying out site-directed mutagenesis of DNA, the starting DNA is altered by first hybridizing an oligonucleotide encoding the desired mutation to a single strand of such starting DNA. After hybridization, a DNA polymerase is used to synthesize an entire second strand, using the hybridized oligonucleotide as a primer, and using the single strand of the starting DNA as a template. Thus, the oligonucleotide encoding the desired mutation is incorporated in the resulting double-stranded DNA. Site-directed mutagenesis may be carried out within the gene expressing the protein to be mutagenized in an expression plasmid and the resulting plasmid may be sequenced to confirm the introduction of the desired cysteine replacement mutations (Liu et al (1998) J. Biol. Chem. 273:20252-20260). Site-directed of protocols and formats, including those commercially available, e.g. QuikChange® Multi Site-Directed Mutagenesis Kit (Stratagene, La Jolla, Calif.).

PCR mutagenesis is also suitable for making amino acid sequence variants of the starting polypeptide. See Higuchi, (1990) in PCR Protocols, pp. 177-183, Academic Press; Ito et al (1991) Gene 102:67-70; Bernhard et al (1994) Bioconjugate Chem. 5:126-132; and Vallette et al (1989) Nuc. Acids Res. 17:723-733. Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template.

Another method for preparing variants, cassette mutagenesis, is based on the technique described by Wells et al (1985) Gene 34:315-323. The starting material is the plasmid (or other vector) comprising the starting polypeptide DNA to be mutated. The codon(s) in the starting DNA to be mutated are identified. There must be a unique restriction endonuclease site on each side of the identified mutation site(s). If no such restriction sites exist, they may be generated using the above described oligonucleotide-mediated mutagenesis method to introduce them at appropriate locations in the starting polypeptide DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. This plasmid now contains the mutated DNA sequence. Mutant DNA containing the encoded cysteine replacements can be confirmed by DNA sequencing.

Single mutations are also generated by oligonucleotide directed mutagenesis using double stranded plasmid DNA as template by PCR based mutagenesis (Sambrook and Russel, (2001) Molecular Cloning: A Laboratory Manual, 3rd edition; Zoller et al (1983) Methods Enzymol. 100:468-500; Zoller, M. J. and Smith, M. (1982) Nucl. Acids Res. 10:6487-6500).

In the present invention, hu4D5Fabv8 displayed on M13 phage (Gerstner et al (2002) "Sequence Plasticity In The Antigen-Binding Site Of A Therapeutic Anti-HER2 Antibody", J Mol. Biol. 321:851-62) was used for experiments as a model system. Cysteine mutations were introduced in hu4D5Fabv8-phage, hu4D5Fabv8, and ABP-hu4D5Fabv8 constructs. The hu4D5-ThioFab-Phage preps were carried out using the polyethylene glycol (PEG) precipitation method as described earlier (Lowman, Henry B. (1998) Methods in Molecular Biology (Totowa, N.J.) 87 (Combinatorial Peptide Library Protocols) 249-264).

Oligonucleotides are prepared by the phosphoramidite synthesis method (U.S. Pat. Nos. 4,415,732; 4,458,066; Beaucage, S. and Iyer, R. (1992) "Advances in the synthesis of oligonucleotides by the phosphoramidite approach", Tetrahedron 48:2223-2311). The phosphoramidite method entails cyclical addition of nucleotide monomer units with a reactive 3' phosphoramidite moiety to an oligonucleotide chain growing on a solid-support comprised of controlled-pore glass or highly crosslinked polystyrene, and most commonly in the 3' to 5' direction in which the 3' terminus nucleoside is attached to the solid-support at the beginning of synthesis (U.S. Pat. Nos. 5,047,524; 5,262,530). The method is usually practiced using automated, commercially available synthesizers (Applied Biosystems, Foster City, Calif.). Oligonucleotides can be chemically labelled with non-isotopic moieties for detection, capture, stabilization, or other purposes (Andrus, A. "Chemical methods for 5' non-isotopic labelling of PCR probes and primers" (1995) in PCR 2: A Practical Approach, Oxford University Press, Oxford, pp. 39-54; Hermanson, G. in Bioconjugate Techniques (1996) Academic Press, San Diego, pp. 40-55, 643-671; Keller, G. and Manak, M. in DNA Probes Second Edition (1993), Stockton Press, New York, pp. 121-23).

Pheselector Assay

The PHESELECTOR (Phage ELISA for Selection of Reactive Thiols) assay allows for detection of reactive cysteine groups in antibodies in an ELISA phage format. The process of coating the protein (e.g. antibody) of interest on well surfaces, followed incubation with phage particles and then HRP labeled secondary antibody with absorbance detection is detailed in Example 2. Mutant proteins displayed on phage may be screened in a rapid, robust, and high-throughput manner. Libraries of cysteine engineered antibodies can be produced and subjected to binding selection using the same approach to identify appropriately reactive sites of free Cys incorporation from random protein-phage libraries of antibodies or other proteins. This technique includes reacting cysteine mutant proteins displayed on phage with an affinity reagent or reporter group which is also thiol-reactive. FIG. 8 illustrates the PHESELECTOR Assay by a schematic representation depicting the binding of Fab or ThioFab to HER2 (top) and biotinylated ThioFab to streptavidin (bottom).

Protein Expression and Purification

DNA encoding the cysteine engineered antibodies is readily isolated and sequenced using conventional procedures (e.g., by using oligonucleotide probes that are capable of binding specifically to genes encoding the heavy and light chains of murine antibodies). The hybridoma cells serve as a source of such DNA. Once isolated, the DNA may be placed into expression vectors, which are then transfected into host cells such as E. coli cells, simian COS cells, Chinese Hamster Ovary (CHO) cells, or other mammalian host cells, such as myeloma cells (U.S. Pat. No. 5,807,715; US 2005/0048572; US 2004/0229310) that do not otherwise produce the antibody protein, to obtain the synthesis of monoclonal antibodies in the recombinant host cells. The yields of hu4D5Fabv8 cysteine engineered antibodies were similar to wild type hu4D5Fabv8. Review articles on recombinant expression in bacteria of DNA encoding the antibody include Skerra et al (1993) Curr. Opinion in Immunol. 5:256-262 and Pluckthun (1992) Immunol. Revs. 130:151-188.

After design and selection, cysteine engineered antibodies, e.g. ThioFabs, with highly reactive unpaired Cys residues, may be produced by: (i) expression in a bacterial, e.g. E. coli, system or a mammalian cell culture system (WO 01/00245), e.g. Chinese Hamster Ovary cells (CHO); and (ii) purification using common protein purification techniques (Lowman et al (1991) J. Biol. Chem. 266(17):10982-10988).

ThioFabs were expressed upon induction in 34B8, a non-suppressor E. coli strain (Baca et al (1997) Journal Biological Chemistry 272(16):10678-84). See Example 3a. The harvested cell pellet was resuspended in PBS (phosphate buffered saline), total cell lysis was performed by passing through a microfluidizer and the ThioFabs were purified by affinity chromatography with protein G SEPHAROSE™ (Amersham). ThioFabs were conjugated with biotin-PEO-maleimide as described above and the biotinylated-ThioFabs were further purified by Superdex-200™ (Amersham) gel filtration chromatography, which eliminated the free biotin-PEO-maleimide and the oligomeric fraction of ThioFabs.

Mass Spectroscopy Analysis

Liquid chromatography electrospray ionization mass spectrometric (LC-ESI-MS) analysis was employed for the accurate molecular weight determination of biotin conjugated Fab (Cole, R. B. Electro Spray Ionization Mass Spectrometry: Fundamentals, Instrumentation And Applications. (1997) Wiley, N.Y.). The amino acid sequence of biotinylated hu4D5Fabv8 (A121C) peptide was determined by tryptic digestion followed by LC-ESI-Tandem MS analysis (Table 4, Example 3b).

The antibody Fab fragment hu4D5Fabv8 contains about 445 amino acid residues, including 10 Cys residues (five on the light and five on the heavy chain). The high-resolution structure of the humanized 4D5 variable fragment (Fv4D5) has been established, see: Eigenbrot et al "X-Ray Structures Of The Antigen-Binding Domains From Three Variants Of Humanized Anti-P185her2 Antibody 4D5 And Comparison With Molecular Modeling" (1993) J Mol. Biol. 229:969-995). All the Cys residues are present in the form of disulfide bonds, therefore these residues do not have any reactive thiol groups to conjugate with drug-maleimide (unless treated with a reducing agent). Hence, the newly engineered Cys residue, can remain unpaired, and able to react with, i.e. conjugate to, an electrophilic linker reagent or drug-linker intermediate, such as a drug-maleimide. FIG. 1A shows a three-dimensional representation of the hu4D5Fabv8 antibody fragment derived by X-ray crystal coordinates. The structure positions of the engineered Cys residues of the heavy and light chains are numbered according to a sequential numbering system. This sequential numbering system is correlated to the Kabat numbering system (Kabat et al., (1991) Sequences of Proteins of Immunological Interest, 5th Ed. Public Health Service, National Institutes of Health, Bethesda, Md.) for the 4d5v7fabH variant of trastuzumab according to FIG. 1B which shows the sequential numbering scheme (top row), starting at the N-terminus, differs from the Kabat numbering scheme (bottom row) by insertions noted by a, b, c. Using the Kabat numbering system, the actual linear amino acid sequence may contain fewer or additional amino acids corresponding to a shortening of, or insertion into, a FR or CDR of the variable domain. The cysteine engineered heavy chain variant sites are identified by the sequential numbering and Kabat numbering schemes in the following chart:

| 4D5Fab Heavy chain variants | Sequential Numbering | Kabat Numbering |
|---|---|---|
| A40C | Ala-40 | Ala-40 |
| A88C | Ala-88 | Ala-84 |
| S119C | Ser-119 | Ser-112 |
| S120C | Ser-120 | Ser-113 |
| A121C | Ala-121 | Ala-114 |
| S122C | Ser-122 | Ser-115 |
| A175C | Ala-175 | Ala-168 |

M13 phagemid-Cys mutant Fabs (FIGS. 3A and 3B) can be rapidly screened compared to Fab proteins. Phagemid-Thio-Fab binding to antigen and to streptavidin can be tested by coating HER2 and streptavidin, respectively, onto ELISA plates followed by probing with anti-Fab-HRP (Horse radish peroxidase) as described in Example 2 and depicted in FIG. 8. This method allowed simultaneous monitoring of the effect on the antigen binding and the reactivity of the thiol group by the engineered Cys residue/conjugated biotin molecule. Also, the method can be applied to screen the reactive thiol groups for any protein displayed on M13 phage. Conjugated or unconjugated phagemid-ThioFabs are purified by simple PEG precipitation.

The antigen-binding fragment of humanized 4D5 (hu4D5Fab) is well expressed in E. Coli and has been displayed on bacteriophage (Garrard et al (1993) Gene 128:103-109). The antibody Fab fragment hu4D5Fabv8 was displayed on M13 phage as a model system in the ELISA based assay to probe thiol reactivity. FIG. 8 is a graphical representation of the PHESELECTOR assay, depicting binding of a biotinylated ThioFab phage and an anti-phage HRP antibody to HER2 (top) and Streptavidin (bottom). Five amino acid residues (L-Ala43, H-Ala40, H-Ser119, H-Ala121 and H-Ser122) were initially selected from crystal structure information as remote from the antigen binding surface (Eigenbrot et al. (1993) J Mol. Biol. 229:969-995). The Protein Database X-ray crystal structure was designated as 1FVC. Cys residues were engineered at these positions by site directed mutagenesis. ThioFab-phage preparations were isolated and reacted with the biotinylation reagent.

Figure 2B:
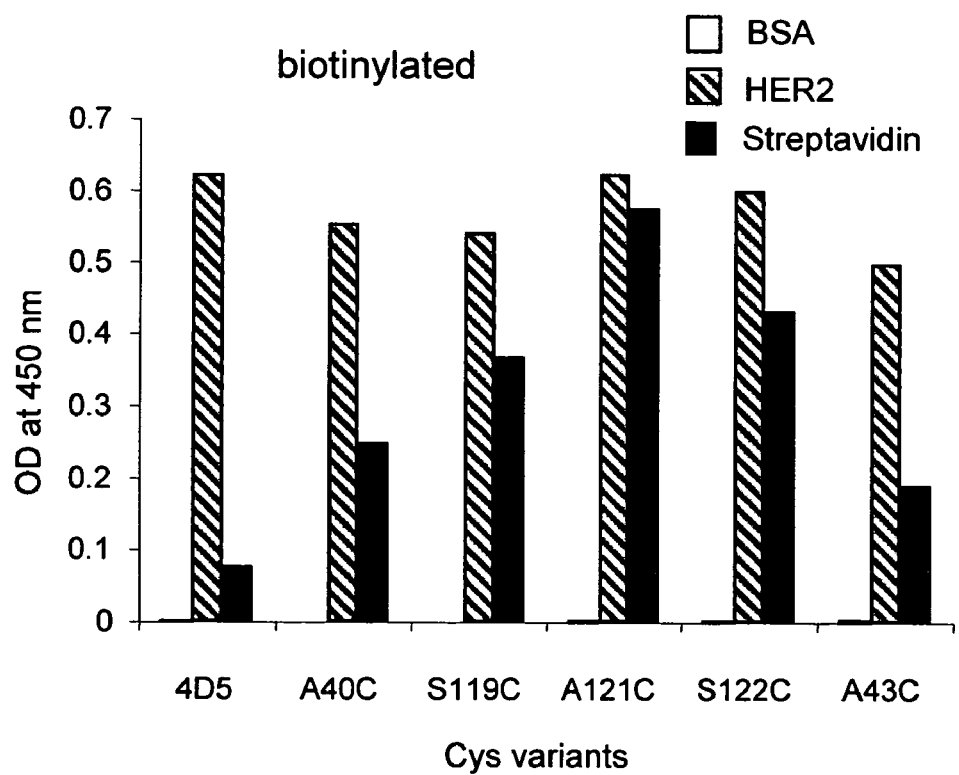

Biotin conjugated and unconjugated variants were tested for HER2 and streptavidin binding using an ELISA based PHESELECTOR assay (FIG. 8, Example 2) with an HRP (horseradish peroxidase)-conjugated anti-phage antibody. The interaction of non-biotinylated phage-hu4D5Fabv8 (FIG. 2A) and biotinylated phage-hu4D5Fabv8 (FIG. 2B) with BSA (open box), HER2 (grey box) or streptavidin (solid box) were monitored through anti-M13-horseradish peroxidase (HRP) antibody by developing a standard HRP reaction and measuring absorbance at 450 nm. The absorbance produced by turnover of a colorimetric substrate was measured at 450 nm. The reactivity of ThioFab with HER2 measures antigen binding. The reactivity of ThioFab with streptavidin measures the extent of biotinylation. The reactivity of ThioFab with BSA is a negative control for nonspecific interaction. As seen in FIG. 2A, all the ThioFab-phage variants have similar binding to HER2 compared to that of wild type hu4D5Fabv8-phage. Furthermore, conjugation with biotin did not interfere in the ThioFab binding to HER2 (FIG. 2B).

Surprisingly and unexpectedly, the ThioFabs-phage samples showed varying levels of streptavidin binding activity. From all the tested phage-ThioFabs, the A121C cysteine engineered antibody exhibited maximal thiol reactivity. Even though wild type hu4D5Fabv8-phage was incubated with the same amounts of biotin-maleimide, these phage had little streptavidin binding indicating that preexisting cysteine residues (involved in disulfide bond formation) from the hu4D5Fabv8 and M13 phage coat proteins did not interfere with the site-specific conjugation of biotin-maleimide. These results demonstrate that the phage ELISA assay can be used successfully to screen reactive thiol groups on the Fab surface.

The PHESELECTOR assay allows screening of reactive thiol groups in antibodies. Identification of the A121C variant by this method is exemplary. The entire Fab molecule may be effectively searched to identify more ThioFab variants with reactive thiol groups. A parameter, fractional surface accessibility, was employed to identify and quantitate the accessibility of solvent to the amino acid residues in a polypeptide. The surface accessibility can be expressed as the surface area ($Å^2$) that can be contacted by a solvent molecule, e.g. water. The occupied space of water is approximated as a 1.4 Å radius sphere. Software is freely available or licensable (Secretary to CCP4, Daresbury Laboratory, Warrington, WA4 4AD, United Kingdom, Fax: (+44) 1925 603825, or by internet: www.ccp4.ac.uk/dist/html/INDEX.html) as the CCP4 Suite of crystallography programs which employ algorithms to calculate the surface accessibility of each amino acid of a protein with known x-ray crystallography derived coordinates ("The CCP4 Suite: Programs for Protein Crystallography" (1994) Acta. Cryst. D50:760-763). Two exemplary software modules that perform surface accessibility calculations are "AREAIMOL" and "SURFACE", based on the algorithms of B. Lee and F. M. Richards (1971) J. Mol. Biol. 55:379-400. AREAIMOL defines the solvent accessible surface of a protein as the locus of the centre of a probe sphere (representing a solvent molecule) as it rolls over the Van der Waals surface of the protein. AREAIMOL calculates the solvent accessible surface area by generating surface points on an extended sphere about each atom (at a distance from the atom centre equal to the sum of the atom and probe radii), and eliminating those that lie within equivalent spheres associated with neighboring atoms. AREAIMOL finds the solvent accessible area of atoms in a PDB coordinate file, and summarizes the accessible area by residue, by chain and for the whole molecule. Accessible areas (or area differences) for individual atoms can be written to a pseudo-PDB output file.

AREAIMOL assumes a single radius for each element, and only recognizes a limited number of different elements. Unknown atom types (i.e. those not in AREAIMOL's internal database) will be assigned the default radius of 1.8 Å. The list of recognized atoms is:

| Atom | Atomic no. | Van der Waals rad. (Å) |
|------|------------|------------------------|
| C    | 6          | 1.80                   |
| N    | 7          | 1.65                   |
| O    | 8          | 1.60                   |
| Mg   | 12         | 1.60                   |
| S    | 16         | 1.85                   |
| P    | 15         | 1.90                   |
| Cl   | 17         | 1.80                   |
| Co   | 27         | 1.80                   |

AREAIMOL and SURFACE report absolute accessibilities, i.e. the number of square Angstroms (Å). Fractional surface accessibility is calculated by reference to a standard state relevant for an amino acid within a polypeptide. The reference state is tripeptide Gly-X-Gly, where X is the amino acid of interest, and the reference state should be an 'extended' conformation, i.e. like those in beta-strands. The extended conformation maximizes the accessibility of X. A calculated accessible area is divided by the accessible area in a Gly-X-Gly tripeptide reference state and reports the quotient, which is the fractional accessibility. Percent accessibility is fractional accessibility multiplied by 100.

Another exemplary algorithm for calculating surface accessibility is based on the SOLV module of the program xsae (Broger, C., F. Hoffman-LaRoche, Basel) which calculates fractional accessibility of an amino acid residue to a water sphere based on the X-ray coordinates of the polypeptide.

The fractional surface accessibility for every amino acid in hu4D5Fabv7 was calculated using the crystal structure information (Eigenbrot et al. (1993) J Mol. Biol. 229:969-995). The fractional surface accessibility values for the amino acids of the light chain and heavy chain of hu4D5Fabv7 are shown in descending order in Table 1.

TABLE 1

| hu4D5Fabv7-light chain | | | | |
|---|---|---|---|---|
| SER | A | 202 | frac acc = | 101.236 |
| GLY | A | 41  | frac acc = | 90.775  |
| GLY | A | 157 | frac acc = | 88.186  |
| ASP | A | 1   | frac acc = | 87.743  |
| SER | A | 156 | frac acc = | 83.742  |
| GLY | A | 57  | frac acc = | 81.611  |
| SER | A | 168 | frac acc = | 79.680  |
| SER | A | 56  | frac acc = | 79.181  |
| LYS | A | 169 | frac acc = | 77.591  |
| SER | A | 60  | frac acc = | 75.291  |
| THR | A | 109 | frac acc = | 74.603  |
| CYS | A | 214 | frac acc = | 72.021  |
| LYS | A | 126 | frac acc = | 71.002  |
| SER | A | 67  | frac acc = | 66.694  |
| ARG | A | 18  | frac acc = | 66.126  |
| ASN | A | 152 | frac acc = | 65.415  |
| SER | A | 127 | frac acc = | 65.345  |
| LYS | A | 190 | frac acc = | 65.189  |
| LYS | A | 145 | frac acc = | 63.342  |
| GLN | A | 199 | frac acc = | 62.470  |
| GLU | A | 143 | frac acc = | 61.681  |
| GLN | A | 3   | frac acc = | 59.976  |
| LYS | A | 188 | frac acc = | 59.680  |
| ARG | A | 24  | frac acc = | 59.458  |

TABLE 1-continued

| | | | | |
|---|---|---|---|---|
| PHE | A | 53 | frac acc = | 58.705 |
| SER | A | 9 | frac acc = | 58.446 |
| GLN | A | 27 | frac acc = | 57.247 |
| ALA | A | 153 | frac acc = | 56.538 |
| SER | A | 203 | frac acc = | 55.864 |
| LYS | A | 42 | frac acc = | 54.730 |
| GLY | A | 16 | frac acc = | 54.612 |
| LYS | A | 45 | frac acc = | 54.464 |
| PRO | A | 204 | frac acc = | 53.172 |
| GLU | A | 213 | frac acc = | 53.084 |
| ALA | A | 184 | frac acc = | 52.556 |
| VAL | A | 15 | frac acc = | 52.460 |
| SER | A | 7 | frac acc = | 51.936 |
| LEU | A | 154 | frac acc = | 51.525 |
| GLN | A | 100 | frac acc = | 51.195 |
| SER | A | 10 | frac acc = | 49.907 |
| THR | A | 5 | frac acc = | 48.879 |
| THR | A | 206 | frac acc = | 48.853 |
| ASP | A | 28 | frac acc = | 48.758 |
| GLY | A | 68 | frac acc = | 48.690 |
| THR | A | 20 | frac acc = | 48.675 |
| ASP | A | 122 | frac acc = | 47.359 |
| PRO | A | 80 | frac acc = | 46.984 |
| SER | A | 52 | frac acc = | 46.917 |
| SER | A | 26 | frac acc = | 46.712 |
| TYR | A | 92 | frac acc = | 46.218 |
| LYS | A | 107 | frac acc = | 45.912 |
| GLU | A | 161 | frac acc = | 45.100 |
| VAL | A | 110 | frac acc = | 44.844 |
| GLU | A | 81 | frac acc = | 44.578 |
| PRO | A | 59 | frac acc = | 44.290 |
| ASN | A | 30 | frac acc = | 42.721 |
| GLN | A | 160 | frac acc = | 42.692 |
| SER | A | 114 | frac acc = | 42.374 |
| PRO | A | 40 | frac acc = | 41.928 |
| ASP | A | 151 | frac acc = | 41.586 |
| SER | A | 12 | frac acc = | 40.633 |
| ASN | A | 210 | frac acc = | 40.158 |
| SER | A | 63 | frac acc = | 39.872 |
| ARG | A | 66 | frac acc = | 39.669 |
| PRO | A | 8 | frac acc = | 39.297 |
| SER | A | 65 | frac acc = | 39.219 |
| SER | A | 77 | frac acc = | 38.820 |
| THR | A | 180 | frac acc = | 38.296 |
| ASP | A | 185 | frac acc = | 38.234 |
| THR | A | 31 | frac acc = | 38.106 |
| THR | A | 94 | frac acc = | 37.452 |
| THR | A | 93 | frac acc = | 37.213 |
| THR | A | 197 | frac acc = | 36.709 |
| SER | A | 182 | frac acc = | 36.424 |
| GLY | A | 128 | frac acc = | 35.779 |
| LYS | A | 207 | frac acc = | 35.638 |
| ASP | A | 17 | frac acc = | 35.413 |
| GLY | A | 200 | frac acc = | 35.274 |
| GLU | A | 165 | frac acc = | 35.067 |
| ALA | A | 112 | frac acc = | 34.912 |
| GLN | A | 79 | frac acc = | 34.601 |
| VAL | A | 191 | frac acc = | 33.935 |
| SER | A | 208 | frac acc = | 33.525 |
| LYS | A | 39 | frac acc = | 33.446 |
| GLU | A | 123 | frac acc = | 32.486 |
| THR | A | 69 | frac acc = | 32.276 |
| SER | A | 76 | frac acc = | 32.108 |
| HIS | A | 189 | frac acc = | 31.984 |
| ARG | A | 108 | frac acc = | 31.915 |
| ASN | A | 158 | frac acc = | 31.447 |
| VAL | A | 205 | frac acc = | 31.305 |
| SER | A | 14 | frac acc = | 31.094 |
| GLN | A | 155 | frac acc = | 30.630 |
| GLU | A | 187 | frac acc = | 30.328 |
| ARG | A | 211 | frac acc = | 30.027 |
| LYS | A | 183 | frac acc = | 29.751 |
| ASN | A | 138 | frac acc = | 29.306 |
| ASP | A | 170 | frac acc = | 29.041 |
| SER | A | 159 | frac acc = | 27.705 |
| GLN | A | 147 | frac acc = | 27.485 |
| THR | A | 22 | frac acc = | 27.121 |
| ALA | A | 43 | frac acc = | 26.801 |
| ARG | A | 142 | frac acc = | 26.447 |

TABLE 1-continued

| | | | | |
|---|---|---|---|---|
| LEU | A | 54 | frac acc = | 25.882 |
| ASP | A | 167 | frac acc = | 25.785 |
| THR | A | 129 | frac acc = | 23.880 |
| ALA | A | 144 | frac acc = | 23.652 |
| VAL | A | 163 | frac acc = | 22.261 |
| PRO | A | 95 | frac acc = | 20.607 |
| ALA | A | 111 | frac acc = | 19.942 |
| LYS | A | 103 | frac acc = | 18.647 |
| LEU | A | 181 | frac acc = | 18.312 |
| THR | A | 72 | frac acc = | 18.226 |
| GLU | A | 195 | frac acc = | 18.006 |
| THR | A | 178 | frac acc = | 17.499 |
| THR | A | 85 | frac acc = | 17.343 |
| ASP | A | 70 | frac acc = | 17.194 |
| LEU | A | 11 | frac acc = | 16.568 |
| PHE | A | 116 | frac acc = | 16.406 |
| THR | A | 97 | frac acc = | 16.204 |
| ARG | A | 61 | frac acc = | 16.192 |
| TYR | A | 49 | frac acc = | 16.076 |
| SER | A | 50 | frac acc = | 15.746 |
| LYS | A | 149 | frac acc = | 15.510 |
| GLU | A | 55 | frac acc = | 14.927 |
| LEU | A | 201 | frac acc = | 14.012 |
| GLY | A | 64 | frac acc = | 13.735 |
| GLY | A | 212 | frac acc = | 13.396 |
| PHE | A | 98 | frac acc = | 12.852 |
| THR | A | 74 | frac acc = | 12.169 |
| SER | A | 171 | frac acc = | 11.536 |
| PRO | A | 141 | frac acc = | 11.073 |
| PHE | A | 83 | frac acc = | 10.871 |
| THR | A | 164 | frac acc = | 10.325 |
| ALA | A | 32 | frac acc = | 9.971 |
| HIS | A | 198 | frac acc = | 9.958 |
| VAL | A | 146 | frac acc = | 9.861 |
| SER | A | 121 | frac acc = | 9.833 |
| ALA | A | 13 | frac acc = | 9.615 |
| GLU | A | 105 | frac acc = | 9.416 |
| SER | A | 162 | frac acc = | 9.304 |
| ILE | A | 117 | frac acc = | 8.780 |
| HIS | A | 91 | frac acc = | 8.557 |
| ALA | A | 193 | frac acc = | 8.547 |
| GLN | A | 37 | frac acc = | 8.442 |
| VAL | A | 58 | frac acc = | 8.281 |
| PRO | A | 120 | frac acc = | 8.095 |
| GLN | A | 38 | frac acc = | 6.643 |
| PRO | A | 113 | frac acc = | 6.594 |
| GLY | A | 101 | frac acc = | 6.558 |
| TYR | A | 140 | frac acc = | 5.894 |
| VAL | A | 115 | frac acc = | 5.712 |
| TYR | A | 87 | frac acc = | 4.539 |
| SER | A | 176 | frac acc = | 4.106 |
| ILE | A | 2 | frac acc = | 4.080 |
| ASN | A | 137 | frac acc = | 3.906 |
| TRP | A | 148 | frac acc = | 3.676 |
| GLY | A | 99 | frac acc = | 3.550 |
| PRO | A | 44 | frac acc = | 3.543 |
| LEU | A | 175 | frac acc = | 3.488 |
| VAL | A | 19 | frac acc = | 3.420 |
| ILE | A | 106 | frac acc = | 3.337 |
| PRO | A | 119 | frac acc = | 2.953 |
| LEU | A | 46 | frac acc = | 2.887 |
| GLN | A | 6 | frac acc = | 2.860 |
| TYR | A | 173 | frac acc = | 2.825 |
| VAL | A | 150 | frac acc = | 2.525 |
| GLN | A | 166 | frac acc = | 2.525 |
| THR | A | 172 | frac acc = | 2.436 |
| LEU | A | 125 | frac acc = | 2.398 |
| PRO | A | 96 | frac acc = | 2.387 |
| LEU | A | 47 | frac acc = | 2.180 |
| ALA | A | 51 | frac acc = | 1.837 |
| PHE | A | 118 | frac acc = | 1.779 |
| PHE | A | 62 | frac acc = | 1.581 |
| ALA | A | 25 | frac acc = | 1.538 |
| VAL | A | 133 | frac acc = | 1.315 |
| ASP | A | 82 | frac acc = | 1.141 |
| LEU | A | 179 | frac acc = | 0.872 |
| GLN | A | 124 | frac acc = | 0.787 |
| MET | A | 4 | frac acc = | 0.778 |
| SER | A | 177 | frac acc = | 0.693 |

TABLE 1-continued

| | | | | |
|---|---|---|---|---|
| SER | A | 131 | frac acc = | 0.693 |
| LEU | A | 135 | frac acc = | 0.654 |
| PHE | A | 71 | frac acc = | 0.593 |
| TRP | A | 35 | frac acc = | 0.448 |
| PHE | A | 209 | frac acc = | 0.395 |
| TYR | A | 186 | frac acc = | 0.259 |
| LEU | A | 78 | frac acc = | 0.157 |
| VAL | A | 196 | frac acc = | 0.000 |
| VAL | A | 132 | frac acc = | 0.000 |
| VAL | A | 104 | frac acc = | 0.000 |
| VAL | A | 33 | frac acc = | 0.000 |
| VAL | A | 29 | frac acc = | 0.000 |
| TYR | A | 192 | frac acc = | 0.000 |
| TYR | A | 86 | frac acc = | 0.000 |
| TYR | A | 36 | frac acc = | 0.000 |
| THR | A | 102 | frac acc = | 0.000 |
| SER | A | 174 | frac acc = | 0.000 |
| PHE | A | 139 | frac acc = | 0.000 |
| LEU | A | 136 | frac acc = | 0.000 |
| LEU | A | 73 | frac acc = | 0.000 |
| ILE | A | 75 | frac acc = | 0.000 |
| ILE | A | 48 | frac acc = | 0.000 |
| ILE | A | 21 | frac acc = | 0.000 |
| GLN | A | 90 | frac acc = | 0.000 |
| GLN | A | 89 | frac acc = | 0.000 |
| CYS | A | 194 | frac acc = | 0.000 |
| CYS | A | 134 | frac acc = | 0.000 |
| CYS | A | 88 | frac acc = | 0.000 |
| CYS | A | 23 | frac acc = | 0.000 |
| ALA | A | 130 | frac acc = | 0.000 |
| ALA | A | 84 | frac acc = | 0.000 |
| ALA | A | 34 | frac acc = | 0.000 |
| hu4D5Fabv7-heavy chain | | | | |
| SER | B | 179 | frac acc = | 99.479 |
| GLY | B | 42 | frac acc = | 95.850 |
| GLU | B | 1 | frac acc = | 87.276 |
| GLY | B | 66 | frac acc = | 84.541 |
| ASP | B | 102 | frac acc = | 83.794 |
| SER | B | 75 | frac acc = | 80.567 |
| GLY | B | 140 | frac acc = | 80.344 |
| ASN | B | 211 | frac acc = | 79.588 |
| GLY | B | 197 | frac acc = | 78.676 |
| ASP | B | 62 | frac acc = | 77.716 |
| GLY | B | 103 | frac acc = | 77.176 |
| SER | B | 163 | frac acc = | 76.664 |
| SER | B | 139 | frac acc = | 74.946 |
| LYS | B | 213 | frac acc = | 74.442 |
| ALA | B | 165 | frac acc = | 74.339 |
| THR | B | 167 | frac acc = | 73.934 |
| SER | B | 122 | frac acc = | 72.870 |
| SER | B | 194 | frac acc = | 71.959 |
| PRO | B | 41 | frac acc = | 71.540 |
| THR | B | 198 | frac acc = | 68.668 |
| SER | B | 222 | frac acc = | 68.128 |
| LYS | B | 43 | frac acc = | 67.782 |
| GLY | B | 26 | frac acc = | 67.782 |
| THR | B | 138 | frac acc = | 65.826 |
| ASP | B | 31 | frac acc = | 64.222 |
| GLY | B | 15 | frac acc = | 64.172 |
| SER | B | 168 | frac acc = | 62.100 |
| SER | B | 120 | frac acc = | 61.332 |
| LYS | B | 76 | frac acc = | 61.092 |
| GLY | B | 141 | frac acc = | 59.419 |
| SER | B | 137 | frac acc = | 59.179 |
| TYR | B | 57 | frac acc = | 58.916 |
| GLU | B | 89 | frac acc = | 58.483 |
| SER | B | 180 | frac acc = | 56.289 |
| LYS | B | 65 | frac acc = | 55.044 |
| ASP | B | 215 | frac acc = | 54.656 |
| GLN | B | 13 | frac acc = | 53.719 |
| GLN | B | 112 | frac acc = | 53.215 |
| TYR | B | 105 | frac acc = | 51.940 |
| ALA | B | 88 | frac acc = | 51.602 |
| GLY | B | 164 | frac acc = | 50.259 |
| PRO | B | 192 | frac acc = | 49.826 |
| THR | B | 158 | frac acc = | 49.694 |
| THR | B | 142 | frac acc = | 48.896 |
| ASN | B | 55 | frac acc = | 48.344 |
| LYS | B | 136 | frac acc = | 48.312 |
| ARG | B | 19 | frac acc = | 48.082 |
| PRO | B | 156 | frac acc = | 47.366 |
| PRO | B | 174 | frac acc = | 47.157 |
| LYS | B | 217 | frac acc = | 47.102 |
| GLN | B | 199 | frac acc = | 46.650 |
| SER | B | 17 | frac acc = | 45.980 |
| SER | B | 85 | frac acc = | 45.824 |
| PRO | B | 14 | frac acc = | 45.729 |
| THR | B | 54 | frac acc = | 45.503 |
| THR | B | 200 | frac acc = | 45.369 |
| LEU | B | 177 | frac acc = | 45.337 |
| GLY | B | 8 | frac acc = | 44.898 |
| SER | B | 7 | frac acc = | 43.530 |
| THR | B | 69 | frac acc = | 43.503 |
| PRO | B | 220 | frac acc = | 43.378 |
| LYS | B | 208 | frac acc = | 43.138 |
| LYS | B | 30 | frac acc = | 42.380 |
| ALA | B | 23 | frac acc = | 41.952 |
| GLU | B | 46 | frac acc = | 41.430 |
| SER | B | 25 | frac acc = | 41.323 |
| ARG | B | 87 | frac acc = | 41.282 |
| LYS | B | 124 | frac acc = | 40.888 |
| ASN | B | 28 | frac acc = | 40.529 |
| GLN | B | 3 | frac acc = | 39.824 |
| THR | B | 123 | frac acc = | 39.306 |
| SER | B | 63 | frac acc = | 38.867 |
| GLY | B | 56 | frac acc = | 38.582 |
| GLY | B | 169 | frac acc = | 38.469 |
| THR | B | 172 | frac acc = | 38.421 |
| PRO | B | 209 | frac acc = | 38.309 |
| GLY | B | 101 | frac acc = | 38.040 |
| TYR | B | 109 | frac acc = | 36.829 |
| LYS | B | 221 | frac acc = | 36.520 |
| GLY | B | 44 | frac acc = | 35.147 |
| GLY | B | 181 | frac acc = | 34.735 |
| THR | B | 58 | frac acc = | 34.457 |
| GLY | B | 9 | frac acc = | 34.254 |
| VAL | B | 5 | frac acc = | 34.198 |
| ALA | B | 121 | frac acc = | 33.049 |
| SER | B | 127 | frac acc = | 32.390 |
| GLY | B | 10 | frac acc = | 32.230 |
| SER | B | 71 | frac acc = | 30.659 |
| ASP | B | 73 | frac acc = | 30.245 |
| LEU | B | 115 | frac acc = | 29.867 |
| LEU | B | 11 | frac acc = | 29.825 |
| ASN | B | 84 | frac acc = | 29.765 |
| SER | B | 210 | frac acc = | 28.656 |
| GLU | B | 155 | frac acc = | 28.162 |
| SER | B | 160 | frac acc = | 26.526 |
| CYS | B | 223 | frac acc = | 26.270 |
| GLY | B | 16 | frac acc = | 26.158 |
| ILE | B | 202 | frac acc = | 26.068 |
| GLN | B | 82 | frac acc = | 25.836 |
| SER | B | 193 | frac acc = | 25.550 |
| ASN | B | 77 | frac acc = | 25.418 |
| ARG | B | 59 | frac acc = | 25.301 |
| VAL | B | 93 | frac acc = | 25.254 |
| THR | B | 74 | frac acc = | 24.902 |
| GLU | B | 219 | frac acc = | 24.778 |
| ASN | B | 206 | frac acc = | 24.647 |
| VAL | B | 170 | frac acc = | 24.549 |
| TYR | B | 52 | frac acc = | 24.298 |
| ALA | B | 175 | frac acc = | 23.804 |
| LYS | B | 216 | frac acc = | 23.277 |
| VAL | B | 214 | frac acc = | 23.150 |
| GLY | B | 125 | frac acc = | 22.802 |
| ASN | B | 162 | frac acc = | 22.245 |
| ALA | B | 72 | frac acc = | 22.166 |
| ALA | B | 40 | frac acc = | 21.974 |
| LEU | B | 18 | frac acc = | 20.273 |
| THR | B | 212 | frac acc = | 20.170 |
| LEU | B | 182 | frac acc = | 19.619 |
| TYR | B | 33 | frac acc = | 19.398 |
| THR | B | 190 | frac acc = | 19.365 |
| VAL | B | 176 | frac acc = | 18.941 |
| SER | B | 21 | frac acc = | 18.929 |
| SER | B | 119 | frac acc = | 18.877 |
| THR | B | 91 | frac acc = | 18.237 |

TABLE 1-continued

| | | | | |
|---|---|---|---|---|
| ASP | B | 151 | frac acc = | 17.849 |
| THR | B | 114 | frac acc = | 17.601 |
| SER | B | 134 | frac acc = | 17.571 |
| LEU | B | 196 | frac acc = | 17.090 |
| TYR | B | 60 | frac acc = | 16.575 |
| TYR | B | 183 | frac acc = | 15.968 |
| VAL | B | 2 | frac acc = | 15.901 |
| PRO | B | 130 | frac acc = | 15.342 |
| LEU | B | 166 | frac acc = | 15.268 |
| GLY | B | 100 | frac acc = | 15.003 |
| PHE | B | 27 | frac acc = | 14.383 |
| ASN | B | 204 | frac acc = | 13.873 |
| PHE | B | 104 | frac acc = | 13.836 |
| TYR | B | 80 | frac acc = | 13.490 |
| VAL | B | 159 | frac acc = | 12.782 |
| ARG | B | 67 | frac acc = | 12.362 |
| GLN | B | 178 | frac acc = | 12.131 |
| HIS | B | 171 | frac acc = | 11.412 |
| SER | B | 184 | frac acc = | 11.255 |
| ARG | B | 98 | frac acc = | 11.115 |
| PRO | B | 53 | frac acc = | 11.071 |
| GLN | B | 39 | frac acc = | 11.037 |
| SER | B | 195 | frac acc = | 10.909 |
| ASP | B | 108 | frac acc = | 10.525 |
| LEU | B | 185 | frac acc = | 10.464 |
| GLY | B | 113 | frac acc = | 10.406 |
| THR | B | 78 | frac acc = | 10.213 |
| THR | B | 117 | frac acc = | 9.990 |
| LYS | B | 150 | frac acc = | 9.447 |
| VAL | B | 157 | frac acc = | 9.323 |
| VAL | B | 12 | frac acc = | 9.207 |
| TRP | B | 110 | frac acc = | 9.069 |
| ALA | B | 143 | frac acc = | 8.903 |
| SER | B | 135 | frac acc = | 8.897 |
| PHE | B | 129 | frac acc = | 8.895 |
| ARG | B | 50 | frac acc = | 8.639 |
| ALA | B | 61 | frac acc = | 8.547 |
| ALA | B | 132 | frac acc = | 7.882 |
| VAL | B | 191 | frac acc = | 7.366 |
| PRO | B | 126 | frac acc = | 7.258 |
| PHE | B | 153 | frac acc = | 6.918 |
| PRO | B | 154 | frac acc = | 6.767 |
| PRO | B | 133 | frac acc = | 6.767 |
| TRP | B | 99 | frac acc = | 6.502 |
| THR | B | 32 | frac acc = | 6.291 |
| LEU | B | 45 | frac acc = | 4.649 |
| VAL | B | 128 | frac acc = | 4.515 |
| ILE | B | 51 | frac acc = | 4.307 |
| SER | B | 186 | frac acc = | 4.084 |
| PHE | B | 173 | frac acc = | 3.969 |
| ARG | B | 38 | frac acc = | 3.734 |
| TRP | B | 47 | frac acc = | 3.561 |
| VAL | B | 118 | frac acc = | 3.409 |
| ALA | B | 24 | frac acc = | 3.376 |
| TYR | B | 95 | frac acc = | 3.242 |
| GLU | B | 6 | frac acc = | 3.216 |
| ALA | B | 144 | frac acc = | 3.167 |
| ILE | B | 70 | frac acc = | 1.958 |
| GLY | B | 111 | frac acc = | 1.868 |
| LEU | B | 4 | frac acc = | 1.808 |
| TYR | B | 201 | frac acc = | 1.758 |
| LEU | B | 148 | frac acc = | 1.744 |
| PHE | B | 68 | frac acc = | 1.708 |
| VAL | B | 188 | frac acc = | 1.315 |
| CYS | B | 22 | frac acc = | 0.935 |
| TRP | B | 161 | frac acc = | 0.876 |
| LEU | B | 131 | frac acc = | 0.654 |
| VAL | B | 205 | frac acc = | 0.495 |
| ALA | B | 92 | frac acc = | 0.356 |
| ALA | B | 79 | frac acc = | 0.356 |
| VAL | B | 64 | frac acc = | 0.263 |
| ILE | B | 29 | frac acc = | 0.227 |
| VAL | B | 218 | frac acc = | 0.000 |
| VAL | B | 189 | frac acc = | 0.000 |
| VAL | B | 149 | frac acc = | 0.000 |
| VAL | B | 116 | frac acc = | 0.000 |
| VAL | B | 48 | frac acc = | 0.000 |
| VAL | B | 37 | frac acc = | 0.000 |
| TYR | B | 152 | frac acc = | 0.000 |
| TYR | B | 94 | frac acc = | 0.000 |
| TRP | B | 36 | frac acc = | 0.000 |
| SER | B | 187 | frac acc = | 0.000 |
| SER | B | 97 | frac acc = | 0.000 |
| MET | B | 107 | frac acc = | 0.000 |
| MET | B | 83 | frac acc = | 0.000 |
| LEU | B | 145 | frac acc = | 0.000 |
| LEU | B | 86 | frac acc = | 0.000 |
| LEU | B | 81 | frac acc = | 0.000 |
| LEU | B | 20 | frac acc = | 0.000 |
| ILE | B | 34 | frac acc = | 0.000 |
| HIS | B | 207 | frac acc = | 0.000 |
| HIS | B | 35 | frac acc = | 0.000 |
| GLY | B | 146 | frac acc = | 0.000 |
| CYS | B | 203 | frac acc = | 0.000 |
| CYS | B | 147 | frac acc = | 0.000 |
| CYS | B | 96 | frac acc = | 0.000 |
| ASP | B | 90 | frac acc = | 0.000 |
| ALA | B | 106 | frac acc = | 0.000 |
| ALA | B | 49 | frac acc = | 0.000 |

The following two criteria were applied to identify the residues of hu4D5Fabv8 that can be engineered to replace with Cys residues:

1. Amino acid residues that are completely buried are eliminated, i.e. less than 10% fractional surface accessibility. Table 1 shows there are 134 (light chain) and 151 (heavy chain) residues of hu4D5Fabv8 that are more than 10% accessible (fractional surface accessibility). The top ten most accessible Ser, Ala and Val residues were selected due to their close structural similarity to Cys over other amino acids, introducing only minimal structural constraints in the antibody by newly engineered Cys. Other cysteine replacement sites can also be screened, and may be useful for conjugation.

2. Residues are sorted based on their role in functional and structural interactions of Fab. The residues which are not involved in antigen interactions and distant from the existing disulfide bonds were further selected. The newly engineered Cys residues should be distinct from, and not interfere with, antigen binding nor mispair with cysteines involved in disulfide bond formation.

The following residues of hu4D5Fabv8 possessed the above criteria and were selected to be replaced with Cys: L-V15, L-A43, L-V110, L-A144, L-S168, H-A88, H-A121, H-S122, H-A175 and H-S 179 (shown in FIG. 1).

Thiol reactivity may be generalized to any antibody where substitution of amino acids with reactive cysteine amino acids may be made within the ranges in the light chain selected from: L-10 to L-20; L-38 to L-48; L-105 to L-115; L-139 to L-149; L-163 to L-173; and within the ranges in the heavy chain selected from: H-35 to H-45; H-83 to H-93; H-114 to H-127; and H-170 to H-184, and in the Fc region within the ranges selected from H-268 to H-291; H-319 to H-344; H-370 to H-380; and H-395 to H-405.

Thiol reactivity may also be generalized to certain domains of an antibody, such as the light chain constant domain (CL) and heavy chain constant domains, CH1, CH2 and CH3. Cysteine replacements resulting in thiol reactivity values of 0.6 and higher may be made in the heavy chain constant domains α, δ, ε, γ, and μ of intact antibodies: IgA, IgD, IgE, IgG, and IgM, respectively, including the IgG subclasses: IgG1, IgG2, IgG3, IgG4, IgA, and IgA2.

Figure 3A:
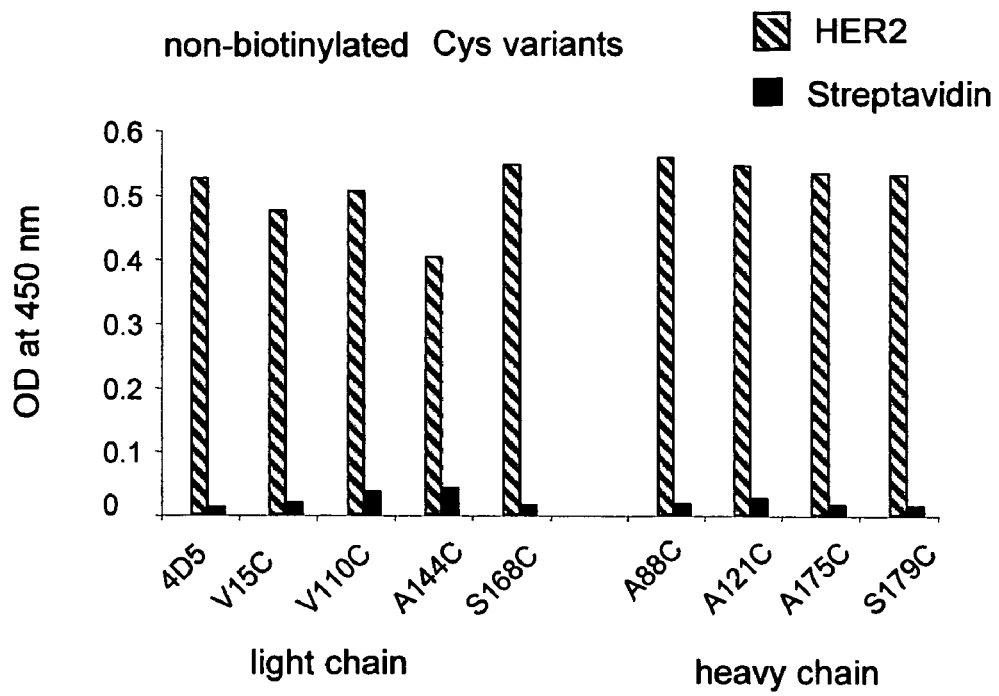
FIGS. 3A and 3B show binding measurements with detection of absorbance at 450 nm of hu4D5Fabv8 (left) and hu4D5Fabv8 Cys mutant (ThioFab) variants: (A) non-biotinylated phage-hu4D5Fabv8 and (B) biotinylated phage-hu4D5Fabv8 by the PHESELECTOR assay for interactions with: BSA (open bar), HER2 (striped bar) and streptavidin (solid bar). Light chain variants are on the left side and heavy chain variants are on the right side. Thiol reactivity=$OD_{450\,nm}$ for streptavidin binding÷$OD_{450\,nm}$ for HER2 (antibody) binding
Figure 3B:
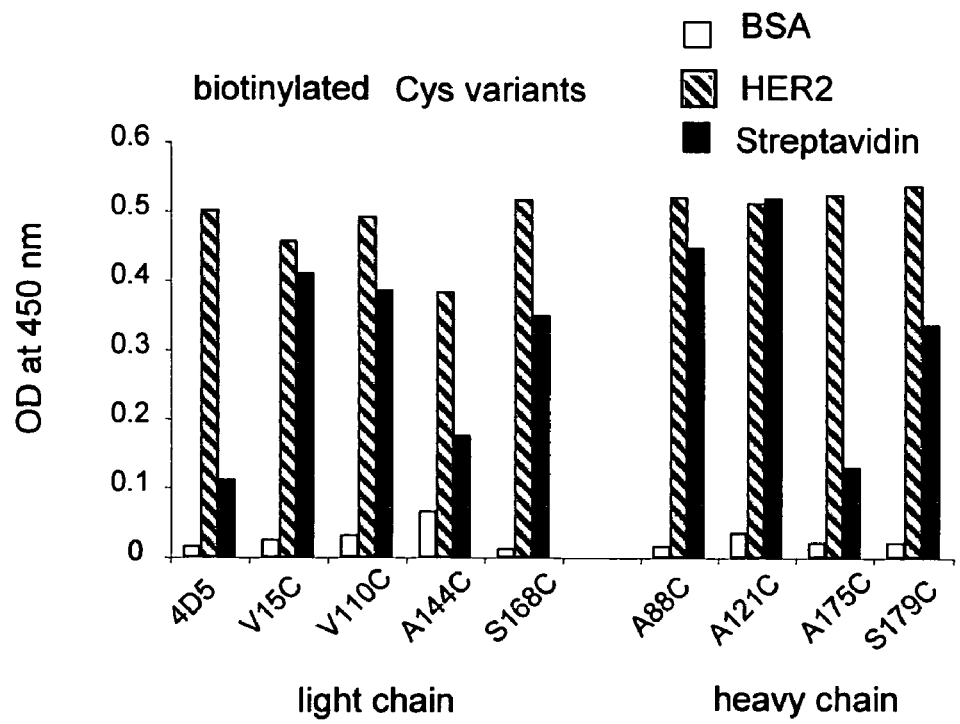

It is evident from the crystal structure data that the selected 10 Cys mutants are far away from the antigen-combining site, such as the interface with HER2 in this case. These mutants can be tested experimentally for indirect effects on functional interactions. The thiol reactivities of all the Cys Fab variants were measured and calculated as described in Examples 1 and 2, and presented in Table 2. The residues L-V15C, L-V110C, H-A88C and H-A121C have reactive and stable thiol groups (FIGS. 3A and 3B). Mutants V15C, V110C, A144C, S168C are light chain Cys variants. Mutants A88C, A121C, A175C, S179C are heavy chain Cys variants. It was surprising and unexpected that the sites with high fractional surface accessibility did not have the highest thiol reactivity as calculated by the PHESELECTOR assay (Table 2). In other words, fractional surface accessibility (Tables 1, 2) did not correlate with thiol reactivity (Table 2). In fact, the Cys residues engineered at the sites with moderate surface accessibility of 20% to 80% (FIG. 4A, Table 1), or partially exposed sites, like Ala or Val residues, exhibited better thiol reactivity, i.e. >0.6, (FIG. 3B, Table 2) than the Cys introduced at Ser residues, thus necessitating the use of PHESELECTOR assay in the screening of thiol reactive sites since the crystal structure information alone is not sufficient to select these sites (FIGS. 3B and 4A).

Thiol reactivity data is shown in FIGS. 3A and 3B for amino acid residues of 4D5 ThioFab Cys mutants: (3A) non-biotinylated (control) and (3B) biotinylated phage-ThioFabs. Reactive thiol groups on antibody/Fab surface were identified by PHESELECTOR assay analyses for the interaction of non-biotinylated phage-hu4D5Fabv8 (3A) and biotinylated phage-hu4D5Fabv8 (3B) with BSA (open box), HER2 (grey box) or streptavidin (solid box). The assay was carried out as described in Example 2. Light chain variants are on the left side and heavy chain variants are on the right side. The binding of non-biotinylated 4D5 ThioFab Cys mutants is low as expected, but strong binding to HER2 is retained. The ratio of binding to streptavidin and to HER2 of the biotinylated 4D5 ThioFab Cys mutants gives the thiol reactivity values in Table 2. Background absorbance at 450 nm or small amounts of non-specific protein binding of the biotinylated 4D5 ThioFab Cys mutants to BSA is also evident in FIG. 3B. Fractional Surface Accessibility values of the selected amino acid residues that were replaced with a Cys residue are shown in FIG. 4A. Fractional surface accessibility was calculated from the available hu4D5Fabv7 structure and shown on Table 1 (Eigenbrot et al. (1993) J Mol. Biol. 229:969-995). The conformational parameters of the hu4D5Fabv7 and hu4D5Fabv8 structures are highly consistent and allow for determination of any correlation between fractional surface accessibility calculations of hu4D5Fabv7 and thiol reactivity of hu4D5Fabv8 cysteine mutants. The measured thiol reactivity of phage ThioFab Cys residues introduced at partially exposed residues (Ala or Val) have better thiol reactivity compared to the ones introduced at Ser residues (Table 2). It can be seen from the ThioFab Cys mutants of Table 2 that there is little or no correlation between thio reactivity values and fractional surface accessibility.

Amino acids at positions L-15, L-43, L-110, L-144, L-168, H-40, H-88, H-119, H-121, H-122, H-175, and H-179 of an antibody may generally be mutated (replaced) with free cysteine amino acids. Ranges within about 5 amino acid residues on each side of these positions may also be replaced with free cysteine acids, i.e. L-10 to L-20; L-38 to L-48; L-105 to L-115; L-139 to L-149; L-163 to L-173; H-35 to H-45; H-83 to H-93; H-114 to H-127; and H-170 to H-184, as well as the ranges in the Fc region selected from H-268 to H-291; H-319 to H-344; H-370 to H-380; and H-395 to H-405, to yield the cysteine engineered antibodies of the invention.

TABLE 2

Thiol reactivity of phage-ThioFabs

| Phage-ThioFab construct | Thiol Reactivity* | Fractional Surface Accessibility (%) (from Table 1) |
|---|---|---|
| hu4D5Fabv8-wt | 0.125 | — |
| L-V15C | 0.934 | 52.46 |
| L-A43C | 0.385 | 26.80 |
| L-V110C | 0.850 | 44.84 |
| L-A144C | 0.373 | 23.65 |
| L-S168C | 0.514 | 79.68 |
| H-A40C | 0.450 | 21.97 |
| H-A88C | 0.914 | 51.60 |
| H-S119C | 0.680 | 18.88 |
| H-A121C | 0.925 | 33.05 |
| H-S122C | 0.720 | 72.87 |
| H-A175C | 0.19 | 23.80 |
| H-S179C | 0.446 | 99.48 |

L = light chain,
H = heavy chain,
A = alanine,
S = serine,
V = valine,
C = cysteine
*Thiol reactivity is measured as the ratio of $OD_{450\,nm}$ for streptavidin binding to $OD_{450\,nm}$ for HER2 (antibody) binding (Example 2). Thiol reactivity value of 1 indicates complete biotinylation of the cysteine thiol.

Two Cys variants from light chain (L-V15C and L-V110C) and two from heavy chain (H-A88C and H-A121C) were selected for further analysis as these variants showed the highest thiol reactivity (Table 2).

Unlike phage purification, Fab preparation may require 2-3 days, depending on the scale of production. During this time, thiol groups may lose reactivity due to oxidation. To probe the stability of thiol groups on hu4D5Fabv8-phage, stability of the thiol reactivity of phage-thioFabs was measured (FIG. 4B). After ThioFab-phage purification, on day 1, day 2 and day 4, all the samples were conjugated with biotin-PEO-maleimide and probed with phage ELISA assay (PHESELECTOR) to test HER2 and streptavidin binding. L-V15C, L-V110C, H-A88C and H-A121C retain significant amounts of thiol reactivity compared to other ThioFab variants (FIG. 4B).

Labelled Cysteine Engineered Antibodies

The cysteine engineered antibodies of the invention may be conjugated with any label moiety which can be covalently attached to the antibody through a reactive cysteine thiol group (Singh et al (2002) Anal. Biochem. 304:147-15; Harlow E. and Lane, D. (1999) Using Antibodies: A Laboratory Manual, Cold Springs Harbor Laboratory Press, Cold Spring Harbor, N.Y.; Lundblad R. L. (1991) Chemical Reagents for Protein Modification, 2nd ed. CRC Press, Boca Raton, Fla.). The attached label may function to: (i) provide a detectable signal; (ii) interact with a second label to modify the detectable signal provided by the first or second label, e.g. to give FRET (fluorescence resonance energy transfer); (iii) stabilize interactions or increase affinity of binding, with antigen or ligand; (iv) affect mobility, e.g. electrophoretic mobility or cell-permeability, by charge, hydrophobicity, shape, or other physical parameters, or (v) provide a capture moiety, to modulate ligand affinity, antibody/antigen binding, or ionic complexation.

Labelled cysteine engineered antibodies may be useful in diagnostic assays, e.g., for detecting expression of an antigen of interest in specific cells, tissues, or serum. For diagnostic applications, the antibody will typically be labeled with a detectable moiety. Numerous labels are available which can be generally grouped into the following categories:

(a) Radioisotopes (radionuclides), such as $^{3}$H, $^{11}$C, $^{14}$C, $^{18}$F, $^{32}$P, $^{35}$S, $^{64}$Cu, $^{68}$Ga, $^{86}$Y, $^{99}$Tc, $^{111}$In, $^{123}$I, $^{124}$I, $^{125}$I, $^{131}$I, $^{133}$Xe, $^{177}$Lu, $^{211}$At, or $^{213}$Bi. Radioisotope labelled antibodies are useful in receptor targeted imaging experiments. The antibody can be labeled with ligand reagents that bind, chelate or otherwise complex a radioisotope metal where the reagent is reactive with the engineered cysteine thiol of the antibody, using the techniques described in Current Protocols in Immunology, Volumes 1 and 2, Coligen et al, Ed. Wiley-Interscience, New York, N.Y., Pubs. (1991). Chelating ligands which may complex a metal ion include DOTA, DOTP, DOTMA, DTPA and TETA (Macrocyclics, Dallas, Tex.). Radionuclides can be targeted via complexation with the antibody-drug conjugates of the invention (Wu et al (2005) Nature Biotechnology 23(9):1137-1146).

Metal-chelate complexes suitable as antibody labels for imaging experiments are disclosed: U.S. Pat. Nos. 5,342,606; 5,428,155; 5,316,757; 5,480,990; 5,462,725; 5,428,139; 5,385,893; 5,739,294; 5,750,660; 5,834,456; Hnatowich et al (1983) J. Immunol. Methods 65:147-157; Meares et al (1984) Anal. Biochem. 142:68-78; Mirzadeh et al (1990) Bioconjugate Chem. 1:59-65; Meares et al (1990) J. Cancer 1990, Suppl. 10:21-26; Izard et al (1992) Bioconjugate Chem. 3:346-350; Nikula et al (1995) Nucl. Med. Biol. 22:387-90; Camera et al (1993) Nucl. Med. Biol. 20:955-62; Kukis et al (1998) J. Nucl. Med. 39:2105-2110; Verel et al (2003) J. Nucl. Med. 44:1663-1670; Camera et al (1994) J. Nucl. Med. 21:640-646; Ruegg et al (1990) Cancer Res. 50:4221-4226; Verel et al (2003) J. Nucl. Med. 44:1663-1670; Lee et al (2001) Cancer Res. 61:4474-4482; Mitchell, et al (2003)J. Nucl. Med. 44:1105-1112; Kobayashi et al (1999) Bioconjugate Chem. 10:103-111; Miederer et al (2004) J. Nucl. Med. 45:129-137; DeNardo et al (1998) Clinical Cancer Research 4:2483-90; Blend et al (2003) Cancer Biotherapy & Radiopharmaceuticals 18:355-363; Nikula et al (1999) J. Nucl. Med. 40:166-76; Kobayashi et al (1998) J. Nucl. Med. 39:829-36; Mardirossian et al (1993) Nucl. Med. Biol. 20:65-74; Roselli et al (1999) Cancer Biotherapy & Radiopharmaceuticals, 14:209-20.

(b) Fluorescent labels such as rare earth chelates (europium chelates), fluorescein types including FITC, 5-carboxyfluorescein, 6-carboxy fluorescein; rhodamine types including TAMRA; dansyl; Lissamine; cyanines; phycoerythrins; Texas Red; and analogs thereof. The fluorescent labels can be conjugated to antibodies using the techniques disclosed in Current Protocols in Immunology, supra, for example. Fluorescent dyes and fluorescent label reagents include those which are commercially available from Invitrogen/Molecular Probes (Eugene, Oreg.) and Pierce Biotechnology, Inc. (Rockford, Ill.).

(c) Various enzyme-substrate labels are available or disclosed (U.S. Pat. No. 4,275,149). The enzyme generally catalyzes a chemical alteration of a chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRP), alkaline phosphatase (AP), β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al (1981) "Methods for the Preparation of Enzyme-Antibody Conjugates for use in Enzyme Immunoassay", in *Methods in Enzym.* (ed J. Langone & H. Van Vunakis), Academic Press, New York, 73:147-166.

Examples of enzyme-substrate combinations include, for example:

(i) Horseradish peroxidase (HRP) with hydrogen peroxidase as a substrate, wherein the hydrogen peroxidase oxidizes a dye precursor (e.g., orthophenylene diamine (OPD) or 3,3', 5,5'-tetramethylbenzidine hydrochloride (TMB));

(ii) alkaline phosphatase (AP) with para-nitrophenyl phosphate as chromogenic substrate; and (iii) β-D-galactosidase (β-D-Gal) with a chromogenic substrate (e.g., p-nitrophenyl-β-D-galactosidase) or fluorogenic substrate 4-methylumbelliferyl-β-D-galactosidase.

Numerous other enzyme-substrate combinations are available to those skilled in the art. For a general review, see U.S. Pat. Nos. 4,275,149 and 4,318,980.

A label may be indirectly conjugated with a cysteine engineered antibody. For example, the antibody can be conjugated with biotin and any of the three broad categories of labels mentioned above can be conjugated with avidin or streptavidin, or vice versa. Biotin binds selectively to streptavidin and thus, the label can be conjugated with the antibody in this indirect manner. Alternatively, to achieve indirect conjugation of the label with the polypeptide variant, the polypeptide variant is conjugated with a small hapten (e.g., digoxin) and one of the different types of labels mentioned above is conjugated with an anti-hapten polypeptide variant (e.g., anti-digoxin antibody). Thus, indirect conjugation of the label with the polypeptide variant can be achieved (Hermanson, G. (1996) in *Bioconjugate Techniques* Academic Press, San Diego).

The polypeptide variant of the present invention may be employed in any known assay method, such as ELISA, competitive binding assays, direct and indirect sandwich assays, and immunoprecipitation assays (Zola, (1987) *Monoclonal Antibodies: A Manual of Techniques*, pp. 147-158, CRC Press, Inc.).

A detection label may be useful for localizing, visualizing, and quantitating a binding or recognition event. The labelled antibodies of the invention can detect cell-surface receptors. Another use for detectably labelled antibodies is a method of bead-based immunocapture comprising conjugating a bead with a fluorescent labelled antibody and detecting a fluorescence signal upon binding of a ligand. Similar binding detection methodologies utilize the surface plasmon resonance (SPR) effect to measure and detect antibody-antigen interactions.

Detection labels such as fluorescent dyes and chemiluminescent dyes (Briggs et al (1997) "Synthesis of Functionalised Fluorescent Dyes and Their Coupling to Amines and Amino Acids," J. Chem. Soc., Perkin-Trans. 1:1051-1058) provide a detectable signal and are generally applicable for labelling antibodies, preferably with the following properties: (i) the labelled antibody should produce a very high signal with low background so that small quantities of antibodies can be sensitively detected in both cell-free and cell-based assays; and (ii) the labelled antibody should be photostable so that the fluorescent signal may be observed, monitored and recorded without significant photo bleaching. For applications involving cell surface binding of labelled antibody to membranes or cell surfaces, especially live cells, the labels preferably (iii) have good water-solubility to achieve effective conjugate concentration and detection sensitivity and (iv) are non-toxic to living cells so as not to disrupt the normal metabolic processes of the cells or cause premature cell death.

Direct quantification of cellular fluorescence intensity and enumeration of fluorescently labelled events, e.g. cell surface binding of peptide-dye conjugates may be conducted on an system (FMAT® 8100 HTS System, Applied Biosystems, Foster City, Calif.) that automates mix-and-read, non-radioactive assays with live cells or beads (Miraglia, "Homogeneous cell- and bead-based assays for high throughput screening using fluorometric microvolume assay technology", (1999) J. of Biomolecular Screening 4:193-204). Uses of labelled antibodies also include cell surface receptor binding assays, immunocapture assays, fluorescence linked immunosorbent assays (FLISA), caspase-cleavage (Zheng, "Caspase-3 controls both cytoplasmic and nuclear events associated with Fas-mediated apoptosis in vivo", (1998) Proc. Natl. Acad. Sci. USA 95:618-23; U.S. Pat. No. 6,372, 907), apoptosis (Vermes, "A novel assay for apoptosis. Flow cytometric detection of phosphatidylserine expression on early apoptotic cells using fluorescein labelled Annexin V" (1995) J. Immunol. Methods 184:39-51) and cytotoxicity assays. Fluorometric microvolume assay technology can be used to identify the up or down regulation by a molecule that is targeted to the cell surface (Swartzman, "A homogeneous and multiplexed immunoassay for high-throughput screening using fluorometric microvolume assay technology", (1999) Anal. Biochem. 271:143-51).

Labelled cysteine engineered antibodies of the invention are useful as imaging biomarkers and probes by the various methods and techniques of biomedical and molecular imaging such as: (i) MRI (magnetic resonance imaging); (ii) MicroCT (computerized tomography); (iii) SPECT (single photon emission computed tomography); (iv) PET (positron emission tomography) Chen et al (2004) Bioconjugate Chem. 15:41-49; (v) bioluminescence; (vi) fluorescence; and (vii) ultrasound. Immunoscintigraphy is an imaging procedure in which antibodies labeled with radioactive substances are administered to an animal or human patient and a picture is taken of sites in the body where the antibody localizes (U.S. Pat. No. 6,528,624). Imaging biomarkers may be objectively measured and evaluated as an indicator of normal biological processes, pathogenic processes, or pharmacological responses to a therapeutic intervention. Biomarkers may be of several types: Type 0 are natural history markers of a disease and correlate longitudinally with known clinical indices, e.g. MRI assessment of synovial inflammation in rheumatoid arthritis; Type I markers capture the effect of an intervention in accordance with a mechanism-of-action, even though the mechanism may not be associated with clinical outcome; Type II markers function as surrogate endpoints where the change in, or signal from, the biomarker predicts a clinical benefit to "validate" the targeted response, such as measured bone erosion in rheumatoid arthritis by CT. Imaging biomarkers thus can provide pharmacodynamic (PD) therapeutic information about: (i) expression of a target protein, (ii) binding of a therapeutic to the target protein, i.e. selectivity, and (iii) clearance and half-life pharmacokinetic data. Advantages of in vivo imaging biomarkers relative to lab-based biomarkers include: non-invasive treatment, quantifiable, whole body assessment, repetitive dosing and assessment, i.e. multiple time points, and potentially transferable effects from preclinical (small animal) to clinical (human) results. For some applications, bioimaging supplants or minimizes the number of animal experiments in preclinical studies.

Radionuclide imaging labels include radionuclides such as $^{3}$H, $^{11}$C, $^{14}$C, $^{18}$F, $^{32}$P, $^{35}$S, $^{64}$Cu, $^{68}$Ga, $^{86}$Y, $^{99}$Tc, $^{111}$In, $^{123}$I, $^{124}$I, $^{125}$I, $^{131}$I, $^{133}$Xe, $^{177}$Lu, $^{211}$At, or $^{213}$Bi. The radionuclide metal ion can be complexed with a chelating linker such as DOTA. Linker reagents such as DOTA-maleimide (4-maleimidobutyramidobenzyl-DOTA) can be prepared by the reaction of aminobenzyl-DOTA with 4-maleimidobutyric acid (Fluka) activated with isopropylchloroformate (Aldrich), following the procedure of Axworthy et al (2000) Proc. Natl. Acad. Sci. USA 97(4):1802-1807). DOTA-maleimide reagents react with the free cysteine amino acids of the cysteine engineered antibodies and provide a metal complexing ligand on the antibody (Lewis et al (1998) Bioconj. Chem. 9:72-86). Chelating linker labelling reagents such as DOTA-NHS (1,4,7,10-tetraazacyclododecane-1,4,7,10-tetraacetic acid mono (N-hydroxysuccinimide ester) are commercially available (Macrocyclics, Dallas, Tex.). Receptor target imaging with radionuclide labelled antibodies can provide a marker of pathway activation by detection and quantitation of progressive accumulation of antibodies in tumor tissue (Albert et al (1998) Bioorg. Med. Chem. Lett. 8:1207-1210). The conjugated radio-metals may remain intracellular following lysosomal degradation.

Peptide labelling methods are well known. See Haugland, 2003, *Molecular Probes Handbook of Fluorescent Probes and Research Chemicals*, Molecular Probes, Inc.; Brinkley, 1992, Bioconjugate Chem. 3:2; Garman, (1997) *Non-Radioactive Labelling: A Practical Approach*, Academic Press, London; Means (1990) Bioconjugate Chem. 1:2; Glazer et al (1975) *Chemical Modification of Proteins. Laboratory Techniques in Biochemistry and Molecular Biology* (T. S. Work and E. Work, Eds.) American Elsevier Publishing Co., New York; Lundblad, R. L. and Noyes, C. M. (1984) *Chemical Reagents for Protein Modification*, Vols. I and II, CRC Press, New York; Pfleiderer, G. (1985) "Chemical Modification of Proteins", *Modern Methods in Protein Chemistry*, H. Tschesche, Ed., Walter DeGryter, Berlin and New York; and Wong (1991) *Chemistry of Protein Conjugation and Cross-linking*, CRC Press, Boca Raton, Fla.); De Leon-Rodriguez et al (2004) Chem. Eur. J. 10:1149-1155; Lewis et al (2001) Bioconjugate Chem. 12:320-324; Li et al (2002) Bioconjugate Chem. 13:110-115; Mier et al (2005) Bioconjugate Chem. 16:240-237.

Peptides and proteins labelled with two moieties, a fluorescent reporter and quencher in sufficient proximity undergo fluorescence resonance energy transfer (FRET). Reporter groups are typically fluorescent dyes that are excited by light at a certain wavelength and transfer energy to an acceptor, or quencher, group, with the appropriate Stokes shift for emission at maximal brightness. Fluorescent dyes include molecules with extended aromaticity, such as fluorescein and rhodamine, and their derivatives. The fluorescent reporter may be partially or significantly quenched by the quencher moiety in an intact peptide. Upon cleavage of the peptide by a peptidase or protease, a detectable increase in fluorescence may be measured (Knight, C. (1995) "Fluorimetric Assays of Proteolytic Enzymes", Methods in Enzymology, Academic Press, 248:18-34).

The labelled antibodies of the invention may also be used as an affinity purification agent. In this process, the labelled antibody is immobilized on a solid phase such a Sephadex resin or filter paper, using methods well known in the art. The immobilized antibody is contacted with a sample containing the antigen to be purified, and thereafter the support is washed with a suitable solvent that will remove substantially all the material in the sample except the antigen to be purified, which is bound to the immobilized polypeptide variant. Finally, the support is washed with another suitable solvent, such as glycine buffer, pH 5.0, that will release the antigen from the polypeptide variant.

Labelling reagents typically bear reactive functionality which may react (i) directly with a cysteine thiol of a cysteine engineered antibody to form the labelled antibody, (ii) with a linker reagent to form a linker-label intermediate, or (iii) with a linker antibody to form the labelled antibody. Reactive functionality of labelling reagents include: maleimide, haloacetyl, iodoacetamide succinimidyl ester (e.g. NHS, N-hydroxysuccinimide), isothiocyanate, sulfonyl chloride, 2,6-dichlorotriazinyl, pentafluorophenyl ester, and phosphoramidite, although other functional groups can also be used.

An exemplary reactive functional group is N-hydroxysuccinimidyl ester (NHS) of a carboxyl group substituent of a detectable label, e.g. biotin or a fluorescent dye. The NHS ester of the label may be preformed, isolated, purified, and/or characterized, or it may be formed in situ and reacted with a nucleophilic group of an antibody. Typically, the carboxyl form of the label is activated by reacting with some combination of a carbodiimide reagent, e.g. dicyclohexylcarbodiimide, diisopropylcarbodiimide, or a uronium reagent, e.g. TSTU (O—(N-Succinimidyl)-N,N,N',N'-tetramethyluronium tetrafluoroborate, HBTU (O-benzotriazol-1-yl)-N,N,N',N'-tetramethyluronium hexafluorophosphate), or HATU (O-(7-azabenzotriazol-1-yl)-N,N,N',N'-tetramethyluronium hexafluorophosphate), an activator, such as 1-hydroxybenzotriazole (HOBt), and N-hydroxysuccinimide to give the NHS ester of the label. In some cases, the label and the antibody may be coupled by in situ activation of the label and reaction with the antibody to form the label-antibody conjugate in one step. Other activating and coupling reagents include TBTU (2-(1H-benzotriazo-1-yl)-1-1,3,3-tetramethyluronium hexafluorophosphate), TFFH(N,N',N'',N'''-tetramethyluronium 2-fluoro-hexafluorophosphate), PyBOP (benzotriazole-1-yl-oxy-tris-pyrrolidino-phosphonium hexafluorophosphate, EEDQ (2-ethoxy-1-ethoxycarbonyl-1,2-dihydroquinoline), DCC (dicyclohexylcarbodiimide); DIPCDI (diisopropylcarbodiimide), MSNT (1-(mesitylene-2-sulfonyl)-3-nitro-1H-1,2,4-triazole, and aryl sulfonyl halides, e.g. triisopropylbenzenesulfonyl chloride.

Conjugation of Biotin-Maleimide to Thiofabs

The above-described ThioFab properties were established in the presence of phage because fusion of the Fab to the phage coat protein could potentially alter Cys thiol accessibility or reactivity. Therefore, the ThioFab constructs were cloned into an expression vector under alkaline phosphatase promoter (Chang et al (1987) Gene 55:189-196) and the ThioFab expression was induced by growing *E. coli* cells in the phosphate-free medium. ThioFabs were purified on a Protein G SEPHAROSE™ column and analyzed on reducing and non-reducing SDS-PAGE gels. These analyses allow assessment of whether ThioFabs retained their reactive thiol group or were rendered inactive by forming intramolecular or intermolecular disulfide bonds. ThioFabs L-V15C, L-V110C, H-A88C, and H-A121C were expressed and purified by Protein-G SEPHAROSE™ column chromatography (see methods sections for details). Purified proteins were analyzed on SDS-PAGE gel in reducing (with DTT) and non-reducing (without DTT) conditions. Other reducing agents such as BME (beta-mercaptoethanol) can used in the gel to cleave interchain disulfide groups. It is evident from SDS-PAGE gel analysis that the major (~90%) fraction of ThioFab is in the monomeric form, while wild type hu4D5Fabv8 is essentially in the monomeric form (47 kDa).

ThioFab (A121C) and wild type hu4D5Fabv8 were incubated with 100 fold excess of biotin-maleimide for 3 hours at room temperature and the biotinylated Fabs were loaded onto a Superdex-200™ gel filtration column. This purification step was useful in separating monomeric Fab from oligomeric Fab and also from excess free biotin-maleimide (or free cytotoxic drug).

Figure 5:
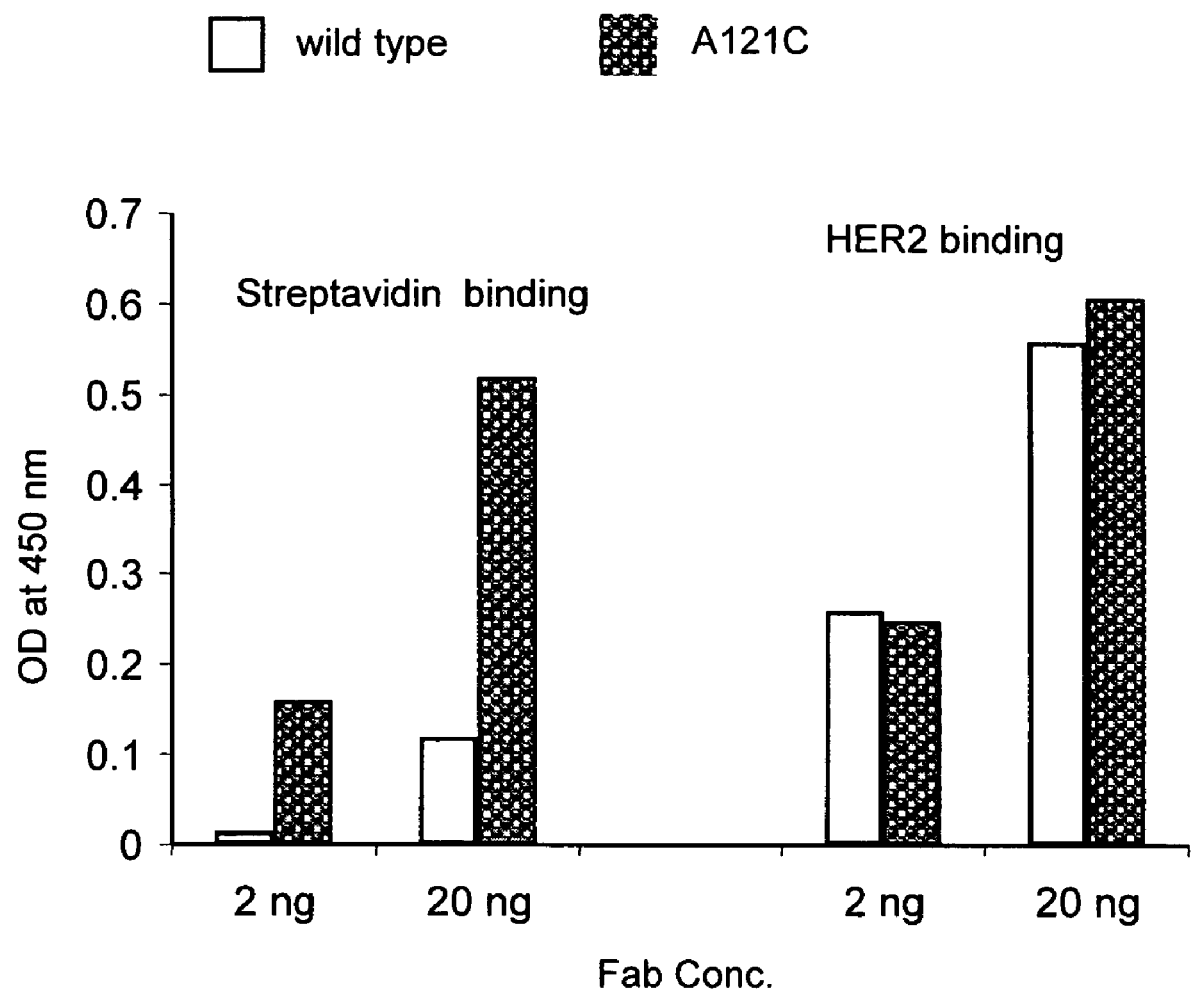
FIG. 5 shows binding measurements with detection of absorbance at 450 nm of biotin-maleimide conjugated-hu4D5Fabv8 (A121C) and non-biotinylated wild type hu4D5Fabv8 for binding to streptavidin and HER2. Each Fab was tested at 2 ng and 20 ng.

FIG. 5 shows validation of the properties of ThioFab variants in the absence of the phage context. The proteins without phage fusion, hu4D5Fabv8 and hu4D5Fabv8-A121C (ThioFab-A121C), were expressed and purified using protein-G agarose beads followed by incubation with 100 fold molar excess of biotin-maleimide. Streptavidin and HER2 binding of a biotinylated cys engineered ThioFab and a non-biotinylated wild type Fab was compared. The extent of biotin conjugation (interaction with streptavidin) and their binding ability to HER2 were monitored by ELISA analyses. Each Fab was tested at 2 ng and 20 ng.

Biotinylated A121C ThioFab retained comparable HER2 binding to that of wild type hu4D5Fabv8 (FIG. 5). Wild type Fab and A121C-ThioFab were purified by gel filtration column chromatography. The two samples were tested for HER2 and streptavidin binding by ELISA using goat anti-Fab-HRP as secondary antibody. Both wild type (open box) and ThioFab (dotted box) have similar binding to HER2 but only ThioFab retained streptavidin binding. Only a background level of interaction with streptavidin was observed with non-biotinylated wild type hu4D5Fabv8 (FIG. 5). Mass spectral (LC-ESI-MS) analysis of biotinylated-ThioFab (A121C) resulted in a major peak with 48294.5 daltons compared to the wild type hu4D5Fabv8 (47737 daltons). The 537.5 daltons difference between the two molecules exactly corresponds to a single biotin-maleimide conjugated to the ThioFab. Mass spec protein sequencing (LC-ESI-Tandem mass spec analysis) results further confirmed that the conjugated biotin molecule was at the newly engineered Cys residue (Table 4, Example 3).

Site Specific Conjugation of Biotin-Maleimide to Albumin Binding Peptide (ABP)-Thiofabs Plasma-protein binding can be an effective means of improving the pharmacokinetic properties of short lived molecules. Albumin is the most abundant protein in plasma. Serum albumin binding peptides (ABP) can alter the pharmacodynamics of fused active domain proteins, including alteration of tissue uptake, penetration, and diffusion. These pharmacodynamic parameters can be modulated by specific selection of the appropriate serum albumin binding peptide sequence (US 20040001827). A series of albumin binding peptides were identified by phage display screening (Dennis et al. (2002) "Albumin Binding As A General Strategy For Improving The Pharmacokinetics Of Proteins" J Biol. Chem. 277:35035-35043; WO 01/45746). Compounds of the invention include ABP sequences taught by: (i) Dennis et al (2002) J Biol. Chem. 277:35035-35043 at Tables III and IV, page 35038; (ii) US 20040001827 at [0076] SEQ ID NOS: 9-22; and (iii) WO 01/45746 at pages 12-13, SEQ ID NOS: z1-z14, and all of which are incorporated herein by reference.

Albumin Binding (ABP)-Fabs were engineered by fusing an albumin binding peptide to the C-terminus of Fab heavy chain in 1:1 stoichiometric ratio (1 ABP/1 Fab). It was shown that association of these ABP-Fabs with albumin increased their half life by more than 25 fold in rabbits and mice. The above described reactive Cys residues can therefore be introduced in these ABP-Fabs and used for site-specific conjugation with cytotoxic drugs followed by in vivo animal studies. FIG. 9 shows a graphical albumin binding peptide-Fab fusion (ABP-Fab) linker drug conjugate.

Exemplary albumin binding peptide sequences include, but are not limited to the amino acid sequences listed in SEQ ID NOS: 1-5:

```
CDKTHTGGGSQRLMEDICLPRWGCLWEDDF    SEQ ID NO:1

QRLMEDICLPRWGCLWEDDF              SEQ ID NO:2

QRLIEDICLPRWGCLWEDDF              SEQ ID NO:3

RLIEDICLPRWGCLWEDD                SEQ ID NO:4

DICLPRWGCLW                       SEQ ID NO:5
```

The albumin binding peptide (ABP) sequences bind albumin from multiple species (mouse, rat, rabbit, bovine, rhesus, baboon, and human) with Kd (rabbit)=0.3 μM. The albumin binding peptide does not compete with ligands known to bind albumin and has a half life (T½) in rabbit of 2.3 hr. ABP-ThioFab proteins were purified on BSA-SEPHAROSE™ followed by biotin-maleimide conjugation and purification on Superdex-S200 column chromatography as described in previous sections. Purified biotinylated proteins were homogeneous and devoid of any oligomeric forms (Example 4).

FIG. 6 shows the properties of Albumin Binding Peptide (ABP)-ThioFab variants. ELISA analyses were carried out to test the binding ability of ABP-hu4D5Fabv8-wt, ABP-hu4D5Fabv8-V110C and ABP-hu4D5Fabv8-A121C with rabbit albumin, streptavidin and HER2. Biotinylated ABP-ThioFabs are capable of binding to albumin and HER2 with similar affinity to that of wild type ABP-hu4D5Fabv8 as confirmed by ELISA (FIG. 6) and BIAcore binding kinetics analysis (Table 3). An ELISA plate was coated with albumin, HER2 and SA as described. Binding of biotinylated ABP-ThioFabs to albumin, HER2 and SA was probed with anti-Fab HRP. Biotinylated ABP-ThioFabs were capable of binding to streptavidin compared to non biotinylated control ABP-hu4D5Fabv8-wt indicating that ABP-ThioFabs were conjugated with biotin maleimide like ThioFabs in a site specific manner as the same Cys mutants were used for both the variants (FIG. 6).

TABLE 3

BIAcore kinetic analysis for HER2 and rabbit albumin binding to biotinylated ABP-hu4D5Fabv8 wild type and ThioFabs

| Antibody | $k_{on}$ (M$^{-1}$s$^{-1}$) | $k_{off}$ (s$^{-1}$) | $K_d$ (nM) |
|---|---|---|---|
| HER2 binding | | | |
| wild type | $4.57 \times 10^5$ | $4.19 \times 10^{-5}$ | 0.0917 |
| V110C | $4.18 \times 10^5$ | $4.05 \times 10^{-5}$ | 0.097 |
| A121C | $3.91 \times 10^5$ | $4.15 \times 10^{-5}$ | 0.106 |
| Rabbit albumin binding | | | |
| wild type | $1.66 \times 10^5$ | 0.0206 | 124 |
| V110C | $2.43 \times 10^5$ | 0.0331 | 136 |
| A121C | $1.70 \times 10^5$ | 0.0238 | 140 |

ABP = albumin binding peptide

Alternatively, an albumin-binding peptide may be linked to the antibody by covalent attachment through a linker moiety.

Engineering of ABP-Thiofabs with Two Free Thiol Groups Per Fab

The above results indicate that all four (L-V15C, L-V110C, H-A88C and H-A121C) thioFab (cysteine engineered Fab antibodies) variants have reactive thiol groups that can be used for site specific conjugation with a label reagent, linker reagent, or drug-linker intermediate. L-V15C can be expressed and purified but with relatively low yields. However the expression and purification yields of L-V110C, H-A88C and H-A121C variants were similar to that of hu4D5Fabv8. Therefore these mutants can be used for further analysis and recombined to get more than one thiol group per Fab. Towards this objective, one thiol group on the light and one on heavy chain were constructed to obtain two thiol groups per Fab molecule (L-V110C/H-A88C and L-V110C/H-A121C). These two double Cys variants were expressed in an E. coli expression system and purified. The homogeneity of purified biotinylated ABP-ThioFabs was found to be similar to that of single Cys variants.

The effects of engineering two reactive Cys residues per Fab was investigated (FIG. 7). The presence of a second biotin was tested by probing the binding of biotinylated ABP-Thio-Fab to SA using streptavidin-HRP (FIG. 7). For HER2/Fab analysis, an ELISA plate was coated with HER2 and probed with anti-Fab HRP. For SA/Fab analysis, an ELISA plate was coated with SA and probed with anti-Fab HRP. For SA/SA analysis, an ELISA plate was coated with SA and probed with SA-HRP. FIG. 7. ELISA analyses for the interaction of biotinylated ABP-hu4D5Fabv8 cys variants with HER2, streptavidin (SA). HER2/Fab, SA/Fab and SA/SA indicate that their interactions were monitored by anti-Fab-HRP, SA-HRP, respectively. SA/Fab monitors the presence of single biotin per Fab and more than one biotin per Fab is monitored by SA/SA analysis. Binding of HER2 with double cys mutants is similar to that of single Cys variants (FIG. 7). However the extent of biotinylation on double Cys mutants was higher compared to single Cys variants due to more than one free thiol group per Fab molecule (FIG. 7).

Engineering of Thio IgG Variants of Trastuzumab

Cysteine was introduced into the full-length monoclonal antibody, trastuzumab (HERCEPTIN®, Genentech Inc.) at certain residues. The single cys mutants H-A88C, H-A121C and L-V110C. of trastuzumab, and double cys mutants V110C-A121C and V110C-A121C of trastuzumab were expressed in CHO (Chinese Hamster Ovary) cells by transient fermentation in media containing 1 mM cysteine. The A88C mutant heavy chain sequence (450 aa) is SEQ ID NO:6. The A121C mutant heavy chain sequence (450 aa) is SEQ ID NO:7. The V110C. mutant light chain sequence (214 aa) is SEQ ID NO:8.

EVQLVESGGGLVQPGGSLRLSCAASGFNIKDTYIHWVRQ SEQ ID NO:6

APGKGLEWVARIYPTNGYTRYADSVKGRFTISADTSKNT

AYLQMNSLRCEDTAVYYCSRWGGDGFYAMDYWGQGTLVT

VSSASTKGPSVFPLAPSSKSTSGGTAALGCLVKDYFPEP

VTVSWNSGALTSGVHTFPAVLQSSGLYSLSSVVTVPSSS

LGTQTYICNVNHKPSNTKVDKKVEPKSCDKTHRCPPCPA

PELLGGPSVFLFPPKPKDTLMISRTPEVTCVVVDVSHED

PEVKFNWYVDGVEVHNAKTKPREEQYNSTYRVVSVLTVL

```
                                      -continued
HQDWLNGKEYKCKVSNKALPAPIEKTISKAKGQPREPQV

YTLPPSREEMTKNQVSLTCLVKGFYPSDIAVEWESNGQP

ENNYKTTPPVLDSDGSFFLYSKLTVDKSRWQQGNVFSCS

VMHEALHNHYTQKSLSLSPGK

EVQLVESGGGLVQPGGSLRLSCAASGFNIKDTYIHWVRQ   SEQ ID NO:7

APGKGLEWVARIYPTNGYTRYADSVKGRFTISADTSKNT

AYLQMNSLRAEDTAVYYCSRWGGDGFYAMDYWGQGTLVT

VSSCSTKGPSVFPLAPSSKSTSGGTAALGCLVKDYFPEP

VTVSWNSGALTSGVHTFPAVLQSSGLYSLSSVVTVPSSS

LGTQTYICNVNHKPSNTKVDKKVEPKSCDKTHTCPPCPA

PELLGGPSVFLFPPKPKDTLMISRTPEVTCVVVDVSHED

PEVKFNWYVDGVEVHNAKTKPREEQYNSTYRVVSVLTVL

HQDWLNGKEYKCKVSNKALPAPIEKTISKAKGQPREPQV

YTLPPSREEMTKNQVSLTCLVKGFYPSDIAVEWESNGQP

ENNYKTTPPVLDSDGSFFLYSKLTVDKSRWQQGNVFSCS

VMHEALHNHYTQKSLSLSPGK

DIQMTQSPSSLSASVGDRVTITCRASQDVNTAVAWYQQK   SEQ ID NO:8

PGKAPKLLIYSASFLYSGVPSRFSGSRSGTDFTLTISSL

QPEDFATYYCQQHYTTPPTFGQGTKVEIKRTCAAPSVFI

FPPSDEQLKSGTASVVCLLNNFYPREAKVQWKVDNALQS

GNSQESVTEQDSKDSTYSLSSTLTLSKADYEKHKVYACE

VTHQGLSSPVTKSFNRGEC
```

According to one embodiment, the cysteine engineered thio-trastuzumab antibodies comprise one or more of the following variable region heavy chain sequences with a free cysteine amino acid (SEQ ID NOS: 9-16).

| Mutant | Sequence      | SEQ ID NO:     |
|--------|---------------|----------------|
| A40C   | WVRQCPGKGL    | SEQ ID NO:9    |
| A88C   | NSLRCEDTAV    | SEQ ID NO:10   |
| S119C  | LVTVCSASTKGPS | SEQ ID NO:11   |
| S120C  | LVTVSCASTKGPS | SEQ ID NO:12   |
| A121C  | LVTVSSCSTKGPS | SEQ ID NO:13   |
| S122C  | LVTVSSACTKGPS | SEQ ID NO:14   |
| A175C  | HTFPCVLQSSGLYS| SEQ ID NO:15   |
| S179C  | HTFPAVLQCSGLYS| SEQ ID NO:16   |

According to another embodiment, the cysteine engineered thio-trastuzumab antibodies comprise one or more of the following variable region light chain sequences with a free cysteine amino acid (SEQ ID NOS: 17-27).

| Mutant | Sequence      | SEQ ID NO:     |
|--------|---------------|----------------|
| V15C   | SLSASCGDRVT   | SEQ ID NO:17   |
| A43C   | QKPGKCPKLLI   | SEQ ID NO:18   |
| V110C  | EIKRTCAAPSV   | SEQ ID NO:19   |
| S114C  | TCAAPCVFIFPP  | SEQ ID NO:20   |
| S121C  | FIFPPCDEQLK   | SEQ ID NO:21   |
| S127C  | DEQLKCGTASV   | SEQ ID NO:22   |
| A144C  | FYPRECKVQWK   | SEQ ID NO:23   |
| A153C  | WKVDNCLQSGN   | SEQ ID NO:24   |
| N158C  | ALQSGCSQESV   | SEQ ID NO:25   |
| S168C  | VTEQDCKDSTY   | SEQ ID NO:26   |
| V205C  | GLSSPCTKSFN   | SEQ ID NO:27   |

Figure 13B:
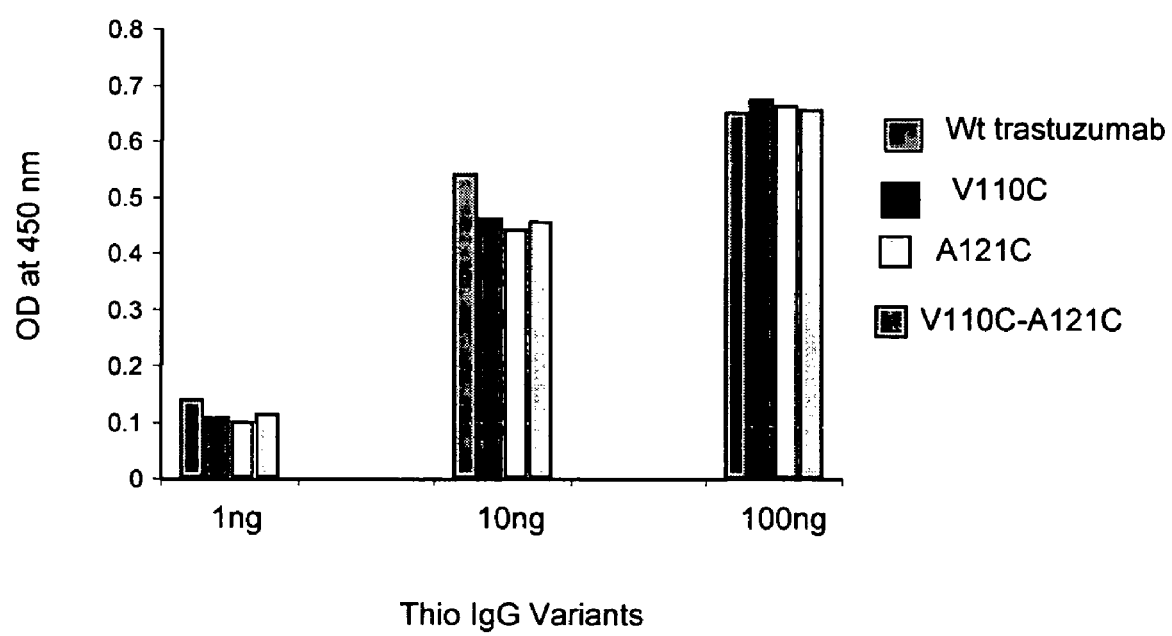
FIG. 13B shows binding measurements with detection of absorbance at 450 nm of biotin-maleimide conjugated thio-trastuzumab variants and non-biotinylated wild type trastuzumab in binding to immobilized HER2. From left to right: V110C (single cys), A121C (single cys), V110C/A121C (double cys), and trastuzumab. Each thio IgG variant and trastuzumab was tested at 1, 10, and 100 ng.

The resulting full-length, thio-trastuzumab IgG variants were assayed for thiol reactivity and HER2 binding activity. FIG. 13A shows a cartoon depiction of biotinylated antibody binding to immobilized HER2 and HRP labeled secondary antibody for absorbance detection. FIG. 13B shows binding measurements to immobilized HER2 with detection of absorbance at 450 nm of (left to right): non-biotinylated wild type trastuzumab (Wt), biotin-maleimide conjugated thio-trastuzumab variants V110C (single cys), A121C (single cys), and V110C-A121C (double cys). Each thio IgG variant and trastuzumab was tested at 1, 10, and 100 ng. The measurements show that biotinylated anti-HER2 ThioMabs retain HER2 binding activity.

Figure 14A:
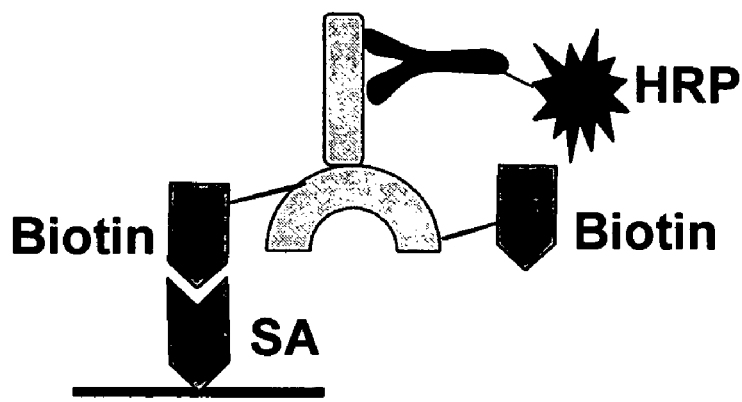
FIG. 14A shows a cartoon depiction of biotinylated antibody binding to immobilized HER2 with binding of biotin to anti-IgG-HRP for absorbance detection.
Figure 14B:
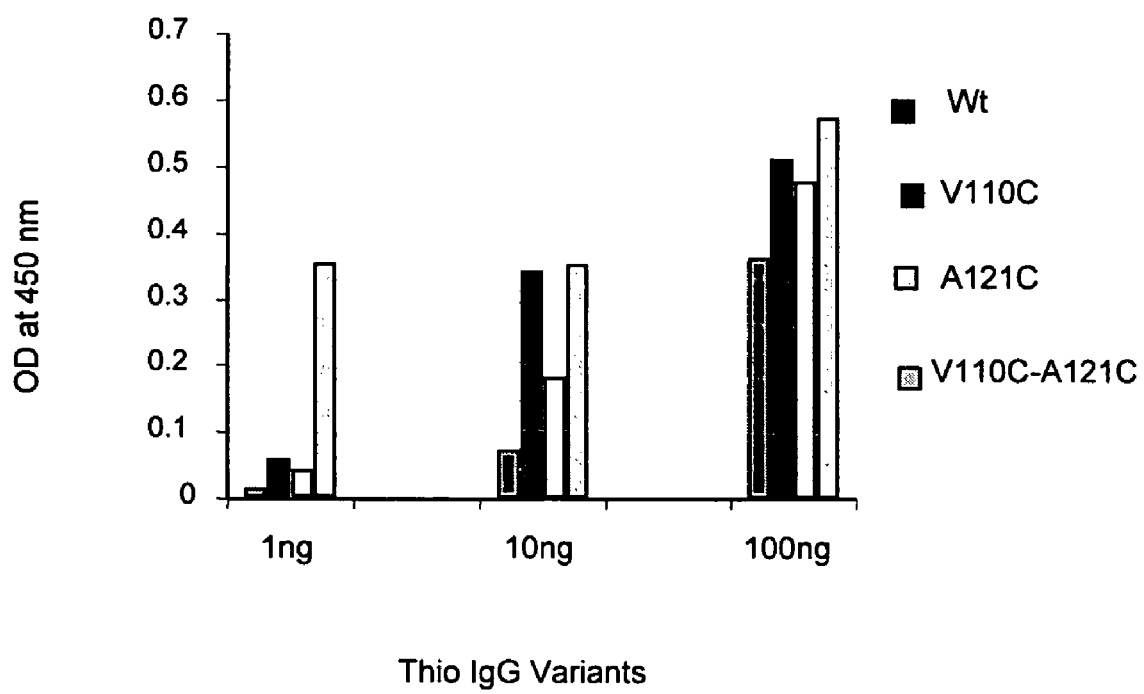
FIG. 14B shows binding measurements with detection of absorbance at 450 nm of biotin-maleimide conjugated-thio trastuzumab variants and non-biotinylated wild type trastuzumab in binding to immobilized streptavidin. From left to right: V110C (single cys), A121C (single cys), V110C/A121C (double cys), and trastuzumab. Each thio IgG variant and trastuzumab was tested at 1, 10, and 100 ng.

FIG. 14A shows a cartoon depiction of a biotinylated antibody binding to immobilized HER2 with binding of biotin to anti-IgG-HRP for absorbance detection. FIG. 14B shows binding measurements with detection of absorbance at 450 nm of biotin-maleimide conjugated thio-trastuzumab variants and non-biotinylated wild type trastuzumab in binding to streptavidin. From left to right: V110C (single cys), A121C (single cys), V110C/A121C (double cys), and trastuzumab. Each thio IgG trastuzumab variant and parent trastuzumab was tested at 1, 10, and 100 ng. The measurements show that the HER2 ThioMabs have high thiol reactivity.

Cysteine was introduced into the full-length 2H9 anti-EphB2R antibody at certain residues. The single cys mutant H-A121C of 2H9 was expressed in CHO (Chinese Hamster Ovary) cells by transient fermentation in media containing 1 mM cysteine. The A121C 2H9 mutant heavy chain sequence (450 aa) is SEQ ID NO:28.

```
EVQLVESGGGLVQPGGSLRLSCAASGYTFTSYWMHWV   SEQ ID NO:28

RQAPGKGLEWVGFINPSTGYTDYNQKFKDRFTISADT

SKNTAYLQMNSLRAEDTAVYYCTRRPKIPRHANVFWG

QGTLVTVSSCSTKGPSVFPLAPSSKSTSGGTAALGCL

VKDYFPEPVTVSWNSGALTSGVHTFPAVLQSSGLYSL

SSVVTVPSSSLGTQTYICNVNHKPSNTKVDKKVEPKS

CDKTHTCPPCPAPELLGGPSVFLFPPKPKDTLMISRT
```

```
                                    -continued
PEVTCVVVDVSHEDPEVKFNWYVDGVEVHNAKTKPRE

EQYNSTYRVVSVLTVLHQDWLNGKEYKCKVSNKALPA

PIEKTISKAKGQPREPQVYTLPPSREEMTKNQVSLTC

LVKGFYPSDIAVEWESNGQPENNYKTTPPVLDSDGSF

FLYSKLTVDKSRWQQGNVFSCSVMHEALHNHYTQKSL

SLSPGK
```

Cysteine engineered thio-2H9 antibodies comprise the following Fc constant region heavy chain sequences with a free cysteine amino acid (SEQ ID NOS: 29-38).

| Mutant | Sequence | SEQ ID NO: |
|---|---|---|
| V273C | HEDPECKFNWYVDGVEVHNAKTKPR | SEQ ID NO:29 |
| V279C | HEDPEVKFNWYCDGVEVHNAKTKPR | SEQ ID NO:30 |
| V282C | HEDPEVKFNWYVDGCEVHNAKTKPR | SEQ ID NO:31 |
| V284C | HEDPEVKFNWYVDGVECHNAKTKPR | SEQ ID NO:32 |
| A287C | HEDPEVKFNWYVDGVEVHNCKTKPR | SEQ ID NO:33 |
| S324C | YKCKVCNKALP | SEQ ID NO:34 |
| S337C | IEKTICKAKGQPR | SEQ ID NO:35 |
| A339C | IEKTISKCKGQPR | SEQ ID NO:36 |
| S375C | KGFYPCDIAVE | SEQ ID NO:37 |
| S400C | PPVLDCDGSFF | SEQ ID NO:38 |

Figure 16:
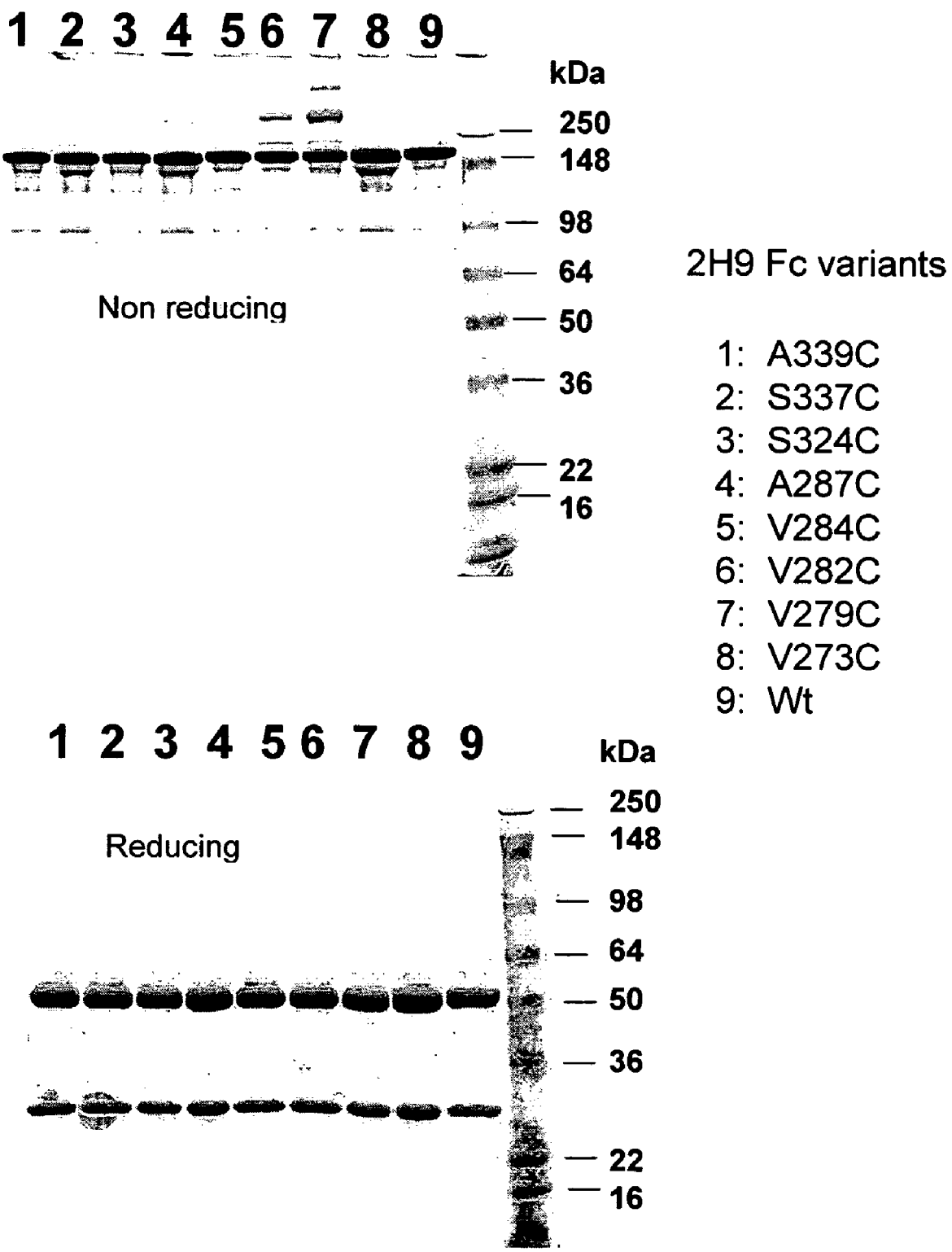
FIG. 16 shows non-reducing (top) and reducing (bottom) denaturing polyacrylamide gel electrophoresis analysis of 2H9 ThioMab Fc variants (left to right, lanes 1-9): A339C; S337C; S324C; A287C; V284C; V282C; V279C; V273C, and 2H9 wild type after purification on immobilized Protein A. The lane on the right is a size marker ladder, indicating the intact proteins are about 150 kDa, heavy chain fragments about 50 kDa, and light chain fragments about 25 kDa.
Figure 17A:
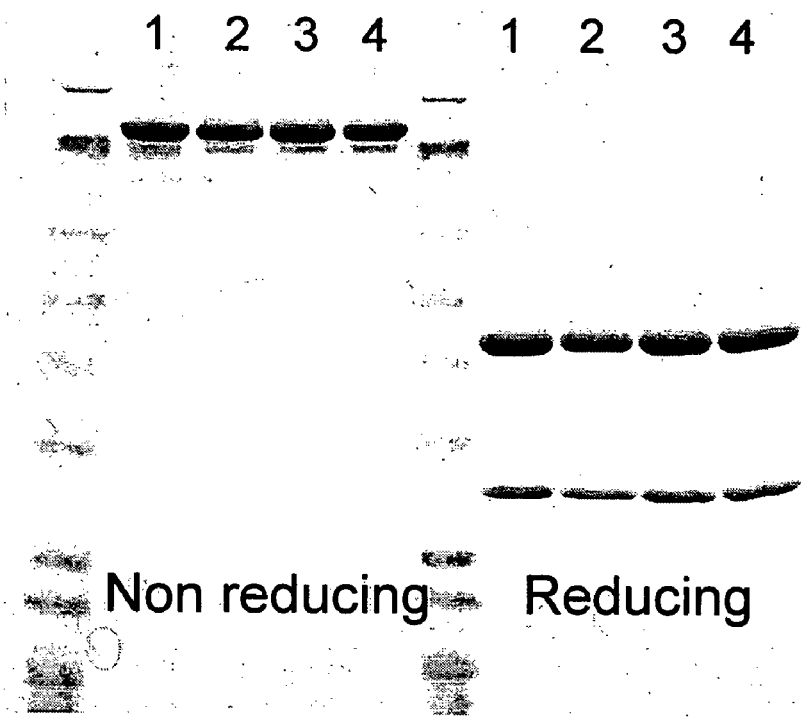
FIG. 17A shows non-reducing (left) and reducing (+DTT) (right) denaturing polyacrylamide gel electrophoresis analysis of 2H9 ThioMab variants (left to right, lanes 1-4): L-V15C; S179C; S375C; S400C, after purification on immobilized Protein A.
Figure 17B:
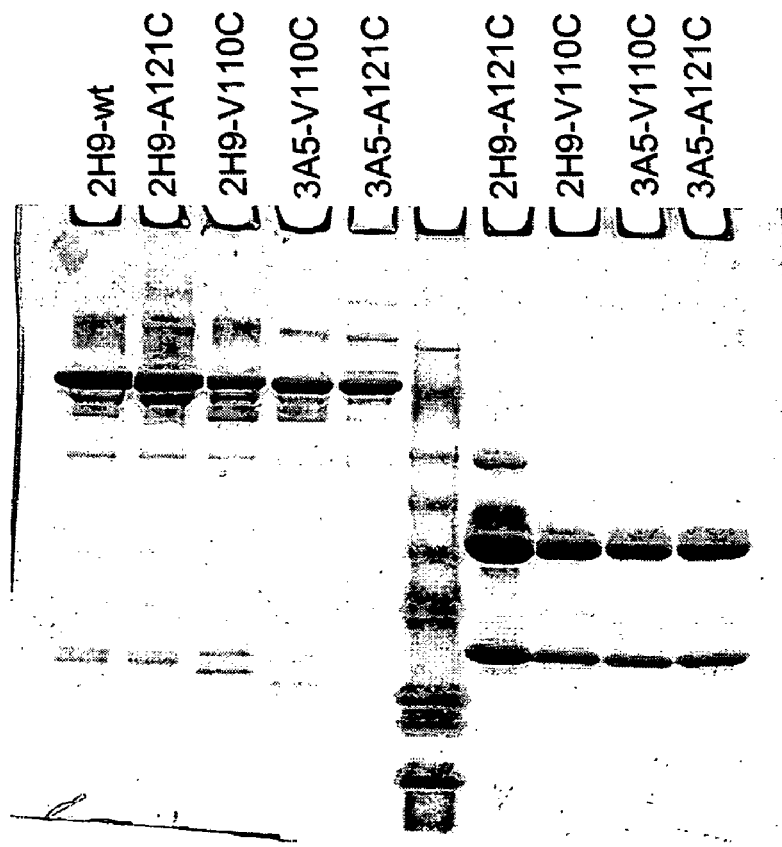
FIG. 17B shows non-reducing (left) and reducing (+DTT) (right) denaturing polyacrylamide gel electrophoresis analysis of 2H9 and 3A5 ThioMab variants after purification on immobilized Protein A.

FIG. 16 shows non-reducing (top) and reducing (bottom) denaturing SDS-PAGE (polyacrylamide gel electrophoresis) analysis of 2H9 ThioMab Fc variants (left to right, lanes 1-9): A339C; S337C; S324C; A287C; V284C; V282C; V279C; and V273C, with 2H9 wild type, after purification on immobilized Protein A. The lane on the right is a size marker ladder, indicating the intact proteins are about 150 kDa, heavy chain fragments about 50 kDa, and light chain fragments about 25 kDa. FIG. 17A shows non-reducing (left) and reducing (right) denaturing polyacrylamide gel electrophoresis analysis of 2H9 ThioMab variants (left to right, lanes 1-4): L-V15C; S179C; S375C; S400C, after purification on immobilized Protein A. FIG. 17B shows non-reducing (left) and reducing (+DTT) (right) denaturing polyacrylamide gel electrophoresis analysis of additional 2H9 and 3A5 ThioMab variants after purification on immobilized Protein A. The 2H9 ThioMab variants (in the Fab as well as Fc region) were expressed and purified as described. As seen in FIGS. 16, 17A and 17B, all the proteins are homogenous on SDS-PAGE followed by the reduction and oxidation procedure of Example 11 to prepare reactive ThioMabs for conjugation (Example 12).

Cysteine was introduced into the full-length 3A5 anti-MUC16 antibody at certain residues. The single cys mutant H-A121C of 3A5 was expressed in CHO (Chinese Hamster Ovary) cells by transient fermentation in media containing 1 mM cysteine. The A121C 3A5 mutant heavy chain sequence (446 aa) comprises SEQ ID NO:39.

```
DVQLQESGPGLVNPSQSLSLTCTVTGYSITNDYAWNW     SEQ ID NO:39

IRQFPGNKLEWMGYINYSGYTTYNPSLKSRISITRDT

SKNQFFLHLNSVTTEDTATYYCARWDGGLTYWGQGTL

VTVSACSTKGPSVFPLAPSSKSTSGGTAALGCLVKDY

FPEPVTVSWNSGALTSGVHTFPAVLQSSGLYSLSSVV

TVPSSSLGTQTYICNVNHKPSNTKVDKKVEPKSCDKT

HTCPPCPAPELLGGPSVFLFPPKPKDTLMISRTPEVT

CVVVDVSHEDPEVKFNWYVDGVEVHNAKTKPREEQYN

STYRVVSVLTVLHQDWLNGKEYKCKVSNKALPAPIEK

TISKAKGQPREPQVYTLPPSREEMTKNQVSLTCLVKG

FYPSDIAVEWESNGQPENNYKTTPPVLDSDGSFFLYS

KLTVDKSRWQQGNVFSCSVMHEALHNHYTQKSLSLSP

GK
```

Cysteine engineered thio-3A5 anti-MUC16 antibodies comprise the following variable region heavy chain sequences with a free cysteine amino acid (SEQ ID NOS: 40-44).

| Mutant | Sequence | SEQ ID NO: |
|---|---|---|
| F45C | NWIRQCPGNK | SEQ ID NO:40 |
| A90C | LNSCTTEDTAT | SEQ ID NO:41 |
| A121C | GQGTLVTVSACSTKGPSVFPL | SEQ ID NO:42 |
| A175C | HTFPCVLQSSGLYS | SEQ ID NO:43 |
| V176C | HTFPACLQSSGLYS | SEQ ID NO:44 |

Cysteine engineered thio-3A5 anti-MUC16 antibodies comprise the following variable region light chain sequences with a free cysteine amino acid (SEQ ID NOS: 45-49).

| Mutant | Sequence | SEQ ID NO: |
|---|---|---|
| L15C | FLSVSCGGRVT | SEQ ID NO:45 |
| A43C | QKPGNCPRLLI | SEQ ID NO:46 |
| V110C | EIKRTCAAPSV | SEQ ID NO:47 |
| A144C | FYPRECKVQWK | SEQ ID NO:48 |
| S168C | VTEQDCKDSTY | SEQ ID NO:49 |

Thiol Reactivity of Thiomabs

Figure 18:
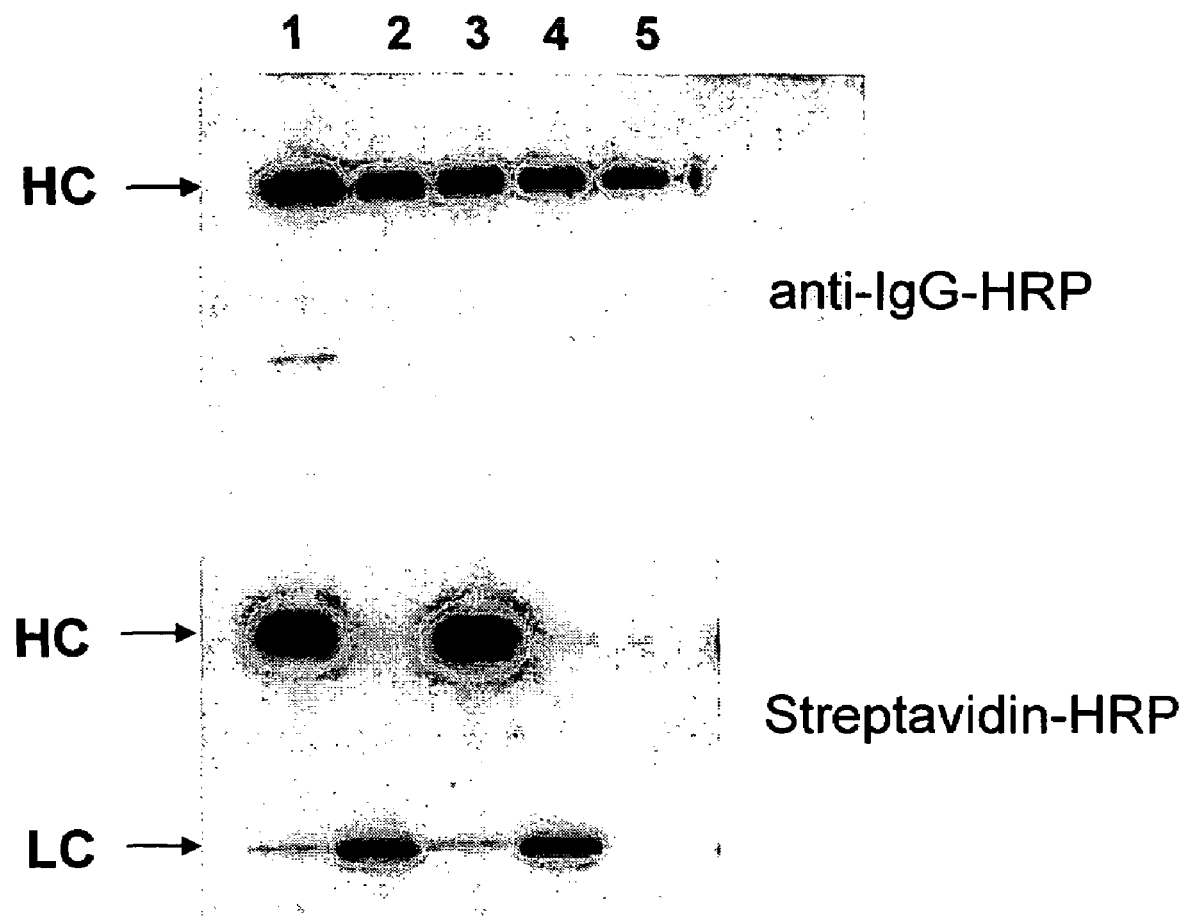
FIG. 18 shows western blot analysis of biotinylated Thio-IgG variants. 2H9 and 3A5 ThioMab variants were analyzed on reduced denaturing polyacrylamide gel electrophoresis, the proteins were transferred to nitrocellulose membrane. The presence of antibody and conjugated biotin were probed with anti-IgG-HRP (top) and streptavidin-HRP (bottom), respectively. Lane 1: 3A5H-A121C. Lane 2: 3A5 L-V110C. Lane3: 2H9H-A121C. Lane4: 2H9L-V110C. Lane5: 2H9 wildtype.

The thiol reactivity of full length, IgG cysteine engineered antibodies (ThioMabs) was measured by biotinylation and streptavidin binding. A western blot assay was set up to screen the ThioMab that is specifically conjugated with biotin-maleimide. In this assay, the antibodies are analyzed on reducing SDS-PAGE and the presence of Biotin is specifically probed by incubating with streptavidin-HRP. As seen from FIG. 18, the streptavidin-HRP interaction is either observed in heavy chain or light chain depending on which engineered cys variant is being used and no interaction is seen with wild type, indicating that ThioMab variants specifically conjugated the biotin at engineered Cys residue. FIG. 18 shows denaturing gel analysis of reduced, biotinylated Thio-IgG variants after capture on immobilized anti-IgG-HRP (top gel) and streptavidin-HRP (bottom gel). Lane 1: 3A5H-A121C. Lane 2: 3A5 L-V110C. Lane 3: 2H9H-A121C. Lane 4: 2H9 L-V110C. Lane 5: anti-EphB2R 2H9 parent, wild type. Each mutant (lanes 1-4) was captured by anti-IgG with HRP detection (top) indicating that selectivity and affinity were retained. Capture by immobilized streptavidin with HRP detection (bottom) confirmed the location of biotin on heavy and light chains. The location of cysteine mutation on the cysteine engineered antibodies in lanes 1 and 3 is the heavy chain. The location of cysteine mutation on the cysteine engineered antibodies in lanes 2 and 4 is the light chain. The cysteine mutation site undergoes conjugation with the biotin-maleimide reagent.

Analysis of the ThioMab cysteine engineered antibodies of FIG. 18 and a 2H9 V15C variant by LC/MS gave quantitative indication of thiol reactivity (Table 5).

TABLE 5

LC/MS quantitation of biotinylation of ThioMabs - Thiol reactivity

| ThioMab variant | number of biotin per ThioMab |
|---|---|
| 2H9 wt | 0.0 |
| 2H9 L-V15C | 0.6 |
| 2H9 L-V110C | 0.5 |
| 2H9 H-A121C | 2.0 |
| 3A5 L-V110C | 1.0 |
| 3A5 H-A121C | 2.0 |

Figure 19:
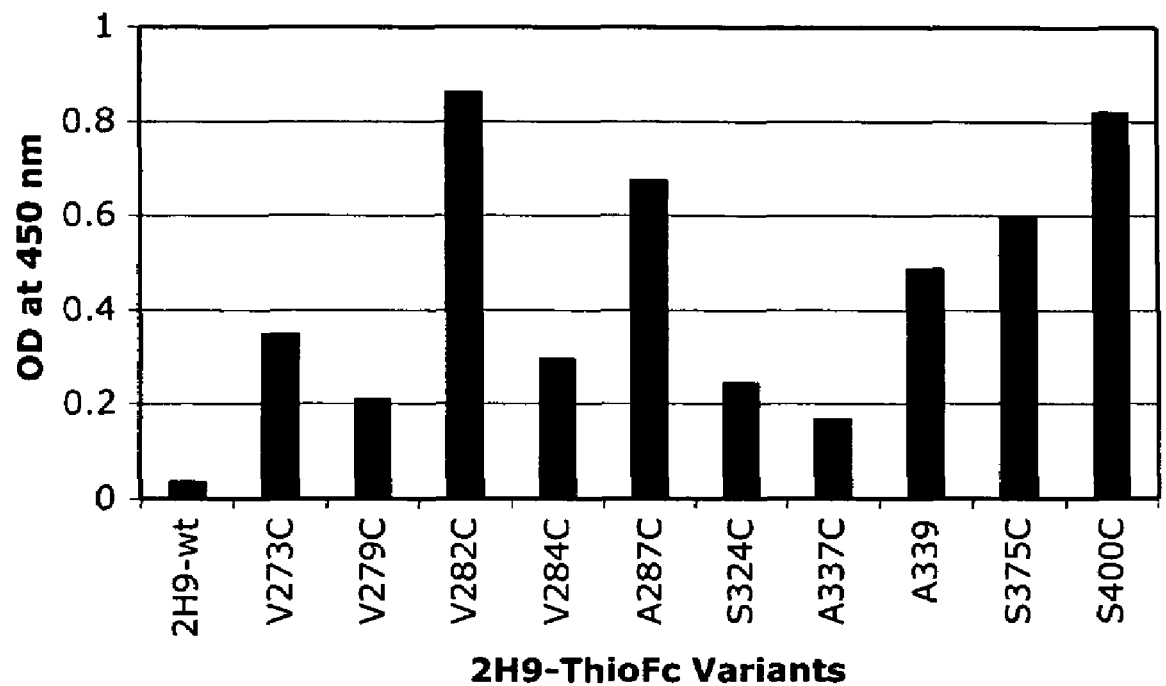
FIG. 19 shows ELISA analysis for the binding of biotinylated 2H9 variants to streptavidin by probing with anti-IgG-HRP and measuring the absorbance at 450 nm of (top bar diagram). Bottom schematic diagram depicts the experimental design used in the ELISA analysis.
Figure 19:
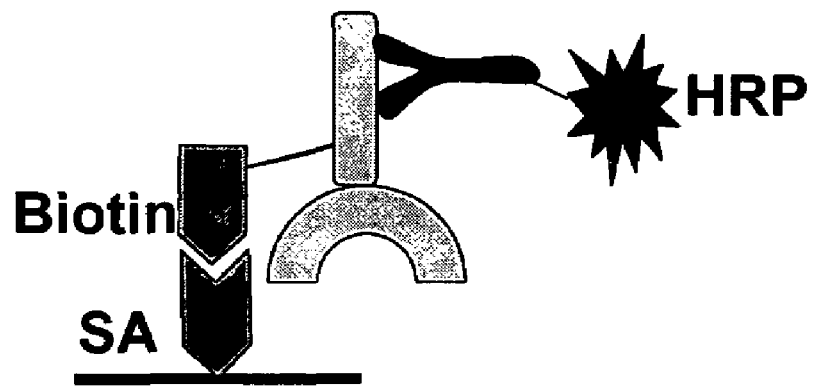

Cysteine engineering was conducted in the constant domain, i.e. Fc region, of IgG antibodies. A variety of amino acid sites were converted to cysteine sites and the expressed mutants, i.e. cysteine engineered antibodies, were assessed for their thiol reactivity. Biotinylated 2H9 ThioMab Fc variants were assessed for thiol reactivity by HRP quantitation by capture on immobilized streptavidin in an ELISA assay (FIG. 19). An ELISA assay was established to rapidly screen the Cys residues with reactive Thiol groups. As depicted in FIG. 19 schematic diagram, the streptavidin-biotin interaction is monitored by probing with anti-IgG-HRP followed by measuring absorbance at 450 nm. These results confirmed 2H9-ThioFc variants V282C, A287C, A339C, S375C and S400C had moderate to highest Thiol reactivity. The extent of biotin conjugation of 2H9 ThioMab Fc variants was quantitated by LS/MS analysis as reported in Table 6. The LS/MS analysis confirmed that the A282C, S375C and S400C variants had 100% biotin conjugation and V284C and A339C had 50% conjugation, indicating the presence of a reactive cysteine thiol group. The other ThioFc variants, and the parent, wild type 2H9, had either very little biotinylation or none.

TABLE 6

LC/MS quantitation of biotinylation of 2H9 Fc ThioMabs

| 2H9 ThioMab Fc variant | % biotinylation |
|---|---|
| V273C | 0 |
| V279C | 31 |
| V282C | 100 |
| V284C | 50 |
| A287C | 0 |
| S324C | 71 |
| S337C | 0 |
| A339C | 54 |

TABLE 6-continued

LC/MS quantitation of biotinylation of 2H9 Fc ThioMabs

| 2H9 ThioMab Fc variant | % biotinylation |
|---|---|
| S375C | 100 |
| S400C | 100 |
| (wild type 2H9) | 0 |

Thiol Reactivity of Thio-4D5 Fab Light Chain Variants

Screening of a variety of cysteine engineered light chain variant Fabs of the antiErbB2 antibody 4D5 gave a number of variants with a thiol reactivity value of 0.6 and higher (Table 7), as measured by the PHESELECTOR assay of FIG. 8. The thiol reactivity values of Table 7 are normalized to the heavy chain 4D5 ThioFab variant (HC-A121C) which is set at 100%, assuming complete biotinylation of HC-A121C variant, and represented as percent values.

TABLE 7

Thiol reactivity percent values of 4D5 ThioFab light chain variants

| 4D5 ThioFab variant | Thiol reactivity value (%) |
|---|---|
| V15C | 100 |
| V110C | 95 |
| S114C | 78 |
| S121C | 75 |
| S127C | 75 |
| A153C | 82 |
| N158C | 77 |
| V205C | 78 |
| (HC-A121C) | 100 |
| (4D5 wild type) | 25 |

Antibody-Drug Conjugates

The cysteine engineered antibodies of the invention may be conjugated with any therapeutic agent, i.e. drug moiety, which can be covalently attached to the antibody through a reactive cysteine thiol group.

An exemplary embodiment of an antibody-drug conjugate (ADC) compound comprises a cysteine engineered antibody (Ab), and a drug moiety (D) wherein the antibody has one or more free cysteine amino acids having a thiol reactivity value in the range of 0.6 to 1.0, and the antibody is attached through the one or more free cysteine amino acids by a linker moiety (L) to D; the composition having Formula I:

Ab-(L-D)$_p$    I where p is 1, 2, 3, or 4. The number of drug moieties which may be conjugated via a thiol reactive linker moiety to an antibody molecule is limited by the number of cysteine residues which are introduced by the methods described herein. Exemplary ADC of Formula I therefore comprise antibodies which have 1, 2, 3, or 4 engineered cysteine amino acids.

Another exemplary embodiment of an antibody-drug conjugate compound (ADC) comprises a cysteine engineered antibody (Ab), an albumin-binding peptide (ABP) and a drug moiety (D) wherein the antibody is attached to the drug moiety by a linker moiety (L) and the antibody is attached to the albumin-binding peptide by an amide bond or a second linker moiety; the composition having Formula Ia:

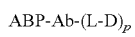

ABP-Ab-(L-D)$_p$    Ia where p is 1,2,3, or 4.

The ADC compounds of the invention include those with utility for anticancer activity. In particular, the compounds include a cysteine-engineered antibody conjugated, i.e. covalently attached by a linker, to a drug moiety, i.e. toxin. When the drug is not conjugated to an antibody, the drug has a cytotoxic or cytostatic effect. The biological activity of the drug moiety is thus modulated by conjugation to an antibody. The antibody-drug conjugates (ADC) of the invention selectively deliver an effective dose of a cytotoxic agent to tumor tissue whereby greater selectivity, i.e. a lower efficacious dose, may be achieved.

In one embodiment, the bioavailability of the ADC of the invention, or an intracellular metabolite of the ADC, is improved in a mammal when compared to a drug compound comprising the drug moiety of the ADC. Also, the bioavailability of the ADC, or an intracellular metabolite of the ADC is improved in a mammal when compared to the analog of the ADC not having the drug moiety.

Drug Moieties

The drug moiety (D) of the antibody-drug conjugates (ADC) includes any compound, moiety or group which has a cytotoxic or cytostatic effect. Drug moieties include: (i) chemotherapeutic agents, which may function as microtubulin inhibitors, mitosis inhibitors, topoisomerase inhibitors, or DNA intercalators; (ii) protein toxins, which may function enzymatically; and (iii) radioisotopes.

Exemplary drug moieties include, but are not limited to, a maytansinoid, an auristatin, a dolastatin, a trichothecene, CC1065, a calicheamicin and other enediyne antibiotics, a taxane, an anthracycline, and stereoisomers, isosteres, analogs or derivatives thereof.

Maytansine compounds suitable for use as maytansinoid drug moieties are well known in the art, and can be isolated from natural sources according to known methods, produced using genetic engineering techniques (see Yu et al (2002) PROC. NAT. ACAD. SCI. (USA) 99:7968-7973), or maytansinol and maytansinol analogues prepared synthetically according to known methods.

Exemplary maytansinoid drug moieties include those having a modified aromatic ring, such as: C-19-dechloro (U.S. Pat. No. 4,256,746) (prepared by lithium aluminum hydride reduction of ansamytocin P2); C-20-hydroxy (or C-20-demethyl) +/−C-19-dechloro (U.S. Pat. Nos. 4,361,650 and 4,307,016) (prepared by demethylation using *Streptomyces* or *Actinomyces* or dechlorination using LAH); and C-20-demethoxy, C-20-acyloxy (—OCOR), +/−dechloro (U.S. Pat. No. 4,294,757) (prepared by acylation using acyl chlorides) and those having modifications at other positions Exemplary maytansinoid drug moieties also include those having modifications such as: C-9-SH (U.S. Pat. No. 4,424,219) (prepared by the reaction of maytansinol with $H_2S$ or $P_2S_5$); C-14-alkoxymethyl(demethoxy/$CH_2$ OR)(U.S. Pat. No. 4,331,598); C-14-hydroxymethyl or acyloxymethyl ($CH_2OH$ or $CH_2OAc$) (U.S. Pat. No. 4,450,254) (prepared from *Nocardia*); C—l 5-hydroxy/acyloxy (U.S. Pat. No. 4,364,866) (prepared by the conversion of maytansinol by *Streptomyces*); C-15-methoxy (U.S. Pat. Nos. 4,313,946 and 4,315,929) (isolated from Trewia nudlflora); C-18-N-demethyl (U.S. Pat. Nos. 4,362,663 and 4,322,348) (prepared by the demethylation of maytansinol by *Streptomyces*); and 4,5-deoxy (U.S. Pat. No. 4,371,533) (prepared by the titanium trichloride/LAH reduction of maytansinol). Many positions on maytansine compounds are known to be useful as the linkage position, depending upon the type of link. For example, for forming an ester linkage, the C-3 position having a hydroxyl group, the C-14 position modified with hydroxymethyl, the C-15 position modified with a hydroxyl group and the C-20 position having a hydroxyl group are all suitable.

The drug moiety (D) of the antibody-drug conjugates (ADC) of Formula I include maytansinoids having the structure:

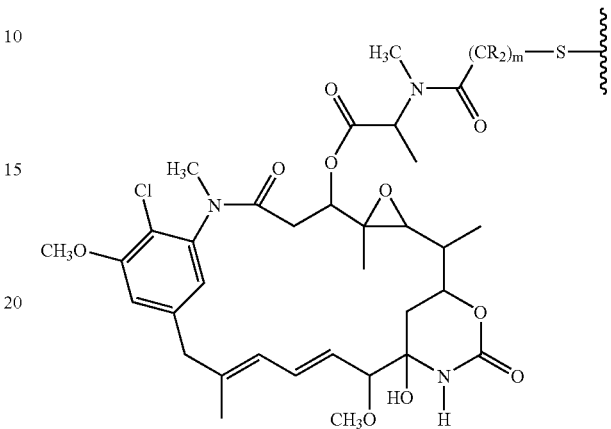

where the wavy line indicates the covalent attachment of the sulfur atom of D to a linker (L) of an antibody-drug conjugate (ADC). R may independently be H or a $C_1$-$C_6$ alkyl selected from methyl, ethyl, 1-propyl, 2-propyl, 1-butyl, 2-methyl-1-propyl, 2-butyl, 2-methyl-2-propyl, 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, and 3,3-dimethyl-2-butyl. The alkylene chain attaching the amide group to the sulfur atom may be methanyl, ethanyl, or propyl, i.e. m is 1, 2, or 3.

Maytansine compounds inhibit cell proliferation by inhibiting the formation of microtubules during mitosis through inhibition of polymerization of the microtubulin protein, tubulin (Remillard et al (1975) Science 189:1002-1005). Maytansine and maytansinoids are highly cytotoxic but their clinical use in cancer therapy has been greatly limited by their severe systemic side-effects primarily attributed to their poor selectivity for tumors. Clinical trials with maytansine had been discontinued due to serious adverse effects on the central nervous system and gastrointestinal system (Issel et al (1978) Can. Treatment. Rev. 5:199-207).

Maytansinoid drug moieties are attractive drug moieties in antibody-drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines (US 2005/0169933; WO 2005/037992; U.S. Pat. No. 5,208,020).

As with other drug moieties, all stereoisomers of the maytansinoid drug moiety are contemplated for the compounds of the invention, i.e. any combination of R and S configurations at the chiral carbons of D. In one embodiment, the maytansinoid drug moiety (D) will have the following stereochemistry:

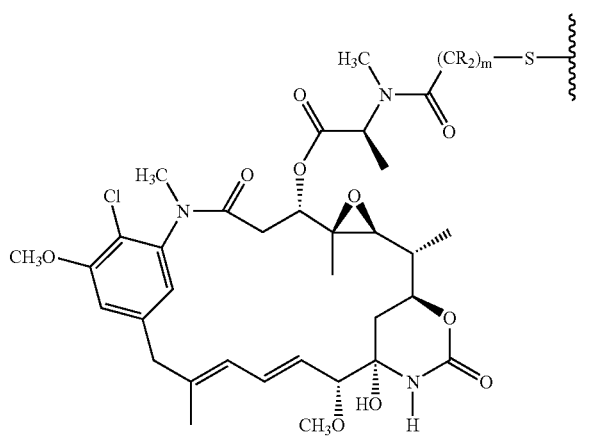

Exemplary embodiments of maytansinoid drug moieties include: DM1, $(CR_2)_m$=$CH_2CH_2$; DM3, $(CR_2)_m$= $CH_2CH_2CH(CH_3)$; and DM4, $(CR_2)_m$=$CH_2CH_2C(CH_3)_2$, having the structures:

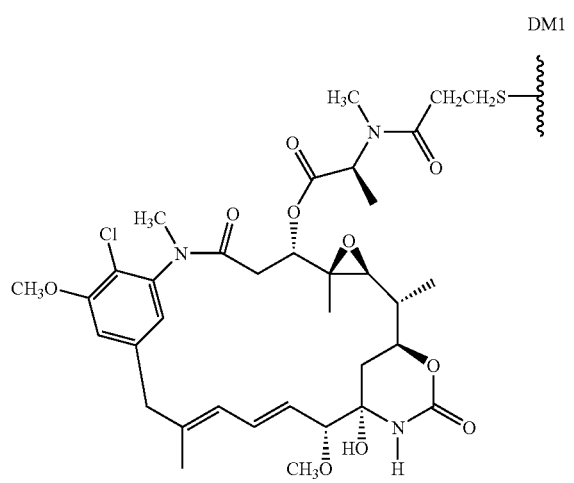

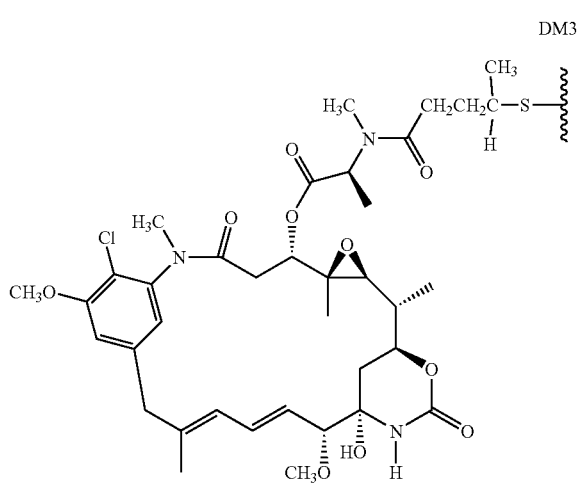

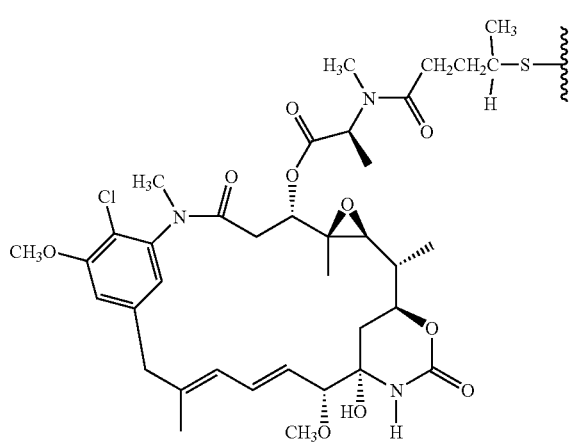

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

The drug moiety (D) of the antibody-drug conjugates (ADC) of Formula I also include dolastatins and their peptidic analogs and derivatives, the auristatins (U.S. Pat. Nos. 5,635, 483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). Various forms of a dolastatin or auristatin drug moiety may be covalently attached to an antibody through the N (amino) terminus or the C (carboxyl) terminus of the peptidic drug moiety (WO 02/088172; Doronina et al (2003) Nature Biotechnology 21(7):778-784; Francisco et al (2003) Blood 102 (4):1458-1465).

Drug moieties include dolastatins, auristatins (U.S. Pat. Nos. 5,635,483; 5,780,588; 5,767,237; 6,124,431), and analogs and derivatives thereof. Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in: WO 2005/081711; Senter et al, Proceedings of the American Association for Cancer Research, Volume 45, Abstract Number 623, presented Mar. 28, 2004, the disclosure of each which are expressly incorporated by reference in their entirety.

The drug moiety (D) of the antibody-drug conjugates (ADC) of Formula I include the monomethylauristatin drug moieties MMAE and MMAF linked through the N-terminus to the antibody, and having the structures:

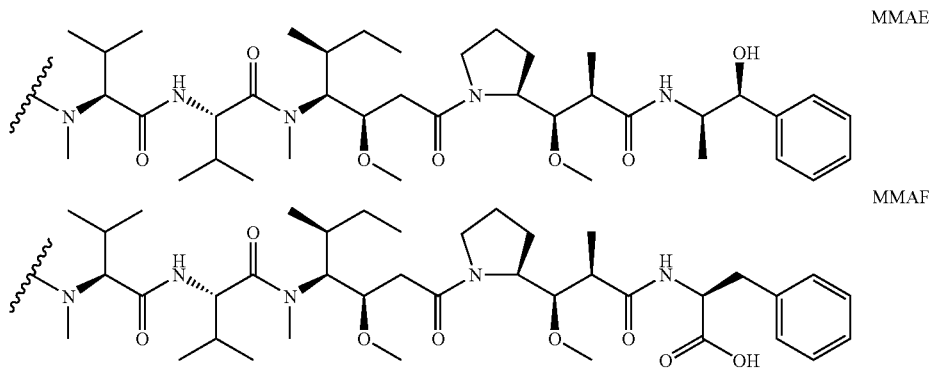

MMAE

MMAF

Typically, peptide-based drug moieties can be prepared by forming a peptide bond between two or more amino acids and/or peptide fragments. Such peptide bonds can be prepared, for example, according to the liquid phase synthesis method (see E. Schröder and K. Lüibke, "The Peptides", volume 1, pp 76-136, 1965, Academic Press) that is well known in the field of peptide chemistry.

The drug moiety includes calicheamicin, and analogs and derivatives thereof. The calicheamicin family of antibiotics are capable of producing double-stranded DNA breaks at sub-picomolar concentrations. For the preparation of conjugates of the calicheamicin family, see U.S. Pat. Nos. 5,712,374; 5,714,586; 5,739,116; 5,767,285; 5,770,701, 5,770,710; 5,773,001; 5,877,296. Structural analogues of calicheamicin which may be used include, but are not limited to, $\gamma_1^I$, $\alpha_2^I$, $\alpha_3^I$, N-acetyl-$\gamma_1^I$, PSAG and $\theta^I_1$ (Hinman et al Cancer Research 53:3336-3342 (1993), Lode et al Cancer Research 58:2925-2928 (1998).

Protein toxins include: diphtheria A chain, nonbinding active fragments of diphtheria toxin, exotoxin A chain (from *Pseudomonas aeruginosa*), ricin A chain (Vitetta et al (1987) Science, 238:1098), abrin A chain, modeccin A chain, alpha-sarcin, Aleurites fordii proteins, dianthin proteins, Phytolaca americana proteins (PAPI, PAPII, and PAP-S), momordica charantia inhibitor, curcin, crotin, sapaonaria officinalis inhibitor, gelonin, mitogellin, restrictocin, phenomycin, eno-mycin, and the tricothecenes (WO 93/21232).

Therapeutic radioisotopes include: $^{32}P$, $^{33}P$ $^{90}Y$ $^{125}I$, $^{131}I$, $^{131}In$, $^{153}Sm$, 186Re, $^{188}Re$, $^{211}At$, $^{212}Bi$, $^{212}Pb$, and radioactive isotopes of Lu.

The radioisotope or other labels may be incorporated in the conjugate in known ways (Fraker et al (1978) Biochem. Biophys. Res. Commun. 80: 49-57; "Monoclonal Antibodies in Immunoscintigraphy" Chatal, CRC Press 1989). Carbon-14-labeled 1-isothiocyanatobenzyl-3-methyldiethylene tri-aminepentaacetic acid (MX-DTPA) is an exemplary chelating agent for conjugation of a radionuclide to the antibody (WO 94/11026).

Linkers

A "Linker" (L) is a bifunctional or multifunctional moiety which can be used to link one or more Drug moieties (D) and an antibody unit (Ab) to form antibody-drug conjugates (ADC) of Formula I. Antibody-drug conjugates (ADC) can be conveniently prepared using a Linker having reactive functionality for binding to the Drug and to the Antibody. A cysteine thiol of a cysteine engineered antibody (Ab) can form a bond with a functional group of a linker reagent, a drug moiety or drug-linker intermediate.

In one aspect, a Linker has a reactive site which has an electrophilic group that is reactive to a nucleophilic cysteine present on an antibody. The cysteine thiol of the antibody is reactive with an electrophilic group on a Linker and forms a covalent bond to a Linker. Useful electrophilic groups include, but are not limited to, maleimide and haloacetamide groups.

Cysteine engineered antibodies react with linker reagents or drug-linker intermediates, with electrophilic functional groups such as maleimide or α-halo carbonyl, according to the conjugation method at page 766 of Klussman, et al (2004), Bioconjugate Chemistry 15(4):765-773, and according to the protocol of Example 4.

In one embodiment, linker L of an ADC has the formula:

$$-A_a\text{-}W_w\text{—}Y_y\text{—}$$

wherein:

-A- is a Stretcher unit covalently attached to a cysteine thiol of the antibody (Ab);

a is 0 or 1;

each —W— is independently an Amino Acid unit;

w is independently an integer ranging from 0 to 12;

—Y— is a Spacer unit covalently attached to the drug moiety; and y is 0, 1 or 2.

Stretcher Unit

The Stretcher unit (-A-), when present, is capable of linking an antibody unit to an amino acid unit (—W—). In this regard an antibody (Ab) has a free cysteine thiol group that can form a bond with an electrophilic functional group of a Stretcher Unit. Representative Stretcher units of this embodiment are depicted within the square brackets of Formulas IIIa and IIIb, wherein Ab-, —W—, —Y—, -D, w and y are as defined above, and $R^{17}$ is a divalent radical selected from $(CH_2)_r$, $C_3$-$C_8$ carbocyclyl, O—$(CH_2)_r$, arylene, $(CH_2)_r$-arylene, -arylene-$(CH_2)_r$—, $(CH_2)_r$—$(C_3$-$C_8$ carbocyclyl), $(C_3$-$C_8$ carbocyclyl)-$(CH_2)_r$, $C_3$-$C_8$ heterocyclyl, $(CH_2)_r$—$(C_3$-$C_8$ heterocyclyl), —$(C_3$-$C_8$ heterocyclyl)-$(CH_2)_r$—, —$(CH_2)_rC(O)NR^b(CH_2)_r$—, —$(CH_2CH_2O)_r$—, —$(CH_2CH_2O)_r$—$CH_2$—, —$(CH_2)_rC(O)NR^b(CH_2CH_2O)_r$—, —$(CH_2)_rC(O)NR^b(CH_2CH_2O)_rCH_2$—, —$(CH_2CH_2O)_rC(O)NR^b(CH_2CH_2O)_r$—, —$(CH_2CH_2O)_rC(O)NR^b(CH_2$ $CH_2O)_r$—$CH_2$—, and —$(CH_2CH_2O)_rC(O)NR^b(CH_2)_r$—; where $R^b$ is H, $C_1$-$C_6$ alkyl, phenyl, or benzyl; and r is independently an integer ranging from 1-10.

Arylene includes divalent aromatic hydrocarbon radicals of 6-20 carbon atoms derived by the removal of two hydrogen atoms from a parent aromatic ring system. Typical arylene groups include, but are not limited to, radicals derived from benzene, substituted benzene, naphthalene, anthracene, biphenyl, and the like.

Heterocyclyl groups include a ring system in which one or more ring atoms is a heteroatom, e.g. nitrogen, oxygen, and sulfur. The heterocycle radical comprises 1 to 20 carbon atoms and 1 to 3 heteroatoms selected from N, O, P, and S. A heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* (1960) 82:5566.

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4Ah-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

Carbocyclyl groups include a saturated or unsaturated ring having 3 to 7 carbon atoms as a monocycle or 7 to 12 carbon atoms as a bicycle. Monocyclic carbocycles have 3 to 6 ring atoms, still more typically 5 or 6 ring atoms. Bicyclic carbocycles have 7 to 12 ring atoms, e.g. arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cycloheptyl, and cyclooctyl.

It is to be understood from all the exemplary embodiments of Formula I ADC such as III-VI, that even where not denoted expressly, from 1 to 4 drug moieties are linked to an antibody (p=1-4), depending on the number of engineered cysteine residues.

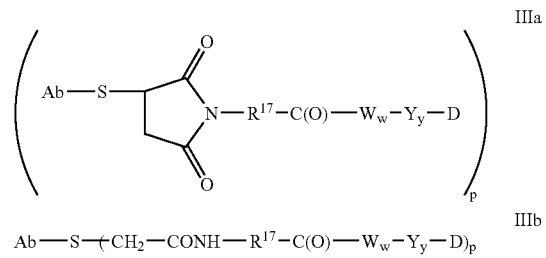

An illustrative Stretcher unit is that of Formula IIIa, and is derived from maleimido-caproyl (MC) wherein $R^{17}$ is —$(CH_2)_5$—:

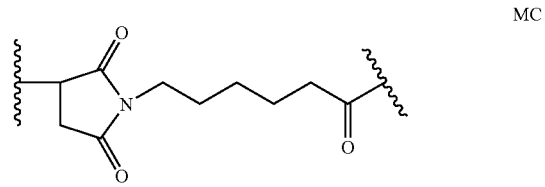

An illustrative Stretcher unit is that of Formula IIIa, and is derived from maleimido-propanoyl (MP) wherein $R^{17}$ is —$(CH_2)_2$—:

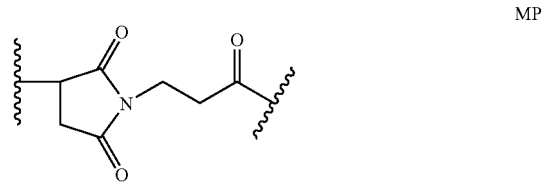

Another illustrative Stretcher unit is that of Formula IIIa wherein $R^{17}$ is —$(CH_2CH_2O)_r$—$CH_2$— and r is

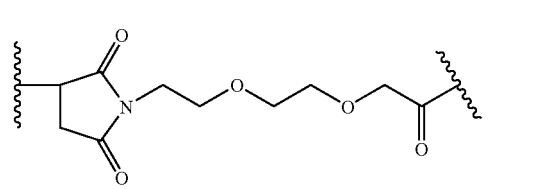

Another illustrative Stretcher unit is that of Formula IIIa wherein $R^{17}$ is —$(CH_2)_rC(O)NR^b(CH_2CH_2O)_r$—$CH_2$— where $R^b$ is H and each r is 2:

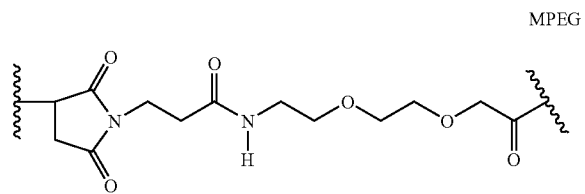

Another illustrative Stretcher unit is that of Formula IIIb wherein $R^{17}$ is —$(CH_2)_5$—:

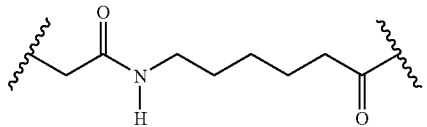

In another embodiment, the Stretcher unit is linked to the Antibody unit via a disulfide bond between a sulfur atom of the Antibody unit and a sulfur atom of the Stretcher unit. A representative Stretcher unit of this embodiment is depicted within the square brackets of Formula IV, wherein $R^{17}$, Ab-, —W—, —Y—, -D, w and y are as defined above.

Ab-S-(—S—$R^{17}$—C(O)—$W_w$—$Y_y$-D$)_p$    IV

In yet another embodiment, the reactive group of the Stretcher contains a thiol-reactive functional group that can form a bond with a free cysteine thiol of an antibody. Examples of thiol-reaction functional groups include, but are not limited to, maleimide, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates and isothiocyanates. Representative Stretcher units of this embodiment are depicted within the square brackets of Formulas Va and Vb, wherein —$R^{17}$—, Ab-, —W—, —Y—, -D, w and y are as defined above;

Ab-(—S—C(O)NH—$R^{17}$—C(O)—$W_w$—$Y_y$-D$)_p$    Va

Ab-(—S—C(S)NH—$R^{17}$—C(O)—$W_w$—$Y_y$-D$)_p$    Vb

In another embodiment, the linker may be a dendritic type linker for covalent attachment of more than one drug moiety through a branching, multifunctional linker moiety to an antibody (Sun et al (2002) Bioorganic & Medicinal Chemistry Letters 12:2213-2215; Sun et al (2003) Bioorganic & Medicinal Chemistry 11:1761-1768; King (2002) Tetrahedron Letters 43:1987-1990). Dendritic linkers can increase the molar ratio of drug to antibody, i.e. loading, which is related to the potency of the ADC. Thus, where a cysteine engineered antibody bears only one reactive cysteine thiol group, a multitude of drug moieties may be attached through a dendritic linker.

Amino Acid Unit

The linker may comprise amino acid residues. The Amino Acid unit (—$W_w$—), when present, links the antibody (Ab) to the drug moiety (D) of the cysteine engineered antibody-drug conjugate (ADC) of the invention.

—$W_w$— is a dipeptide, tripeptide, tetrapeptide, pentapeptide, hexapeptide, heptapeptide, octapeptide, nonapeptide, decapeptide, undecapeptide or dodecapeptide unit. Amino acid residues which comprise the Amino Acid unit include those occurring naturally, as well as minor amino acids and non-naturally occurring amino acid analogs, such as citrulline. Each —W— unit independently has the formula denoted below in the square brackets, and w is an integer ranging from 0 to 12:

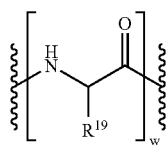

wherein $R^{19}$ is hydrogen, methyl, isopropyl, isobutyl, sec-butyl, benzyl, p-hydroxybenzyl, —$CH_2OH$, —$CH(OH)CH_3$, —$CH_2CH_2SCH_3$, —$CH_2CONH_2$, —$CH_2COOH$, —$CH_2CH_2CONH_2$, —$CH_2CH_2COOH$, —$(CH_2)_3NHC(=NH)NH_2$, —$(CH_2)_3NH_2$, —$(CH_2)_3NHCOCH_3$, —$(CH_2)_3NHCHO$, —$(CH_2)_4NHC(=NH)NH_2$, —$(CH_2)_4NH_2$, —$(CH_2)_4NHCOCH_3$, —$(CH_2)_4NHCHO$, —$(CH_2)_3NHCONH_2$, —$(CH_2)_4NHCONH_2$, —$CH_2CH_2CH(OH)CH_2NH_2$, 2-pyridylmethyl-, 3-pyridylmethyl-, 4-pyridylmethyl-, phenyl, cyclohexyl,

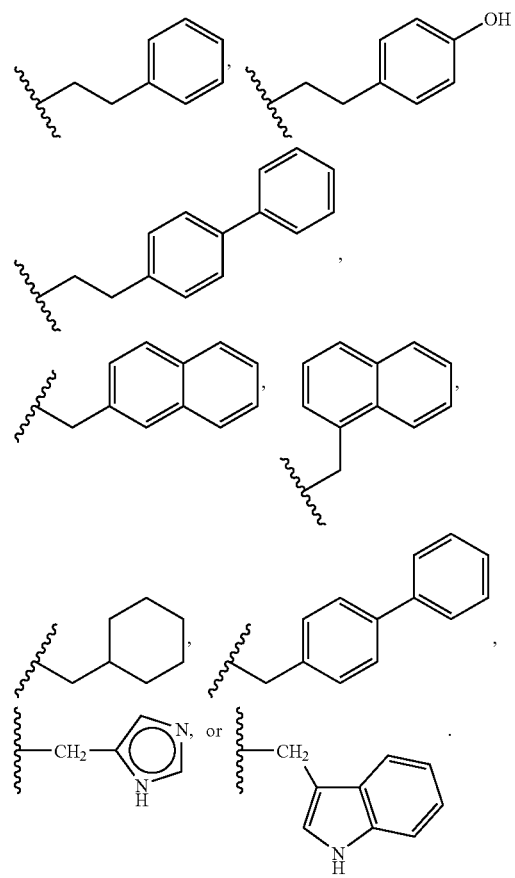

The Amino Acid unit can be enzymatically cleaved by one or more enzymes, including a tumor-associated protease, to liberate the Drug moiety (-D), which in one embodiment is protonated in vivo upon release to provide a Drug (D).

Useful —$W_w$— units can be designed and optimized in their selectivity for enzymatic cleavage by a particular enzymes, for example, a tumor-associated protease. In one embodiment, a —$W_w$— unit is that whose cleavage is catalyzed by cathepsin B, C and D, or a plasmin protease.

Exemplary —$W_w$— Amino Acid units include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly).

When $R^{19}$ is other than hydrogen, the carbon atom to which $R^{19}$ is attached is chiral. Each carbon atom to which $R^{19}$ is attached is independently in the (S) or (R) configuration, or a racemic mixture. Amino acid units may thus be enantiomerically pure, racemic, or diastereomeric.

Spacer Unit

The Spacer unit (—$Y_y$—), when present (y=1 or 2), links an Amino Acid unit (—$W_w$—) to the drug moiety (D) when an Amino Acid unit is present (w=1-12). Alternately, the Spacer unit links the Stretcher unit to the Drug moiety when the Amino Acid unit is absent. The Spacer unit also links the drug moiety to the antibody unit when both the Amino Acid unit and Stretcher unit are absent (w, y=0). Spacer units are of two general types: self-immolative and non self-immolative. A non self-immolative Spacer unit is one in which part or all of the Spacer unit remains bound to the Drug moiety after cleavage, particularly enzymatic, of an Amino Acid unit from the antibody-drug conjugate or the Drug moiety-linker. When an ADC containing a glycine-glycine Spacer unit or a glycine Spacer unit undergoes enzymatic cleavage via a tumor-cell associated-protease, a cancer-cell-associated protease or a lymphocyte-associated protease, a glycine-glycine-Drug moiety or a glycine-Drug moiety is cleaved from Ab-$A_a$-$W_w$—. In one embodiment, an independent hydrolysis reaction takes place within the target cell, cleaving the glycine-Drug moiety bond and liberating the Drug.

In another embodiment, —$Y_y$— is a p-aminobenzylcarbamoyl (PAB) unit (see Schemes 2 and 3) whose phenylene portion is substituted with $Q_m$ wherein Q is —$C_1$-$C_8$ alkyl, —O—($C_1$-$C_8$ alkyl), -halogen, -nitro or -cyano; and m is an integer ranging from 0-4.

Exemplary embodiments of a non self-immolative Spacer unit (—Y—) are: -Gly-Gly-; -Gly-; -Ala-Phe-; -Val-Cit-.

In one embodiment, a Drug moiety-linker or an ADC is provided in which the Spacer unit is absent (y=0), or a pharmaceutically acceptable salt or solvate thereof.

Alternatively, an ADC containing a self-immolative Spacer unit can release -D. In one embodiment, —Y— is a PAB group that is linked to —$W_w$— via the amino nitrogen atom of the PAB group, and connected directly to -D via a carbonate, carbamate or ether group, where the ADC has the exemplary structure:

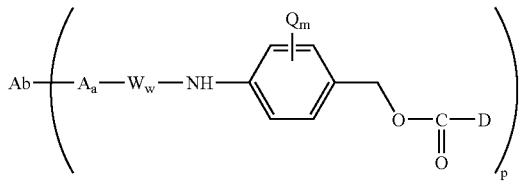

wherein Q is —$C_1$-$C_8$ alkyl, —O—($C_1$-$C_8$ alkyl), -halogen, -nitro or -cyano; m is an integer ranging from 0-4; and p ranges from 1 to 4.

Other examples of self-immolative spacers include, but are not limited to, aromatic compounds that are electronically similar to the PAB group such as 2-aminoimidazol-5-methanol derivatives (Hay et al. (1999) Bioorg. Med. Chem. Lett. 9:2237) and ortho or para-aminobenzylacetals. Spacers can be used that undergo cyclization upon amide bond hydrolysis, such as substituted and unsubstituted 4-aminobutyric acid amides (Rodrigues et al (1995) Chemistry Biology 2:223), appropriately substituted bicyclo[2.2.1] and bicyclo[2.2.2] ring systems (Storm et al (1972) J. Amer. Chem. Soc. 94:5815) and 2-aminophenylpropionic acid amides (Amsberry, et al (1990) J. Org. Chem. 55:5867). Elimination of amine-containing drugs that are substituted at glycine (Kingsbury et al (1984) J. Med. Chem. 27:1447) are also examples of self-immolative spacer useful in ADCs.

In one embodiment, the Spacer unit is a branched bis (hydroxymethyl)styrene (BHMS), which can be used to incorporate and release multiple drugs, having the structure:

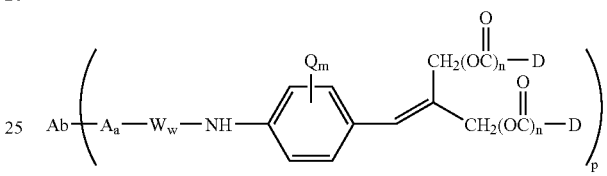

comprising a 2-(4-aminobenzylidene)propane-1,3-diol dendrimer unit (WO 2004/043493; de Groot et al (2003) Angew. Chem. Int. Ed. 42:4490-4494), wherein Q is —$C_1$-$C_8$ alkyl, —O—($C_1$-$C_8$ alkyl), -halogen, -nitro or -cyano; m is an integer ranging from 0-4; n is 0 or 1; and p ranges ranging from 1 to 4.

Dendritic Linkers

In another embodiment, linker L may be a dendritic type linker for covalent attachment of more than one drug moiety through a branching, multifunctional linker moiety to an antibody (Sun et al (2002) Bioorganic & Medicinal Chemistry Letters 12:2213-2215; Sun et al (2003) Bioorganic & Medicinal Chemistry 11:1761-1768). Dendritic linkers can increase the molar ratio of drug to antibody, i.e. loading, which is related to the potency of the ADC. Thus, where a cysteine engineered antibody bears only one reactive cysteine thiol group, a multitude of drug moieties may be attached through a dendritic linker.

The following exemplary embodiments of dendritic linker reagents allow up to nine nucleophilic drug moiety reagents to be conjugated by reaction with the chloroethyl nitrogen mustard functional groups:

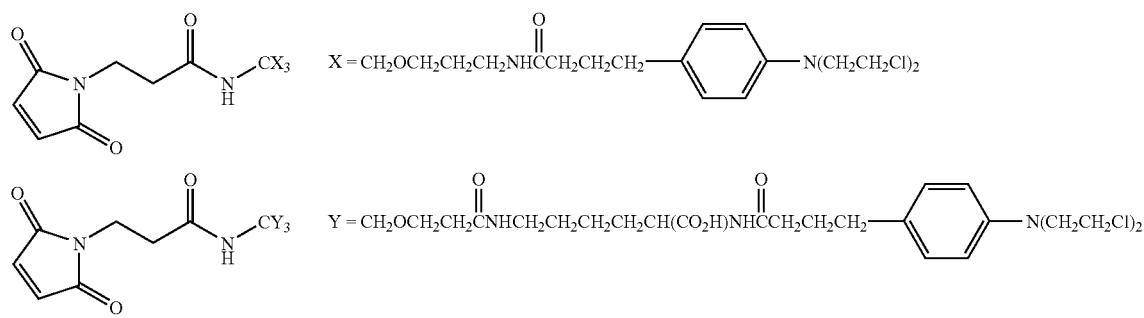

-continued

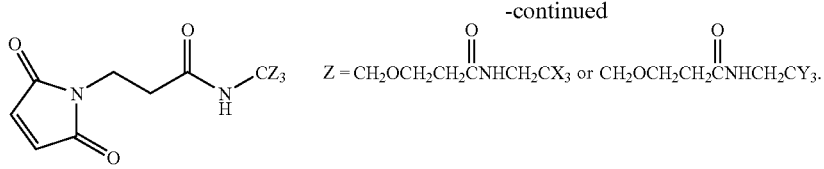

In another embodiment of a Spacer unit, branched, dendritic linkers with self-immolative 2,6-bis(hydroxymethyl)-p-cresol and 2,4,6-tris(hydroxymethyl)-phenol dendrimer units (WO 2004/01993; Szalai et al (2003) J. Amer. Chem. Soc. 125:15688-15689; Shamis et al (2004) J. Amer. Chem. Soc. 126:1726-1731; Amir et al (2003) Angew. Chem. Int. Ed. 42:4494-4499) may be employed as linkers in the compounds of the invention.

In another embodiment, the D moieties are the same.

In yet another embodiment, the D moieties are different.

In one aspect, Spacer units ($-Y_y-$) are represented by Formulas (X)-(XII):

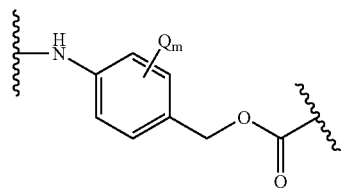

X wherein Q is $-C_1-C_8$ alkyl, $-O-(C_1-C_8$ alkyl), -halogen, -nitro or -cyano; and m is an integer ranging from 0-4;

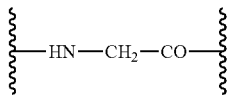

XI

XII

Embodiments of the Formula I antibody-drug conjugate compounds include XIIIa (val-cit), XIIIb (MC-val-cit), XIIIc (MC-val-cit-PAB):

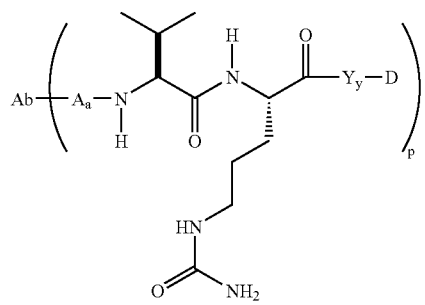

XIIIa

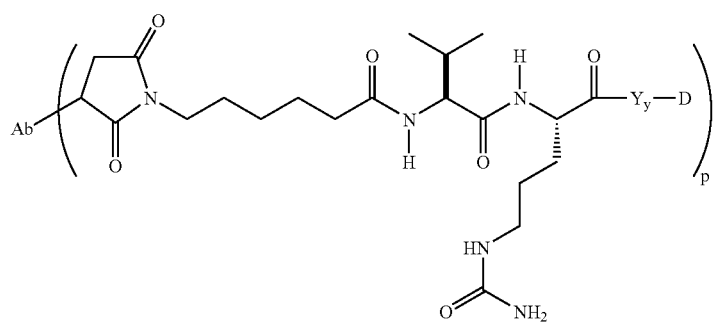

(XIIIb)

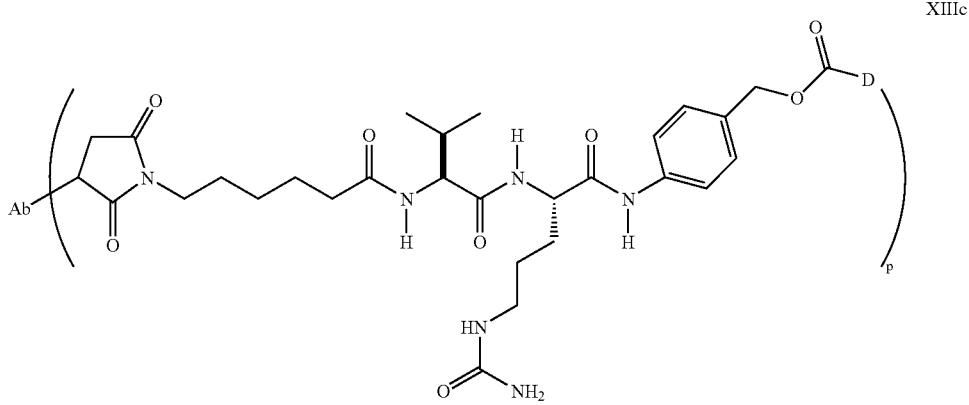

Other exemplary embodiments of the Formula Ia antibody-drug conjugate compounds include XIVa-e:

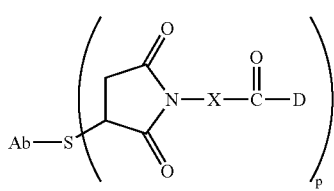   XIVa

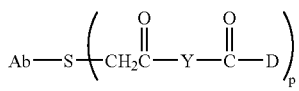   XIVb

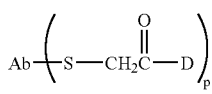   XIVc

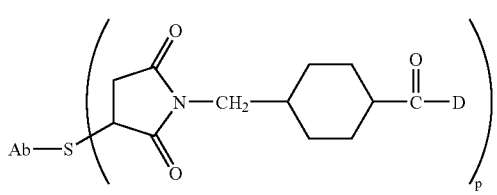   XIVd

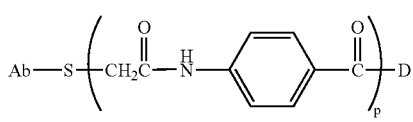   XIVe where X is:

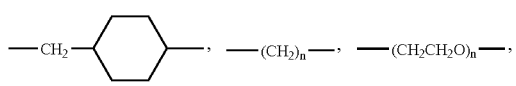

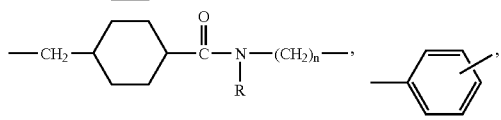

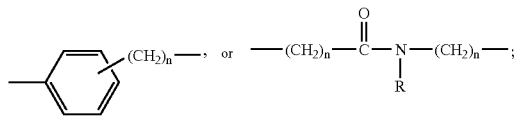

Y is:

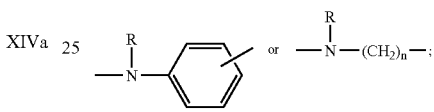

and R is independently H or $C_1$-$C_6$ alkyl; and n is 1 to 12.

In another embodiment, a Linker has a reactive functional group which has a nucleophilic group that is reactive to an electrophilic group present on an antibody. Useful electrophilic groups on an antibody include, but are not limited to, aldehyde and ketone carbonyl groups. The heteroatom of a nucleophilic group of a Linker can react with an electrophilic group on an antibody and form a covalent bond to an antibody unit. Useful nucleophilic groups on a Linker include, but are not limited to, hydrazide, oxime, amino, hydrazine, thiosemicarbazone, hydrazine carboxylate, and arylhydrazide. The electrophilic group on an antibody provides a convenient site for attachment to a Linker.

Typically, peptide-type Linkers can be prepared by forming a peptide bond between two or more amino acids and/or peptide fragments. Such peptide bonds can be prepared, for example, according to the liquid phase synthesis method (E. Schröder and K. Lüibke (1965) "The Peptides", volume 1, pp 76-136, Academic Press) which is well known in the field of peptide chemistry.

Linker intermediates may be assembled with any combination or sequence of reactions including Spacer, Stretcher, and Amino Acid units. The Spacer, Stretcher, and Amino Acid units may employ reactive functional groups which are electrophilic, nucleophilic, or free radical in nature. Reactive functional groups include, but are not limited to:

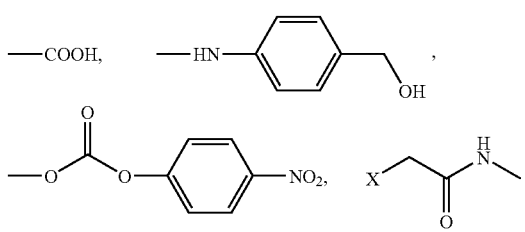

where X is a leaving group, e.g. O-mesyl, O-tosyl, —Cl, —Br, —I; or maleimide.

In another embodiment, the Linker may be substituted with groups which modulated solubility or reactivity. For example, a charged substituent such as sulfonate (—SO$_3^-$) or ammonium, may increase water solubility of the reagent and facilitate the coupling reaction of the linker reagent with the antibody or the drug moiety, or facilitate the coupling reaction of Ab-L (antibody-linker intermediate) with D, or D-L (drug-linker intermediate) with Ab, depending on the synthetic route employed to prepare the ADC.

The compounds of the invention expressly contemplate, but are not limited to, ADC prepared with linker reagents: BMPEO, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate), and including bis-maleimide reagents: DTME, BMB, BMDB, BMH, BMOE, BM(PEO)$_3$, and BM(PEO)$_4$, which are commercially available from Pierce Biotechnology, Inc., Customer Service Department, P.O. Box 117, Rockford, Ill. 61105 U.S.A, U.S.A 1-800-874-3723, International +815-968-0747. See pages 467-498, 2003-2004 Applications Handbook and Catalog. Bis-maleimide reagents allow the attachment of the thiol group of a cysteine engineered antibody to a thiol-containing drug moiety, label, or linker intermediate, in a sequential or concurrent fashion. Other functional groups besides maleimide, which are reactive with a thiol group of a cysteine engineered antibody, drug moiety, label, or linker intermediate include iodoacetamide, bromoacetamide, vinyl pyridine, disulfide, pyridyl disulfide, isocyanate, and isothiocyanate.

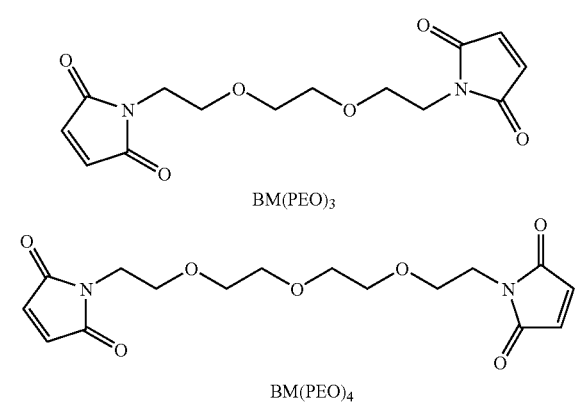

BM(PEO)$_3$

BM(PEO)$_4$

Useful linker reagents can also be obtained via other commercial sources, such as Molecular Biosciences Inc. (Boulder, Colo.), or synthesized in accordance with procedures described in Toki et al (2002) J. Org. Chem. 67:1866-1872; Walker, M. A. (1995) J. Org. Chem. 60:5352-5355; Frisch et al (1996) Bioconjugate Chem. 7:180-186; U.S. Pat. No. 6,214,345; WO 02/088172; US 2003130189; US2003096743; WO 03/026577; WO 03/043583; and WO 04/032828.

Stretchers of formula (IIIa) can be introduced into a Linker by reacting the following linker reagents with the N-terminus of an Amino Acid unit:

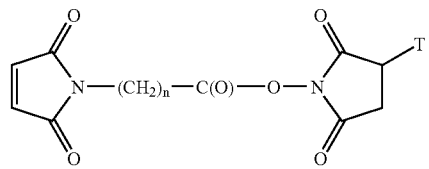

where n is an integer ranging from 1-10 and T is —H or —SO$_3$Na;

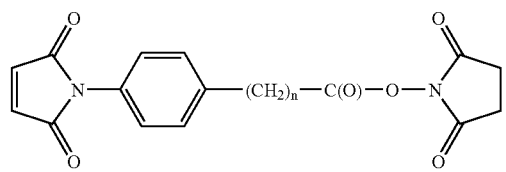

where n is an integer ranging from 0-3;

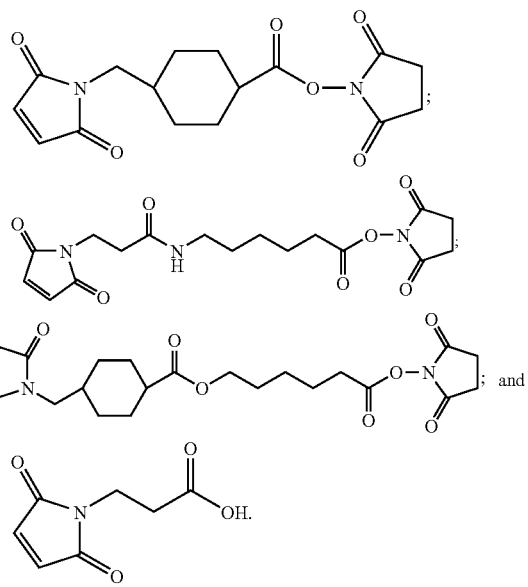

Stretcher units of can be introduced into a Linker by reacting the following bifunctional reagents with the N-terminus of an Amino Acid unit:

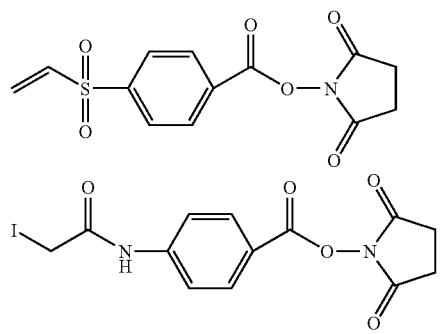

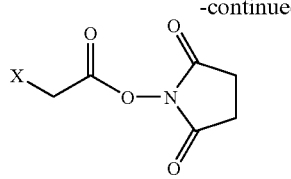

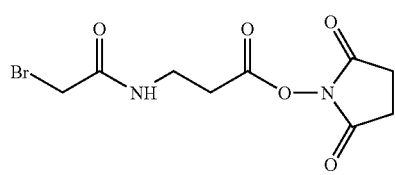

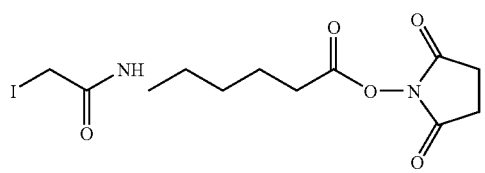

where X is Br or I. Stretcher units of formula can also be introduced into a Linker by reacting the following bifunctional reagents with the N-terminus of an Amino Acid unit:

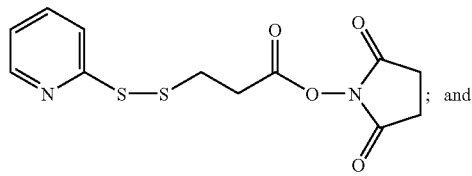

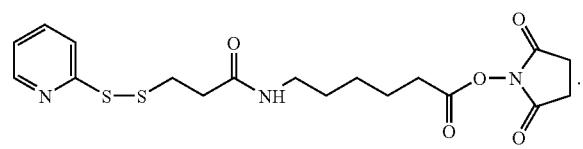

Stretcher units of formula (Va) can be introduced into a Linker by reacting the following intermediates with the N-terminus of an Amino Acid unit:

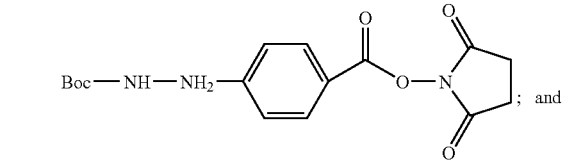

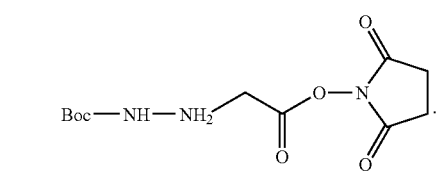

Isothiocyanate Stretchers of the formula shown below may be prepared from isothiocyanatocarboxylic acid chlorides as described in Angew. Chem., (1975) 87(14), 517.

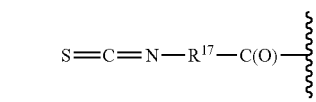

wherein $-R^{17}-$ is as described herein.

An exemplary valine-citrulline (val-cit or vc) dipeptide linker reagent having a maleimide Stretcher and a para-aminobenzylcarbamoyl (PAB) self-immolative Spacer has the structure:

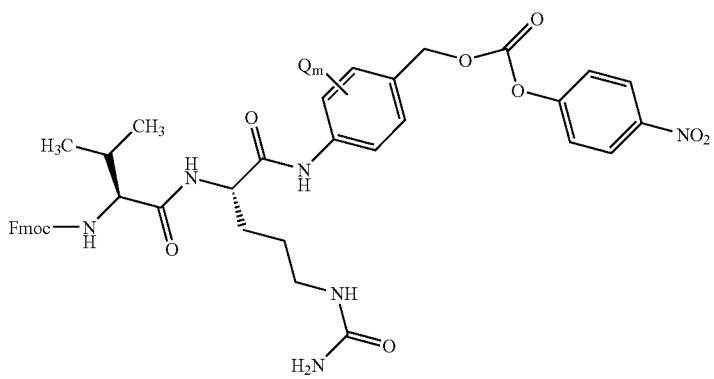

where Q is $-C_1\text{-}C_8$ alkyl, $-O-(C_1\text{-}C_8$ alkyl), -halogen, -nitro or -cyano; and m is an integer ranging from 0-4.

An exemplary phe-lys(Mtr) dipeptide linker reagent having a maleimide Stretcher unit and a p-aminobenzyl self-immolative Spacer unit can be prepared according to Dubowchik, et al. (1997) Tetrahedron Letters, 38:5257-60, and has the structure:

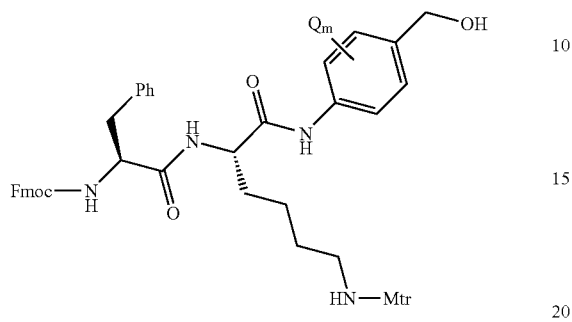

where Mtr is mono-4-methoxytrityl, Q is —$C_1$-$C_8$ alkyl, —O—($C_1$-$C_8$ alkyl), -halogen, -nitro or -cyano; and m is an integer ranging from 0-4.

Exemplary antibody-drug conjugate compounds of the invention include:

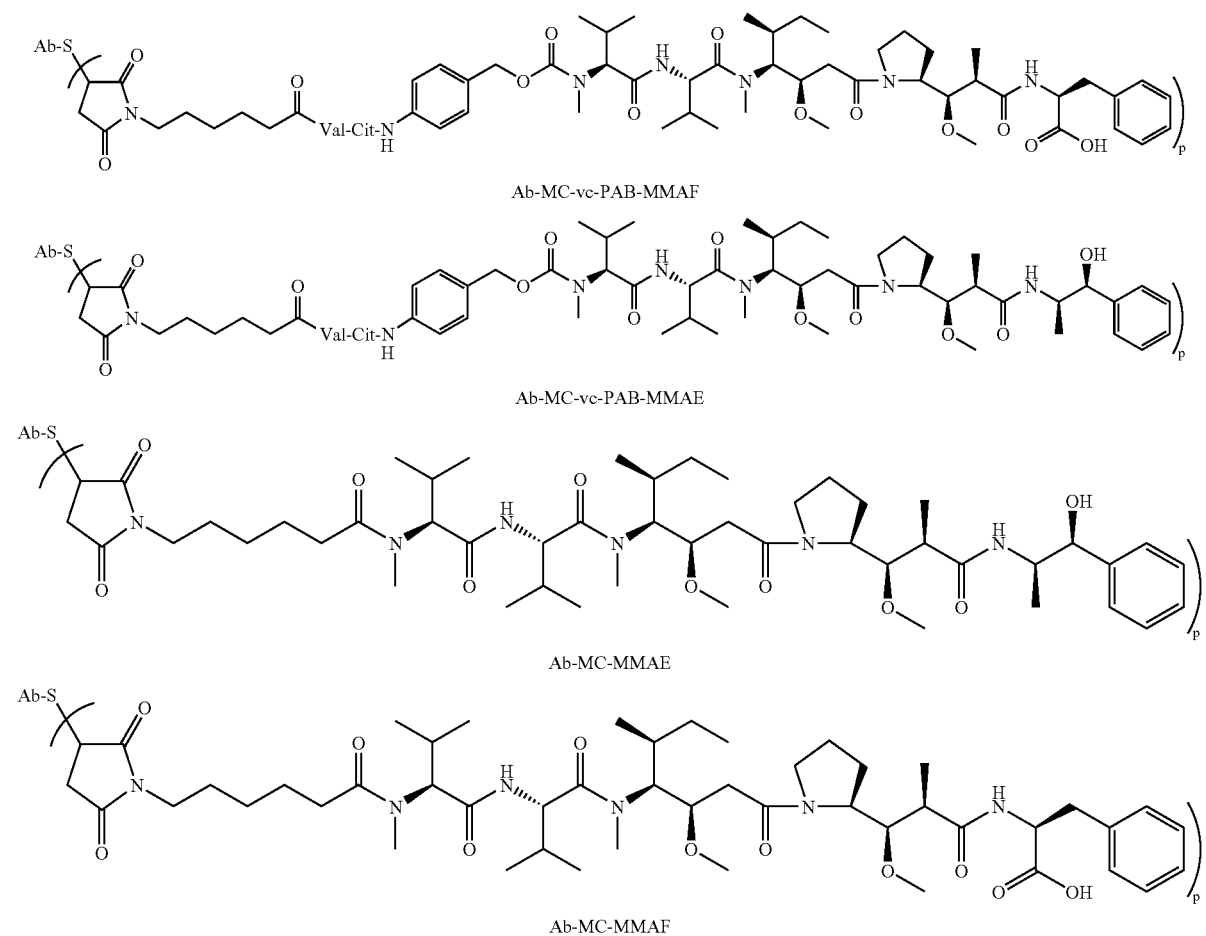

Ab-MC-vc-PAB-MMAF

Ab-MC-vc-PAB-MMAE

Ab-MC-MMAE

Ab-MC-MMAF where Val is valine; Cit is citrulline; p is 1, 2, 3, or 4; and Ab is a cysteine engineered antibody. Other exemplary antibody drug conjugates where maytansinoid drug moiety DM1 is linked through a BMPEO linker to a thiol group of trastuzumab have the structure:

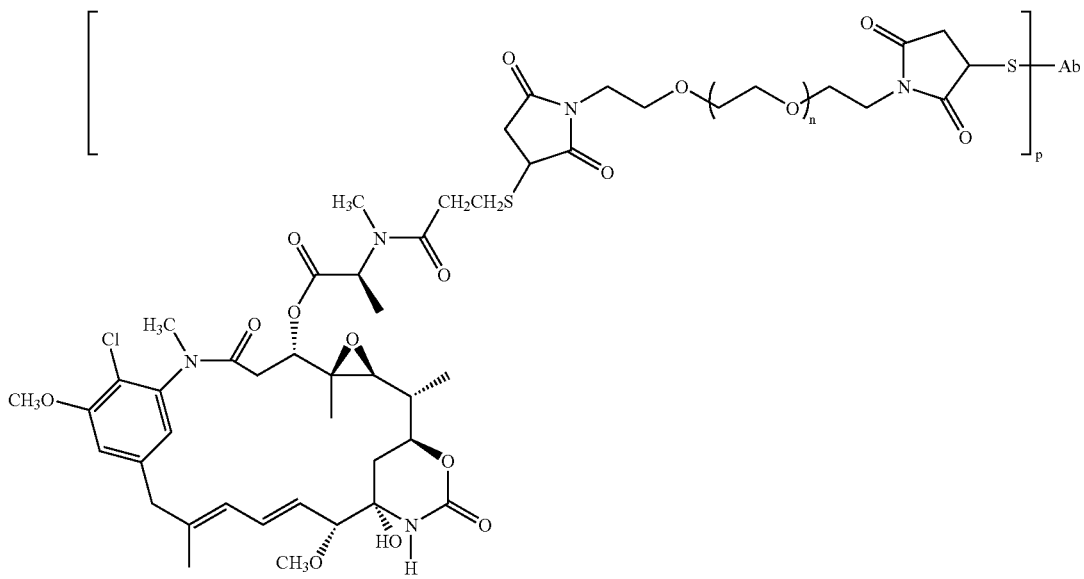

where Ab is a cysteine engineered antibody; n is 0, 1, or 2; and p is 1, 2, 3, or 4.

Preparation of Antibody-Drug Conjugates

The ADC of Formula I may be prepared by several routes, employing organic chemistry reactions, conditions, and reagents known to those skilled in the art, including: (1) reaction of a cysteine group of a cysteine engineered antibody with a linker reagent, to form antibody-linker intermediate Ab-L, via a covalent bond, followed by reaction with an activated drug moiety D; and (2) reaction of a nucleophilic group of a drug moiety with a linker reagent, to form drug-linker intermediate D-L, via a covalent bond, followed by reaction with a cysteine group of a cysteine engineered antibody. Conjugation methods (1) and (2) may be employed with a variety of cysteine engineered antibodies, drug moieties, and linkers to prepare the antibody-drug conjugates of Formula I.

Antibody cysteine thiol groups are nucleophilic and capable of reacting to form covalent bonds with electrophilic groups on linker reagents and drug-linker intermediates including: (i) active esters such as NHS esters, HOBt esters, haloformates, and acid halides; (ii) alkyl and benzyl halides, such as haloacetamides; (iii) aldehydes, ketones, carboxyl, and maleimide groups; and (iv) disulfides, including pyridyl disulfides, via sulfide exchange. Nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents.

Maytansine may, for example, be converted to May-SSCH$_3$, which can be reduced to the free thiol, May-SH, and reacted with a modified antibody (Chari et al (1992) Cancer Research 52:127-131) to generate a maytansinoid-antibody immunoconjugate with a disulfide linker. Antibody-maytansinoid conjugates with disulfide linkers have been reported (WO 04/016801; U.S. Pat. No. 6,884,874; US 2004/039176 A1; WO 03/068144; US 2004/001838 A1; U.S. Pat. Nos. 6,441,163, 5,208,020, 5,416,064; WO 01/024763). The disulfide linker SPP is constructed with linker reagent N-succinimidyl 4-(2-pyridylthio)pentanoate.

Under certain conditions, the cysteine engineered antibodies may be made reactive for conjugation with linker reagents by treatment with a reducing agent such as DTT (Cleland's reagent, dithiothreitol) or TCEP (tris(2-carboxyethyl)phosphine hydrochloride; Getz et al (1999) Anal. Biochem. Vol 273:73-80; Soltec Ventures, Beverly, Mass.). Full length, cysteine engineered monoclonal antibodies (ThioMabs) expressed in CHO cells were reduced with about a 50 fold excess of TCEP for 3 hrs at 37° C. to reduce disulfide bonds which may form between the newly introduced cysteine residues and the cysteine present in the culture media. The reduced ThioMab was diluted and loaded onto HiTrap S column in 10 mM sodium acetate, pH 5, and eluted with PBS containing 0.3M sodium chloride. Disulfide bonds were reestablished between cysteine residues present in the parent Mab with dilute (200 nM) aqueous copper sulfate (CuSO$_4$) at room temperature, overnight. Other oxidants, i.e. oxidizing agents, and oxidizing conditions, which are known in the art may be used. Ambient air oxidation is also effective. This mild, partial reoxidation step forms intrachain disulfides efficiently with high fidelity. An approximate 10 fold excess of drug-linker intermediate, e.g. BM(PEO)$_4$-DM1 was added, mixed, and let stand for about an hour at room temperature to effect conjugation and form the ThioMab antibody-drug conjugate. The conjugation mixture was gel filtered and loaded and eluted through a HiTrap S column to remove excess drug-linker intermediate and other impurities.

Figure 15:
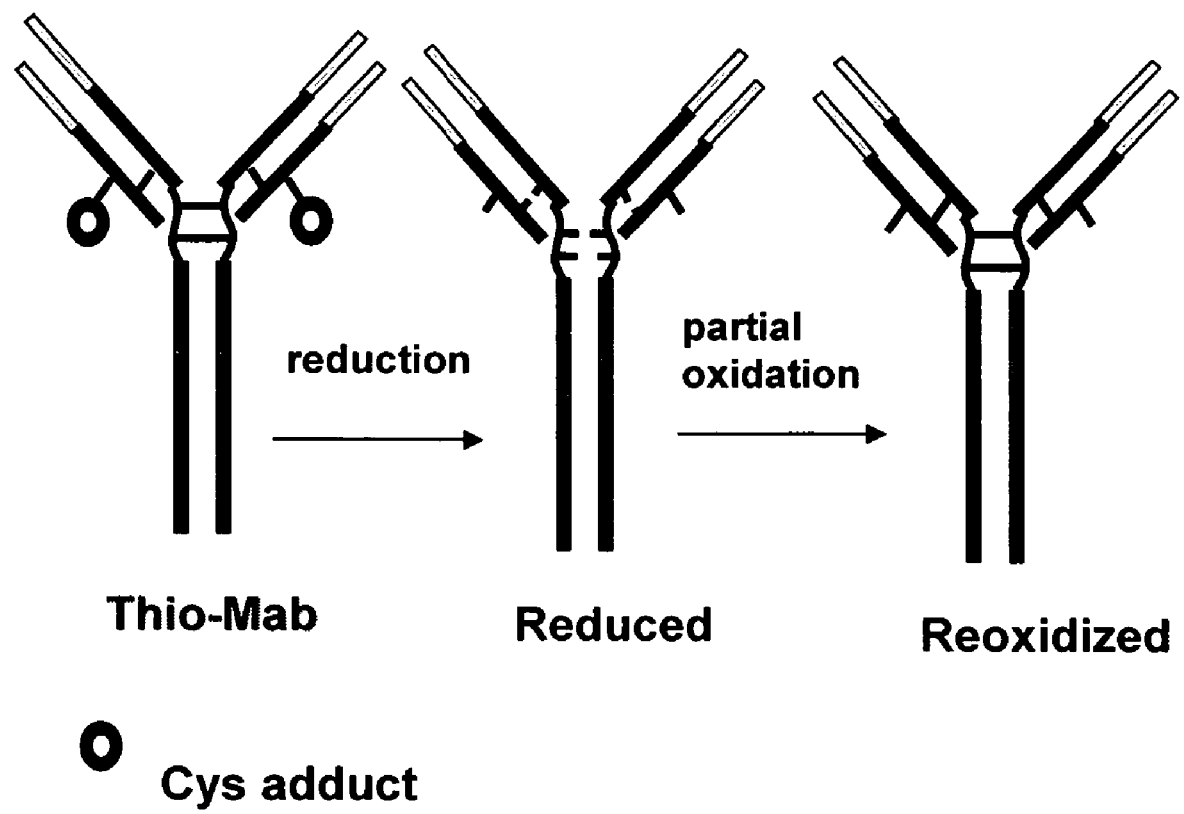
FIG. 15 shows the general process to prepare a cysteine engineered antibody (ThioMab) expressed from cell culture for conjugation.

FIG. 15 shows the general process to prepare a cysteine engineered antibody expressed from cell culture for conjugation. Cysteine adducts, presumably along with various interchain disulfide bonds, are reductively cleaved to give a reduced form of the antibody. The interchain disulfide bonds between paired cysteine residues are reformed under partial oxidation conditions, such as exposure to ambient oxygen. The newly introduced, engineered, and unpaired cysteine residues remain available for reaction with linker reagents or drug-linker intermediates to form the antibody conjugates of the invention. The ThioMabs expressed in mammalian cell lines result in externally conjugated Cys adduct to an engineered Cys through —S—S— bond formation. Hence the purified ThioMabs have to be treated with reduction and oxidation procedures as described in Example 11 to produce reactive ThioMabs. These ThioMabs are used to conjugate with maleimide containing cytotoxic drugs, fluorophores, and other labels.

A variety of ThioFab and ThioMab antibody-drug conjugates were prepared (Examples 4-8). Cysteine mutant hu4D5Fabv8 (V110C) was conjugated with the maytansinoid drug moiety DM1 with a bis-maleimido linker reagent BMPEO to form hu4D5Fabv8 (V110C)-BMPEO-DM1 (Example 8).

In Vitro Cell Proliferation Assays

Generally, the cytotoxic or cytostatic activity of an antibody-drug conjugate (ADC) is measured by: exposing mammalian cells having receptor proteins, e.g. HER2, to the antibody of the ADC in a cell culture medium; culturing the cells for a period from about 6 hours to about 5 days; and measuring cell viability. Cell-based in vitro assays were used to measure viability (proliferation), cytotoxicity, and induction of apoptosis (caspase activation) of the ADC of the invention.

Figure 11:
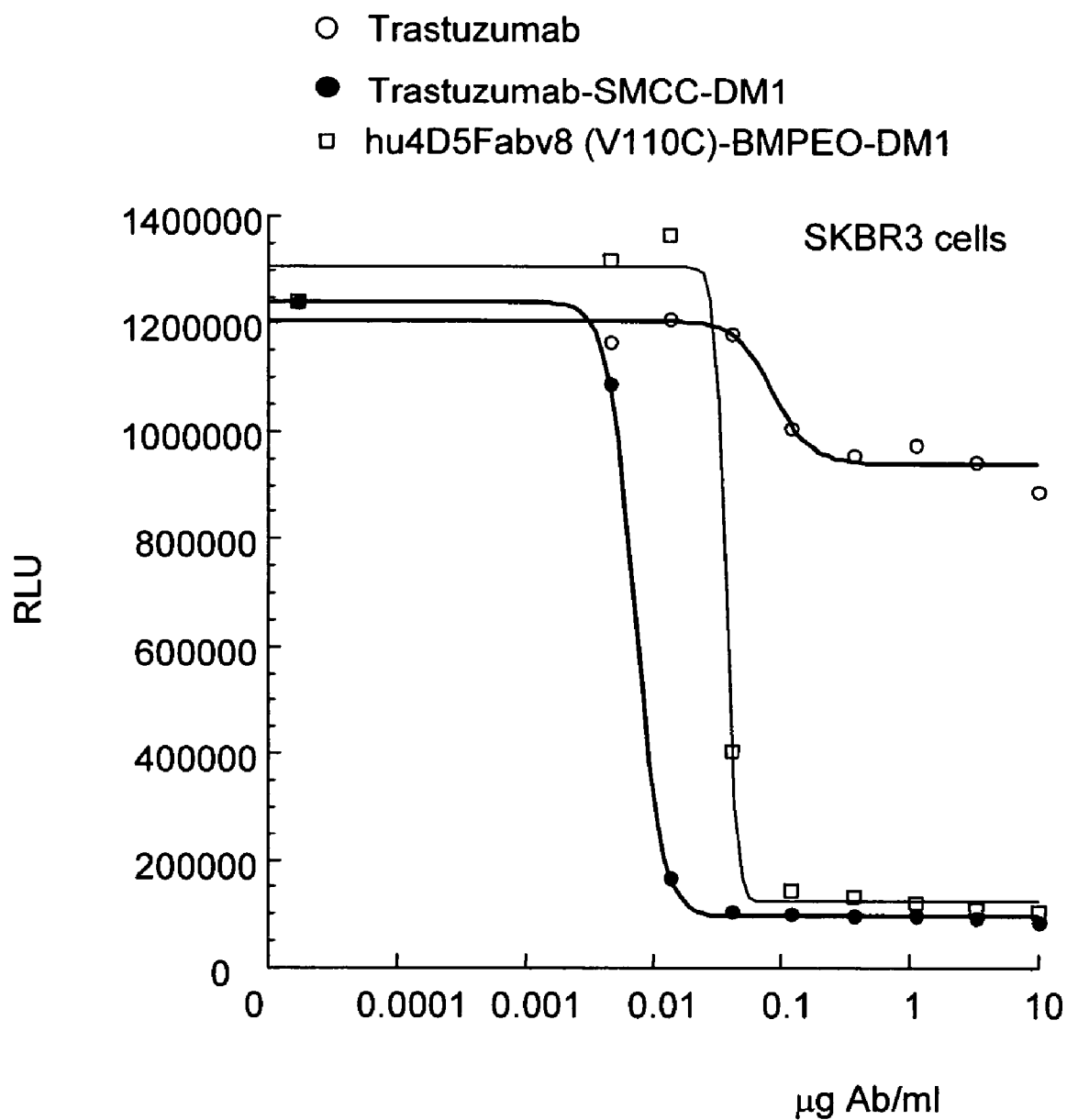
FIG. 11 shows an in vitro, cell proliferation assay of SK-BR-3 cells treated with: -o- trastuzumab; -●- trastuzumab-SMCC-DM1; and --□- hu4D5Fabv8 cysteine mutant (V110C)-BMPEO-DM1.

The in vitro potency of antibody-drug conjugates was measured by a cell proliferation assay (FIGS. 10 and 11, Example 9). The CellTiter-Glo® Luminescent Cell Viability Assay is a commercially available (Promega Corp., Madison, Wis.), homogeneous assay method based on the recombinant expression of Coleoptera luciferase (U.S. Pat. Nos. 5,583,024; 5,674,713 and 5,700,670). This cell proliferation assay determines the number of viable cells in culture based on quantitation of the ATP present, an indicator of metabolically active cells (Crouch et al (1993) J. Immunol. Meth. 160:81-88; U.S. Pat. No. 6,602,677). The CellTiter-Glo® Assay was conducted in 96 well format, making it amenable to automated high-throughput screening (HTS) (Cree et al (1995) AntiCancer Drugs 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing. The cells may be treated continuously with ADC, or they may be treated and separated from ADC. Generally, cells treated briefly, i.e. 3 hours, showed the same potency effects as continuously treated cells.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons. The extended half-life eliminates the need to use reagent injectors and provides flexibility for continuous or batch mode processing of multiple plates. This cell proliferation assay can be used with various multiwell formats, e.g. 96 or 384 well format. Data can be recorded by luminometer or CCD camera imaging device. The luminescence output is presented as relative light units (RLU), measured over time. Alternatively, photons from luminescence can be counted in a scintillation counter in the presence of a scintillant. The light units can be represented then as CPS—counts per second.

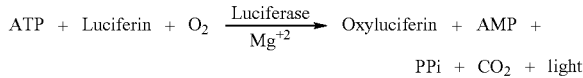

$$ATP + \text{Luciferin} + O_2 \xrightarrow[Mg^{+2}]{\text{Luciferase}} \text{Oxyluciferin} + AMP + PPi + CO_2 + \text{light}$$

The anti-proliferative effects of antibody-drug conjugates were measured by the cell proliferation, in vitro cell killing assay above against the SK-BR-3 breast tumor cell line (FIGS. 10 and 11). $IC_{50}$ values of the ADC were established against SK-BR-3 cells, which are known to overexpress HER2 receptor protein.

FIG. 10 shows that trastuzumab-SMCC-DM1 ($IC_{50}$=0.008-0.015 µg/ml) was more potent than the heavy chain cysteine mutant conjugate hu4D5Fabv8-(A121C)-BMPEO-DM1 ($IC_{50}$=0.04 µg/ml). Both conjugates were significantly more potent in cell killing than naked trastuzumab ($IC_{50}$=0.1 µg/ml). Drug loading for trastuzumab-SMCC-DM1 was 2.8 DM1/Ab and for hu4D5Fabv8 (A121C)-BMPEO-DM1 was 0.6 DM1/Ab.

FIG. 11 shows that trastuzumab-SMCC-DM1 ($IC_{50}$=0.008-0.015 µg/ml) was more potent than the light chain cysteine mutant hu4D5Fabv8 (V110C)-BMPEO-DM1 ($IC_{50}$=0.07 µg/ml). Both conjugates were more potent in cell killing than naked trastuzumab ($IC_{50}$=0.1 µg/ml). Drug loading for trastuzumab-SMCC-DM1 was 2.8 DM1/Ab and for hu4D5Fabv8 (V110C)-BMPEO-DM1 was 0.9 DM1/Ab.

Figure 20:
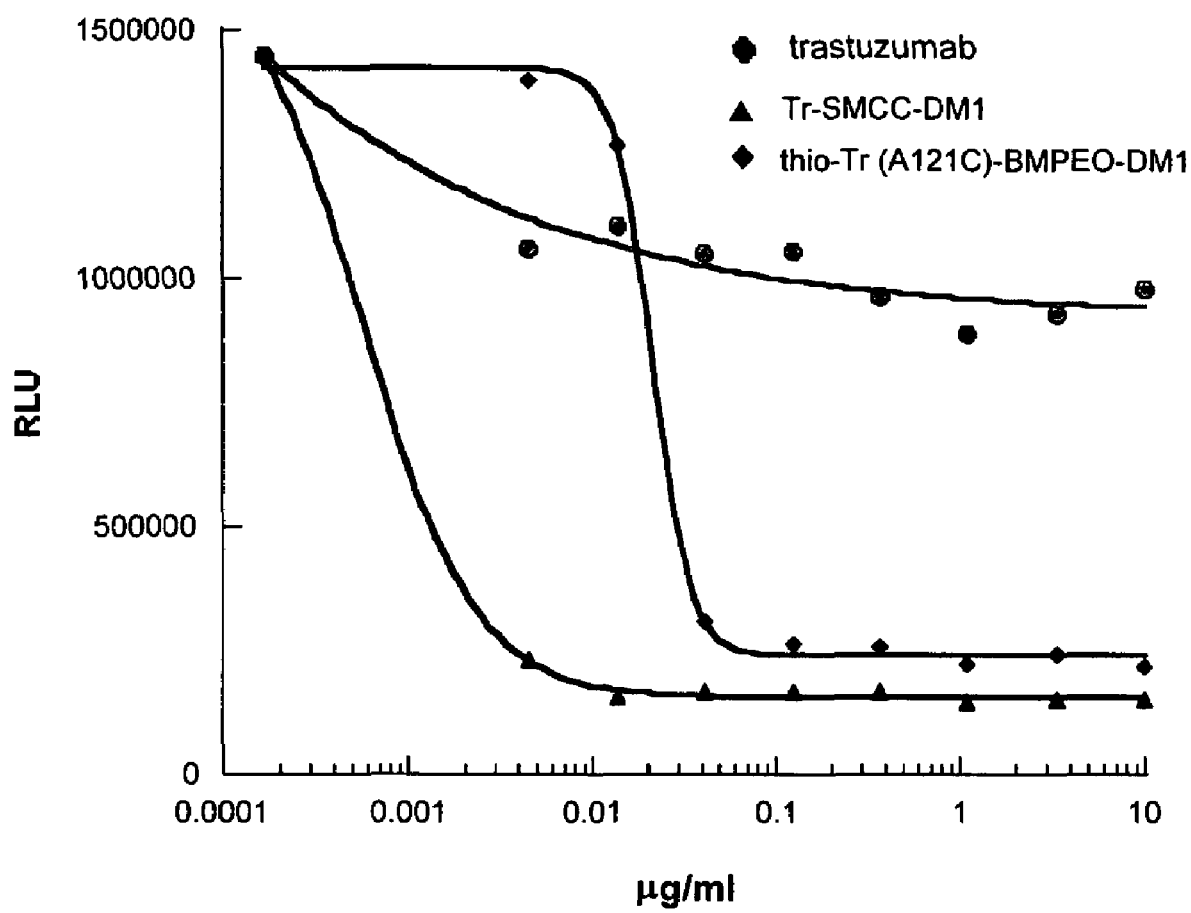
FIG. 20 shows an in vitro, cell proliferation assay of SK-BR-3 cells treated with: -●- trastuzumab; -▲-trastuzumab-SMCC-DM1 with a drug loading of 3.4 DM1/Ab; and -♦- thio-trastuzumab (A121C)-BMPEO-DM1 with a drug loading of 1.6 DM1/Ab.
Figure 21A:
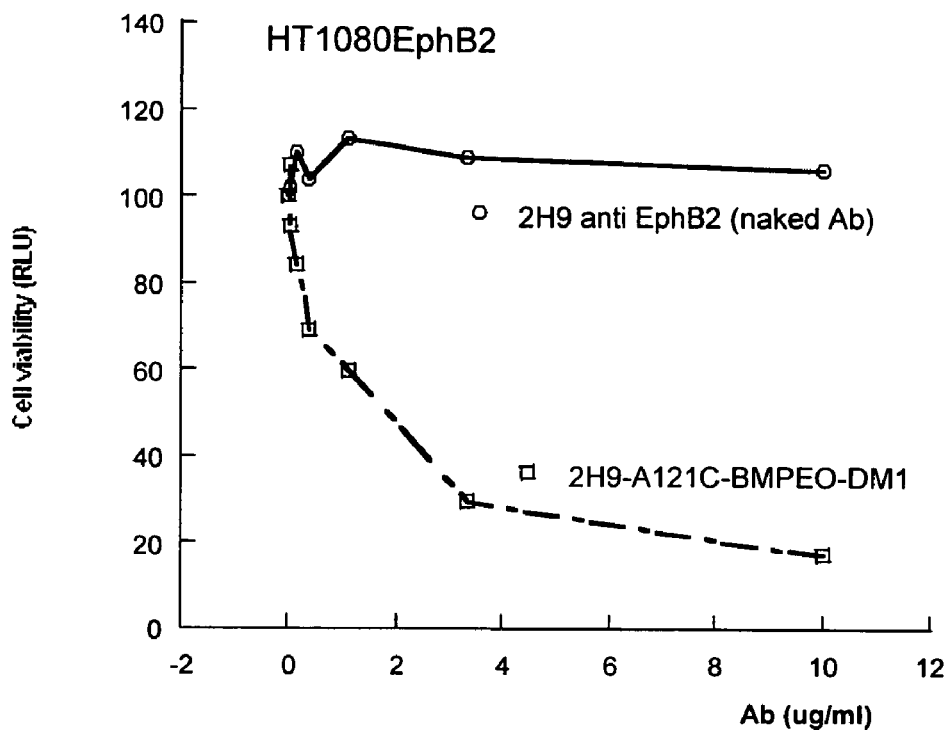
FIG. 21A shows an in vitro, cell proliferation assay of HT 1080EphB2 cells treated with: -○- parent 2H9 anti-EphB2R; and -□- thio 2H9 (A121C) BMPEO-DM1.
Figure 21B:
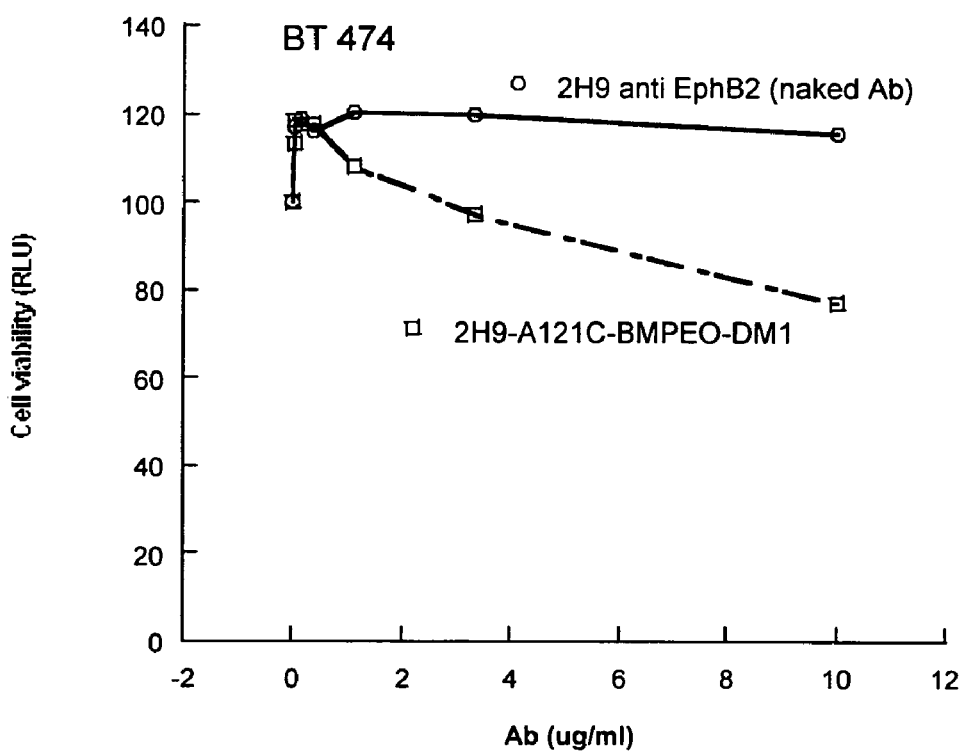
FIG. 21B shows an in vitro, cell proliferation assay of BT 474 cells treated with: -○- parent 2H9 anti-EphB2R; and -□- thio 2H9 (A121C) BMPEO-DM1.

Full-length IgG ThioMab conjugates were tested for in vitro, cell proliferation efficacy and compared with parent antibodies. FIG. 20 shows the results of an assay of SK-BR-3 cells treated with: parent antibody trastuzumab (HERCEPTIN®, Genentech, Inc.); trastuzumab-SMCC-DM1 with a drug loading of about 3.4 DM1/Ab; and thio-trastuzumab (A121C)-BMPEO-DM1 with a drug loading of about 1.6 DM1/Ab. The trastuzumab-SMCC-DM1 conjugate is linked to the antibody via the amino reactive, NHS ester SMCC linker reagent, whereas the thio-trastuzumab (A121C)-BMPEO-DM1 conjugates is linked via the thiol reactive, maleimide BMPEO linker reagent. Both conjugates were potent against SK-BR-3 cells and showed comparable activity, whereas trastuzumab did not exert a cytotoxic effect. FIG. 21A shows the results of an assay of HT 1080EphB2 cells treated with: parent 2H9 anti-EphB2R; and thio 2H9 (A121C) BMPEO-DM1 conjugate. FIG. 21B shows the results of an assay of BT 474 cells treated with: parent 2H9 anti-EphB2R; and thio 2H9 (A121C) BMPEO-DM1 conjugate. Against both HT 1080EphB2 and BT 474 cells, the 2H9 ThioMab conjugate was more potent than the parent 2H9 antibody conjugate. The conjugate Thio-2H9-BMPEO-DM1 showed functional cell killing activity in EphB2 specific cell line (HT1080EphB2) compared to a non EphB2 cell line, BT474 in which only marginal activity is observed.

Figure 22:
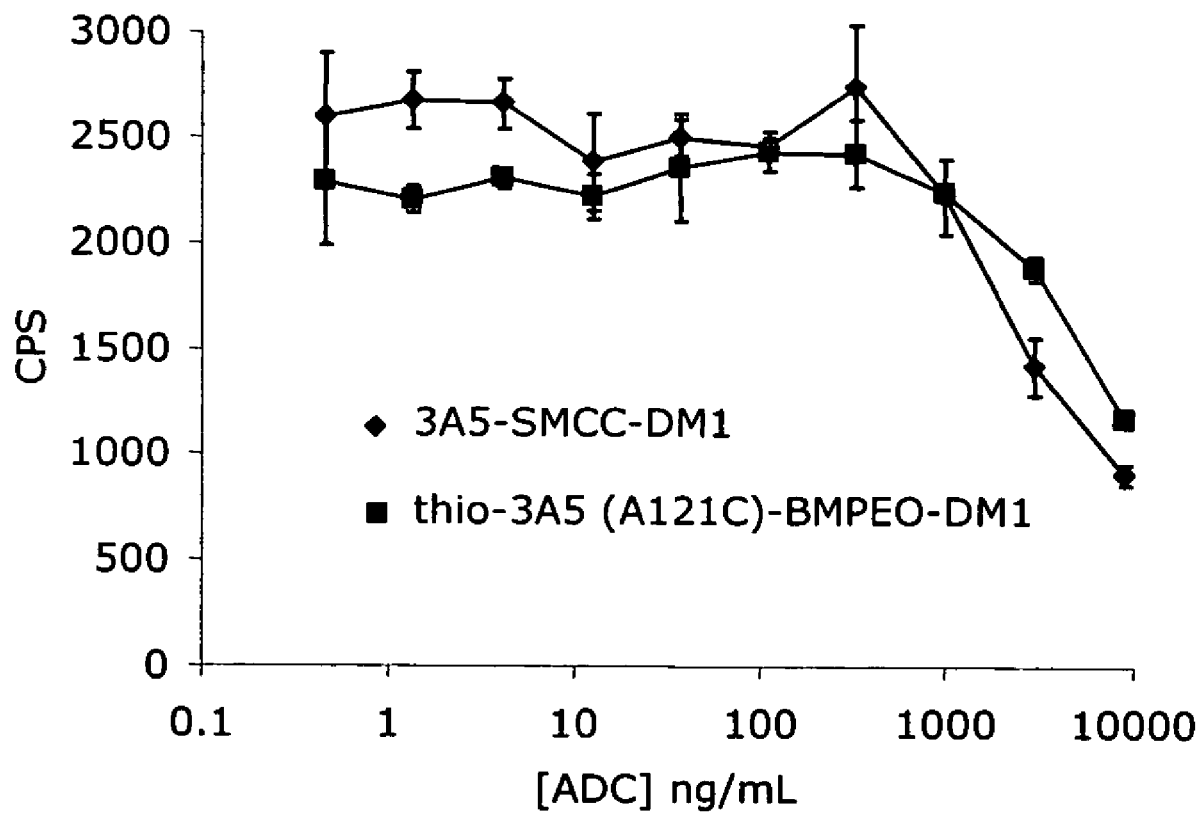
FIG. 22 shows an in vitro, cell proliferation assay of PC3/ neo cells treated with: -♦- 3A5 anti MUC16-SMCC-DM1; and -■- thio 3A5 (A121C) BMPEO-DM1.
Figure 23:
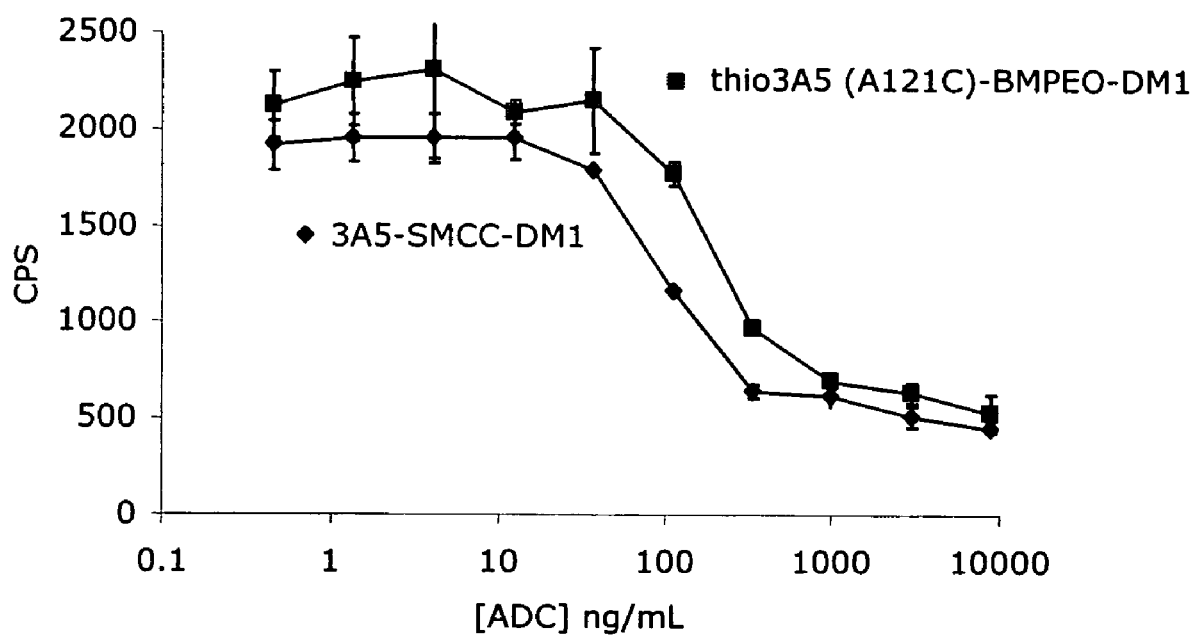
FIG. 23 shows an in vitro, cell proliferation assay of PC3/MUC16 cells treated with: -♦- 3A5 anti MUC16-SMCC-DM1; and -■- thio 3A5 (A121C) BMPEO-DM1.
Figure 24:
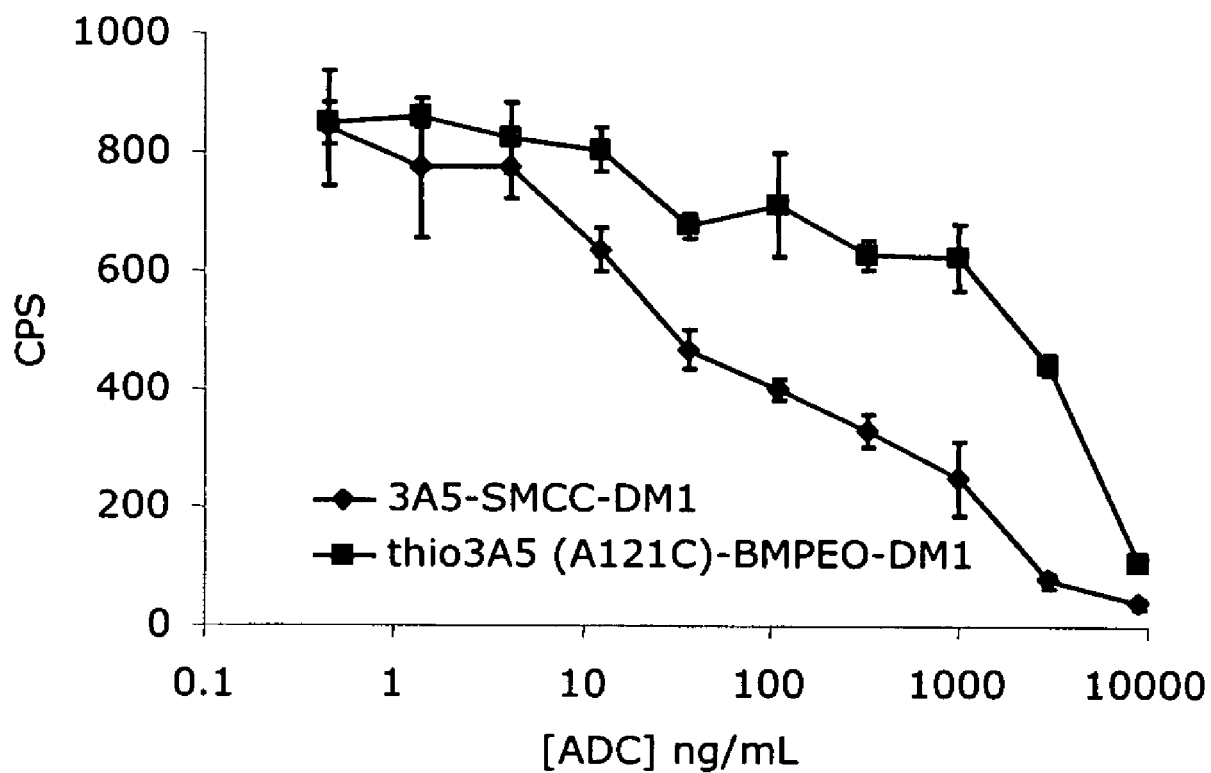
FIG. 24 shows an in vitro, cell proliferation assay of OVCAR-3 cells treated with: -♦-3A5 anti MUC16-SMCC-DM1; and -■- thio 3A5 (A121C) BMPEO-DM1.

Antibody drug conjugates were compared where the antibody is a parent antibody and where the antibody is a cysteine engineered antibody. FIG. 22 shows the results of an assay of PC3/neo cells treated with: 3A5 anti MUC16-SMCC-DM1; and thio 3A5 (A121C) BMPEO-DM1. FIG. 23 shows the results of an assay of PC3/MUC16 cells treated with: 3A5 anti MUC16-SMCC-DM1; and thio 3A5 (A121C) BMPEO-DM1. FIG. 24 shows the results of an assay of OVCAR-3 cells treated with: 3A5 anti MUC16-SMCC-DM1; and thio 3A5 (A121C) BMPEO-DM1. Thio-3A5-BMPEO-DM1 did not show any significant cell killing activity in the control PC3/neo cell line, whereas it showed comparable activity to 3A5-SMCC-DM1 in the PC3/MUC16 cell line. Thio-3A5-DM1 conjugate also showed activity in the OVCAR-3 that expresses endogenous MUC16 antigen.

In Vivo Efficacy

The in vivo efficacy of two albumin binding peptide-DM1 (maytansinoid)-antibody-drug conjugates (ADC) of the invention was measured by a high expressing HER2 transgenic explant mouse model (FIG. 12, Example 10). An allograft was propagated from the Fo5 mmtv transgenic mouse which does not respond to, or responds poorly to, HERCEPTIN® therapy. Subjects were treated once with ABP-rhuFab4D5-cys(light chain)-DM1; ABP-rhuFab4D5-cys(heavy chain)-DM1; and placebo PBS buffer control (Vehicle) and monitored over 3 weeks to measure the time to tumor doubling, log cell kill, and tumor shrinkage.

| Sample | Dose | Ti | PR | CR | TDV (days) |
|---|---|---|---|---|---|
| Vehicle (PBS buffer) | | 7/7 | 0/7 | 0/7 | 3 |
| ABP-rhuFab4D5-V110C (light chain)-DM1 (0.9 DM1/Ab) | 25 mg per kg (1012 µg/m² of DM1) | 7/7 | 1/7 | 0/7 | 14 |
| ABP-rhuFab4D5-A121C(heavy chain)-DM1 (0.6 DM1/Ab) | 37.5 mg per kg (1012 µg/m² of DM1) | 7/7 | 4/7 | 0/7 | 16 |

The term Ti is the number of animals in the study group with tumor at T=0÷total animals in group. The term PR is the number of animals attaining partial remission of tumor÷animals with tumor at T=0 in the group. The term CR is the number of animals attaining complete remission of tumor÷animals with tumor at T=0 in the group. The term TDV is the tumor doubling time, i.e. time in days for the control tumor volume to double.

The seven mice treated with 25 mg per kg (1012 ug/m² of DM1) of ABP-rhuFab4D5-cys(light chain)-DM1 were all tumor-positive and gave one animal with partial remission after 20 days. The seven mice treated with 37.5 mg per kg (1012 ug/m² of DM1) of ABP-rhuFab4D5-cys(heavy chain)-DM1 were all tumor-positive and gave four animals with partial remission after 20 days.

Figure 25:
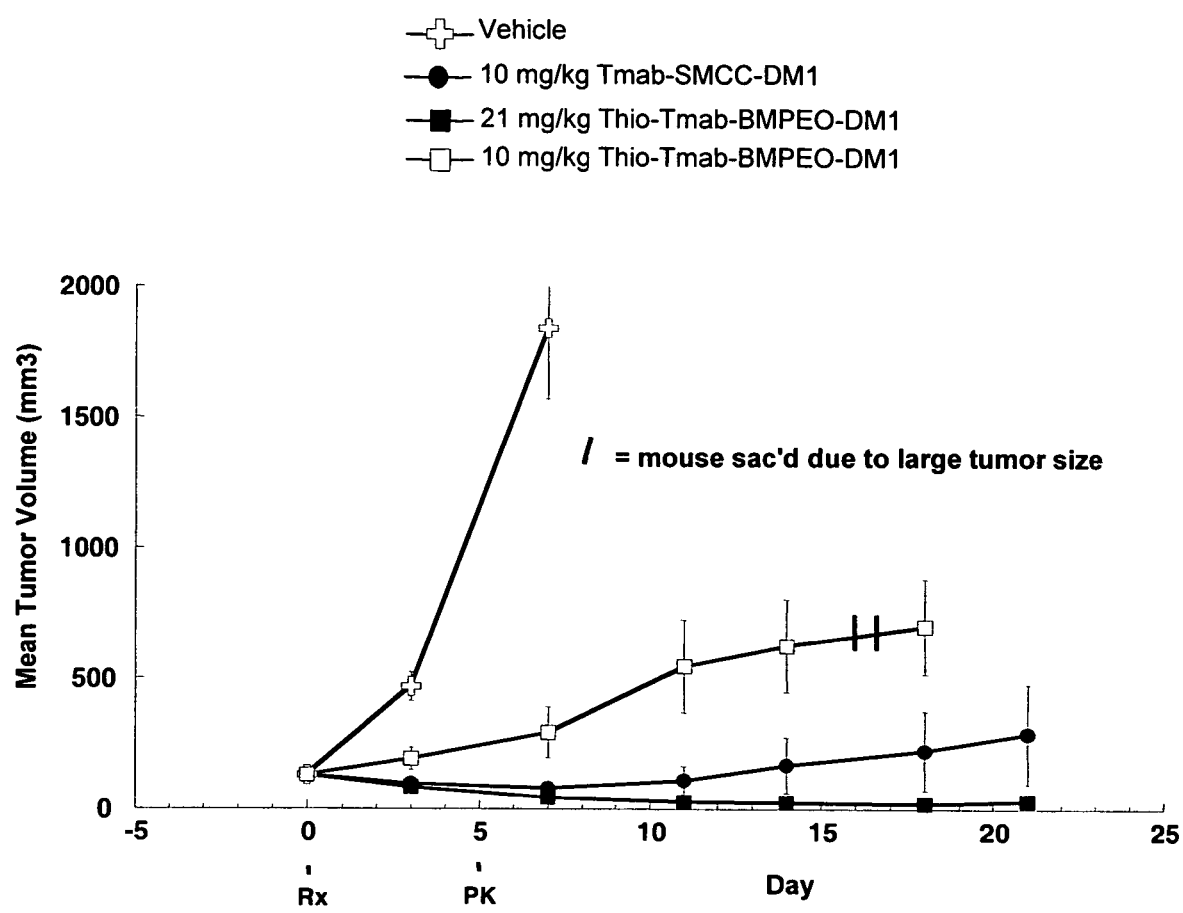
FIG. 25 shows the mean tumor volume change over 21 days in athymic nude mice with MMTV-HER2 Fo5 mammary tumor allografts, after a single dose on Day 0 with: ⊕Vehicle (Buffer); -●- trastuzumab-SMCC-DM1 10 mg/kg, with a drug loading of 3.4 DM1/Ab; -■- thio trastuzumab (A121C)-SMCC-DM1 21 mg/kg, with a drug loading of 1.6 DM1/Ab; and -□- thio trastuzumab (A121C)-SMCC-DM1 10 mg/kg, with a drug loading of 1.6 DM1/Ab.

The full length IgG ThioMab antibody variant with the A121C cysteine mutation and conjugated to the BMPEO linker and DM1 drug moiety was tested against the parent trastuzumab-SMCC-DM1 conjugate in MMTV-HER2 Fo5 tumor-bearing mice. Tumor size at day 0 of injection was about 100-200 mm in size. FIG. 25 shows the mean tumor volume change over 21 days in athymic nude mice with MMTV-HER2 Fo5 mammary tumor allografts, after a single dose on Day 0 with: Vehicle (Buffer); trastuzumab-SMCC-DM1 10 mg/kg; thio trastuzumab (A121C)—SMCC-DM1 21 mg/kg and thio trastuzumab (A121C)—SMCC-DM1 10 mg/kg.

| Sample | Dose | Ti | PR | CR |
|---|---|---|---|---|
| Vehicle (PBS buffer) | — | 10/10 | 0/10 | 0/10 |
| trastuzumab-SMCC-DM1 3.4 DM1/Ab | 10 mg Ab per kg mouse (490 µg/m² of DM1) | 10/10 | 7/10 | 0/10 |
| thio-trastuzumab (A121C)-BMPEO-DM1 1.6 DM1/Ab | 21 mg Ab per kg mouse (496 µg/m² of DM1) | 8/10 | 6/10 | 4/10 |
| thio-trastuzumab (A121C)-BMPEO-DM1 1.6 DM1/Ab | 10 mg Ab per kg mouse (236 µg/m² of DM1) | 10/10 | 0/10 | 0/10 |

It can be seen from FIG. 25 that each conjugate exerts a significant effect of retarding tumor growth relative to placebo (Vehicle). Each of the ten mice in the four groups above received a single injection at day 1. The parent trastuzumab-SMCC-DM1 conjugate was loaded with more than twice (3.4 DM1/Ab) the number of drug moieties than the cysteine engineered thio-trastuzumab (A121C)-BMPEO-DM1 conjugate (1.6 DM1/Ab). The effective amount of DM1 was thus approximately equal between parent trastuzumab-SMCC-DM1 and the higher dose (21 mg Ab) thio-trastuzumab (A121C)-BMPEO-DM1. These two sample showed the most potency. After 14 days post-injection, most of the animals receiving these conjugates were in partial or complete remission. The lower efficacy of the lower dose thio-trastuzumab (A121C)-BMPEO-DM1 sample confirmed a DM1 dose-related response. Thio-Trastuzumab-DM1 either dosed in equivalent antibody (10 mg/kg) or DM1 drug (21 mg/kg) quantity to that of control trastuzumab-SMCC-DM1 conjugate. As seen from the FIG. 25, Thio-BMPEO-DM1 (21 mg/kg) showed slightly better response than that of trastuzumab-SMCC-DM1 group as some of the animals showed complete response with Thiomab-DM1 whereas there was only partial response with trastuzumab-SMCC-DM1.

Administration of Antibody-Drug Conjugates

The antibody-drug conjugates (ADC) of the invention may be administered by any route appropriate to the condition to be treated. The ADC will typically be administered parenterally, i.e. infusion, subcutaneous, intramuscular, intravenous, intradermal, intrathecal and epidural.

Pharmaceutical Formulations

Pharmaceutical formulations of therapeutic antibody-drug conjugates (ADC) of the invention are typically prepared for parenteral administration, i.e. bolus, intravenous, intratumor injection with a pharmaceutically acceptable parenteral vehicle and in a unit dosage injectable form. An antibody-drug conjugate (ADC) having the desired degree of purity is optionally mixed with pharmaceutically acceptable diluents, carriers, excipients or stabilizers (Remington's Pharmaceutical Sciences (1980) 16th edition, Osol, A. Ed.), in the form of a lyophilized formulation or an aqueous solution.

Acceptable diluents, carriers, excipients, and stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). For example, lyophilized anti-ErbB2 antibody formulations are described in WO 97/04801, expressly incorporated herein by reference.

The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semi permeable matrices of solid hydrophobic polymers containing the ADC, which matrices are in the form of shaped articles, e.g. films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile, which is readily accomplished by filtration through sterile filtration membranes.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Aqueous suspensions of the invention contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of ADC may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Although oral administration of protein therapeutics are disfavored due to hydrolysis or denaturation in the gut, formulations of ADC suitable for oral administration may be prepared as discrete units such as capsules, cachets or tablets each containing a predetermined amount of the ADC.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Antibody-Drug Conjugate Treatments

It is contemplated that the antibody-drug conjugates (ADC) of the present invention may be used to treat various diseases or disorders, e.g. characterized by the overexpression of a tumor antigen. Exemplary conditions or hyperproliferative disorders include benign or malignant tumors; leukemia and lymphoid malignancies. Others include neuronal, glial, astrocytal, hypothalamic, glandular, macrophagal, epithelial, stromal, blastocoelic, inflammatory, angiogenic and immunologic, including autoimmune, disorders.

The ADC compounds which are identified in the animal models and cell-based assays can be further tested in tumor-bearing higher primates and human clinical trials. Human clinical trials can be designed similar to the clinical trials testing the efficacy of the anti-HER2 monoclonal antibody HERCEPTIN® in patients with HER2 overexpressing metastatic breast cancers that had received extensive prior anticancer therapy as reported by Baselga et al. (1996) J. Clin. Oncol. 14:737-744. The clinical trial may be designed to evaluate the efficacy of an ADC in combinations with known therapeutic regimens, such as radiation and/or chemotherapy involving known chemotherapeutic and/or cytotoxic agents.

Generally, the disease or disorder to be treated is a hyperproliferative disease such as cancer. Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

The cancer may comprise HER2-expressing cells, such that the ADC of the present invention are able to bind to the cancer cells. To determine ErbB2 expression in the cancer, various diagnostic/prognostic assays are available. In one embodiment, ErbB2 overexpression may be analyzed by IHC, e.g. using the HERCEPTEST (Dako). Parrafin embedded tissue sections from a tumor biopsy may be subjected to the IHC assay and accorded a ErbB2 protein staining intensity criteria as follows: Score 0, no staining is observed or membrane staining is observed in less than 10% of tumor cells; Score 1+, a faint/barely perceptible membrane staining is detected in more than 10% of the tumor cells, the cells are only stained in part of their membrane; Score 2+, a weak to moderate complete membrane staining is observed in more than 10% of the tumor cells; Score 3+, a moderate to strong complete membrane staining is observed in more than 10% of the tumor cells. Those tumors with 0 or 1+scores for ErbB2 overexpression assessment may be characterized as not overexpressing ErbB2, whereas those tumors with 2+ or 3+scores may be characterized as overexpressing ErbB2.

Alternatively, or additionally, FISH assays such as the INFORM™ (Ventana Co., Arizona) or PATHVISION™ (Vysis, Ill.) may be carried out on formalin-fixed, paraffin-embedded tumor tissue to determine the extent (if any) of ErbB2 overexpression in the tumor.

Autoimmune diseases for which the ADC compounds may be used in treatment include rheumatologic disorders (such as, for example, rheumatoid arthritis, Sjögren's syndrome, scleroderma, lupus such as SLE and lupus nephritis, polymyositis/dermatomyositis, cryoglobulinemia, anti-phospholipid antibody syndrome, and psoriatic arthritis), osteoarthritis, autoimmune gastrointestinal and liver disorders (such as, for example, inflammatory bowel diseases (e.g., ulcerative colitis and Crohn's disease), autoimmune gastritis and pernicious anemia, autoimmune hepatitis, primary biliary cirrhosis, primary sclerosing cholangitis, and celiac disease), vasculitis (such as, for example, ANCA-associated vasculitis, including Churg-Strauss vasculitis, Wegener's granulomatosis, and polyarteriitis), autoimmune neurological disorders (such as, for example, multiple sclerosis, opsoclonus myoclonus syndrome, myasthenia gravis, neuromyelitis optica, Parkinson's disease, Alzheimer's disease, and autoimmune polyneuropathies), renal disorders (such as, for example, glomerulonephritis, Goodpasture's syndrome, and Berger's disease), autoimmune dermatologic disorders (such as, for example, psoriasis, urticaria, hives, pemphigus vulgaris, bullous pemphigoid, and cutaneous lupus erythematosus), hematologic disorders (such as, for example, thrombocytopenic purpura, thrombotic thrombocytopenic purpura, post-transfusion purpura, and autoimmune hemolytic anemia), atherosclerosis, uveitis, autoimmune hearing diseases (such as, for example, inner ear disease and hearing loss), Behcet's disease, Raynaud's syndrome, organ transplant, and autoimmune endocrine disorders (such as, for example, diabetic-related autoimmune diseases such as insulin-dependent diabetes mellitus (IDDM), Addison's disease, and autoimmune thyroid disease (e.g., Graves' disease and thyroiditis)). More preferred such diseases include, for example, rheumatoid arthritis, ulcerative colitis, ANCA-associated vasculitis, lupus, multiple sclerosis, Sjögren's syndrome, Graves' disease, IDDM, pernicious anemia, thyroiditis, and glomerulonephritis.

For the prevention or treatment of disease, the appropriate dosage of an ADC will depend on the type of disease to be treated, as defined above, the severity and course of the disease, whether the molecule is administered for preventive or therapeutic purposes, previous therapy, the patient's clinical history and response to the antibody, and the discretion of the attending physician. The molecule is suitably administered to the patient at one time or over a series of treatments. Depending on the type and severity of the disease, about 1 µg/kg to 15 mg/kg (e.g. 0.1-20 mg/kg) of molecule is an initial candidate dosage for administration to the patient, whether, for example, by one or more separate administrations, or by continuous infusion. A typical daily dosage might range from about 1 µg/kg to 100 mg/kg or more, depending on the factors mentioned above. An exemplary dosage of ADC to be administered to a patient is in the range of about 0.1 to about 10 mg/kg of patient weight.

For repeated administrations over several days or longer, depending on the condition, the treatment is sustained until a desired suppression of disease symptoms occurs. An exemplary dosing regimen comprises administering an initial loading dose of about 4 mg/kg, followed by a weekly maintenance dose of about 2 mg/kg of an anti-ErbB2 antibody. Other dosage regimens may be useful. The progress of this therapy is easily monitored by conventional techniques and assays.

Combination Therapy

An antibody-drug conjugate (ADC) of the invention may be combined in a pharmaceutical combination formulation, or dosing regimen as combination therapy, with a second compound having anti-cancer properties. The second compound of the pharmaceutical combination formulation or dosing regimen preferably has complementary activities to the ADC of the combination such that they do not adversely affect each other.

The second compound may be a chemotherapeutic agent, cytotoxic agent, cytokine, growth inhibitory agent, anti-hormonal agent, and/or cardioprotectant. Such molecules are suitably present in combination in amounts that are effective for the purpose intended. A pharmaceutical composition containing an ADC of the invention may also have a therapeutically effective amount of a chemotherapeutic agent such as a tubulin-forming inhibitor, a topoisomerase inhibitor, or a DNA binder.

Other therapeutic regimens may be combined with the administration of an anticancer agent identified in accordance with this invention. The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

In one embodiment, treatment with an ADC involves the combined administration of an anticancer agent identified herein, and one or more chemotherapeutic agents or growth inhibitory agents, including coadministration of cocktails of different chemotherapeutic agents. Chemotherapeutic agents include taxanes (such as paclitaxel and docetaxel) and/or anthracycline antibiotics. Preparation and dosing schedules for such chemotherapeutic agents may be used according to manufacturer's instructions or as determined empirically by the skilled practitioner. Preparation and dosing schedules for such chemotherapy are also described in "Chemotherapy Service", (1992) Ed., M. C. Perry, Williams & Wilkins, Baltimore, Md.

The ADC may be combined with an anti-hormonal compound; e.g., an anti-estrogen compound such as tamoxifen; an anti-progesterone such as onapristone (EP 616812); or an anti-androgen such as flutamide, in dosages known for such molecules. Where the cancer to be treated is hormone independent cancer, the patient may previously have been subjected to anti-hormonal therapy and, after the cancer becomes hormone independent, the ADC (and optionally other agents as described herein) may be administered to the patient. It may be beneficial to also coadminister a cardioprotectant (to prevent or reduce myocardial dysfunction associated with the therapy) or one or more cytokines to the patient. In addition to the above therapeutic regimes, the patient may be subjected to surgical removal of cancer cells and/or radiation therapy.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g. by different injections in separate syringes. In general, during alternation therapy, an effective dosage of each active ingredient is administered sequentially, i.e. serially, whereas in combination therapy, effective dosages of two or more active ingredients are administered together.

Metabolites of the Antibody-Drug Conjugates

Also falling within the scope of this invention are the in vivo metabolic products of the ADC compounds described herein, to the extent such products are novel and unobvious over the prior art. Such products may result for example from the oxidation, reduction, hydrolysis, amidation, esterification, enzymatic cleavage, and the like, of the administered compound. Accordingly, the invention includes novel and unobvious compounds produced by a process comprising contacting a compound of this invention with a mammal for a period of time sufficient to yield a metabolic product thereof.

Metabolite products typically are identified by preparing a radiolabelled (e.g. $^{14}$C or $^{3}$H) ADC, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS, LC/MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the ADC compounds of the invention.

Labelled Antibody Imaging Methods

In another embodiment of the invention, cysteine engineered antibodies may be labelled through the cysteine thiol with radionuclides, fluorescent dyes, bioluminescence-triggering substrate moieties, chemiluminescence-triggering substrate moieties, enzymes, and other detection labels for imaging experiments with diagnostic, pharmacodynamic, and therapeutic applications. Generally, the labelled cysteine engineered antibody, i.e. "biomarker" or "probe", is administered by injection, perfusion, or oral ingestion to a living organism, e.g. human, rodent, or other small animal, a perfused organ, or tissue sample. The distribution of the probe is detected over a time course and represented by an image.

Articles of Manufacture

In another embodiment of the invention, an article of manufacture, or "kit", containing materials useful for the treatment of the disorders described above is provided. The article of manufacture comprises a container and a label or package insert on or associated with the container. Suitable containers include, for example, bottles, vials, syringes, blister pack, etc. The containers may be formed from a variety of materials such as glass or plastic. The container holds an antibody-drug conjugate (ADC) composition which is effective for treating the condition and may have a sterile access port (for example the container may be an intravenous solution bag or a vial having a stopper pierceable by a hypodermic injection needle). At least one active agent in the composition is an ADC. The label or package insert indicates that the composition is used for treating the condition of choice, such as cancer. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

EXAMPLES

Example 1

Preparation of Biotinylated ThioFab Phage

ThioFab-phage ($5 \times 10^{12}$ phage particles) were reacted with 150 fold excess of biotin-PEO-maleimide ((+)-biotinyl-3-maleimidopropionamidyl-3,6-dioxaoctainediamine, Oda et al (2001) Nature Biotechnology 19:379-382, Pierce Biotechnology, Inc.) for 3 hours at room temperature. Excess biotin-PEO-maleimide was removed from biotin-conjugated phage by repeated PEG precipitations (3-4 times). Other commercially available biotinylation reagents with electrophilic groups which are reactive with cysteine thiol groups may be used, including Biotin-BMCC, PEO-Iodoacetyl Biotin, Iodoacetyl-LC-Biotin, and Biotin-HPDP (Pierce Biotechnology, Inc.), and $N^{\alpha}$-(3-maleimidylpropionyl)biocytin (MPB, Molecular Probes, Eugene, Oreg.). Other commercial sources for biotinylation, bifunctional and multifunctional linker reagents include Molecular Probes, Eugene, Oreg., and Sigma, St. Louis, Mo.

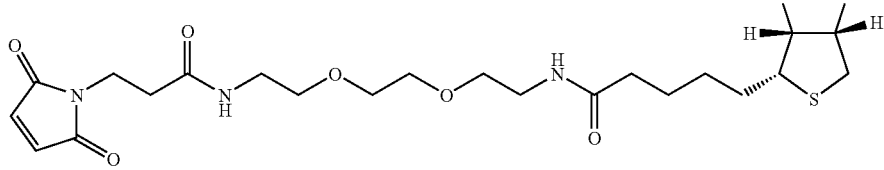

Biotin-PEO-maleimide

Example 2

Pheselector Assay

Bovine serum albumin (BSA), erbB2 extracellular domain (HER2) and streptavidin (100 µl of 2 µg/ml) were separately coated on Maxisorp 96 well plates. After blocking with 0.5% Tween-20 (in PBS), biotinylated and non-biotinylated hu4D5Fabv8-ThioFab-Phage ($2 \times 10^{10}$ phage particles) were incubated for 1 hour at room temperature followed by incubation with horseradish peroxidase (HRP) labeled secondary antibody (anti-M13 phage coat protein, pVIII protein antibody). FIG. 8 illustrates the PHESELECTOR Assay by a schematic representation depicting the binding of Fab or ThioFab to HER2 (top) and biotinylated ThioFab to streptavidin (bottom).

Standard HRP reaction was carried out and the absorbance was measured at 450 nm. Thiol reactivity was measured by calculating the ratio between $OD_{450}$ for streptavidin/$OD_{450}$ for HER2. A thiol reactivity value of 1 indicates complete biotinylation of the cysteine thiol. In the case of Fab protein binding measurements, hu4D5Fabv8 (2-20 ng) was used followed by incubation with HRP labeled goat polyclonal anti-Fab antibodies.

Example 3a

Expression and Purification of ThioFabs

ThioFabs were expressed upon induction in 34B8, a non-suppressor *E. coli* strain (Baca et al (1997) Journal Biological Chemistry 272(16):10678-84). The harvested cell pellet was resuspended in PBS (phosphate buffered saline), total cell lysis was performed by passing through a microfluidizer and the ThioFabs were purified by affinity chromatography with protein G SEPHAROSE™ (Amersham).

ThioFabs L-V15C, L-V110C, H-A88C, and H-A121C were expressed and purified by Protein-G SEPHAROSE™ column chromatography. Oligomeric-Fab was present in fractions 26 to 30, and most of the monomeric form was in fractions 31-34. Fractions consisting of the monomeric form were pooled and analyzed by SDS-PAGE along with wild type hu4D5Fabv8 and analyzed on SDS-PAGE gel in reducing (with DTT or BME) and non-reducing (without DTT or BME) conditions. Gel filtration fractions of A121C-ThioFab were analyzed on non-reducing SDS-PAGE.

ThioFabs were conjugated with biotin-PEO-maleimide as described above and the biotinylated-ThioFabs were further purified by Superdex-200™ (Amersham) gel filtration chromatography, which eliminated the free biotin-PEO-maleimide and the oligomeric fraction of ThioFabs. Wild type hu4D5Fabv8 and hu4D5Fabv8 A121C-ThioFab (0.5 mg in quantity) were each and separately incubated with 100 fold molar excess of biotin-PEO-maleimide for 3 hours at room temperature and loaded onto a Superdex-200 gel filtration column to separate free biotin as well as oligomeric Fabs from the monomeric form.

Example 3b

Analysis of ThioFabs

Enzymatic digest fragments of biotinylated hu4D5Fabv8 (A121C) ThioFab and wild type hu4D5Fabv8 were analyzed by liquid chromatography electrospray ionization mass spectroscopy (LS-ESI-MS) The difference between the 48294.5 primary mass of biotinylated hu4D5Fabv8 (A121C) and the 47737.0 primary mass of wild type hu4D5Fabv8 was 557.5 mass units. This fragment indicates the presence of a single biotin-PEO-maleimide moiety ($C_{23}H_{36}N_5O_7S_2$). Table 4 shows assignment of the fragmentation values which confirms the sequence.

TABLE 4

LC-ESI-Mass spec analysis of biotinylated hu4D5Fabv8 ThioFab A121C after tryptic digestion

| Amino acid | b Fragment | y Fragment |
| --- | --- | --- |
| A (Alanine) | 72 | |
| M (Methionine) | 203 | 2505 |
| D (Aspartic acid) | 318 | 2374 |
| Y (Tyrosine) | 481 | 2259 |
| W (Tryptophan) | 667 | 2096 |
| G (Glycine) | 724 | 1910 |
| Q (glutamine) | 852 | 1853 |
| G (Glycine) | 909 | 1725 |
| T (Threonine) | 1010 | 1668 |
| L (Leucine) | 1123 | 1567 |
| V (Valine) | 1222 | 1454 |
| T (Threonine) | 1323 | 1355 |
| V (Valine) | 1422 | 1254 |
| S (Serine) | 1509 | 1155 |
| S (Serine) | 1596 | 1068 |
| C (Cysteine) + biotin | 2242 | 981 |
| S (Serine) | 2329 | 335 |
| T (Threonine) | 2430 | 248 |
| K (Lysine) | | 175 |

Before and after Superdex-200 gel filtration, SDS-PAGE gel analyses, with and without reduction by DTT or BME, of biotinylated ABP-hu4D5Fabv8-A121C, biotinylated ABP-hu4D5Fabv8-V110C, biotinylated double Cys ABP-hu4D5Fabv8-(V110C-A88C), and biotinylated double Cys ABP-hu4D5Fabv8-(V110C-A121C) were conducted.

Mass spectroscopy analysis (MS/MS) of hu4D5Fabv8-(V110C)-BMPEO-DM1 (after Superdex-200 gel filtration purification): Fab+1 51607.5, Fab 50515.5. This data shows 91.2% conjugation. MS/MS analysis of hu4D5Fabv8-(V110C)-BMPEO-DM1 (reduced): LC 23447.2, LC+1 24537.3, HC (Fab) 27072.5. This data shows that all DM1 conjugation is on the light chain of the Fab.

Example 4

Preparation of ABP-hu4D5Fabv8-(V110C)-MC-MMAE by Conjugation of ABP-hu4D5Fabv8-(V110C) and MC-MMAE The drug linker reagent, maleimidocaproyl-monomethyl auristatin E (MMAE), i.e. MC-MMAE, dissolved in DMSO, is diluted in acetonitrile and water at known concentration, and added to chilled ABP-hu4D5Fabv8-(V110C) ThioFab in phosphate buffered saline (PBS). After about one hour, an excess of maleimide is added to quench the reaction and cap any unreacted antibody thiol groups. The reaction mixture is concentrated by centrifugal ultrafiltration and ABP-hu4D5Fabv8-(V110C)-MC-MMAE is purified and desalted by elution through G25 resin in PBS, filtered through 0.2 μm filters under sterile conditions, and frozen for storage.

Example 5

Preparation of ABP-hu4D5Fabv8-(V110C)-MC-MMAF by Conjugation of ABP-hu4D5Fabv8-(V110C) and MC-MMAF ABP-hu4D5Fabv8-(V110C)-MC-MMAF is prepared by conjugation of ABP-hu4D5Fabv8-(V110C) ThioFab and MC-MMAF following the procedure of Example 4.

Example 6

Preparation of ABP-A121C-ThioFab-MC-val-cit-PAB-MMAE by Conjugation of ABP-A121C-ThioFab and MC-val-cit-PAB-MMAE ABP-hu4D5Fabv8-(A121C)-MC-val-cit-PAB-MMAE is prepared by conjugation of ABP-hu4D5Fabv8-(A121C) and MC-val-cit-PAB-MMAE following the procedure of Example 4.

Example 7

Preparation of ABP-A121C-ThioFab-MC-val-cit-PAB-MMAF by Conjugation of ABP-A121C-ThioFab and MC-val-cit-PAB-MMAF ABP-hu4D5Fabv8-(A121C)-MC-val-cit-PAB-MMAF is prepared by conjugation of ABP-hu4D5Fabv8-(A121C) and MC-val-cit-PAB-MMAF following the procedure of Example 4.

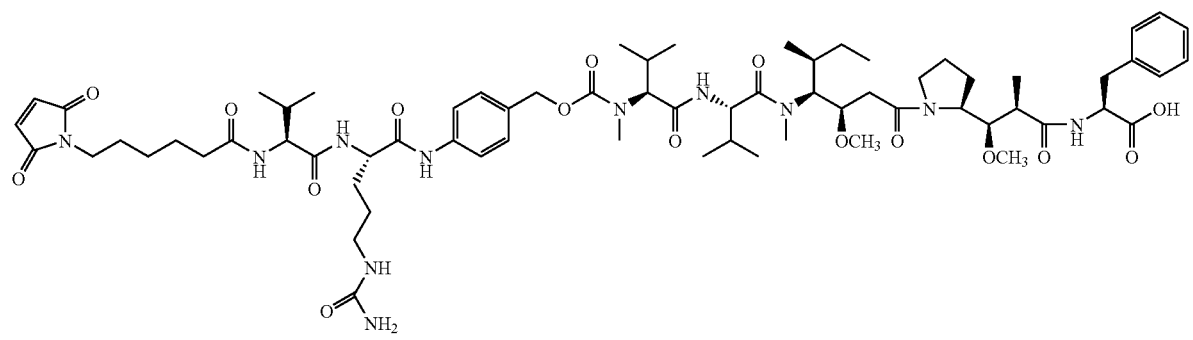

MC-val-cit-PAB-MMAF

Example 8

Preparation of hu4D5Fabv8-(V110C) ThioFab-BMPEO-DM1

The free cysteine on hu4D5Fabv8-(V110C) ThioFab was modified by the bis-maleimido reagent BM(PEO)$_4$ (Pierce Chemical), leaving an unreacted maleimido group on the surface of the antibody. This was accomplished by dissolving BM(PEO)4 in a 50% ethanol/water mixture to a concentration of 10 mM and adding a tenfold molar excess of BM(PEO)4 to a solution containing hu4D5Fabv8-(V110C) ThioFab in phosphate buffered saline at a concentration of approximately 1.6 mg/ml (10 micromolar) and allowing it to react for 1 hour. Excess BM(PEO)4 was removed by gel filtration (HiTrap column, Pharmacia) in 30 mM citrate, pH 6 with 150 mM NaCl buffer. An approximate 10 fold molar excess DM1 dissolved in dimethyl acetamide (DMA) was added to the hu4D5Fabv8-(V110C) ThioFab-BMPEO intermediate. Dimethylformamide (DMF) may also be employed to dissolve the drug moiety reagent. The reaction mixture was allowed to react overnight before gel filtration or dialysis into PBS to remove unreacted drug. Gel filtration on S200 columns in PBS was used to remove high molecular weight aggregates and furnish purified hu4D5Fabv8-(V110C) Thio-Fab-BMPEO-DM1.

By the same protocol, hu4D5Fabv8 (A121C) ThioFab-BMPEO-DM1 was prepared.

Example 9

In Vitro Cell Proliferation Assay

Efficacy of ADC were measured by a cell proliferation assay employing the following protocol (CellTiter Glo Luminiscent Cell Viability Assay, Promega Corp. Technical Bulletin TB288; Mendoza et al (2002) Cancer Res. 62:5485-5488):
1. An aliquot of 100 µl of cell culture containing about $10^4$ cells (SKBR-3, BT474, MCF7 or MDA-MB-468) in medium was deposited in each well of a 96-well, opaque-walled plate.
2. Control wells were prepared containing medium and without cells.
3. ADC was added to the experimental wells and incubated for 3-5 days.
4. The plates were equilibrated to room temperature for approximately 30 minutes.
5. A volume of CellTiter-Glo Reagent equal to the volume of cell culture medium present in each well was added.
6. The contents were mixed for 2 minutes on an orbital shaker to induce cell lysis.
7. The plate was incubated at room temperature for 10 minutes to stabilize the luminescence signal.
8. Luminescence was recorded and reported in graphs as RLU=relative luminescence units.

Certain cells are seeded at 1000-2000/well (PC3 lines) or 2000-3000/well (OVCAR-3) in a 96-well plate, 50 uL/well. After one (PC3) or two (OVCAR-3) days, ADC are added in 50 µL volumes to final concentration of 9000, 3000, 1000, 333, 111, 37, 12.4, 4.1, or 1.4 ng/mL, with "no ADC" control wells receiving medium alone. Conditions are in duplicate or triplicate After 3 (PC3) or 4-5 (OVCAR-3) days, 100 µL/well Cell TiterGlo II is added (luciferase-based assay; proliferation measured by ATP levels) and cell counts are determined using a luminometer. Data are plotted as the mean of luminescence for each set of replicates, with standard deviation error bars. The protocol is a modification of the CellTiter Glo Luminiscent Cell Viability Assay (Promega):
1. Plate 1000 cells/well of PC3/Muc16, PC3/neo (in 50 µL/well) of media. Ovcar3 cells should be plated at 2000 cells/well (in 50 µL) of their media. (recipes below) Allow cells to attach overnight.
2. ADC is serially diluted 1:3 in media beginning at working concentration 18 µg/ml (this results in a final concentration of 9 µg/ml). 50 µL of diluted ADC is added to the 50 µL of cells and media already in the well.
3. Incubate 72-96 hrs (the standard is 72 hours, but watch the 0 ug/mL concentration to stop assay when the cells are 85-95% confluent).
4. Add 100 µL/well of Promega Cell Titer Glo reagent, shake 3 min. and read on luminometer Media: PC3/neo and PC3/MUC16 grow in 50/50/10% FBS/glutamine/250 µg/mL G-418 OVCAR-3 grow in RPMI/20% FBS/glutamine

Example 10

Tumor Growth Inhibition, in Vivo Efficacy in High Expressing HER2 transgenic explant mice Animals suitable for transgenic experiments can be obtained from standard commercial sources such as Taconic (Germantown, N.Y.). Many strains are suitable, but FVB female mice are preferred because of their higher susceptibility to tumor formation. FVB males were used for mating and vasectomized CD.1 studs were used to stimulate pseudopregnancy. Vasectomized mice can be obtained from any commercial supplier. Founders were bred with either FVB mice or with 129/BL6×FVB p53 heterozygous mice. The mice with heterozygosity at p53 allele were used to potentially increase tumor formation. However, this has proven unnecessary. Therefore, some F1 tumors are of mixed strain. Founder tumors are FVB only. Six founders were obtained with some developing tumors without having litters.

Animals having tumors (allograft propagated from Fo5 mmtv transgenic mice) were treated with a single or multiple dose by IV injection of ADC. Tumor volume was assessed at various time points after injection.

Tumors arise readily in transgenic mice that express a mutationally activated form of neu, the rat homolog of HER2, but the HER2 that is overexpressed in human breast cancers is not mutated and tumor formation is much less robust in transgenic mice that overexpress nonmutated HER2 (Webster et al (1994) Semin. Cancer Biol. 5:69-76).

To improve tumor formation with nonmutated HER2, transgenic mice were produced using a HER2 cDNA plasmid in which an upstream ATG was deleted in order to prevent initiation of translation at such upstream ATG codons, which would otherwise reduce the frequency of translation initiation from the downstream authentic initiation codon of HER2 (for example, see Child et al (1999) J. Biol. Chem. 274: 24335-24341). Additionally, a chimeric intron was added to the 5' end, which should also enhance the level of expression as reported earlier (Neuberger and Williams (1988) Nucleic Acids Res. 16:6713; Buchman and Berg (1988) Mol. Cell.

Biol. 8:4395; Brinster et al (1988) Proc. Natl. Acad. Sci. USA 85:836). The chimeric intron was derived from a Promega vector, Pci-neo mammalian expression vector (bp 890-1022). The cDNA 3'-end is flanked by human growth hormone exons 4 and 5, and polyadenylation sequences. Moreover, FVB mice were used because this strain is more susceptible to tumor development. The promoter from MMTV-LTR was used to ensure tissue-specific HER2 expression in the mammary gland. Animals were fed the AIN 76A diet in order to increase susceptibility to tumor formation (Rao et al (1997) Breast Cancer Res. and Treatment 45:149-158).

Example 11

Reduction/Oxidation of ThioMabs for Conjugation

Full length, cysteine engineered monoclonal antibodies (ThioMabs) expressed in CHO cells were reduced with about a 50 fold excess of TCEP (tris(2-carboxyethyl)phosphine hydrochloride; Getz et al (1999) Anal. Biochem. Vol 273:73-80; Soltec Ventures, Beverly, Mass.) for 3 hrs at 37° C. The reduced ThioMab (FIG. 15) was diluted and loaded onto a HiTrap S column in 10 mM sodium acetate, pH 5, and eluted with PBS containing 0.3M sodium chloride. The eluted reduced ThioMab was treated with 200 nM aqueous copper sulfate ($CuSO_4$) at room temperature, overnight. Ambient air oxidation was also effective.

Example 12

Conjugation of ThioMabs

The reoxidized ThioMabs from Example 11, including thio-trastuzumab (A121C), thio-2H9 (A121C), and thio-3A5 (A121C), were combined with a 10 fold excess of drug-linker intermediate, $BM(PEO)_4$-DM1, mixed, and let stand for about an hour at room temperature to effect conjugation and form the ThioMab antibody-drug conjugates, including thio-trastuzumab (A121C)-BMPEO-DM1, thio-2H9 (A121C)-BMPEO-DM1, and thio-3A5 (A121C)-BMPEO-DM1. The conjugation mixture was gel filtered, or loaded and eluted through a HiTrap S column to remove excess drug-linker intermediate and other impurities.

The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

All patents, patent applications, and references cited throughout the specification are expressly incorporated by reference.

We claim:

1. A cysteine engineered antibody comprising a free cysteine amino acid having a thiol reactivity value in the range of 0.6 to 1.0; and a sequence in the heavy chain selected from SEQ ID NOS: 11, 12, 13, and 15:

```
LVTVCSASTKGPS      SEQ ID NO:11

LVTVSCASTKGPS      SEQ ID NO:12

LVTVSSCSTKGPS      SEQ ID NO:13

HTFPCVLQSSGLYS     SEQ ID NO:15
``` where the cysteine in SEQ ID NOS: 11, 12, 13, and 15 are the free cysteine amino acid.

2. The cysteine engineered antibody of claim 1 wherein the cysteine engineered antibody is more reactive with a thiol-reactive reagent than the parent antibody.

3. The cysteine engineered antibody of claim 1 wherein the process further comprises determining the thiol reactivity of the cysteine engineered antibody by reacting the cysteine engineered antibody with a thiol-reactive reagent;
wherein the cysteine engineered antibody is more reactive with the thiol-reactive reagent than the parent antibody.

4. The cysteine engineered antibody of claim 1 wherein the thiol reactivity value is in the range of 0.7 to 1.0.

5. The cysteine engineered antibody of claim 1 wherein the thiol reactivity value is in the range of 0.8 to 1.0.

6. The cysteine engineered antibody of claim 1 prepared by a process comprising:
(i) mutagenizing a nucleic acid sequence encoding the cysteine engineered antibody;
(ii) expressing the cysteine engineered antibody; and
(iii) isolating and purifying the cysteine engineered antibody.

7. The cysteine engineered antibody of claim 6 wherein mutagenizing comprises site-directed mutagenesis.

8. The cysteine engineered antibody of claim 6 wherein the cysteine engineered antibody is expressed on a viral particle selected from a phage or a phagemid particle.

9. The cysteine engineered antibody of claim 6 further comprising:
(i) reacting the cysteine engineered antibody with a thiol-reactive affinity reagent to generate an affinity labelled, cysteine engineered antibody; and
(ii) measuring the binding of the affinity labelled, cysteine engineered antibody to a capture media.

10. The cysteine engineered antibody of claim 9 wherein the thiol-reactive affinity reagent comprises a biotin moiety.

11. The cysteine engineered antibody of claim 10 wherein the thiol-reactive reagent comprises a maleimide moiety.

12. The cysteine engineered antibody of claim 9 wherein the capture media comprises streptavidin.

13. The cysteine engineered antibody of claim 1 wherein the parent antibody is a fusion protein comprising the albumin-binding peptide (ABP).

14. The cysteine engineered antibody of claim 13 wherein the ABP comprises a sequence selected from SEQ ID NO: 1, SEQ ID NO: 2, SEQ ID NO: 3, SEQ ID NO: 4, and SEQ ID NO: 5.

15. The cysteine engineered antibody of claim 1 wherein the parent antibody is selected from a monoclonal antibody, a bispecific antibody, a chimeric antibody, a human antibody, and a humanized antibody.

16. The cysteine engineered antibody of claim 15 wherein the parent antibody is huMAb4D5-8 (trastuzumab).

17. The cysteine engineered antibody of claim 15 wherein the parent antibody is an anti-EphB2R antibody.

18. The cysteine engineered antibody of claim 15 wherein the parent antibody is an anti-MUC16 antibody.

19. The cysteine engineered antibody of claim 1 wherein the parent antibody is an intact antibody selected from IgA, IgD, IgE, IgG, and IgM.

20. The cysteine engineered antibody of claim 19 wherein the IgG is selected from subclasses IgG1, IgG2, IgG3, and IgG4.

21. The cysteine engineered antibody of claim 1 wherein the parent antibody is an antibody fragment.

22. The cysteine engineered antibody of claim 21 wherein the antibody fragment is a Fab fragment.

23. The cysteine engineered antibody of claim 22 wherein the Fab fragment is hu4D5Fabv8.

24. The cysteine engineered antibody of claim 1 wherein the cysteine engineered antibody or the parent antibody binds to one or more of receptors (1)-(36):
(1) BMPR1B (bone morphogenetic protein receptor-type IB);
(2) E16 (LAT1, SLC7A5);
(3) STEAP1 (six transmembrane epithelial antigen of prostate);
(4) 0772P (CA125, MUC16);
(5) MPF (MPF, MSLN, SMR, megakaryocyte potentiating factor, mesothelin);
(6) Napi3b (NAPI-3B, NPTIIb, SLC34A2, solute carrier family 34 (sodium phosphate), member 2, type II sodium-dependent phosphate transporter 3b);
(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B);
(8) PSCA hlg (2700050C12Rik, C530008O16Rik, RIKEN cDNA 2700050C12, RIKEN cDNA 2700050C12 gene);
(9) ETBR (Endothelin type B receptor);
(10) MSG783 (RNF124, hypothetical protein FLJ20315);
(11) STEAP2 (HGNC_8639 IPCA-1, PCANAP1, STAMP1, STEAP2, STMP, prostate cancer associated gene 1, prostate cancer associated protein 1, six transmembrane epithelial antigen of prostate 2, six transmembrane prostate protein);
(12) TrpM4 (BR22450, FLJ20041, TRPM4, TRPM4B, transient receptor potential cation channel, subfamily M, member 4);
(13) CRIPTO (CR, CR1, CRGF, CRIPTO, TDGF1, teratocarcinoma-derived growth factor);
(14) CD21 (CR2 (Complement receptor 2) or C3DR (C3d/Epstein Barr virus receptor) or Hs.73792);
(15) CD79b (CD79B, CD79β, IGb (immunoglobulin-associated beta), B29);
(16) FcRH2 (IFGP4, IRTA4, SPAP1A (SH2 domain containing phosphatase anchor protein 1a), SPAP1B, SPAP1C);
(17) HER2;
(18) NCA;
(19) MDP;
(20) IL20Rα;
(21) Brevican;
(22) EphB2R;
(23) ASLG659;
(24) PSCA;
(25) GEDA;

(26) BAFF-R (B cell-activating factor receptor, BLyS receptor 3, BR3;
(27) CD22 (B-cell receptor CD22-B isoform);
(28) CD79a (CD79A, CD79α, immunoglobulin-associated alpha, a B cell-specific protein that covalently interacts with Ig beta (CD79B) and forms a complex on the surface with IgM molecules, transduces a signal involved in B-cell differentiation);
(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia);
(30) HLA-DOB (Beta subunit of MHC class II molecule (Ia antigen) that binds peptides and presents them to CD4+ T lymphocytes);
(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability);
(32) CD72 (B-cell differentiation antigen CD72, Lyb-2);
(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis);
(34) FcRH1 (Fc receptor-like protein 1, a putative receptor for the immunoglobulin Fc domain that contains C2 type Ig-like and ITAM domains, may have a role in B-lymphocyte differentiation);
(35) IRTA2 (Immunoglobulin superfamily receptor translocation associated 2, a putative immunoreceptor with possible roles in B cell development and lymphomagenesis; deregulation of the gene by translocation occurs in some B cell malignancies); and
(36) TENB2 (putative transmembrane proteoglycan, related to the EGF/heregulin family of growth factors and follistatin).

25. The cysteine engineered antibody of claim 1 wherein the antibody is covalently attached to a capture label, a detection label, or a solid support.

26. The cysteine engineered antibody of claim 25 wherein the antibody is covalently attached to a biotin capture label.

27. The cysteine engineered antibody of claim 25 wherein the antibody is covalently attached to a fluorescent dye detection label.

28. The cysteine engineered antibody of claim 27 wherein the fluorescent dye is selected from a fluorescein type, a rhodamine type, dansyl, Lissamine, a cyanine, a phycoerythrin, Texas Red, and an analog thereof.

29. The cysteine engineered antibody of claim 25 wherein the antibody is covalently attached to a radionuclide detection label selected from $^3$H, $^{11}$C, $^{14}$C, $^{18}$F, $^{32}$P, $^{35}$S, $^{64}$Cu, $^{68}$Ga, $^{86}$Y, $^{99}$Tc, $^{111}$In, $^{123}$I, $^{124}$I, $^{125}$I, $^{131}$I, $^{133}$Xe, $^{177}$Lu, $^{211}$At, and $^{213}$Bi.

30. The cysteine engineered antibody of claim 25 wherein the antibody is covalently attached to a detection label by a chelating ligand.

31. The cysteine engineered antibody of claim 30 wherein the chelating ligand is selected from DOTA, DOTP, DOTMA, DTPA and TETA.

32. An antibody-drug conjugate compound comprising a cysteine engineered antibody (Ab) comprising a free cysteine amino acid having a thiol reactivity value in the range of 0.6 to 1.0; and a sequence in the heavy chain selected from SEQ ID NOS: 11, 12, 13, and 15:

```
LVTVCSASTKGPS         SEQ ID NO:11

LVTVSCASTKGPS         SEQ ID NO:12

LVTVSSCSTKGPS         SEQ ID NO:13

HTFPCVLQSSGLYS        SEQ ID NO:15
``` where the cysteine in SEQ ID NOS: 11, 12, 13, and 15 are the free cysteine amino acid, and a drug moiety (D) selected from a maytansinoid, an auristatin, a dolastatin, and a calicheamicin, wherein the cysteine engineered antibody is attached through one or more free cysteine amino acids by a linker moiety (L) to D; the compound having Formula I:

Ab-(L-D)$_p$ where p is 1, 2, 3, or 4; and wherein the cysteine engineered antibody is prepared by a process comprising replacing one or more amino acid residues of a parent antibody with the one or more free cysteine amino acids, where the parent antibody selectively binds to an antigen and the cysteine engineered antibody selectively binds to the same antigen as the parent antibody.

33. The antibody-drug conjugate compound of claim 32 wherein the cysteine engineered antibody is prepared by a process comprising:
(a) replacing one or more amino acid residues of a parent antibody by cysteine; and
(b) determining the thiol reactivity of the cysteine engineered antibody by reacting the cysteine engineered antibody with a thiol-reactive reagent;
wherein the cysteine engineered antibody is more reactive than the parent antibody with the thiol-reactive reagent.

34. The antibody-drug conjugate compound of claim 32 further comprising an albumin-binding peptide (ABP) sequence.

35. The antibody-drug conjugate compound of claim 34 wherein the ABP comprises a sequence selected from SEQ ID NO: 1, SEQ ID NO: 2, SEQ ID NO: 3, SEQ ID NO: 4, and SEQ ID NO: 5.

36. The antibody-drug conjugate compound of claim 32 wherein the cysteine engineered antibody binds to an ErbB receptor selected from EGFR, HER2, HER3, and HER4.

37. The antibody-drug conjugate compound of claim 32 wherein the cysteine engineered antibody or the parent antibody binds to one or more of receptors (1)-(36):
(1) BMPR1B (bone morphogenetic protein receptor-type IB);
(2) E16 (LAT1, SLC7A5);
(3) STEAP1 (six transmembrane epithelial antigen of prostate);
(4) 0772P (CA125, MUC16);
(5) MPF (MPF, MSLN, SMR, megakaryocyte potentiating factor, mesothelin);
(6) Napi3b (NAPI-3B, NPTIIb, SLC34A2, solute carrier family 34 (sodium phosphate), member 2, type II sodium-dependent phosphate transporter 3b);
(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B);

(8) PSCA hlg (2700050C12Rik, C530008O16Rik, RIKEN cDNA 2700050C12, RIKEN cDNA 2700050C12 gene);
(9) ETBR (Endothelin type B receptor);
(10) MSG783 (RNF124, hypothetical protein FLJ20315);
(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein);
(12) TrpM4 (BR22450, FLJ20041, TRPM4, TRPM4B, transient receptor potential cation channel, subfamily M, member 4);
(13) CRIPTO (CR, CR1, CRGF, CRIPTO, TDGF1, teratocarcinoma-derived growth factor);
(14) CD21 (CR2 (Complement receptor 2) or C3DR (C3d/Epstein Barr virus receptor) or Hs.73792);
(15) CD79b (CD79B, CD79β, IGb (immunoglobulin-associated beta), B29);
(16) FcRH2 (IFGP4, IRTA4, SPAP1A (SH2 domain containing phosphatase anchor protein 1a), SPAP1B, SPAP1C);
(17) HER2;
(18) NCA;
(19) MDP;
(20) IL20Rα;
(21) Brevican;
(22) EphB2R;
(23) ASLG659;
(24) PSCA;
(25) GEDA;
(26) BAFF-R (B cell-activating factor receptor, BLyS receptor 3, BR3);
(27) CD22 (B-cell receptor CD22-B isoform);
(28) CD79a (CD79A, CD79α, immunoglobulin-associated alpha, a B cell-specific protein that covalently interacts with Ig beta (CD79B) and forms a complex on the surface with IgM molecules, transduces a signal involved in B-cell differentiation);
(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia);
(30) HLA-DOB (Beta subunit of MHC class II molecule (Ia antigen) that binds peptides and presents them to CD4+ T lymphocytes);
(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability);
(32) CD72 (B-cell differentiation antigen CD72, Lyb-2);
(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis);
(34) FcRH1 (Fc receptor-like protein 1, a putative receptor for the immunoglobulin Fc domain that contains C2 type Ig-like and ITAM domains, may have a role in B-lymphocyte differentiation);
(35) IRTA2 (Immunoglobulin superfamily receptor translocation associated 2, a putative immunoreceptor with possible roles in B cell development and lymphomagenesis; deregulation of the gene by translocation occurs in some B cell malignancies); and
(36) TENB2 (putative transmembrane proteoglycan, related to the EGF/heregulin family of growth factors and follistatin).

38. The antibody-drug conjugate compound of claim 32 wherein p is 1.

39. The antibody-drug conjugate compound of claim 32 wherein p is 2.

40. The antibody-drug conjugate compound of claim 32 wherein L has the formula:

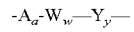

where:
A is a Stretcher unit covalently attached to a cysteine thiol of the cysteine engineered antibody (Ab);
a is 0 or 1;
each W is independently an Amino Acid unit;
w is an integer ranging from 0 to 12;
Y is a Spacer unit covalently attached to the drug moiety; and
y is 0, 1 or 2.

41. The antibody-drug conjugate compound of claim 40 having the formula:

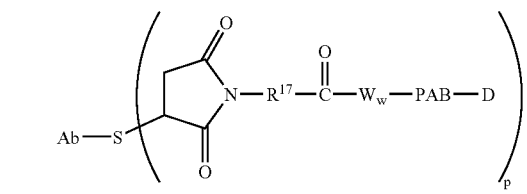

where PAB is para-aminobenzylcarbamoyl, and $R^{17}$ is a divalent radical selected from $(CH_2)_r$, $C_3$-$C_8$ carbocyclyl, $O$—$(CH_2)_r$, arylene, $(CH_2)_r$-arylene, -arylene-$CH_2)_r$—, $(CH_2)_r$—$(C_3$-$C_8$ carbocyclyl), $(C_3$-$C_8$ carbocyclyl)-$(CH_2)_r$, $C_3$-$C_8$ heterocyclyl, $(CH_2)_r$—$(C_3$-$C_8$ heterocyclyl), —$C_3$-$C_8$ heterocyclyl)—$(CH_2)_r$—, —$(CH_2)_rC(O)NR^b(CH_2)_r$—, —$(CH_2CH_2O)_r$—, —$(CH_2CH_2O)_r$—$CH_2$—, —$(CH_2)_rC(O)NR^b(CH_2CH_2O)_r$—, —$(CH_2)_rC(O)NR^b(CH_2CH_2O)_r$—$CH_2$—, —$(CH_2CH_2O)_rC(O)NR^b(CH_2CH_2O)_r$—, —$(CH_2CH_2O)_rC(O)NR^b(CH_2CH_2O)_r$—$CH_2$—, and —$(CH_2CH_2O)_rC(O)NR^b(CH_2)_r$—; where $R^b$ is H, $C_1$-$C_6$ alkyl, phenyl, or benzyl; and r is independently an integer ranging from 1 to 10.

42. The antibody-drug conjugate compound of claim 41 wherein $W_w$ is valine-citrulline.

43. The antibody-drug conjugate compound of claim 41 wherein $R^{17}$ is $(CH_2)_5$ or $(CH_2)_2$.

44. The antibody-drug conjugate compound of claim 40 having the formula:

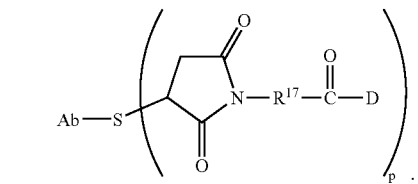

45. The antibody-drug conjugate compound of claim 44 wherein $R^{17}$ is $(CH_2)_5$ or $(CH_2)_2$.

46. The antibody-drug conjugate compound of claim 40 having the formula:

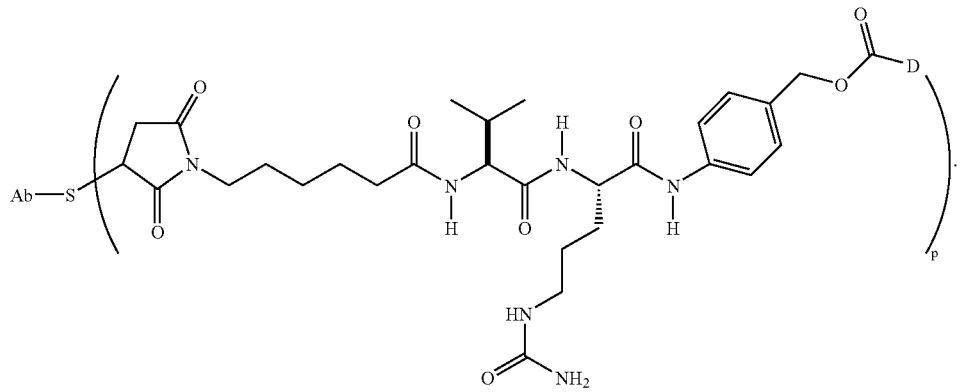

47. The antibody-drug conjugate compound of claim 32 wherein L is SMCC.

48. The antibody-drug conjugate compound of claim 32 wherein L is BMPEO.

49. The antibody-drug conjugate compound of claim 32 wherein D is MMAE, having the structure:

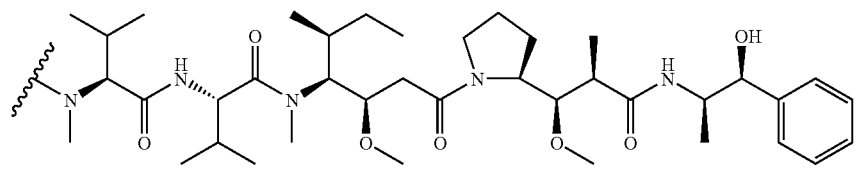

where the wavy line indicates the attachment site to the linker L.

50. The antibody-drug conjugate compound of claim 32 wherein D is MMAF, having the structure:

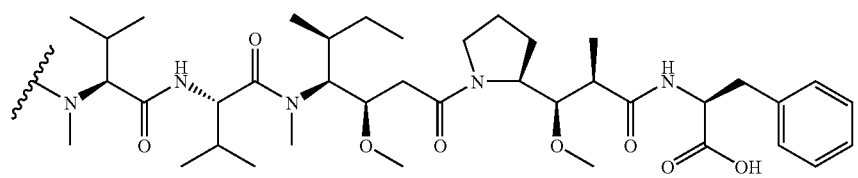

where the wavy line indicates the attachment site to the linker L.

51. The antibody-drug conjugate compound of claim 32 wherein D is DM1, having the structure:

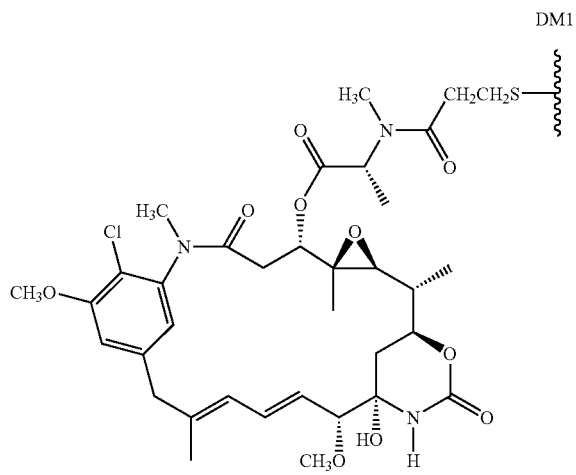

where the wavy line indicates the attachment site to the linker L.

52. The antibody-drug conjugate compound of claim 32 wherein the parent antibody is a fusion protein comprising the albumin-binding peptide (ABP).

53. The antibody-drug conjugate compound of claim 32 wherein the parent antibody is selected from a monoclonal antibody, a bispecific antibody, a chimeric antibody, a human antibody, and a humanized antibody.

54. The antibody-drug conjugate compound of claim 32 wherein the parent antibody is huMAb4D5-8 (trastuzumab).

55. The antibody-drug conjugate compound of claim 32 wherein the parent antibody is an anti-ErbB2 antibody.

56. The antibody-drug conjugate compound of claim 32 wherein the parent antibody is an anti-EphB2R antibody.

57. The antibody-drug conjugate compound of claim 32 wherein the parent antibody is an anti-CD22 antibody.

58. The antibody-drug conjugate compound of claim 32 wherein the parent antibody is an anti-MUC16 antibody.

59. The antibody-drug conjugate compound of claim 32 wherein the parent antibody is an intact antibody selected from IgA, IgD, IgE, IgG, and IgM.

60. The antibody-drug conjugate compound of claim 59 wherein the IgG is selected from subclasses: IgG1, IgG2, IgG3, and IgG4.

61. The antibody-drug conjugate compound of claim 32 wherein the parent antibody is an antibody fragment.

62. The antibody-drug conjugate compound of claim 61 wherein the antibody fragment is a Fab fragment.

63. The antibody-drug conjugate compound of claim 62 wherein the Fab fragment is hu4D5Fabv8.

64. The antibody-drug conjugate compound of claim 32 having the structure:

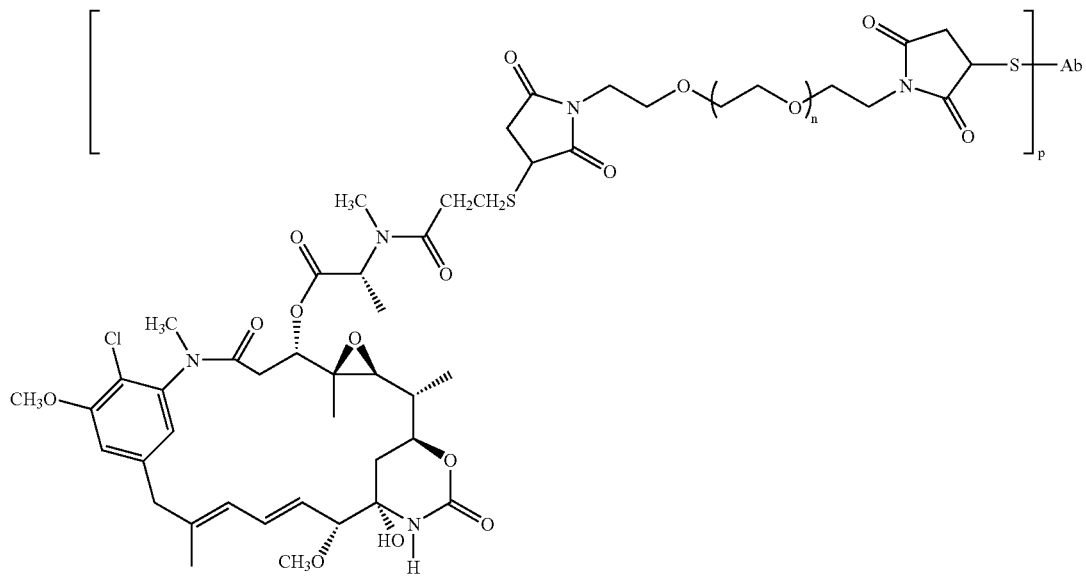

wherein n is 0, 1, or 2; and Ab is a cysteine engineered antibody.

65. A pharmaceutical composition comprising the antibody-drug conjugate compound of claim 32 or a pharmaceutically acceptable salt thereof, and a pharmaceutically acceptable diluent, carrier or excipient.

66. The pharmaceutical composition of claim 65 further comprising a therapeutically effective amount of an additional chemotherapeutic agent.

67. An article of manufacture comprising an antibody-drug conjugate compound of claim 32, a container, and a package insert or label indicating that the compound can be used to treat cancer.

68. The antibody-drug conjugate compound of claim 32 selected from the structures:

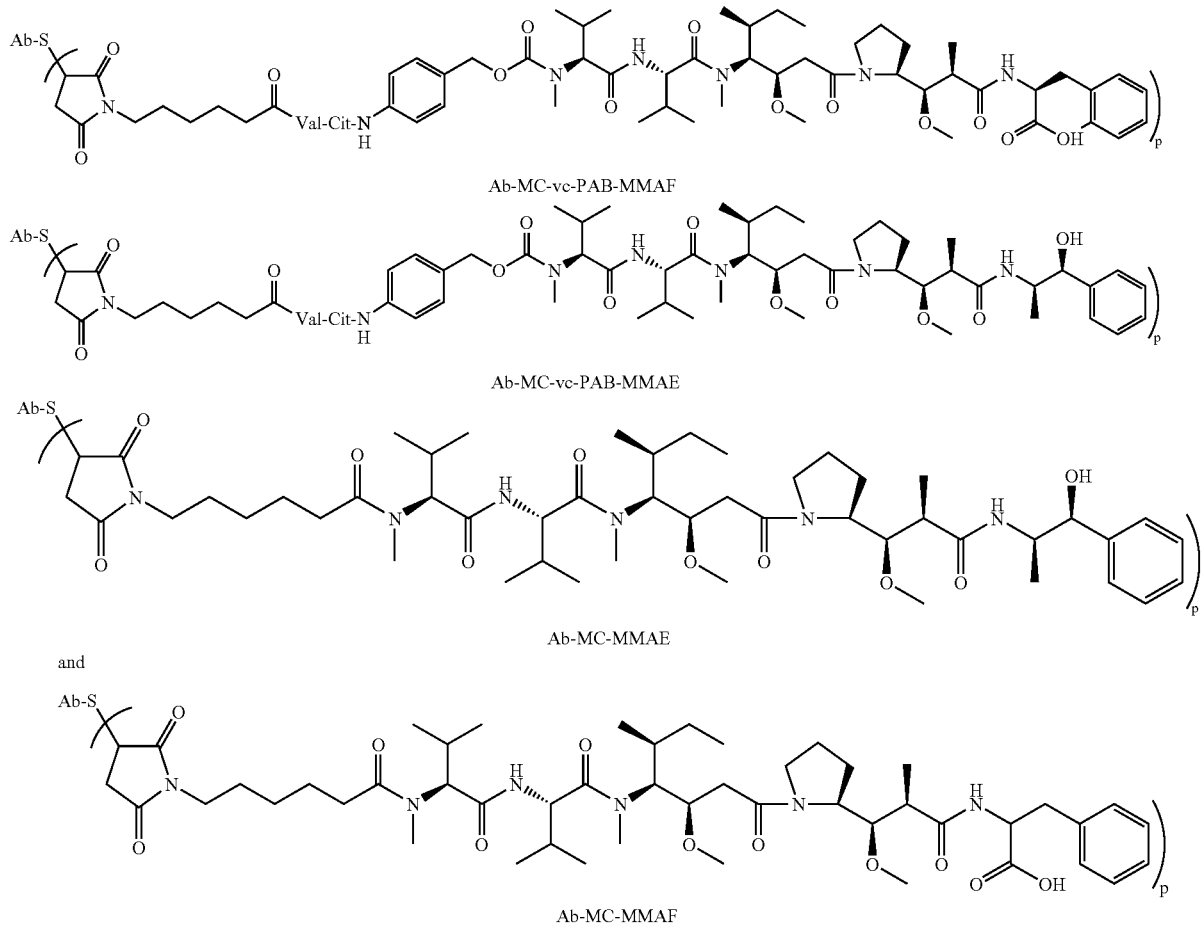

wherein Val is valine and Cit is citrulline.

* * * * *

UNITED STATES PATENT AND TRADEMARK OFFICE
CERTIFICATE OF CORRECTION

PATENT NO. : 7,521,541 B2  Page 1 of 5
APPLICATION NO. : 11/233258
DATED : April 21, 2009
INVENTOR(S) : Eigenbrot et al.

It is certified that error appears in the above-identified patent and that said Letters Patent is hereby corrected as shown below:

Corrections to the Issued Claims should read as follows:

Col. 131, claim 13, line 55

13. The cysteine engineered antibody of claim 1 wherein the ~~parent antibody~~ cysteine engineered antibody is a fusion protein comprising the albumin-binding peptide (ABP).

Col. 131, claim 15, line 62

15. The cysteine engineered antibody of claim 1 wherein the ~~parent antibody~~ cysteine engineered antibody is selected from a monoclonal antibody, a bispecific antibody, a chimeric antibody, a human antibody, and a humanized antibody.

Col. 131, claim 16, line 66

16. The cysteine engineered antibody of claim 15 wherein the ~~parent antibody~~ cysteine engineered antibody is ~~huMAb4D5-8 (trastuzumab)~~ an anti-HER2 antibody.

Col. 132, claim 17, line 1

17. The cysteine engineered antibody of claim 15 wherein the ~~parent antibody~~ cysteine engineered antibody is an anti-EphB2R antibody.

Col. 132, claim 18, line 3

18. The cysteine engineered antibody of claim 15 wherein the ~~parent antibody~~ cysteine engineered antibody is an anti-MUC16 antibody.

Col. 132, claim 19, line 5

19. The cysteine engineered antibody of claim 1 wherein the ~~parent antibody~~ cysteine engineered antibody is an intact antibody selected from IgA, IgD, IgE, IgG, and IgM.

Signed and Sealed this

Twentieth Day of July, 2010

David J. Kappos
*Director of the United States Patent and Trademark Office*

Col. 132, claim 21, line 8

21. The cysteine engineered antibody of claim 1 wherein the ~~parent antibody~~ cysteine engineered antibody is an antibody fragment.

Col. 132, claim 24, line 17

24. The cysteine engineered antibody of claim 1 wherein the cysteine engineered antibody ~~or the parent antibody~~ binds to one or more of receptors (1)-(36):

(1) BMPR1B (bone morphogenetic protein receptor-type IB);

(2) E16 (LAT1, SLC7A5);

(3) STEAP1 (six transmembrane epithelial antigen of prostate);

(4) 0772P (CA125, MUC16);

(5) MPF (MPF, MSLN, SMR, megakaryocyte potentiating factor, mesothelin);

(6) Napi3b (NAPI-3B, NPTIIb, SLC34A2, solute carrier family 34 (sodium phosphate), member 2, type II sodium-dependent phosphate transporter 3b);

(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B);

(8) PSCA hlg (2700050C12Rik, C530008O16Rik, RIKEN cDNA 2700050C12, RIKEN cDNA 2700050C12 gene);

(9) ETBR (Endothelin type B receptor);

(10) MSG783 (RNF124, hypothetical protein FLJ20315);

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein);

(12) TrpM4 (BR22450, FLJ20041, TRPM4, TRPM4B, transient receptor potential cation channel, subfamily M, member 4);

(13) CRIPTO (CR, CR1, CRGF, CRIPTO, TDGF1, teratocarcinoma-derived growth factor);

(14) CD21 (CR2 (Complement receptor 2) or C3DR (C3d/Epstein Barr virus receptor) or Hs.73792);

(15) CD79b (CD79B, CD79β, IGb (immunoglobulin-associated beta), B29);

(16) FcRH2 (IFGP4, IRTA4, SPAP1A (SH2 domain containing phosphatase anchor protein 1a), SPAP1B, SPAP1C);

(17) HER2;

(18) NCA;

(19) MDP;

(20) IL20Rα;

(21) Brevican;

(22) EphB2R;

(23) ASLG659;

(24) PSCA;

(25) GEDA;

(26) BAFF-R (B cell-activating factor receptor, BLyS receptor 3, BR3);

(27) CD22 (B-cell receptor CD22-B isoform);

(28) CD79a (CD79A, CD79a, immunoglobulin-associated alpha, a B cell-specific protein that covalently interacts with Ig beta (CD79B) and forms a complex on the surface with IgM molecules, transduces a signal involved in B-cell differentiation);

(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia);

(30) HLA-DOB (Beta subunit of MHC class II molecule (Ia antigen) that binds peptides and presents them to CD4+ T lymphocytes);

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability);

(32) CD72 (B-cell differentiation antigen CD72, Lyb-2);

(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis);

(34) FcRH1 (Fc receptor-like protein 1, a putative receptor for the immunoglobulin Fc domain that contains C2 type Ig-like and ITAM domains, may have a role in B-lymphocyte differentiation);

(35) IRTA2 (Immunoglobulin superfamily receptor translocation associated 2, a putative immunoreceptor with possible roles in B cell development and lymphomagenesis; deregulation of the gene by translocation occurs in some B cell malignancies); and

CERTIFICATE OF CORRECTION (continued)
U.S. Pat. No. 7,521,541 B2

Page 4 of 5

(36) TENB2 (putative transmembrane proteoglycan, related to the EGF/heregulin family of growth factors and follistatin).

Col. 139, claim 51, line 1

51. The antibody-drug conjugate compound of claim 32 wherein D is DM1, having the structure:

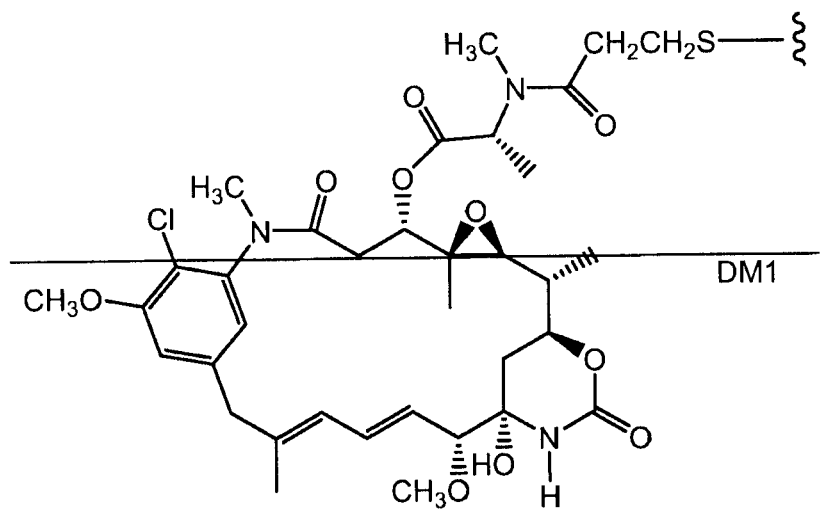

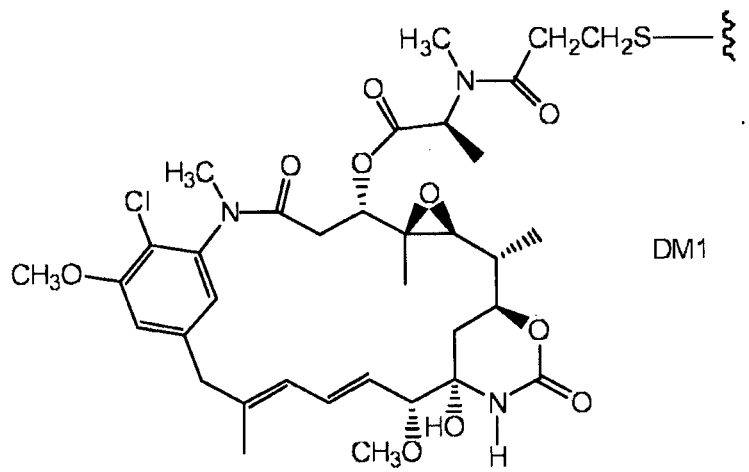

where the wavy line indicates the attachment site to the linker L.

CERTIFICATE OF CORRECTION (continued)
U.S. Pat. No. 7,521,541 B2

Col. 140, claim 64, line 33

64. The antibody-drug conjugate compound of claim 32 having the structure:

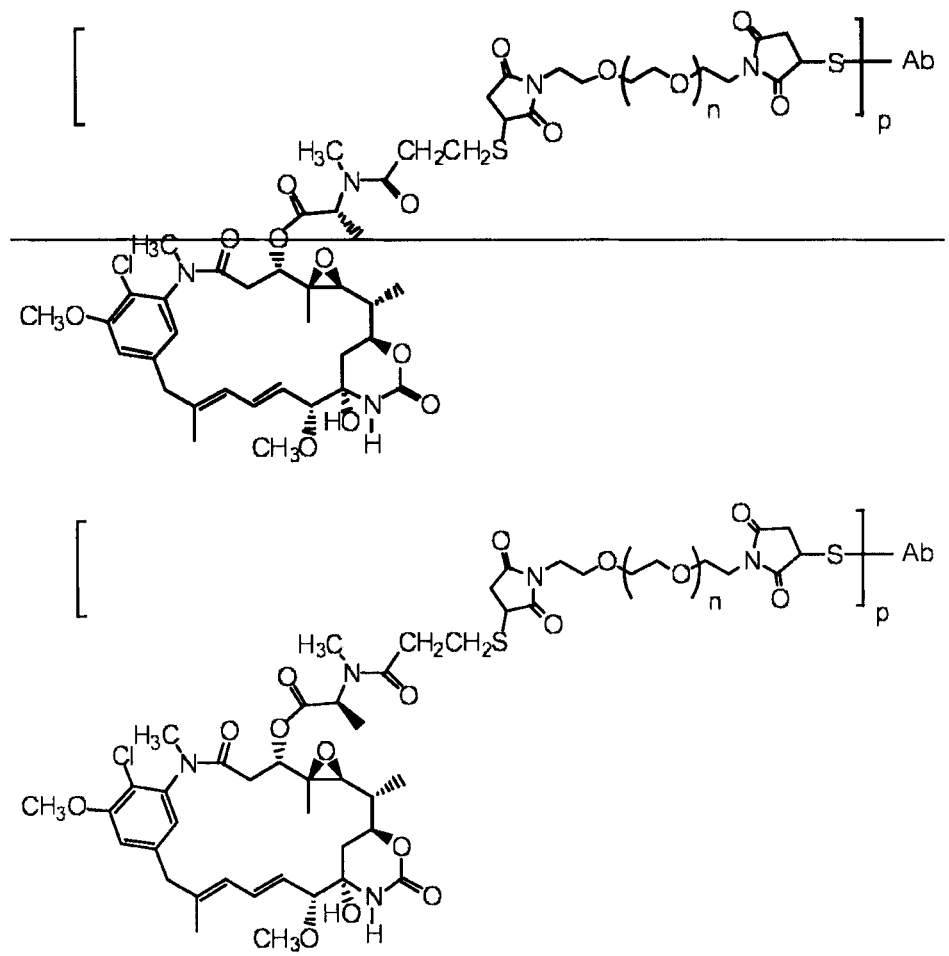

wherein n is 0, 1, or 2; and Ab is a cysteine engineered antibody.

UNITED STATES PATENT AND TRADEMARK OFFICE
CERTIFICATE OF CORRECTION

PATENT NO. : 7,521,541 B2  Page 1 of 1
APPLICATION NO. : 11/233258
DATED : April 21, 2009
INVENTOR(S) : Eigenbrot et al.

It is certified that error appears in the above-identified patent and that said Letters Patent is hereby corrected as shown below:

Title page item 73

Correction to Assignee:

~~Genetech~~ Genentech, Inc., South San Francisco, CA (US)

Signed and Sealed this

Twenty-third Day of November, 2010

David J. Kappos
*Director of the United States Patent and Trademark Office*

SEQUENCE LISTING

<160> NUMBER OF SEQ ID NOS: 49

<210> SEQ ID NO 1
<211> LENGTH: 30
<212> TYPE: PRT
<213> ORGANISM: Artificial sequence
<220> FEATURE:
<223> OTHER INFORMATION: chemically synthesized

<400> SEQUENCE: 1

Cys Asp Lys Thr His Thr Gly Gly Gly Ser Gln Arg Leu Met Glu
 1               5                  10                  15

Asp Ile Cys Leu Pro Arg Trp Gly Cys Leu Trp Glu Asp Asp Phe
                20                  25                  30

<210> SEQ ID NO 2
<211> LENGTH: 20
<212> TYPE: PRT
<213> ORGANISM: Artificial sequence
<220> FEATURE:
<223> OTHER INFORMATION: chemically synthesized

<400> SEQUENCE: 2

Gln Arg Leu Met Glu Asp Ile Cys Leu Pro Arg Trp Gly Cys Leu
 1               5                  10                  15

Trp Glu Asp Asp Phe
                20

<210> SEQ ID NO 3
<211> LENGTH: 20
<212> TYPE: PRT
<213> ORGANISM: Artificial sequence
<220> FEATURE:

<223> OTHER INFORMATION: chemically synthesized

<400> SEQUENCE: 3

Gln Arg Leu Ile Glu Asp Ile Cys Leu Pro Arg Trp Gly Cys Leu
1               5                   10                  15

Trp Glu Asp Asp Phe
            20

<210> SEQ ID NO 4
<211> LENGTH: 18
<212> TYPE: PRT
<213> ORGANISM: Artificial sequence
<220> FEATURE:
<223> OTHER INFORMATION: chemically synthesized

<400> SEQUENCE: 4

Arg Leu Ile Glu Asp Ile Cys Leu Pro Arg Trp Gly Cys Leu Trp
1               5                   10                  15

Glu Asp Asp

<210> SEQ ID NO 5
<211> LENGTH: 11
<212> TYPE: PRT
<213> ORGANISM: Artificial sequence
<220> FEATURE:
<223> OTHER INFORMATION: chemically synthesized

<400> SEQUENCE: 5

Asp Ile Cys Leu Pro Arg Trp Gly Cys Leu Trp
1               5                   10

<210> SEQ ID NO 6
<211> LENGTH: 450
<212> TYPE: PRT
<213> ORGANISM: Artificial sequence
<220> FEATURE:
<223> OTHER INFORMATION: chemically synthesized

<400> SEQUENCE: 6

Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Asn Ile Lys
                20                  25                  30

Asp Thr Tyr Ile His Trp Val Arg Gln Ala Pro Gly Lys Gly Leu
            35                  40                  45

Glu Trp Val Ala Arg Ile Tyr Pro Thr Asn Gly Tyr Thr Arg Tyr
        50                  55                  60

Ala Asp Ser Val Lys Gly Arg Phe Thr Ile Ser Ala Asp Thr Ser
                65                  70                  75

Lys Asn Thr Ala Tyr Leu Gln Met Asn Ser Leu Arg Cys Glu Asp
            80                  85                  90

Thr Ala Val Tyr Tyr Cys Ser Arg Trp Gly Gly Asp Gly Phe Tyr
        95                  100                 105

Ala Met Asp Tyr Trp Gly Gln Gly Thr Leu Val Thr Val Ser Ser
                110                 115                 120

Ala Ser Thr Lys Gly Pro Ser Val Phe Pro Leu Ala Pro Ser Ser
            125                 130                 135

Lys Ser Thr Ser Gly Gly Thr Ala Ala Leu Gly Cys Leu Val Lys
        140                 145                 150

Asp Tyr Phe Pro Glu Pro Val Thr Val Ser Trp Asn Ser Gly Ala

```
                    155                 160                 165
Leu Thr Ser Gly Val His Thr Phe Pro Ala Val Leu Gln Ser Ser
                170                 175                 180

Gly Leu Tyr Ser Leu Ser Ser Val Val Thr Val Pro Ser Ser Ser
                185                 190                 195

Leu Gly Thr Gln Thr Tyr Ile Cys Asn Val Asn His Lys Pro Ser
                200                 205                 210

Asn Thr Lys Val Asp Lys Lys Val Glu Pro Lys Ser Cys Asp Lys
                215                 220                 225

Thr His Thr Cys Pro Pro Cys Pro Ala Pro Glu Leu Leu Gly Gly
                230                 235                 240

Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val
                275                 280                 285

Glu Val His Asn Ala Lys Thr Lys Pro Arg Glu Glu Gln Tyr Asn
                290                 295                 300

Ser Thr Tyr Arg Val Val Ser Val Leu Thr Val Leu His Gln Asp
                305                 310                 315

Trp Leu Asn Gly Lys Glu Tyr Lys Cys Lys Val Ser Asn Lys Ala
                320                 325                 330

Leu Pro Ala Pro Ile Glu Lys Thr Ile Ser Lys Ala Lys Gly Gln
                335                 340                 345

Pro Arg Glu Pro Gln Val Tyr Thr Leu Pro Pro Ser Arg Glu Glu
                350                 355                 360

Met Thr Lys Asn Gln Val Ser Leu Thr Cys Leu Val Lys Gly Phe
                365                 370                 375

Tyr Pro Ser Asp Ile Ala Val Glu Trp Glu Ser Asn Gly Gln Pro
                380                 385                 390

Glu Asn Asn Tyr Lys Thr Thr Pro Pro Val Leu Asp Ser Asp Gly
                395                 400                 405

Ser Phe Phe Leu Tyr Ser Lys Leu Thr Val Asp Lys Ser Arg Trp
                410                 415                 420

Gln Gln Gly Asn Val Phe Ser Cys Ser Val Met His Glu Ala Leu
                425                 430                 435

His Asn His Tyr Thr Gln Lys Ser Leu Ser Leu Ser Pro Gly Lys
                440                 445                 450

<210> SEQ ID NO 7
<211> LENGTH: 450
<212> TYPE: PRT
<213> ORGANISM: Artificial sequence
<220> FEATURE:
<223> OTHER INFORMATION: chemically synthesized

<400> SEQUENCE: 7

Glu Val Gln Leu Val Glu Ser Gly Gly Gly Leu Val Gln Pro Gly
  1               5                  10                  15

Gly Ser Leu Arg Leu Ser Cys Ala Ala Ser Gly Phe Asn Ile Lys
                 20                  25                  30

Asp Thr Tyr Ile His Trp Val Arg Gln Ala Pro Gly Lys Gly Leu
                 35                  40                  45

Glu Trp Val Ala Arg Ile Tyr Pro Thr Asn Gly Tyr Thr Arg Tyr
```

```
                        50                  55                  60
Ala Asp Ser Val Lys Gly Arg Phe Thr Ile Ser Ala Asp Thr Ser
                        65                  70                  75

Lys Asn Thr Ala Tyr Leu Gln Met Asn Ser Leu Arg Ala Glu Asp
                        80                  85                  90

Thr Ala Val Tyr Tyr Cys Ser Arg Trp Gly Asp Gly Phe Tyr
                        95                 100                 105

Ala Met Asp Tyr Trp Gly Gln Gly Thr Leu Val Thr Val Ser Ser
                       110                 115                 120

Cys Ser Thr Lys Gly Pro Ser Val Phe Pro Leu Ala Pro Ser Ser
                       125                 130                 135

Lys Ser Thr Ser Gly Gly Thr Ala Ala Leu Gly Cys Leu Val Lys
                       140                 145                 150

Asp Tyr Phe Pro Glu Pro Val Thr Val Ser Trp Asn Ser Gly Ala
                       155                 160                 165

Leu Thr Ser Gly Val His Thr Phe Pro Ala Val Leu Gln Ser Ser
                       170                 175                 180

Gly Leu Tyr Ser Leu Ser Ser Val Val Thr Val Pro Ser Ser Ser
                       185                 190                 195

Leu Gly Thr Gln Thr Tyr Ile Cys Asn Val Asn His Lys Pro Ser
                       200                 205                 210

Asn Thr Lys Val Asp Lys Lys Val Glu Pro Lys Ser Cys Asp Lys
                       215                 220                 225

Thr His Thr Cys Pro Pro Cys Pro Ala Pro Glu Leu Leu Gly Gly
                       230                 235                 240

Pro Ser Val Phe Leu Phe Pro Pro Lys Pro Lys Asp Thr Leu Met
                       245                 250                 255

Ile Ser Arg Thr Pro Glu Val Thr Cys Val Val Val Asp Val Ser
                       260                 265                 270

His Glu Asp Pro Glu Val Lys Phe Asn Trp Tyr Val Asp Gly Val
                       275                 280                 285

Glu Val His Asn Ala Lys Thr Lys Pro Arg Glu Glu Gln Tyr Asn
                       290                 295                 300

Ser Thr Tyr Arg Val Val Ser Val Leu Thr Val Leu His Gln Asp
                       305                 310                 315

Trp Leu Asn Gly Lys Glu Tyr Lys Cys Lys Val Ser Asn Lys Ala
                       320                 325                 330

Leu Pro Ala Pro Ile Glu Lys Thr Ile Ser Lys Ala Lys Gly Gln
                       335                 340                 345

Pro Arg Glu Pro Gln Val Tyr Thr Leu Pro Pro Ser Arg Glu Glu
                       350                 355                 360

Met Thr Lys Asn Gln Val Ser Leu Thr Cys Leu Val Lys Gly Phe
                       365                 370                 375

Tyr Pro Ser Asp Ile Ala Val Glu Trp Glu Ser Asn Gly Gln Pro
                       380                 385                 390

Glu Asn Asn Tyr Lys Thr Thr Pro Pro Val Leu Asp Ser Asp Gly
                       395                 400                 405

Ser Phe Phe Leu Tyr Ser Lys Leu Thr Val Asp Lys Ser Arg Trp
                       410                 415                 420

Gln Gln Gly Asn Val Phe Ser Cys Ser Val Met His Glu Ala Leu
                       425                 430                 435

His Asn His Tyr Thr Gln Lys Ser Leu Ser Leu Ser Pro Gly Lys
                       440                 445                 450
```

<210> SEQ ID NO 8
<211> LENGTH: 214
<212> TYPE: PRT
<213> ORGANISM: Artificial sequence
<220> FEATURE:
<223> OTHER INFORMATION: chemically synthesized

<400> SEQUENCE: 8

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Asn
             20                  25                  30

Thr Ala Val Ala Trp Tyr Gln Gln Lys Pro Gly Lys Ala Pro Lys
             35                  40                  45

Leu Leu Ile Tyr Ser Ala Ser Phe Leu Tyr Ser Gly Val Pro Ser
             50                  55                  60

Arg Phe Ser Gly Ser Arg Ser Gly Thr Asp Phe Thr Leu Thr Ile
             65                  70                  75

Ser Ser Leu Gln Pro Glu Asp Phe Ala Thr Tyr Tyr Cys Gln Gln
             80                  85                  90

His Tyr Thr Thr Pro Pro Thr Phe Gly Gln Gly Thr Lys Val Glu
             95                 100                 105

Ile Lys Arg Thr Cys Ala Ala Pro Ser Val Phe Ile Phe Pro Pro
            110                 115                 120

Ser Asp Glu Gln Leu Lys Ser Gly Thr Ala Ser Val Val Cys Leu
            125                 130                 135

Leu Asn Asn Phe Tyr Pro Arg Glu Ala Lys Val Gln Trp Lys Val
            140                 145                 150

Asp Asn Ala Leu Gln Ser Gly Asn Ser Gln Glu Ser Val Thr Glu
            155                 160                 165

Gln Asp Ser Lys Asp Ser Thr Tyr Ser Leu Ser Ser Thr Leu Thr
            170                 175                 180

Leu Ser Lys Ala Asp Tyr Glu Lys His Lys Val Tyr Ala Cys Glu
            185                 190                 195

Val Thr His Gln Gly Leu Ser Ser Pro Val Thr Lys Ser Phe Asn
            200                 205                 210

Arg Gly Glu Cys

<210> SEQ ID NO 9
<211> LENGTH: 10
<212> TYPE: PRT
<213> ORGANISM: Artificial sequence
<220> FEATURE:
<223> OTHER INFORMATION: chemically synthesized

<400> SEQUENCE: 9

Trp Val Arg Gln Cys Pro Gly Lys Gly Leu
                 5                  10

<210> SEQ ID NO 10
<211> LENGTH: 10
<212> TYPE: PRT
<213> ORGANISM: Artificial sequence
<220> FEATURE:
<223> OTHER INFORMATION: chemically synthesized

<400> SEQUENCE: 10

Asn Ser Leu Arg Cys Glu Asp Thr Ala Val

<210> SEQ ID NO 11
<211> LENGTH: 13
<212> TYPE: PRT
<213> ORGANISM: Artificial sequence
<220> FEATURE:
<223> OTHER INFORMATION: chemically synthesized

<400> SEQUENCE: 11

Leu Val Thr Val Cys Ser Ala Ser Thr Lys Gly Pro Ser
                5                   10

<210> SEQ ID NO 12
<211> LENGTH: 13
<212> TYPE: PRT
<213> ORGANISM: Artificial sequence
<220> FEATURE:
<223> OTHER INFORMATION: chemically synthesized

<400> SEQUENCE: 12

Leu Val Thr Val Ser Cys Ala Ser Thr Lys Gly Pro Ser
                5                   10

<210> SEQ ID NO 13
<211> LENGTH: 13
<212> TYPE: PRT
<213> ORGANISM: Artificial sequence
<220> FEATURE:
<223> OTHER INFORMATION: chemically synthesized

<400> SEQUENCE: 13

Leu Val Thr Val Ser Ser Cys Ser Thr Lys Gly Pro Ser
                5                   10

<210> SEQ ID NO 14
<211> LENGTH: 13
<212> TYPE: PRT
<213> ORGANISM: Artificial sequence
<220> FEATURE:
<223> OTHER INFORMATION: chemically synthesized

<400> SEQUENCE: 14

Leu Val Thr Val Ser Ser Ala Cys Thr Lys Gly Pro Ser
                5                   10

<210> SEQ ID NO 15
<211> LENGTH: 14
<212> TYPE: PRT
<213> ORGANISM: Artificial sequence
<220> FEATURE:
<223> OTHER INFORMATION: chemically synthesized

<400> SEQUENCE: 15

His Thr Phe Pro Cys Val Leu Gln Ser Ser Gly Leu Tyr Ser
                5                   10

<210> SEQ ID NO 16
<211> LENGTH: 14
<212> TYPE: PRT
<213> ORGANISM: Artificial sequence
<220> FEATURE:
<223> OTHER INFORMATION: chemically synthesized

<400> SEQUENCE: 16

His Thr Phe Pro Ala Val Leu Gln Cys Ser Gly Leu Tyr Ser
                5                   10

<210> SEQ ID NO 17
<211> LENGTH: 11
<212> TYPE: PRT
<213> ORGANISM: Artificial sequence
<220> FEATURE:
<223> OTHER INFORMATION: chemically synthesized

<400> SEQUENCE: 17

Ser Leu Ser Ala Ser Cys Gly Asp Arg Val Thr
                 5                  10

<210> SEQ ID NO 18
<211> LENGTH: 11
<212> TYPE: PRT
<213> ORGANISM: Artificial sequence
<220> FEATURE:
<223> OTHER INFORMATION: chemically synthesized

<400> SEQUENCE: 18

Gln Lys Pro Gly Lys Cys Pro Lys Leu Leu Ile
                 5                  10

<210> SEQ ID NO 19
<211> LENGTH: 11
<212> TYPE: PRT
<213> ORGANISM: Artificial sequence
<220> FEATURE:
<223> OTHER INFORMATION: chemically synthesized

<400> SEQUENCE: 19

Glu Ile Lys Arg Thr Cys Ala Ala Pro Ser Val
                 5                  10

<210> SEQ ID NO 20
<211> LENGTH: 12
<212> TYPE: PRT
<213> ORGANISM: Artificial sequence
<220> FEATURE:
<223> OTHER INFORMATION: chemically synthesized

<400> SEQUENCE: 20

Thr Cys Ala Ala Pro Cys Val Phe Ile Phe Pro Pro
                 5                  10

<210> SEQ ID NO 21
<211> LENGTH: 11
<212> TYPE: PRT
<213> ORGANISM: Artificial sequence
<220> FEATURE:
<223> OTHER INFORMATION: chemically synthesized

<400> SEQUENCE: 21

Phe Ile Phe Pro Pro Cys Asp Glu Gln Leu Lys
                 5                  10

<210> SEQ ID NO 22
<211> LENGTH: 11
<212> TYPE: PRT
<213> ORGANISM: Artificial sequence
<220> FEATURE:
<223> OTHER INFORMATION: chemically synthesized

<400> SEQUENCE: 22

Asp Glu Gln Leu Lys Cys Gly Thr Ala Ser Val
                 5                  10

```
<210> SEQ ID NO 23
<211> LENGTH: 11
<212> TYPE: PRT
<213> ORGANISM: Artificial sequence
<220> FEATURE:
<223> OTHER INFORMATION: chemically synthesized

<400> SEQUENCE: 23

Phe Tyr Pro Arg Glu Cys Lys Val Gln Trp Lys
                  5                  10

<210> SEQ ID NO 24
<211> LENGTH: 11
<212> TYPE: PRT
<213> ORGANISM: Artificial sequence
<220> FEATURE:
<223> OTHER INFORMATION: chemically synthesized

<400> SEQUENCE: 24

Trp Lys Val Asp Asn Cys Leu Gln Ser Gly Asn
                  5                  10

<210> SEQ ID NO 25
<211> LENGTH: 11
<212> TYPE: PRT
<213> ORGANISM: Artificial sequence
<220> FEATURE:
<223> OTHER INFORMATION: chemically synthesized

<400> SEQUENCE: 25

Ala Leu Gln Ser Gly Cys Ser Gln Glu Ser Val
                  5                  10

<210> SEQ ID NO 26
<211> LENGTH: 11
<212> TYPE: PRT
<213> ORGANISM: Artificial sequence
<220> FEATURE:
<223> OTHER INFORMATION: chemically synthesized

<400> SEQUENCE: 26

Val Thr Glu Gln Asp Cys Lys Asp Ser Thr Tyr
                  5                  10

<210> SEQ ID NO 27
<211> LENGTH: 11
<212> TYPE: PRT
<213> ORGANISM: Artificial sequence
<220> FEATURE:
<223> OTHER INFORMATION: chemically synthesized

<400> SEQUENCE: 27

Gly Leu Ser Ser Pro Cys Thr Lys Ser Phe Asn
                  5                  10

<210> SEQ ID NO 28
<211> LENGTH: 450
<212> TYPE: PRT
<213> ORGANISM: Artificial sequence
<220> FEATURE:
<223> OTHER INFORMATION: chemically synthesized

<400> SEQUENCE: 28

Glu Val Gln Leu Val Glu Ser Gly Gly Gly Leu Val Gln Pro Gly
  1               5                  10                  15

Gly Ser Leu Arg Leu Ser Cys Ala Ala Ser Gly Tyr Thr Phe Thr
```

-continued

```
                20                  25                  30
Ser Tyr Trp Met His Trp Val Arg Gln Ala Pro Gly Lys Gly Leu
                35                  40                  45
Glu Trp Val Gly Phe Ile Asn Pro Ser Thr Gly Tyr Thr Asp Tyr
                50                  55                  60
Asn Gln Lys Phe Lys Asp Arg Phe Thr Ile Ser Ala Asp Thr Ser
                65                  70                  75
Lys Asn Thr Ala Tyr Leu Gln Met Asn Ser Leu Arg Ala Glu Asp
                80                  85                  90
Thr Ala Val Tyr Tyr Cys Thr Arg Arg Pro Lys Ile Pro Arg His
                95                 100                 105
Ala Asn Val Phe Trp Gly Gln Gly Thr Leu Val Thr Val Ser Ser
               110                 115                 120
Cys Ser Thr Lys Gly Pro Ser Val Phe Pro Leu Ala Pro Ser Ser
               125                 130                 135
Lys Ser Thr Ser Gly Gly Thr Ala Ala Leu Gly Cys Leu Val Lys
               140                 145                 150
Asp Tyr Phe Pro Glu Pro Val Thr Val Ser Trp Asn Ser Gly Ala
               155                 160                 165
Leu Thr Ser Gly Val His Thr Phe Pro Ala Val Leu Gln Ser Ser
               170                 175                 180
Gly Leu Tyr Ser Leu Ser Ser Val Val Thr Val Pro Ser Ser Ser
               185                 190                 195
Leu Gly Thr Gln Thr Tyr Ile Cys Asn Val Asn His Lys Pro Ser
               200                 205                 210
Asn Thr Lys Val Asp Lys Lys Val Glu Pro Lys Ser Cys Asp Lys
               215                 220                 225
Thr His Thr Cys Pro Pro Cys Pro Ala Pro Glu Leu Leu Gly Gly
               230                 235                 240
Pro Ser Val Phe Leu Phe Pro Pro Lys Pro Lys Asp Thr Leu Met
               245                 250                 255
Ile Ser Arg Thr Pro Glu Val Thr Cys Val Val Val Asp Val Ser
               260                 265                 270
His Glu Asp Pro Glu Val Lys Phe Asn Trp Tyr Val Asp Gly Val
               275                 280                 285
Glu Val His Asn Ala Lys Thr Lys Pro Arg Glu Glu Gln Tyr Asn
               290                 295                 300
Ser Thr Tyr Arg Val Val Ser Val Leu Thr Val Leu His Gln Asp
               305                 310                 315
Trp Leu Asn Gly Lys Glu Tyr Lys Cys Lys Val Ser Asn Lys Ala
               320                 325                 330
Leu Pro Ala Pro Ile Glu Lys Thr Ile Ser Lys Ala Lys Gly Gln
               335                 340                 345
Pro Arg Glu Pro Gln Val Tyr Thr Leu Pro Pro Ser Arg Glu Glu
               350                 355                 360
Met Thr Lys Asn Gln Val Ser Leu Thr Cys Leu Val Lys Gly Phe
               365                 370                 375
Tyr Pro Ser Asp Ile Ala Val Glu Trp Glu Ser Asn Gly Gln Pro
               380                 385                 390
Glu Asn Asn Tyr Lys Thr Thr Pro Pro Val Leu Asp Ser Asp Gly
               395                 400                 405
Ser Phe Phe Leu Tyr Ser Lys Leu Thr Val Asp Lys Ser Arg Trp
               410                 415                 420
```

```
Gln Gln Gly Asn Val Phe Ser Cys Ser Val Met His Glu Ala Leu
                425                 430                 435

His Asn His Tyr Thr Gln Lys Ser Leu Ser Leu Ser Pro Gly Lys
                440                 445                 450
```

<210> SEQ ID NO 29
<211> LENGTH: 25
<212> TYPE: PRT
<213> ORGANISM: Artificial sequence
<220> FEATURE:
<223> OTHER INFORMATION: chemically synthesized

<400> SEQUENCE: 29

```
His Glu Asp Pro Glu Cys Lys Phe Asn Trp Tyr Val Asp Gly Val
  1               5                  10                  15

Glu Val His Asn Ala Lys Thr Lys Pro Arg
                 20                  25
```

<210> SEQ ID NO 30
<211> LENGTH: 25
<212> TYPE: PRT
<213> ORGANISM: Artificial sequence
<220> FEATURE:
<223> OTHER INFORMATION: chemically synthesized

<400> SEQUENCE: 30

```
His Glu Asp Pro Glu Val Lys Phe Asn Trp Tyr Cys Asp Gly Val
  1               5                  10                  15

Glu Val His Asn Ala Lys Thr Lys Pro Arg
                 20                  25
```

<210> SEQ ID NO 31
<211> LENGTH: 25
<212> TYPE: PRT
<213> ORGANISM: Artificial sequence
<220> FEATURE:
<223> OTHER INFORMATION: chemically synthesized

<400> SEQUENCE: 31

```
His Glu Asp Pro Glu Val Lys Phe Asn Trp Tyr Val Asp Gly Cys
  1               5                  10                  15

Glu Val His Asn Ala Lys Thr Lys Pro Arg
                 20                  25
```

<210> SEQ ID NO 32
<211> LENGTH: 25
<212> TYPE: PRT
<213> ORGANISM: Artificial sequence
<220> FEATURE:
<223> OTHER INFORMATION: chemically synthesized

<400> SEQUENCE: 32

```
His Glu Asp Pro Glu Val Lys Phe Asn Trp Tyr Val Asp Gly Val
  1               5                  10                  15

Glu Cys His Asn Ala Lys Thr Lys Pro Arg
                 20                  25
```

<210> SEQ ID NO 33
<211> LENGTH: 25
<212> TYPE: PRT
<213> ORGANISM: Artificial sequence
<220> FEATURE:
<223> OTHER INFORMATION: chemically synthesized

```
<400> SEQUENCE: 33

His Glu Asp Pro Glu Val Lys Phe Asn Trp Tyr Val Asp Gly Val
 1               5                  10                  15

Glu Val His Asn Cys Lys Thr Lys Pro Arg
            20                  25

<210> SEQ ID NO 34
<211> LENGTH: 11
<212> TYPE: PRT
<213> ORGANISM: Artificial sequence
<220> FEATURE:
<223> OTHER INFORMATION: chemically synthesized

<400> SEQUENCE: 34

Tyr Lys Cys Lys Val Cys Asn Lys Ala Leu Pro
 1               5                  10

<210> SEQ ID NO 35
<211> LENGTH: 13
<212> TYPE: PRT
<213> ORGANISM: Artificial sequence
<220> FEATURE:
<223> OTHER INFORMATION: chemically synthesized

<400> SEQUENCE: 35

Ile Glu Lys Thr Ile Cys Lys Ala Lys Gly Gln Pro Arg
 1               5                  10

<210> SEQ ID NO 36
<211> LENGTH: 13
<212> TYPE: PRT
<213> ORGANISM: Artificial sequence
<220> FEATURE:
<223> OTHER INFORMATION: chemically synthesized

<400> SEQUENCE: 36

Ile Glu Lys Thr Ile Ser Lys Cys Lys Gly Gln Pro Arg
 1               5                  10

<210> SEQ ID NO 37
<211> LENGTH: 11
<212> TYPE: PRT
<213> ORGANISM: Artificial sequence
<220> FEATURE:
<223> OTHER INFORMATION: chemically synthesized

<400> SEQUENCE: 37

Lys Gly Phe Tyr Pro Cys Asp Ile Ala Val Glu
 1               5                  10

<210> SEQ ID NO 38
<211> LENGTH: 11
<212> TYPE: PRT
<213> ORGANISM: Artificial sequence
<220> FEATURE:
<223> OTHER INFORMATION: chemically synthesized

<400> SEQUENCE: 38

Pro Pro Val Leu Asp Cys Asp Gly Ser Phe Phe
 1               5                  10

<210> SEQ ID NO 39
<211> LENGTH: 446
<212> TYPE: PRT
<213> ORGANISM: Artificial sequence
<220> FEATURE:
```

<223> OTHER INFORMATION: chemically synthesized

<400> SEQUENCE: 39

```
Asp Val Gln Leu Gln Glu Ser Gly Pro Gly Leu Val Asn Pro Ser
  1               5                  10                  15

Gln Ser Leu Ser Leu Thr Cys Thr Val Thr Gly Tyr Ser Ile Thr
             20                  25                  30

Asn Asp Tyr Ala Trp Asn Trp Ile Arg Gln Phe Pro Gly Asn Lys
             35                  40                  45

Leu Glu Trp Met Gly Tyr Ile Asn Tyr Ser Gly Tyr Thr Thr Tyr
             50                  55                  60

Asn Pro Ser Leu Lys Ser Arg Ile Ser Ile Thr Arg Asp Thr Ser
             65                  70                  75

Lys Asn Gln Phe Phe Leu His Leu Asn Ser Val Thr Thr Glu Asp
             80                  85                  90

Thr Ala Thr Tyr Tyr Cys Ala Arg Trp Asp Gly Gly Leu Thr Tyr
             95                 100                 105

Trp Gly Gln Gly Thr Leu Val Thr Val Ser Ala Cys Ser Thr Lys
            110                 115                 120

Gly Pro Ser Val Phe Pro Leu Ala Pro Ser Ser Lys Ser Thr Ser
            125                 130                 135

Gly Gly Thr Ala Ala Leu Gly Cys Leu Val Lys Asp Tyr Phe Pro
            140                 145                 150

Glu Pro Val Thr Val Ser Trp Asn Ser Gly Ala Leu Thr Ser Gly
            155                 160                 165

Val His Thr Phe Pro Ala Val Leu Gln Ser Ser Gly Leu Tyr Ser
            170                 175                 180

Leu Ser Ser Val Val Thr Val Pro Ser Ser Ser Leu Gly Thr Gln
            185                 190                 195

Thr Tyr Ile Cys Asn Val Asn His Lys Pro Ser Asn Thr Lys Val
            200                 205                 210

Asp Lys Lys Val Glu Pro Lys Ser Cys Asp Lys Thr His Thr Cys
            215                 220                 225

Pro Pro Cys Pro Ala Pro Glu Leu Leu Gly Gly Pro Ser Val Phe
            230                 235                 240

Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro
            260                 265                 270

Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly
            305                 310                 315

Lys Glu Tyr Lys Cys Lys Val Ser Asn Lys Ala Leu Pro Ala Pro
            320                 325                 330

Ile Glu Lys Thr Ile Ser Lys Ala Lys Gly Gln Pro Arg Glu Pro
            335                 340                 345

Gln Val Tyr Thr Leu Pro Pro Ser Arg Glu Glu Met Thr Lys Asn
            350                 355                 360

Gln Val Ser Leu Thr Cys Leu Val Lys Gly Phe Tyr Pro Ser Asp
            365                 370                 375
```

```
Ile Ala Val Glu Trp Glu Ser Asn Gly Gln Pro Glu Asn Asn Tyr
                380                 385                 390

Lys Thr Thr Pro Pro Val Leu Asp Ser Asp Gly Ser Phe Phe Leu
                395                 400                 405

Tyr Ser Lys Leu Thr Val Asp Lys Ser Arg Trp Gln Gln Gly Asn
                410                 415                 420

Val Phe Ser Cys Ser Val Met His Glu Ala Leu His Asn His Tyr
                425                 430                 435

Thr Gln Lys Ser Leu Ser Leu Ser Pro Gly Lys
                440                 445
```

<210> SEQ ID NO 40
<211> LENGTH: 10
<212> TYPE: PRT
<213> ORGANISM: Artificial sequence
<220> FEATURE:
<223> OTHER INFORMATION: chemically synthesized

<400> SEQUENCE: 40

```
Asn Trp Ile Arg Gln Cys Pro Gly Asn Lys
                5                   10
```

<210> SEQ ID NO 41
<211> LENGTH: 11
<212> TYPE: PRT
<213> ORGANISM: Artificial sequence
<220> FEATURE:
<223> OTHER INFORMATION: chemically synthesized

<400> SEQUENCE: 41

```
Leu Asn Ser Cys Thr Thr Glu Asp Thr Ala Thr
                5                   10
```

<210> SEQ ID NO 42
<211> LENGTH: 21
<212> TYPE: PRT
<213> ORGANISM: Artificial sequence
<220> FEATURE:
<223> OTHER INFORMATION: chemically synthesized

<400> SEQUENCE: 42

```
Gly Gln Gly Thr Leu Val Thr Val Ser Ala Cys Ser Thr Lys Gly
  1             5                   10                  15

Pro Ser Val Phe Pro Leu
                20
```

<210> SEQ ID NO 43
<211> LENGTH: 14
<212> TYPE: PRT
<213> ORGANISM: Artificial sequence
<220> FEATURE:
<223> OTHER INFORMATION: chemically synthesized

<400> SEQUENCE: 43

```
His Thr Phe Pro Cys Val Leu Gln Ser Ser Gly Leu Tyr Ser
                5                   10
```

<210> SEQ ID NO 44
<211> LENGTH: 14
<212> TYPE: PRT
<213> ORGANISM: Artificial sequence
<220> FEATURE:
<223> OTHER INFORMATION: chemically synthesized

<400> SEQUENCE: 44

```
His Thr Phe Pro Ala Cys Leu Gln Ser Ser Gly Leu Tyr Ser
                5                  10

<210> SEQ ID NO 45
<211> LENGTH: 11
<212> TYPE: PRT
<213> ORGANISM: Artificial sequence
<220> FEATURE:
<223> OTHER INFORMATION: chemically synthesized

<400> SEQUENCE: 45

Phe Leu Ser Val Ser Cys Gly Gly Arg Val Thr
                5                  10

<210> SEQ ID NO 46
<211> LENGTH: 11
<212> TYPE: PRT
<213> ORGANISM: Artificial sequence
<220> FEATURE:
<223> OTHER INFORMATION: chemically synthesized

<400> SEQUENCE: 46

Gln Lys Pro Gly Asn Cys Pro Arg Leu Leu Ile
                5                  10

<210> SEQ ID NO 47
<211> LENGTH: 11
<212> TYPE: PRT
<213> ORGANISM: Artificial sequence
<220> FEATURE:
<223> OTHER INFORMATION: chemically synthesized

<400> SEQUENCE: 47

Glu Ile Lys Arg Thr Cys Ala Ala Pro Ser Val
                5                  10

<210> SEQ ID NO 48
<211> LENGTH: 11
<212> TYPE: PRT
<213> ORGANISM: Artificial sequence
<220> FEATURE:
<223> OTHER INFORMATION: chemically synthesized

<400> SEQUENCE: 48

Phe Tyr Pro Arg Glu Cys Lys Val Gln Trp Lys
                5                  10

<210> SEQ ID NO 49
<211> LENGTH: 11
<212> TYPE: PRT
<213> ORGANISM: Artificial sequence
<220> FEATURE:
<223> OTHER INFORMATION: chemically synthesized

<400> SEQUENCE: 49

Val Thr Glu Gln Asp Cys Lys Asp Ser Thr Tyr
                5                  10
```